(12) United States Patent
Vargeese et al.

(10) Patent No.: US 7,964,578 B2
(45) Date of Patent: *Jun. 21, 2011

(54) CONJUGATES AND COMPOSITIONS FOR CELLULAR DELIVERY

(75) Inventors: Chandra Vargeese, Schwenksville, PA (US); Peter Haeberli, San Francisco, CA (US); Weimin Wang, Churchville, PA (US); Tongqian Chen, Irvine, CA (US)

(73) Assignee: Sirna Therapeutics, Inc., Boulder, CO (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/253,156

(22) Filed: Oct. 16, 2008

(65) Prior Publication Data

US 2009/0264636 A1    Oct. 22, 2009

Related U.S. Application Data

(63) Continuation of application No. 10/780,447, filed on Feb. 13, 2004, now Pat. No. 7,491,805, which is a continuation-in-part of application No. 10/427,160, filed on Apr. 30, 2003, now Pat. No. 7,833,992, which is a continuation-in-part of application No. PCT/US02/15876, filed on May 17, 2002, said application No. 10/780,447 is a continuation-in-part of application No. PCT/US03/05346, filed on Feb. 20, 2003, and a continuation-in-part of application No. PCT/US03/05028, filed on Feb. 20, 2003.

(60) Provisional application No. 60/292,217, filed on May 18, 2001, provisional application No. 60/362,016, filed on Mar. 6, 2002, provisional application No. 60/306,883, filed on Jul. 20, 2001, provisional application No. 60/311,865, filed on Aug. 13, 2001, provisional application No. 60/358,580, filed on Feb. 20, 2002, provisional application No. 60/363,124, filed on Mar. 11, 2002, provisional application No. 60/386,782, filed on Jun. 6, 2002, provisional application No. 60/406,784, filed on Aug. 29, 2002, provisional application No. 60/408,378, filed on Sep. 5, 2002, provisional application No. 60/409,293, filed on Sep. 9, 2002, provisional application No. 60/440,129, filed on Jan. 15, 2003.

(51) Int. Cl.
C12N 15/113 (2010.01)
C07H 21/02 (2006.01)

(52) U.S. Cl. .................. 514/44 R; 514/44 A; 536/24.1; 536/24.5

(58) Field of Classification Search .................. None
See application file for complete search history.

(56) References Cited

U.S. PATENT DOCUMENTS

| | | |
|---|---|---|
| 4,987,071 A | 1/1991 | Cech et al. |
| 5,108,921 A | 4/1992 | Low et al. |
| 5,334,711 A | 8/1994 | Sproat |
| 5,416,016 A | 5/1995 | Low et al. |
| 5,589,332 A | 12/1996 | Shih et al. |
| 5,627,053 A | 5/1997 | Usman et al. |
| 5,631,359 A | 5/1997 | Chowrira et al. |
| 5,631,360 A | 5/1997 | Usman et al. |
| 5,633,133 A | 5/1997 | Long et al. |
| 5,670,633 A | 9/1997 | Cook et al. |
| 5,672,695 A | 9/1997 | Eckstein et al. |
| 5,716,824 A | 2/1998 | Beigelman et al. |
| 5,741,679 A | 4/1998 | George et al. |
| 5,792,847 A | 8/1998 | Buhr et al. |
| 5,804,683 A | 9/1998 | Usman et al. |
| 5,814,620 A | 9/1998 | Robinson et al. |
| 5,831,071 A | 11/1998 | Usman et al. |
| 5,834,186 A | 11/1998 | George et al. |
| 5,849,902 A | 12/1998 | Arrow et al. |
| 5,871,914 A | 2/1999 | Nathan et al. |
| 5,898,031 A | 4/1999 | Crooke |
| 5,989,912 A | 11/1999 | Arrow et al. |
| 5,998,203 A | 12/1999 | Matulic-Adamic et al. |
| 6,001,311 A | 12/1999 | Brennan |
| 6,005,087 A | 12/1999 | Cook et al. |
| 6,008,400 A | 12/1999 | Scaringe et al. |
| 6,054,576 A | 4/2000 | Bellon et al. |
| 6,107,094 A | 8/2000 | Crooke |
| 6,111,086 A | 8/2000 | Scaringe et al. |
| 6,117,657 A | 9/2000 | Usman et al. |
| 6,153,737 A | 11/2000 | Manoharan et al. |
| 6,162,909 A | 12/2000 | Bellon et al. |
| 6,168,778 B1 | 1/2001 | Janjic et al. |

(Continued)

FOREIGN PATENT DOCUMENTS

CA    2359180    8/2000

(Continued)

OTHER PUBLICATIONS

Yuan et al., "Targeted cleavage of mRNA by human RNase P," Proc. Natl. Acad. Sci. USA 89:8006-8010 (1992).

Zarrinkar et al., "The P9.1-P9.2 peripheral extension helps guide folding of the *Tetrahymena* ribozyme," Nucl. Acids Res. 24:854-858 (1996).

Zimmerly et al., "A Group IIIntran RNA is a Catalytic Component of a DNA Endonuclease Involved in Intran Mobility," Cell 83:529-538 (1995).

(Continued)

*Primary Examiner* — Eric S Olson
(74) *Attorney, Agent, or Firm* — Matthew A. Leff; David A. Muthard

(57) ABSTRACT

This invention features conjugates, degradable linkers, compositions, methods of synthesis, and applications thereof, including cholesterol, folate, galactose, galactosamine, N-acetyl galactosamine, PEG, phospholipid, peptide and human serum albumin (HSA) derived conjugates of biologically active compounds, including antibodies, antivirals, chemotherapeutics, peptides, proteins, hormones, nucleosides, nucleotides, non-nucleosides, and nucleic acids including enzymatic nucleic acids, DNAzymes, allozymes, antisense, dsRNA, siNA, siRNA, triplex oligonucleotides, 2,5-A chimeras, decoys and aptamers.

9 Claims, 51 Drawing Sheets

U.S. PATENT DOCUMENTS

| | | | |
|---|---|---|---|
| 6,303,773 | B1 | 10/2001 | Bellon et al. |
| 6,335,434 | B1 | 1/2002 | Guzaev et al. |
| 6,353,098 | B1 | 3/2002 | Usman et al. |
| 6,362,323 | B1 | 3/2002 | Usman et al. |
| 6,395,492 | B1 | 5/2002 | Manoharan et al. |
| 6,437,117 | B1 | 8/2002 | Usman et al. |
| 6,469,158 | B1 | 10/2002 | Usman et al. |
| 6,476,205 | B1 | 11/2002 | Buhr et al. |
| 6,482,932 | B1 | 11/2002 | Beigelman et al. |
| 6,506,559 | B1 | 1/2003 | Fire et al. |
| 6,528,631 | B1 | 3/2003 | Cook et al. |
| 7,037,646 | B1 * | 5/2006 | Cook et al. ............. 435/6 |
| 2003/0191075 | A1 * | 10/2003 | Cook et al. ............. 514/44 |
| 2004/0110296 | A1 * | 6/2004 | Vargeese et al. ........... 435/458 |
| 2004/0192626 | A1 | 9/2004 | McSwiggen et al. |

FOREIGN PATENT DOCUMENTS

| | | |
|---|---|---|
| EP | 0 360 257 | 2/1990 |
| WO | WO 88/09810 | 12/1988 |
| WO | WO 89/02949 | 3/1989 |
| WO | WO 90/12096 | 10/1990 |
| WO | WO 90/14090 | 11/1990 |
| WO | WO 91/03162 | 3/1991 |
| WO | WO 92/07065 | 4/1992 |
| WO | WO 93/15187 | 8/1993 |
| WO | WO 93/23569 | 11/1993 |
| WO | WO 94/01550 | 1/1994 |
| WO | WO 95/06731 | 3/1995 |
| WO | WO 95/11304 | 4/1995 |
| WO | WO 95/11910 | 5/1995 |
| WO | WO 96/10390 | 4/1996 |
| WO | WO 96/10391 | 4/1996 |
| WO | WO 96-10392 | 4/1996 |
| WO | WO 96-22689 | 8/1996 |
| WO | WO 97/26270 | 7/1997 |
| WO | WO 98/13526 | 4/1998 |
| WO | WO 98/27104 | 6/1998 |
| WO | WO 98/28317 | 7/1998 |
| WO | WO 98/43993 | 10/1998 |
| WO | WO 98/58058 | 12/1998 |
| WO | WO 99/07409 | 2/1999 |
| WO | WO 99/16871 | 4/1999 |
| WO | WO 99/17120 | 4/1999 |
| WO | WO 99/29842 | 6/1999 |
| WO | WO 99/32619 | 7/1999 |
| WO | WO 99/49029 | 9/1999 |
| WO | WO 99/53050 | 10/1999 |
| WO | WO 99/54459 | 10/1999 |
| WO | WO 99/55857 | 11/1999 |
| WO | WO 99/61631 | 12/1999 |
| WO | WO 99/66063 | 12/1999 |
| WO | WO 00/01846 | 1/2000 |
| WO | WO 00/24931 | 5/2000 |
| WO | WO 00/26226 | 5/2000 |
| WO | WO 00/44895 | 6/2000 |
| WO | WO 00/44914 | 8/2000 |
| WO | WO 00/49035 | 8/2000 |
| WO | WO 00/63364 | 10/2000 |
| WO | WO 01/29058 | 4/2001 |
| WO | WO 01/36646 | 5/2001 |
| WO | WO 01/96584 | 12/2001 |
| WO | WO 02/22636 | 3/2002 |
| WO | WO 02/15876 | 5/2002 |
| WO | WO02/096927 | * 12/2002 |
| WO | WO03/028764 | * 4/2003 |
| WO | WO 03/070918 | 8/2003 |
| WO | WO 03/074654 | 9/2003 |
| WO | WO2004/061081 | * 7/2004 |

OTHER PUBLICATIONS

Office Action mailed on Nov. 7, 2006 for U.S. Appl. No. 10/780,447, 4 pages.

Office Action mailed on Jul. 13, 2007 for U.S. Appl. No. 10/780,447, 11 pages.

2006 Chemical Abstracts Service Catalog, published by Chemical Abstracts Service, p. 52.

Ruoslahti, "RGD and Other Recognition Sequences for Integrins," Annu. Rev. Cell Dev. Biol. 12:697-715 (1996).

Salo et al., "Aminooxy Functionalized Oligonucleotides: Preparation, On-Support Derivatization, and Postsynthetic Attachment to Polymer Support," Bioconjugate Chem.10:815-823 (1999).

Sanghvi et al., "Improved Process for the Preparation of Nucleosidic Phosphoramidites Using a Safer and Cheaper Activator," Org. Proc. Res. & Dev. 4:175-181 (2000).

Santoro et al., "A general purpose RNA-cleaving DNA enzyme," Proc. Natl. Acad. Sci. USA 94:4262-4266 (1997).

Santoro et al., "Mechanism and Utility of an RNA-Cleaving DNA Enzyme," Biochem. 37:13330-13342 (1998).

Santoro et al., "RNA Cleavage by a DNA Enzyme with Extended Chemical Functionality," J. Am. Chem. Soc. 122:2433-2439 (2000).

Saville et al., "A Site-Specific Self-Cleavage Reaction Performed by a Novel RNA in *Neurospora* Mitochondria," Cell 61:685-696 (1990).

Saville et al., "RNA-Mediated Ligation of Self-Cleavage Products of a *Neurospora* Mitochondrial Plasmid Transcript," Proc. Natl. Acad: Sci. USA 88:8826-8830 (1991).

Scaringe et al., "Chemical synthesis of biologically active oligoribonucleotides using (3-cyanoethyl protected ribonucleoside phosphoramidites," Nucl. Acids Res. 18:5433-5441 (1990).

Schmajuk et al., "Antisense Oligonucleotides with Different Backbones," J.Biol. Chem. 274:21783-21789 (1999).

Schmidt et al., "Base and sugar requirements for RNA cleavage of essential nucleoside residues in internal loop B of the hairpin ribozyme: implications for secondary structure," Nucl. Acids Res. 24:573-581 (1996).

Schwarz et al., IIEvidence that siRNAs Function as Guides, Not Primers, in the *Drosophila* and Human RNAi Pathways, Mol. Cell 10:537-548 (2002).

Schwarze et al., "In Vivo Protein Transduction: Delivery of a Biologically Active Protein into the Mouse," Science 285:1569-1572 (1999).

Scott et al., "The crystal structure of an All-RNA hammerhead ribozyme: A proposed mechanism for RNA catalytic cleavage," Cell 81:991-1002 (1995).

Seela et al., "Oligodeoxyribonucleotides containing 1,3-propanediol as nucleoside substitute," Nucl. Acids Res. 15:3113-3129 (1987).

Shabarova et al., "Chemical ligation of DNA: The first non-enyzmaticassembly of a biologically active gene," Nucl. Acids Res. 19:4247-4251 (1991).

Sharp et al., "RNAi and double-strand RNA," Genes & Dev. 13:139-141 (1999).

Silverman et al., "Selective RNA Cleavage by Isolated RNase L Activated with 2-5A Antisense Chimeric Oligonucleotides," Meth. in Enzym. 313:522-533 (1999).

Stein et al., "Antisense Oligonucleotides as Therapeutic Agents—Is the Bullet Really Magical?" Science 261:1004-1288 (1993).

Stein et al., "A Specificity Comparison of Four Antisense Types: Morpholino, 2'-O-Methyl RNA, DNA, and Phosphorothioate DNA," Anti. & Nucl. Acid Drug Dev. 7:151-157 (1997).

Strauss, "Molecular Biology: Candidate 'Gene Silencers' Found," Mol. Biol. 286(5441):886 (1999).

Strobel et al., "Site-Specific Cleavage of a Yeast Chromosome by Oligonucleotide-Directed Triple-Helix Formation," Science 249:73-75 (1990).

Strobel et al., "Exocyclic Amine of the Conserved G-U Pair at the Cleavage Site of the *Tetrahymena* Ribozyme Contributes to 5'-Splice Site Selection and Transition State Stabilization," Biochem. 35:1201-1211 (1996).

Strobel et al., "Minor Groove Recognitiori of the Conserved G-U Pair at the *Tetrahymena* Ribozyme Reaction Site," Science 267:675-679 (1995).

Sullenger et al., "Ribozyme-mediated repair of defective mRNA by targeted transsplicing," Nature 371 :619-622 (1994).

Sullenger et al., "Overexpression of TAR Sequences Renders Cells Resistant to Human Immunodeficiency Virus Replication," Cell 63:601-608 (1990).

Sun, "Technology evaluation: SELEX, Giliad Sciences Inc," Curr. Opin. in Mol. Thera. 2:100-105 (2000).

Szostak et al., "Ch. 20—In Vitro Selection of Functional RNA Sequences," in The RNA World, edited by Gesteland and Atkins, Cold Spring Harbor Laboratory Press, pp. 511-533 (1993).

Szostak, "In Vitro Genes," TIBS 17:89-93 (1993).

Tang et al., "Examination of the catalytic fitness of the hammerhead ribozyme by in vitro selection," RNA 3:914-925 (1997).

Torrence et al., "Targeting RNA for degradation with a (2'-5') oligoadenylate-antisense chimera," Proc. Natl. Acad. Sci. USA 90:1300-1304 (1993).

Turner et al., "Improved Parameters for Prediction of RNA Structure," Cold Spring Harbor Symposia on Quantitative Biol., vol. LII, pp. 123-133 (1987).

Turner et al., "Free Energy Increments for Hydrogen Bonds in Nucleic Acid Base Pairs," J. Am. Chem. Soc. 109:3783-3785 (1987).

Tuschl et al., "Small Interfering RNAs: A Revolutionary Tool for Analysis of Gene Function and Gene Therapy," Mol. Interventions, 295(3):158-167 (2002).

Tuschl et al., "Targeted mRNA Degradation by Double-Stranded RNA In Vitro," Genes & Dev. 13: 3191-3197 (1999).

Uhlmann et al., "Antisense Oligonucleotides: A New Therapeutic Principle," Chem. Reviews 90:544-584 (1990).

Usman et al., "Exploiting the chemical synthesis of RNA," TIBS 17:334-339 (1992).

Usman et al., "Automated Chemical Synthesis of Long Oligoribonucleotides Using 2'•0-Silylated Ribonucleoside 3'-0-Phosphoramidites on a Controlled-Pore Glass Support: Synthesis of a 43-Nucleotide Sequence Similar to the 3'-Half Molecule of an *Escherichia coli* Formylmethoionine tRNA," J. Am. Chem. Soc. 109:7845-7854 (1987).

Usman et al., "Chemical modification of hammerhead ribozymes: activity and nuclease resistance," Nucl. Acids Sym. Series 31:163-164 (1994).

Usman et al., "Hammerhead ribozyme engineering," Curr. Opin. in Struct. Biol. 1:527-533(1996).

Vaish et al., "Isolation of Hammerhead Ribozymes with Altered Core Sequences by in Vitro Selection," Biochem. 36:6495-6501 (1997).

Verma et al., "Modified Oligonucleotides: Synthesis and Strategy for Users," Annu. Rev. Biochem. 67:99-134 (1998).

Volpe et al., "Regulation of Heterochromatic Silencing and Histone H3 Lysine-9 Methylation by RNAi," Science 297:1833-1837 (2002).

Wang et aL, "Delivery of Antisense Oligodeoxyribonucleotides Against the Human Epidermal Growth Factor Receptor into Cultured KB Cells with Liposomes Conjugated to Folate via Polyethylene Glycol," Proc. Natl. Acad. Sci. USA 92:3318-3322 (1995).

Waterhouse et al., "Virus resistance and gene silencing in plants can be induced by simultaneous expression of sense and antisense RNA," Proc. Natl. Acad. Sci. USA, 95:13959-13964 (1998).

Werner et al., "The effect of base mismatches in the substrate recognition helices qf hammerhead ribozymes on binding and catalysis," Nucl. Acids Res. 23:2092-2096 (1995).

Wincott et al., "Synthesis, deprotection, analysis and purification of RNA and ribozymes," Nucl. Acids Res. 23(14):2677-2684 (1995).

Wincott et al., "A Practical Method for the Production of RNA and Ribozymes," Meth. in Mol. Biol. 74:59-69 (1997).

Woolf et al., "Specificity of Antisense Oligonucleotides in vivo," Proc. Natl. Acad. Sci. USA 89:7305-7309 (1992).

Wu et al., "Receptor-mediated in Vitro Gene Transformation by a Soluble DNA Carrier System," J. Biol. Chern. 262:4429-4432 (1987).

Lasic et al. "The 'Stealth' Liposome: A Prototypical Biomaterial," Chem. Reviews. 95:2601-2627 (1995).

Lasic et al., "Liposomes Revisited," Science 267:1275-1276 (1995).

Lee et al., "Preparation of Cluster Glycosides of N-Acetylgalactosamine That Have Subnanomolar Binding Constants Towards the Mammalian Hepatic Gal/GalNAc-specific Receptor," Glycoconjugates J. 4:317-328 (1987).

Lee et aL, "Enhancing the Catalytic Repertoire of Nucleic Acids: A Systematic Study of Linker Length and Rigidity," Nucl. Acids Res. 29:1565-1573 (2001).

Leirdal at aL, "Gene silencing in mammalian cells by preformed small RNA duplexes," BBRC 295:744-748 (2002).

Li et al. "Cleavage by RNase P of gene N mRNA reduces bacteriophage λ burst size," Nucl. Acids Res. 24:835-842 (1996).

Li et aL, "Thermodynamic and Activation Parameters for Binding of a Pyrene-Labeled Substrate by the *Tetrahymena* Ribozyme: Docking is Not Diffusion-Controlled and is Driven by a Favorable Entropy Change," Biochem. 34:14394-14399 (1995).

Limbach et al., "Summary: the modified nucleosides of RNA," Nucl. Acids Res. 22(12):2183-2196 (1994).

Lin et al., "A Novel mRNA-cRNA Interference Phenomenon for Silencing bcl-2 Expression in Human LNCaP Cells," BBRC 281:639-644 (2001).

Lin et al., "Policing rogue genes," Nature 402:128-129 (1999).

Lindgren et al., "Translocation Properties of Novel Cell Penetrating Transportan and Penetratin Analogues," Bioconjugate Chem. 11:619-626 (2000).

Lisacek et al., "Automatic Identification of Group I Intron Cores in Genomic DNA Sequences," J. Mol. Biol. 235:1206-1217 (1994).

Liu et al., "Cationic Liposome-mediated Intravenous Gene Delivery," J. Biol. Chem. 270(42):24864-24870 (1995).

Long et al., "Kinetic characterization of intramolecular and intermolecular hammerhead RNAs with stem II deletions," Proc. NatL Acad. Sci. USA 91:6977-6981 (1994).

Ma et al., "Design and Synthesis of RNA Miniduplexes via a Synthetic Linker Approach," Biochem. 32:1751-1758 (1993).

Ma et al., "Design and Synthesis of RNA Miniduplexes via a Synthetic Linker Approach. 2. Generation of Covalently Closed, Double-Stranded Cyclic HIV-1 TAR RNA Analogs with HiQh Tat-Binding Affinitv," Nucl. Acids Res. 21:2585-2589 (1993).

Maher et al., "Kinetic Analysis of Oligodeoxyribonucleotide-Directed Triple-Helix Formation on DNA," Biochem. 29:8820-8826 (1990).

Martinez et al., "Single-Stranded Antisense siRNAs Guide Target RNA Cleavage in RNAi," Cell 110:563-574 (2002).

Matulic-Adamic et al., "Functionalized Nucleoside 5'-triphosphates for in Vitro Selection of New Catalytic Ribonucleic Acids," Bioorg. & Med. Chem. Lett. 10:1299-1302 (2000).

McCurdy et al., "Deozyoligonucleotides with Inverted Polarity: Synthesis and Use in Triple-Helix Formation" Nucleo. & Nucleo. 10:287-290 (1991).

McKay, "Structure and function of the hammerhead ribozyme: an unfinished story," RNA 2:395-403 (1996).

McManus et al., "Gene Silencing Using Micro-RNA Designed Hairpins'," RNA 8:842-850 (2002).

Mesmaeker et al, "Novel Backbone Replacements for Oligonucleotides," Amer. Chem. Soc., pp. 24-39 (1994).

Michel et al., "Slippery substratrates," Nat. Struct. Biol. 1:5-7 (1994).

Michel et al., "Structure and Activities of GroupIIintrons," Annu. Rev. Biochem. 64:435-461 (1995).

Michels et al., "Conversion of a Group II Intron into a New Multiple-Turnover Ribozyme that Selectively Cleaves Oligonucleotides: Elucidation of Reaction Mechanism and Structure/Function Relationships," Biochem. 34:2965-2977 (1995).

Milner et al., "Selecting effective antisense reagents on combinatorial oligonucleotide arrays," Nature Biotech. 15:537-541 (1997).

Mohr et al., "Atyrosyl-tRNA synthetase can function similarly to an RNA structure in the *Tetrahymena* ribozyme," Nature 370:147-150 (1994).

Moore et al., "Site-Specific Modification of Pre-mRNA: The 2'-Hydroxyl Groups at the Splice Sites," Science 256:992-996 (1992).

Morris et aL, "A New peptide Vector for Efficient Delivery of Oligonucleotides into Mammalian Cells," Nucl. Acids Res. 25:2730-2736 (1997).

Nakamaye et al., "AUA-Cleaving Hammerhead Ribozymes: Attempted-Selection for Improved Cleavage," Biochem. 33:1271-1277 (1994).

Nathans et al., "Restriction Endonucleases in the Analysis and Restructuring of DNA Molecules," Ann. Rev. Biochem. 44:273-293 (1975).

Nomura et al., "Development of an Efficient Intermediate, a-(2-(Trimethylsilyl) ethoxy]-2-N-[2-trimethylsilyl) ethoxycarbonyl]folic Acid, for the Synthesis of Folate (y)-Conjugates, and Its Application to the Synthesis of Folate-Nucleoside Conjugates," J. Org. Chem. 65:5016-5021 (2000).

Oku et al., "Real-time analysis of liposomal trafficking in tumor-bearing mice by use of positron emission tomography," Biochim. et Biophys. Acta 1238:86-90 (1995).

Ono et aL, "DNA Triplex Formation of Oligonucleotide Analogues Consisting of Linker Groups and Octamer Segments That Have Opposite Sugar-Phosphate Backbone Polarities," Biochem. 30:9914-9921 (1991).

Pan et al., "Probing of tertiary interactions in RNA: 2'-Hydroxyl-base contacts between the Rnase P and pre-tRNA," Proc. Nat!. Acad. Sci. USA 92:12510~12514(1995).

Perrault et aL, "Mixed Deoxyribo- and Ribo-Oligonucleotides with Catalytic Activity," Nature 344:565-567 (1990).

Perrotta et al., "A pseudoknot-like structure required for efficeint self-Cleavage of hepatitis delta virus RNA," Nature 350:434-436 (1991).

Perrotta et al., "Cleavage of Oligoribonucleotides by a Ribozyme Derived from the Hepatitis S Virus RNA Sequence," Biochem. 31:16-21 (1992).

Pieken et al.. "Kinetic Characterization of Ribonuclease-Resistant 2'-Modified Hammerhead Ribozymes," Science 253:314-317 (1991).

Player et al., The 2-5A System: Modulation of Viral and Cellular Processes Through Acceleration of RNA Degradation, Pharmacol Ther. 78:55-113 (1998).

Ponpipom et al., "Cell-Specific Ligands for Selective Drug Delivery to Tissues and Organs," J. Med. Chem. 24:1388-1395 (1981).

Praseuth et al., "Triple helix formation and the antigene for sequence-specific control of gene expression," Biochim. et Biophys. Acta 1489:181-206 (1999).

Puttaraju et al., "A circular trans-acting hepatitis delta virus ribozyme," Nucl. Acids Res. 21:4253-4258 (1993).

Pyle et al., "Building a Kinetic Framework for Group II Intron Ribozyme Activity: Quantitation of Interdomain Binding and Reaction Rate," Biochem. 33:2716-2725 (1994).

Reinhart et al., "Small RNAsCorrespond to Centromer Heterochromatic Repeats," Science 297:1831 (2002).

Reinhart et al., "MicroRNAs in Plants," Genes & Devel. 16:1616-1626 (2002).

Richardson et al., "Tethered Oligonucleotide Probes. A Strategy for the Recognition of Structured RNA," J. Am. Chem. Soc. 113:5109-5111 (1991).

Robertson et al., "Purification and Properties of a Specific *Escherichia coli* Riobnuclease which Cleaves a Tyrosine Transfer Ribonucleic Acid Precursor," J. Biol. Chem. 247:5243-5251 (1972).

Rossi et al.,"Ribozymes as Anti-HIV-1 Therapeutic Agents: Principles, Applications, and Problems," Aids Res. and Human Retro. 8:183-189 (1992).

Abramovitz et al., "Catalytic Role of 2'-Hydroxyl Groups Within a Group II Intron Active Site," Science 271:1410-1413 (1996).

Allshire, "RNAi and Heterochromatin—A Hushed-up Affair," Science 297:1818-1819 (2002).

Antopolsky et al., "Peptide-Oligonucleotide Phosphorothioate Conjugates with Membrane Translocation and Nuclear Localization Properties," Bioconjugate Chem. 10:598-606 (1999).

Arap et aL, "Cancer Treatment by Targeted Drug Delivery to Tumor Vasculature in a Mouse Model," Science 279:377-380 (1998).

Baenziger et al. "Galactose and N-Acetylgalactosamine-Specific Endocytosis' of Glycopeptides by Isolated Rat Hepatocytes," Cell 22:611-620 (1980).

Bahramian et al., "Transcriptional and Posttranscriptional Silencing of Rodent α1 (I) Collagen by a Homologous Transcriptionally Self-Silenced Transgene," Mol. Cell. Biol. 19:274-283 (1999).

Banerjee et al., "The Time Dependence of Chemical Modification Reveals Slow Steps in the Folding of a Group I Ribozyme," Biochem. 34:6504-6512 (1995).

Bartel et al., "Isolation of New Ribozymes from a Large Pool of Random Sequences," Science 261:1411-1418 (1993).

Bass, "The short answer," Nature 411:428-429 (2001).

Beaucage et al., "The Functionalization of Oligonucleotides Via Phosphoramidite Derivatives," Tetrahedron 49:1925-1963 (1993).

Beaudry et al., "Directed Evolution of an RNA Enzyme," Science 257:635-641 (1992).

Beigelman et al., "Chemical Modification of Hammerhead Ribozymes," J. Biol. Chem. 270:25702-25708 (1995).

Bellon et al., "Amino-Linked Ribozymes: Post-Synthetic Conjugation of Half-Ribozymes," Nucleo. & Nucleo. 16:951-954 (1997).

Bellon et al., "Post-synthetically Ligated Ribozymes: An Alternative Approach to Alternative Solid Phase Synthesis," Bioconjugate Chem. 8:204-212 (1997).

Berzal-Herranz et al., "Essential nucleotide sequences and secondary structure elements of the hairpin ribozyme," EMBO J. 12:2567-2574 (1993).

Berzal-Herranz et al., "In vitro selection of active hairpin ribozymes by sequential RNA-catalyzed cleavage and ligation reactions," Genes & Devel. 6:129-134 (1992).

Bevilacqua et al., "A Mechanistic Framework for the Second Step of Splicing Catalyzed by the *Tetrahymena* Ribozyme," Biochem. 35:648-568 (1996).

Bongartz et al., "Improved biological activity of antisense oligonucleotides conjugated to a fusogenic peptide," Nucl. Acids Res. 22:4681-4688 (1994).

Bonora et al., "Biological Properties of Antisense Oligonucleotides Conjugated to Different High-Molecular Mass Poly(ethylen glycols)," Nucleo. & Nucleo. 18:1723-1725 (1999).

Bonora et al., "Synthesis and Characterization of High-Molecular Mass Polyethylene Glycol-Conjugated Oligonucleotides," Bioconjugate Chem. 8:793-797 (1997).

Breaker et al., "Inventing and improving ribozyme function: rational design versus iterative selection methods," TIBTECH 12:268-275 (1994).

Breaker et al., "A DNA enzyme with MG2:-dependent RNA phosphoesterase activity," Chem. Biol. 2(10):655-660 (1995).

Breaker, "Are engineered proteins getting competition from RNA?" Current Opinion in Biotech. 7:442-448 (1996).

Breaker, "Catalytic DNA: in training and seeking employment," Nature Biotech. 17:422-423 (1999).

Brennan et al., Two-Dimensional Parallel Array Technology as a New Approach to Automated Combinatorial Solid-Phase Organic Synthesis, Biotech. Bioengineer. (Combinatorial Chemistry) 61:33-45 (1998).

Brody et al., "Aptamers as therapeutic and diagnostic agents," Rev. in Molec. Biotech. 74:5-13 (2000).

Burgin et al., "Chemically Modified Hammerhead Ribozymes with Improved Catalytic Rates," Biochem. 35:14090-14097 (1996).

Burlina et al., "Chemical Engineering of RNase Resistant and Catalytically Active Hammerhead Ribozymes," Bio. & Med. Chem. 5:1999-2010 (1997).

Caruthers et al., "Chemical Synthesis of Deoxyoligonucleotides and Deoxyoligonucleotide Analogs," Meth. in Enzymol. 211:3-19 (1992).

Cebon et al., "New DNA Modification Strateg'ies Involving Oxime Formation," Aust. J. Chem. 53:333-339 (2000).

Cech, "Ribozymes and Their MedicalImplications," JAMA 260:3030-3034 (1988).

Chaloin et al., "Design of Carrier Peptide-Oligonucleotide Conjugates With Rapid Membrane Translocation and Nuclear Localization Properties," BBRC 243:601-608 (1998).

Chartrand et al., "An oligodeoxyribonucleotide that supports catalytic activity in the hammerhead ribozyme domain," Nucl. Acids Res. 23(20):4092-4096 (1995).

Chowrira et al., "Novel guanosine requirement for catalysis by the hairpin ribozyme," Nature 354:320-322 (1991).

Cload et al., "Polyether Tethered Oligonucleotide Probes," J. Am. Chern. Soc. 113:6324-6326 (1991).

Collins et al., "Reaction Conditions and Kinetics of Self-Cleavage of a Ribozyme Derived From *Neurospora* VS RNA," Biochem. 32:2795-2799 (1993).

Connolly et al., "Binding and Endocytosis of Cluster Glycosides by Rabbit Hepatocytes," J. Biol. Chern. 257:939-945 (1982).

Crooke, "Advances in Understanding the Pharmacological Properties of Antisense Oligonucleotides," Adv. in Pharmacol. 40:1-49 (1997).

Crooke, "Antisense Therapeutics," Biotech. and Gen. Engineer. Reviews 15:121-157 (1998).

Crooke, "Progress in Antisense Technology: The End of the Beginning," Meth. in Enzymol. 313:3-45 (1999).

Daniels et al., "Two Competing Pathways for Self-splicing by Group II Introns: A Quantitative Analysis of in Vitro Reaction Rates and Products," J. Mol. Biol. 256:31-49 (1996).

Defrancq et al., "Use of an Aminooxy Linker for the Functionalization of Oligodeoxvribonucleotides," Bioorg. & Med. Chem. Lett. 11:931-933 (2001).

Delihas et al., "Natural antisense RNA/target RNA interactions: Possible models for antisense oligonucleotide drug design," Nature Biotech. 15:751-753 (1997).

Durand et al., "Circular Dichroism Studies of an Oligodeoxyribonucleotide Containing a Hairpin Loop Made of a Hexaethylene Glycol Chain: Conformation and Stability," Nucl. Acids Res. 18:6353-6359 (1990).

Duval-Valentin, "Specific inhibition of transcription by triple helix-forming oligonucleotides," Proc. Natl. Acad. Sci. USA 89:504-508 (1992).

Earnshaw et al., "Modified Oligoribonucleotides as Site-Specific Probes oJ RNA Structure and Function," Biopolymers 48:39-55 (1998).

Egholm et al., "PNA hybridizes to complementary oligonucleotides obeying the Watson-Crick hhydrogen-bonding rules," Nature 365:566-568 (1993).

Ferentz et al., "Disulfied Cross-Linked Oligonucleotides," J. Am. Chern. Soc. 113:4000-4002 (1991).

Findeis, "Stepwise Synthesis of a GalNAc-containing Cluster Glycoside Ligand of the Asialoglycoprotein Receptor," Int. J. Pep. Protein Res. 43:477-485 (1994).

Fire et al., "Potent and Specific Genetic Interference by Double-Stranded RNA in Caenorhabditis elegans," Nature 391:806-811(1998).

Forster et al., "External Guide Sequences for an RNA Enzyme," Science 249:783-786 (1990).

Fox, Targeting DNA with Triplexes, Curr. Med. Chem. 7:17-37 (2000).

Freier et al., "Improved free-energy parameters for predictions of RNA duplex stability," Proc. Natl. Acad. Sci. USA 83:9373-9377, (1986).

Futami et al., "Induction of Apoptosis in HeLa Cells with siRNA Expression Vector Targeted AGainst bcl-2," Nucl. Acids Res. Supp. 2:251-252 (2002).

Godwin et al., "The Synthesis of Biologically Active Pteroyloligo-γ-L-Glutamates (Folic Acid Conjugates)," J. Biol. Chem. 247:2266-2271 (1972).

Gold et al., "Diversity of Oligonucleotide Functions," Annu. Rev. Biochem. 64:763-797 (1995).

Grasby et al., "Purine Functional Groups in Essential Residues of the Hairpin Ribozyme Required for Catalytic Cleavage of RNA," Biochem. 34:4068-4076 (1995).

Griffin et al., "Group II intron ribozymes that cleave DNA and RNA linkages with similar efficiency, and lack contacts with substrate 2'-hydroxyl groups," Chem. & Biol. 2:761-770 (1995).

Guerrier-Takada et al., "The RNA Moiety of Ribonuclease P Is the Catalytic Subunit of the Enzyme," Cell 35:849-857 (1983).

Guo et al., "Efficent trans-cleavage of a stem-loop RNA substrate by a ribozyme derived from Neurospora VS RNA," EMBO J. 14:368-376 (1995).

Habus et al., "A Mild and Efficient Solid-Support Synthesis of Novel Oligonucleotide Conjugates," Bioconjug. Chem. 9:283-291 (1998).

Hall et al., "Establishment and Maintenance of a Heterochromatin Domain," Science 297:2232-2237 (2002).

Hamilton et al., "A Species of Small Antisense RNA in Post-transcriptional Gene Silencing in Plants," Science 286:950-952 (1999).

Hammann et al., "Length Variation of Helix III in a Hammerhead Ribozyme and Its Influence on Cleavage Activity," Antisense & Nucl. Acid Drug Dev. 9:25-31 (1999).

Hampel et al., "RNA Catalytic Properties of the Minimum (-)sTRSV Sequence," Biochem. 28:4929-4933 (1989).

Hampel et al., "'Hairpin' Catalytic RNA Model: Evidence for Helices and Sequence Requirement for Substrate RNA," Nucl. Acids Res. 18:299-304 (1990).

Harris et al., "Identification of phosphates involved in catalysis by the ribozyme RNase P RNA," RNA 1:210-218 (1995).

Haseloff et al., "Sequences required for self-catalysed cleavage of the satellite RNA of tobacco ringspot virus," Gene 82:43-52 (1989).

Hegg et al., "Kinetics and Thermodynamics of Intermolecular Catalysis by Hairpin Ribozymes," Biochem. 34:15813-15828 (1995).

Hermann et al., "Adaptive Recognition by Nucleic Acid Aptamers," Science 287:820-825 (2000).

Herschlag et al., "Catalysis of RNA Cleavage by the Tetrahymena thermophila Ribozyme 1. Kinetic Description of the Reaction of an RNA Substrate Complementary to the Active Site," Biochem. 29:10159-10171 (1990).

Herschlag et al., "Catalysis of RNA Cleavage by the Tetrahymena thermophila Ribozyme. 2. Kinetic Description of the Reaction of an RNA Substrate That Forms a Mismatch at the Active Site," Biochem. 29:10172-10180 (1990).

Hertel et al., "A Kinetic Thermodynamic Framework for the Hammerhead Ribozyme Reaction," Biochem. 33:3374-3385 (1994).

Hertel et al., "Numbering System for the Hammerhead," Nucl. Acids Res. 20:3252 (1992).

Hudson et al., "Cellular Delivery of Hammerhead Ribozymes Conjugated to a Transferrin Receptor Antibody," Intl. J. of Pharma. 182:49-58 (1999).

Hunziker et al., "Nucleic Acid Analogues: Synthesis and Properties," in Modem Synthetic Methods, VCH 331-417, (1995).

Hutvagner et al., "A MicroRNA in a Multiple-Turnover RNAi Enzyme Complex," Science 297:2056-2060 (2002).

International Search Report for PCT/US03/05346 mailed Oct. 17, 2003.

International Search Report for PCT/US 03105028 mailed Oct. 17, 2003.

Ishiwata et al., "Physical-Chemistry Characteristics and Biodistribution of Poly(ethyleneglycol)-Coated Liposomes Using Poly(oxyethylene) Cholesteryl Ether," Chem. Pharm. Bull. 43:1005-1011 (1995).

Ishizaka et al., "Isolation of Active Ribozymes from an RNA Pool of Random Sequences Using an Anchored Substrate RNA," Biochem. Biophy. Res. Comm. 214(2):403-409 (1995).

Jarvis et al., "Optimizing the Cell Efficacy of Synthetic Ribozymes," J. Biol. Chem. 271 :29107-29112 (1996).

Jaschke et al., "Automated Incorporation of Polyethylene Glycol into Synthetic Oligonucleotides," Tetrahedron Letters 34:301-304 (1993).

Jaschke et al., "Synthesis and Properties of Oligodeoxyribonuclotide-polyethylene Glycol Conjugates," Nucl. Acids Res. 22:4810-4817 (1994).

Jaschke, "Oligonucleotide-Poly(ethylene glycol) Conjugates: Synthesis, Properties, and Application," Amer. Chem. Soc. 680:265-283 (1997).

Jayasena, "Aptamers: An Emerging Class of Molecules that Rival Antibodies in Diagnostics," Clin. Chem. 45:1628-1650 (1999).

Jenuwein, "An RNA-Guided Pathway for the Epigenome," Science 297:2215-2218 (2002).

Jolliet-Riant et al., "Drug transfer across the blood-brain barrier and improvement of brain delivery," Fundam. Clin. Pharmaco. 13:16-26 (1999).

Joseph et al., "Substrate selection rules for the hairpin ribozyme determined by in vitro selection, mutation, and analysis of mismatched substrates," Genes & Dev. 7:130-138 (1993).

Joyce et al., "Amplification, mutation and selection of catalytic RNA," Gene 82:83-87 (1989).

Joyce, "Directed Molecular Evolution," Sci. Amer. 267:90-97 (1992).

Karpeisky et al, "Highly Efficient Synthesis of 2'-O-Amino Nucleosides And Their Incorporation in Hammerhead Ribozymes," Tetra. Lett. 39:1131-1134 (1998).

Knitt et al., "ph Dependencies of the *Tetrahymena* Ribozyme Reveal an Unconventional Origin of an Apparent pKa," Biochem. 35:1560-1570 (1996).

Kore et al., "Sequence specificity of the hammerhead ribozyme revisited; the NIH rule," Nucl. Acids Res. 26(18):4116-4120 (1998).

Kumar et al., "Artificial evolution and natural ribozymes," FASEB J. 9:1183-1195 (1995).

Kusser, "Chemically modified nucleic acid aptamers for in vitro selections: evolving evolution," Rev. in Mol. Biotech. 74:27-38 (2000).

Kuwabara et al., "Allosterically Controllable Ribozymes with Biosensor Functions," Current Opin. in Chem. Biol. 4:669-677 (2000).

* cited by examiner

Figure 1: Examples of Nuclease Stable Ribozyme Motifs

Figure 2: 2'-O-Me substituted Amberzyme Enzymatic Nucleic Acid Motif

Figure 4: DNAzyme Motif

Figure 5: Synthesis of Folate Linked phosphoramidite

*Figure 6: Fludarabine-Folate conjugates*

Figure 7: Solid Phase Post-synthetic conjugation of pteroic acid

Figure 8: Chemo-enzymatic synthesis of pteroic acid synthon

NA = Nucleic Acid, such as siNA, antisense, or enzymatic nucleic acid
p = phosphorous moiety

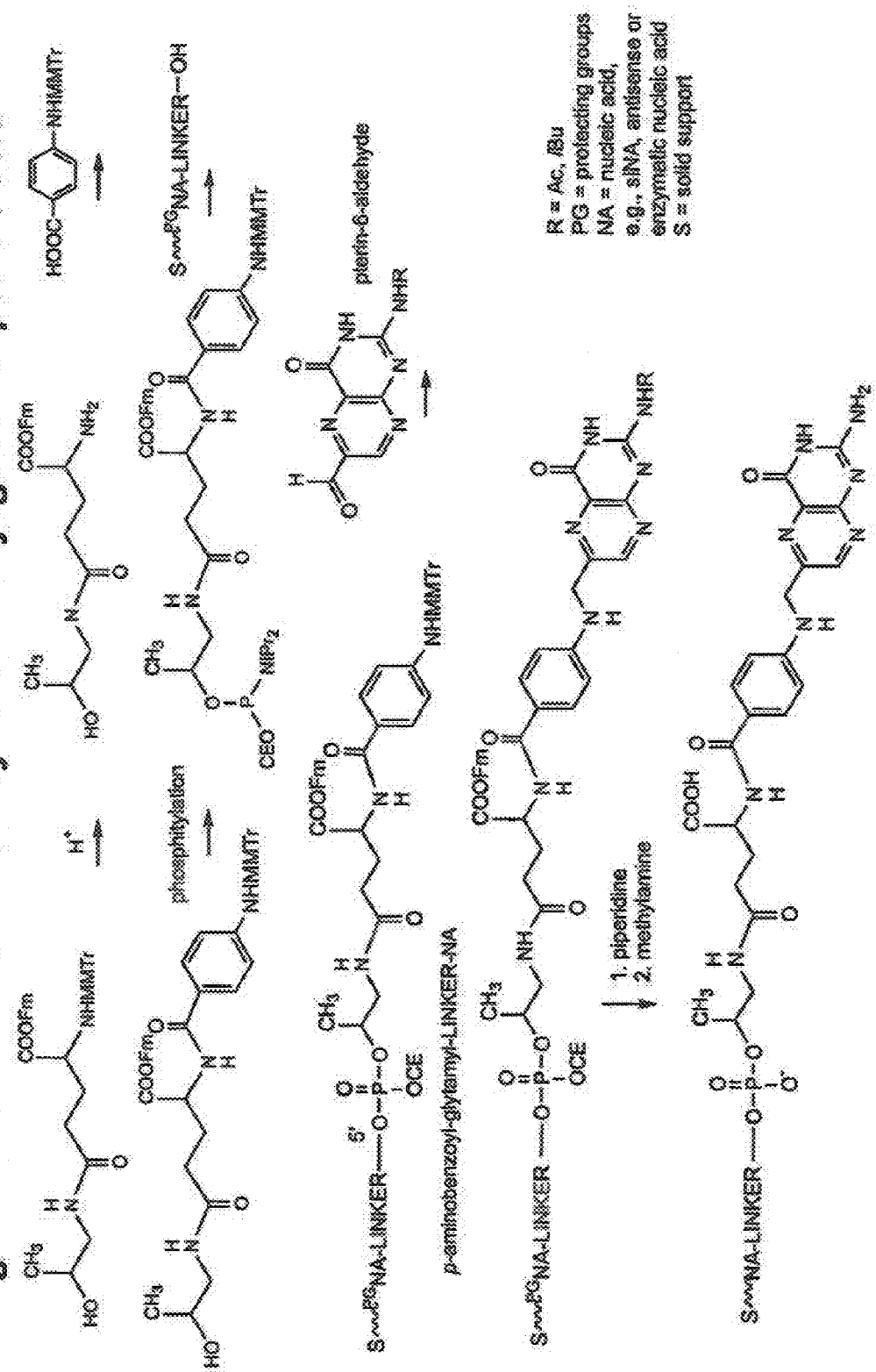
Figure 12: Solid Phase Post-synthetic conjugation of pteroic acid

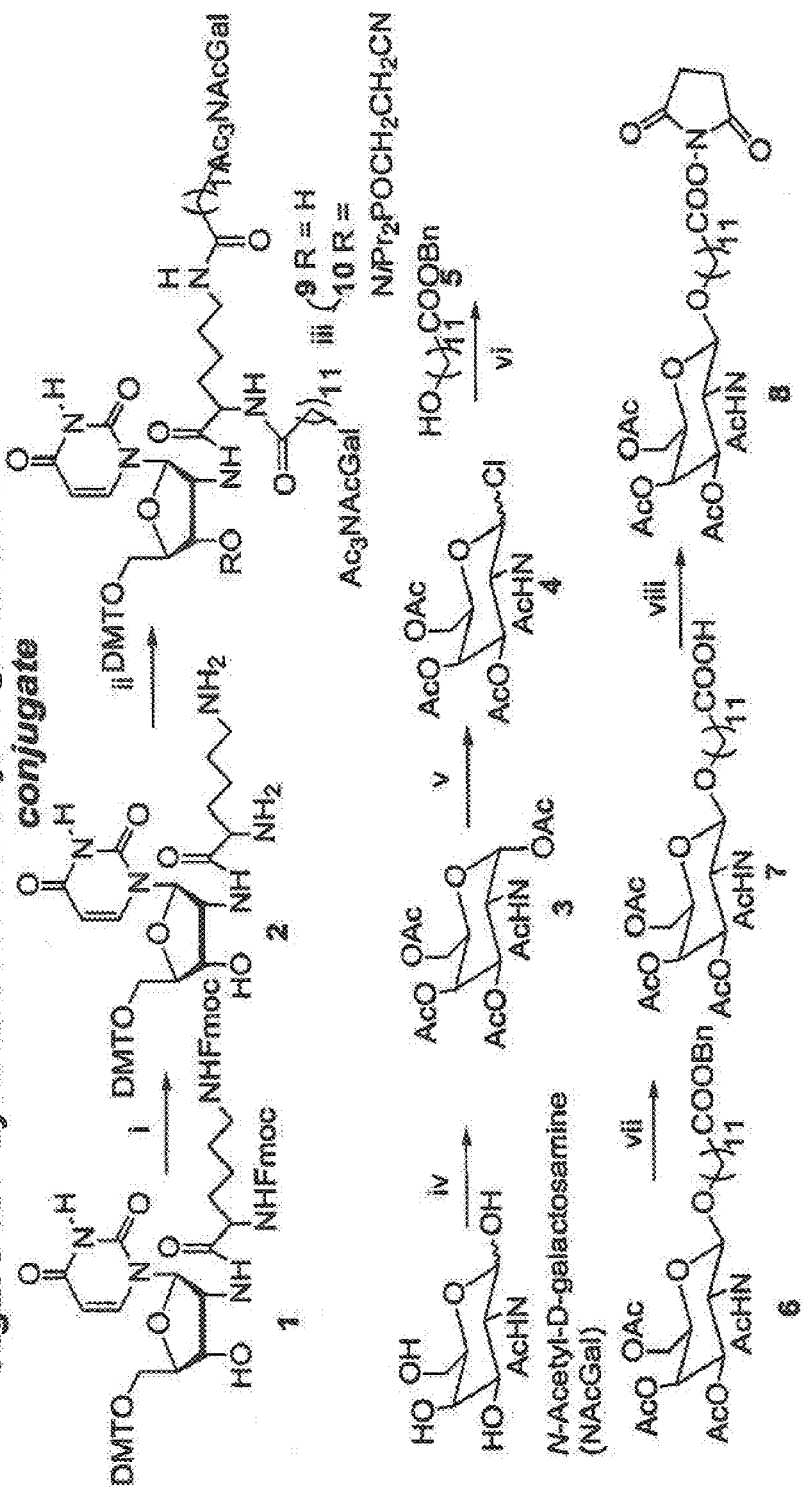
Figure 13: Synthesis of N-acetyl-D-galactosamine-2'-aminouridine conjugate
Reagents and Conditions: (i) diethylamine, DMF; (ii) 8, diisopropylethyl N,N-diisopropylchlorophosphoramidite, 1-methylimidazole, DIPEA, CH₂Cl₂; (iii) 2-cyanoethyl HCl, Ac₂O, (vi) Hg(CN)₂, MS 4A, CH₃NO₂-toluene 1:1, (vii) H₂, 5% Pd-C, ethanol, (viii) N-hydroxysuccinimide, DCC, THF.

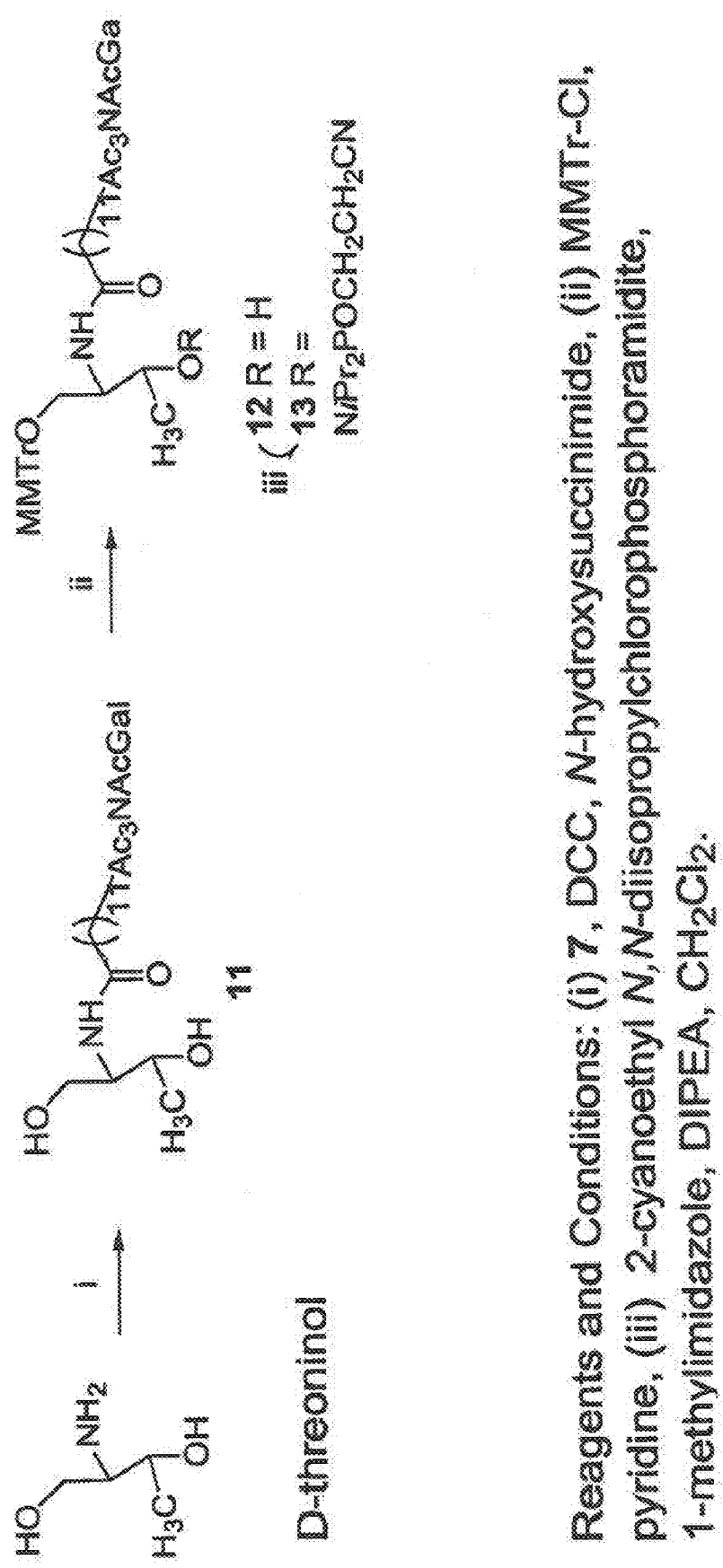
Figure 14: Synthesis of N-acetyl-D-galactosamine-D-threoninol conjugate
Reagents and Conditions: (i) 7, DCC, N-hydroxysuccinimide, (ii) MMTr-Cl, pyridine, (iii) 2-cyanoethyl N,N-diisopropylchlorophosphoramidite, 1-methylimidazole, DIPEA, $CH_2Cl_2$.

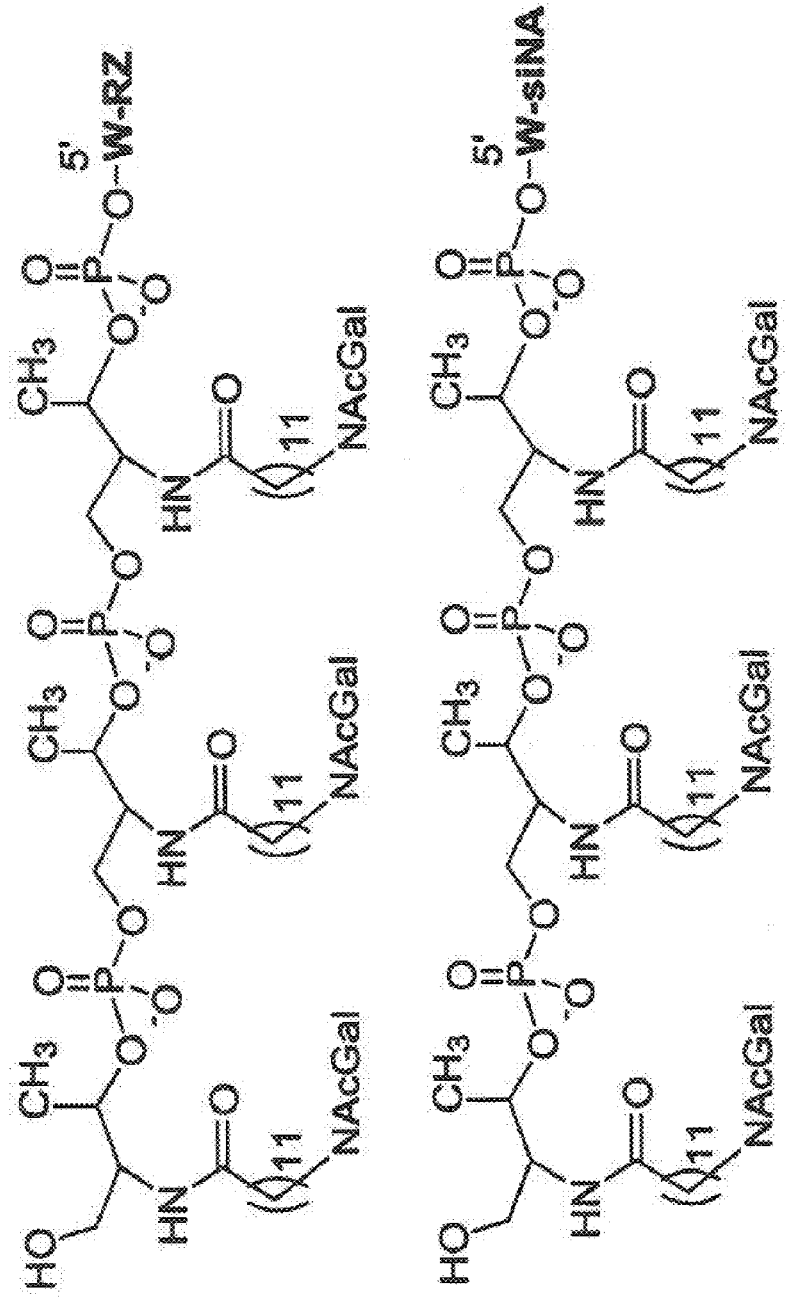
Figure 15: Conjugation of targeting ligands to the 5'-end of a Ribozyme or siNA molecule
N-acetyl-D-galactosamine conjugate

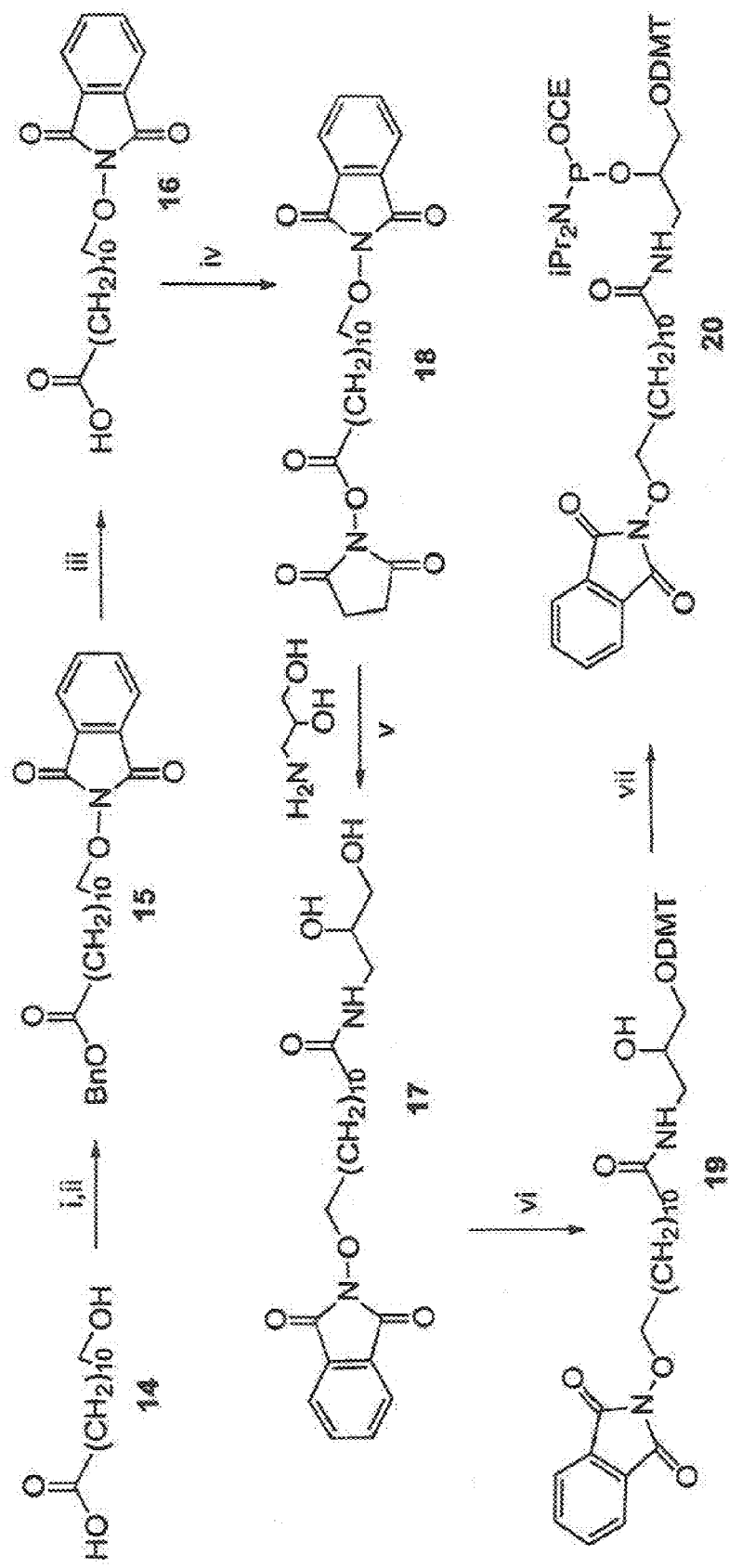
Figure 16: Synthesis of dodecanoic acid linker

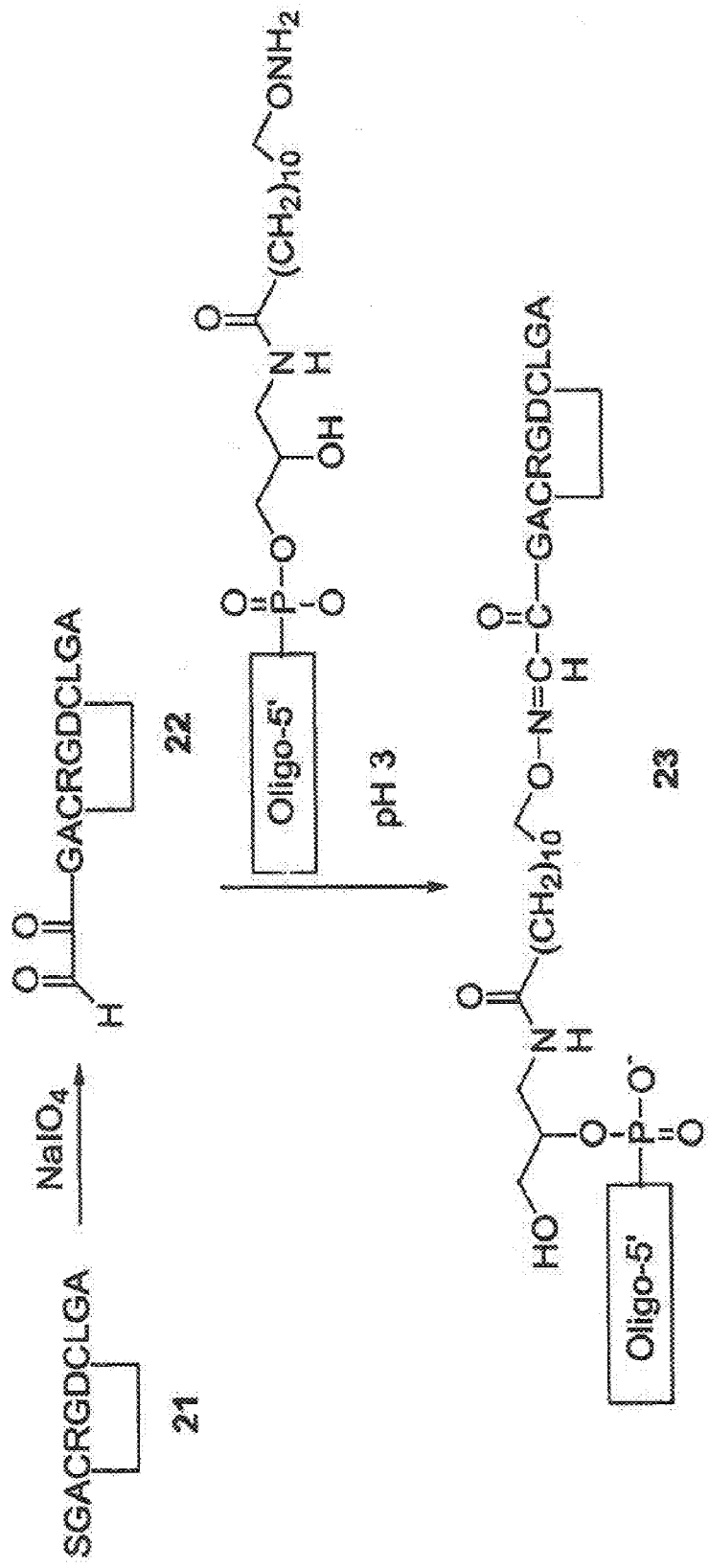
Figure 17: Oxime linked Nucleic Acid/Peptide Conjugate

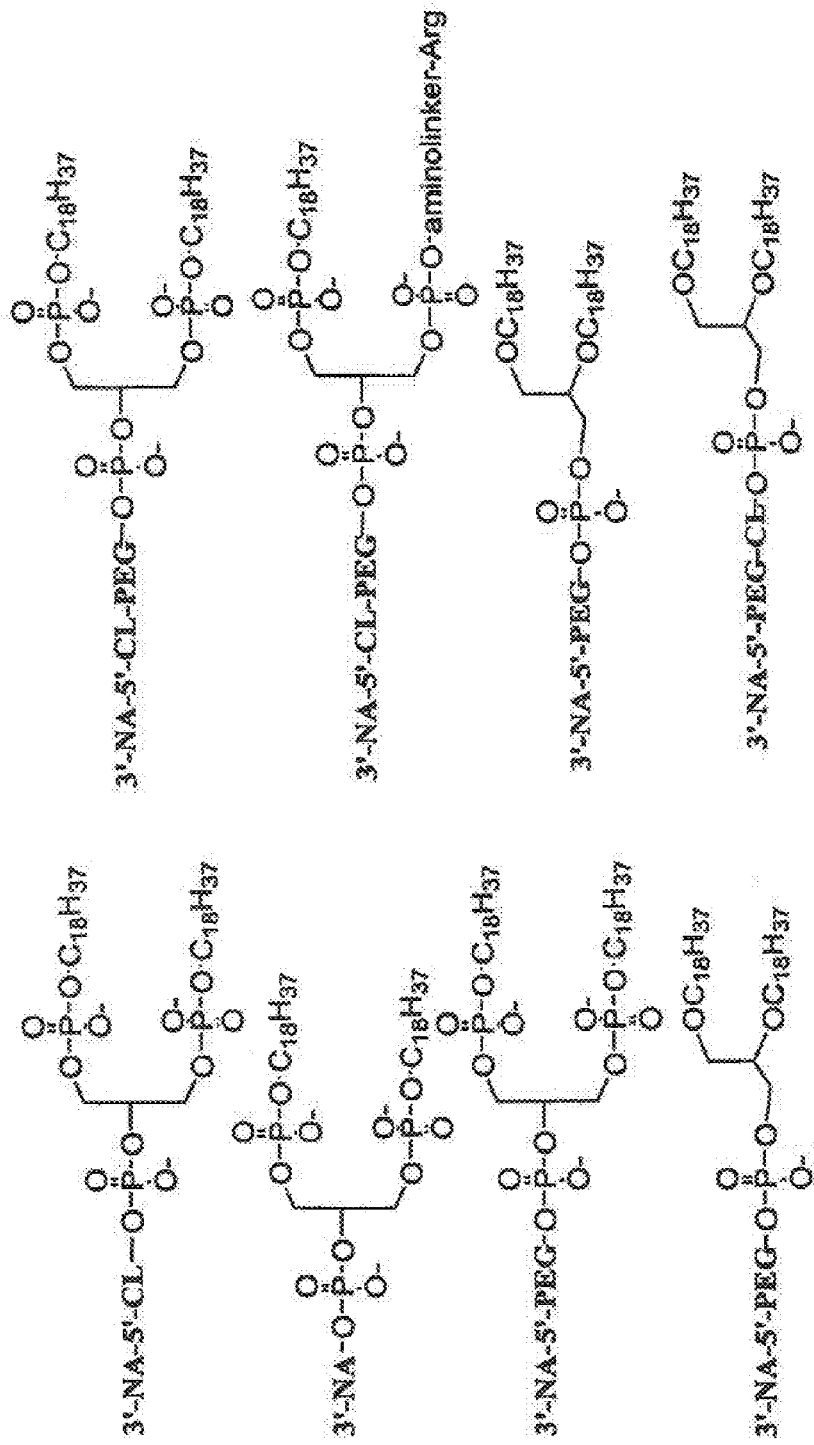
Figure 18: Nucleic Acid/Phospholipid Conjugates

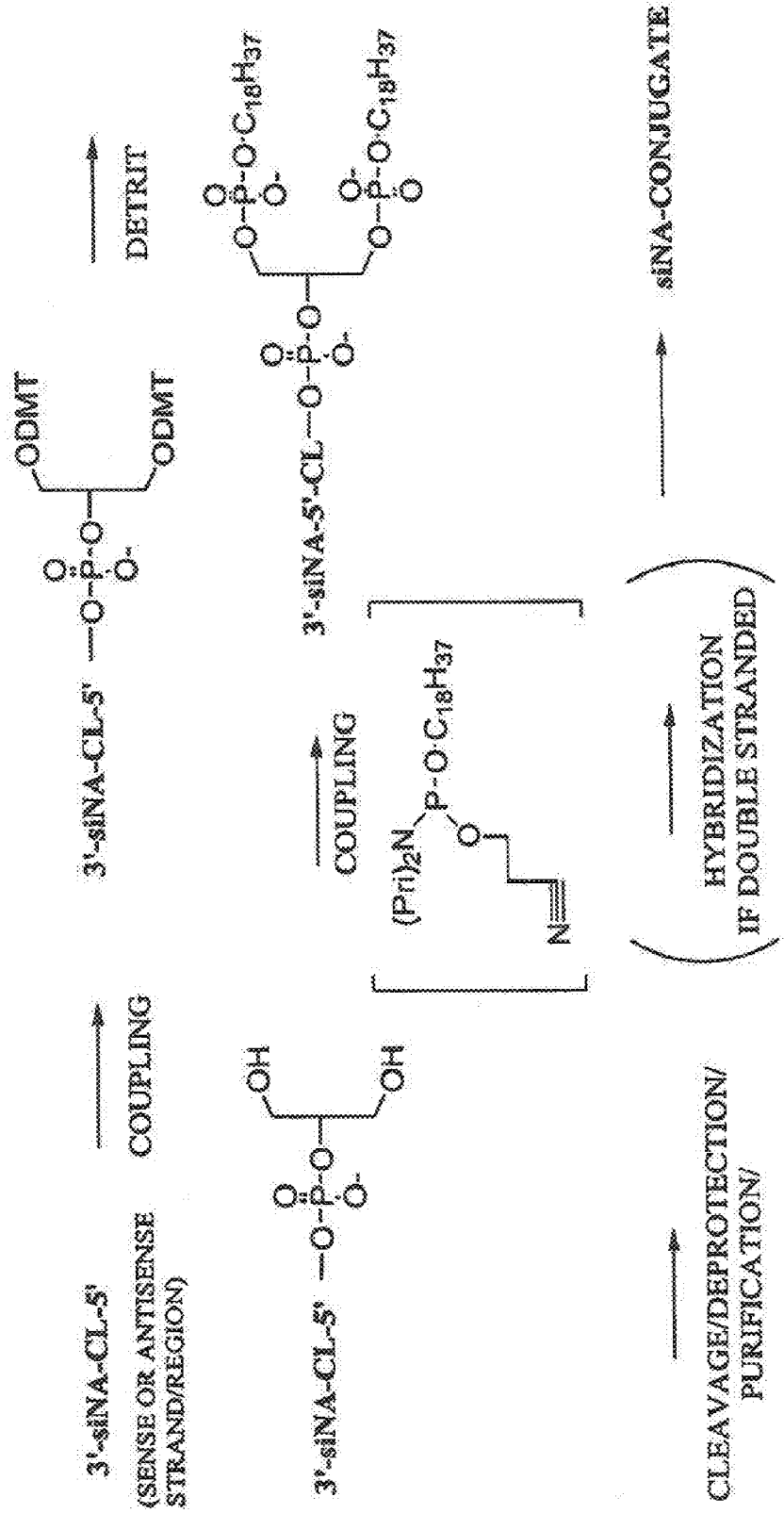
Figure 19: siNA Phospholipid Conjugate

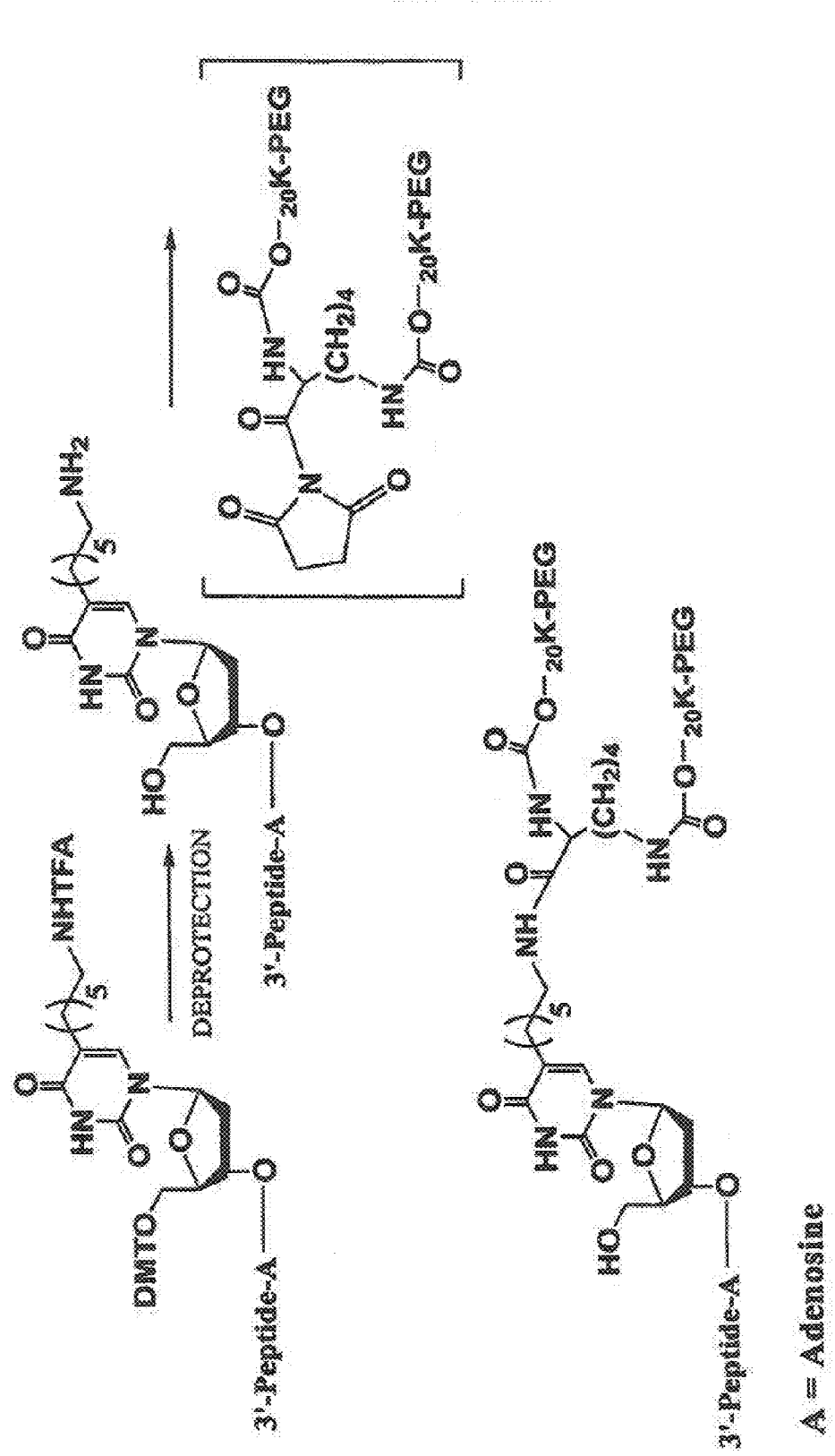
Figure 20: Peptide PEG Conjugate

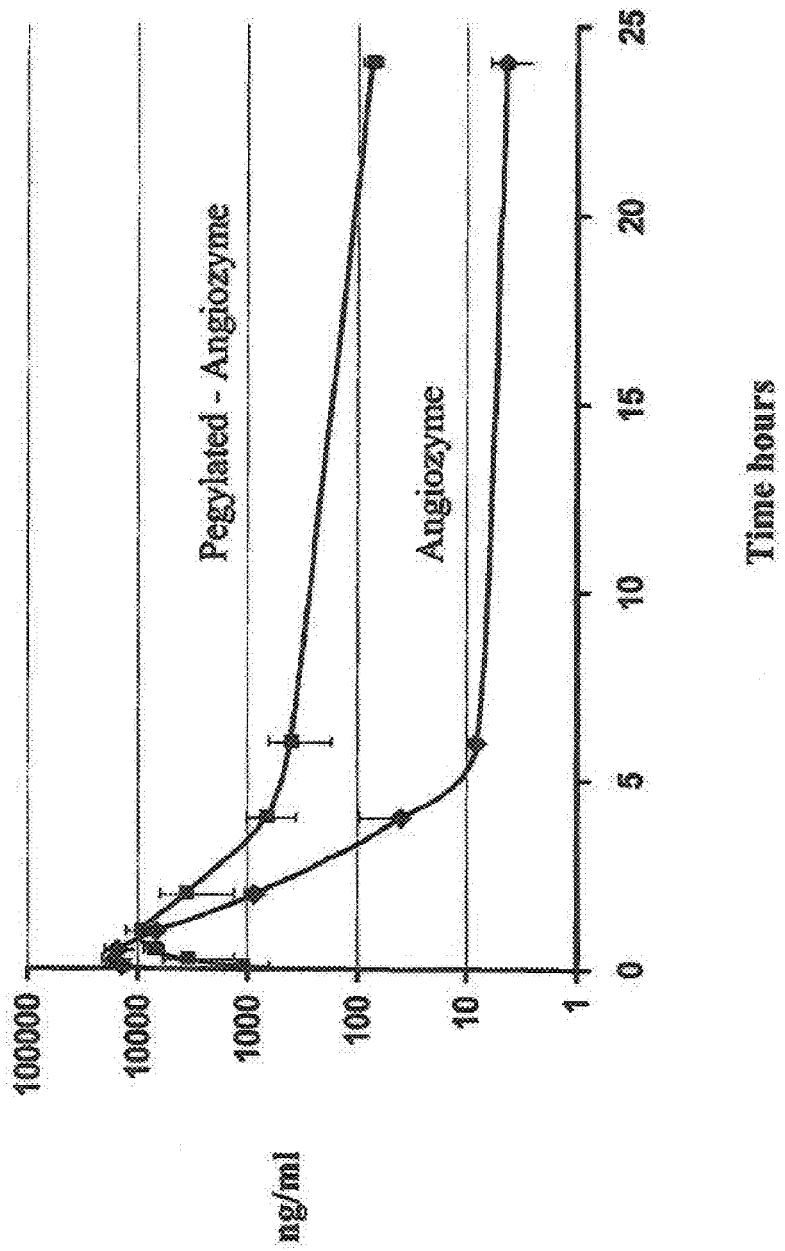

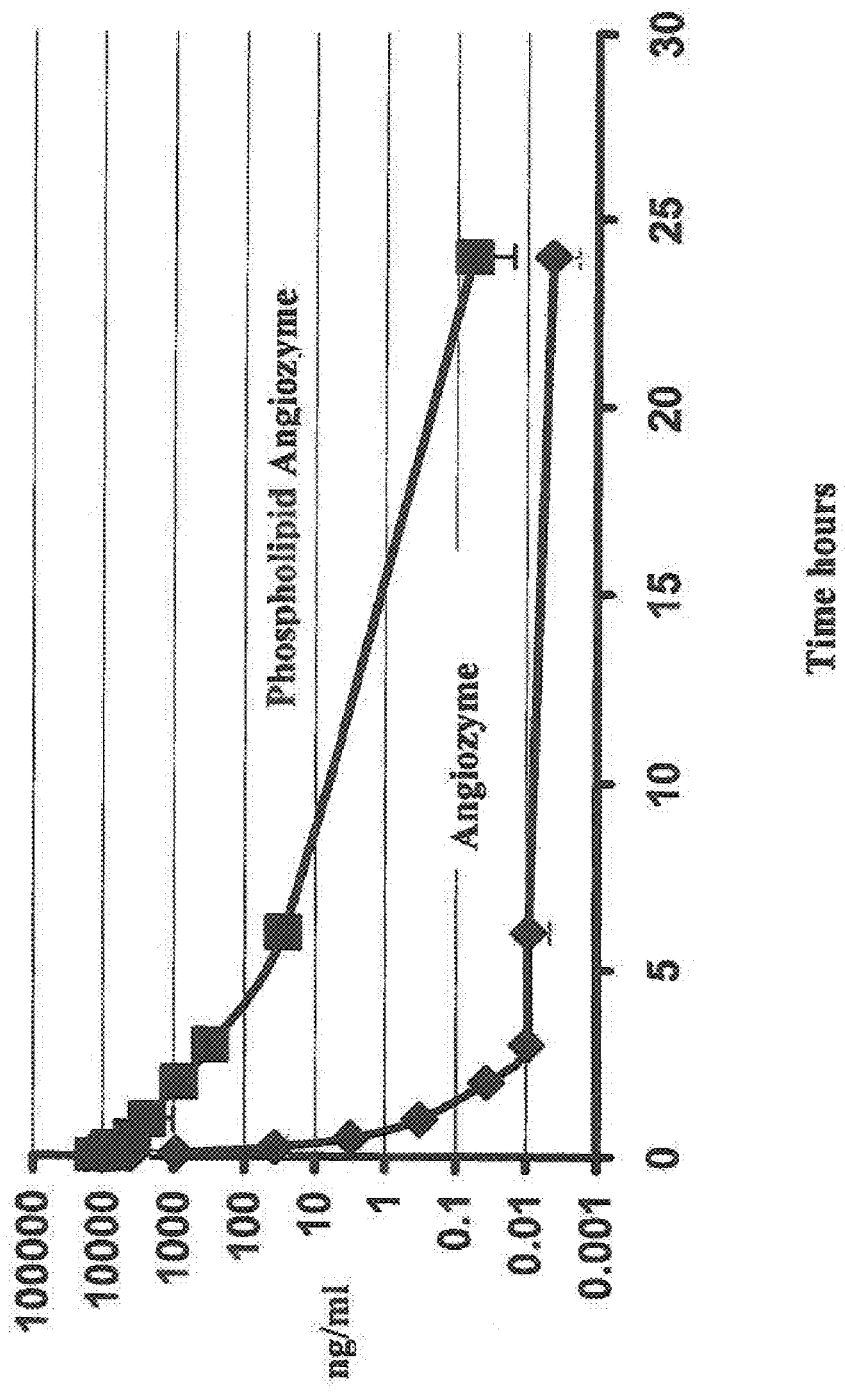
Figure 22: Phospholipid-Angiozyme vs Angiozyme

Figure 23: Oligonucleotide-NAcGalactosamine post-synthetic coupling
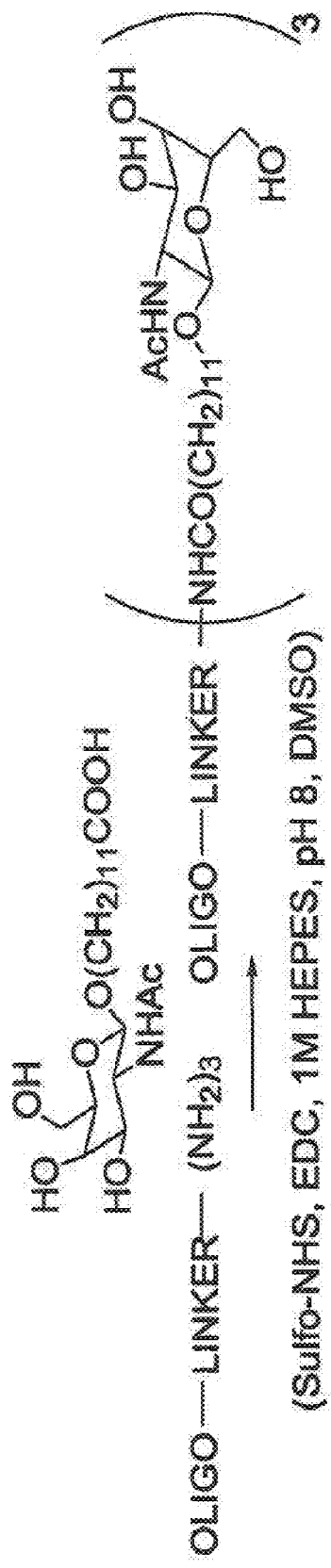
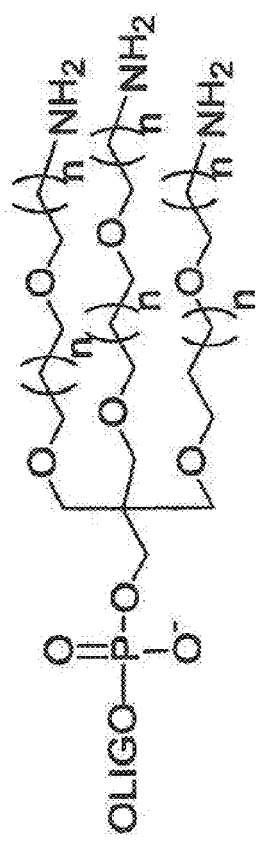
Where n is an integer from 1 to 20

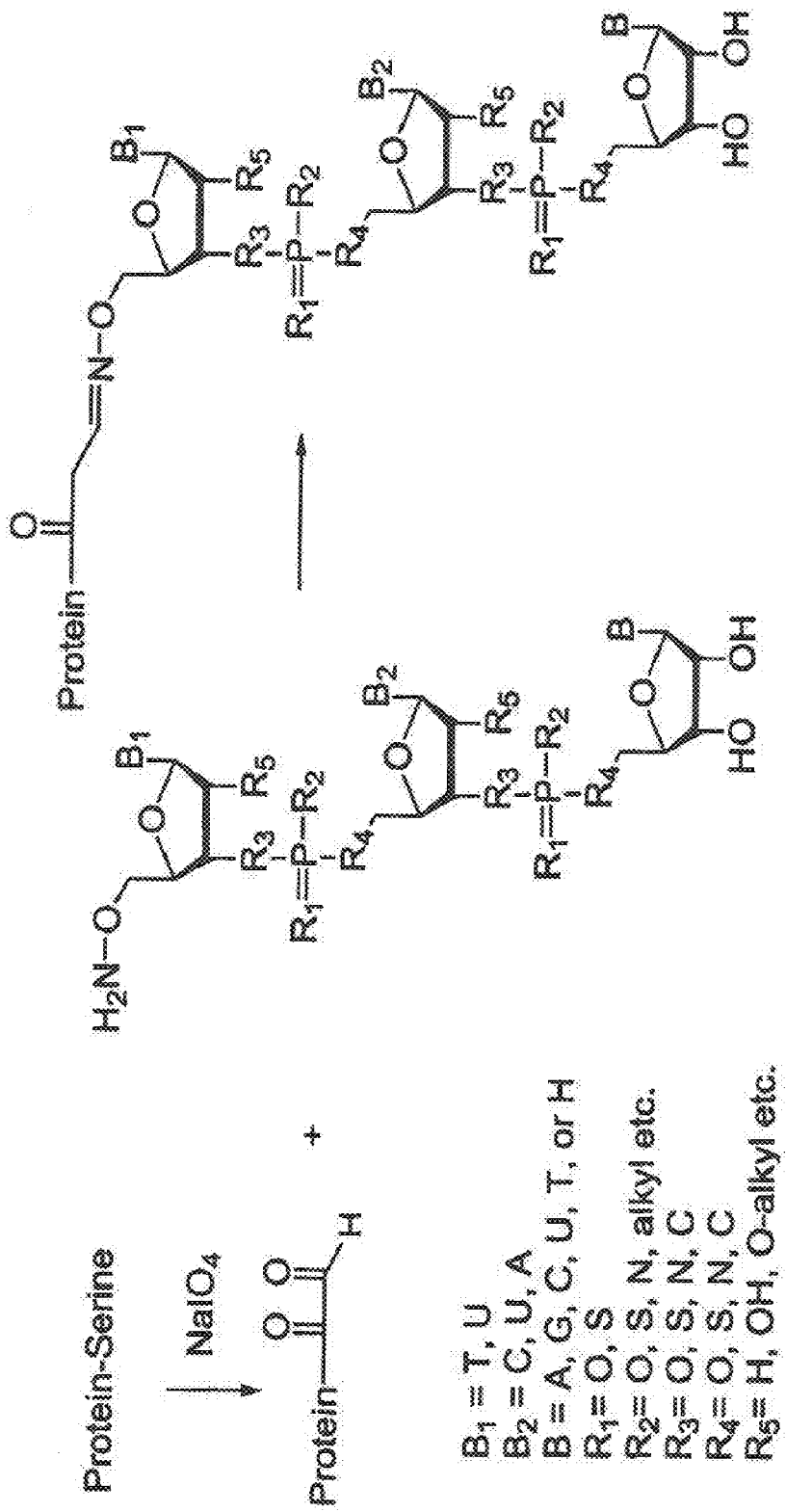
Figure 24a: Protein with cleavable linker

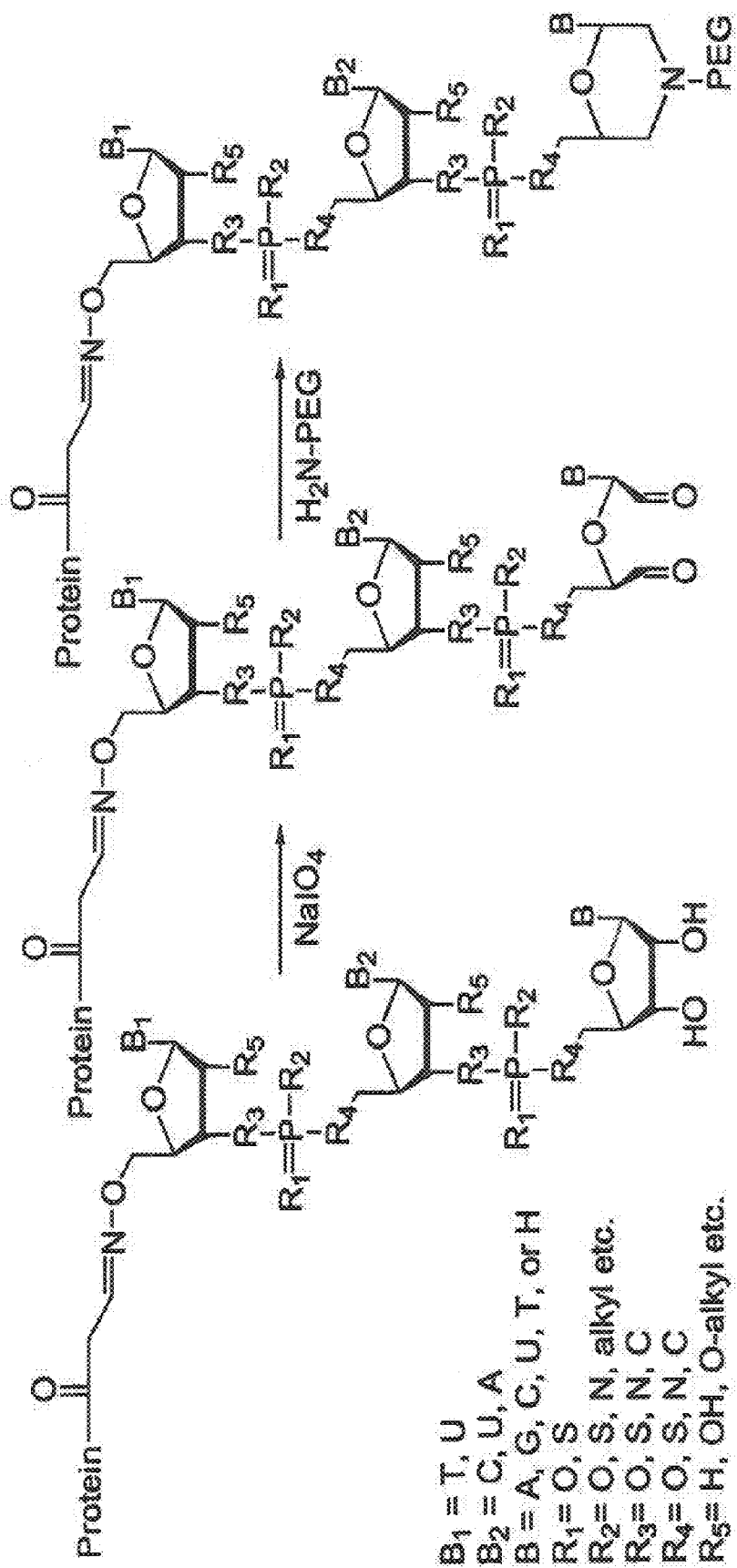
Figure 24b: Protein cleavable linker PEG Conjugate

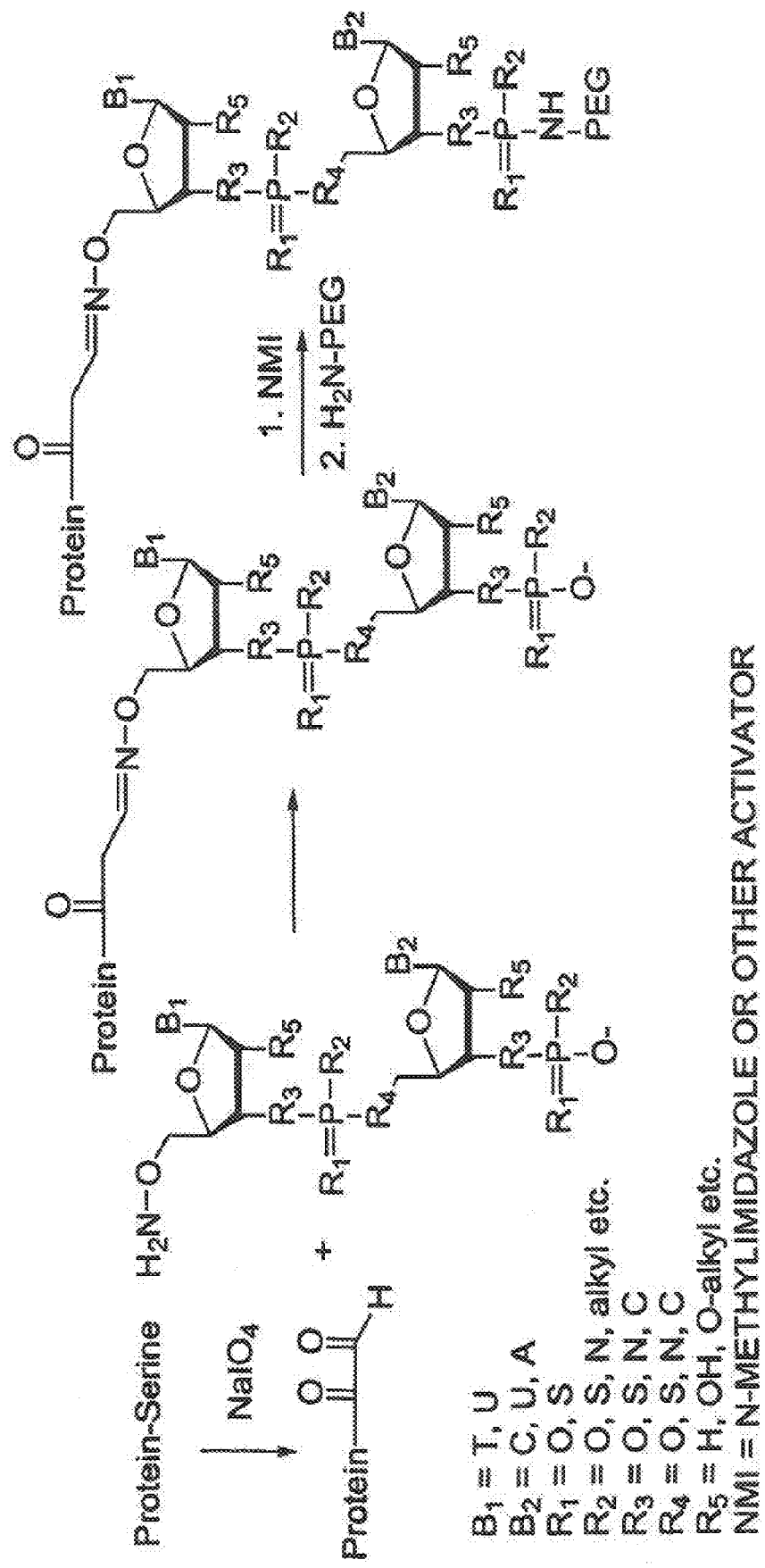
Figure 25: Protein PEG conjugate with cleavable linker

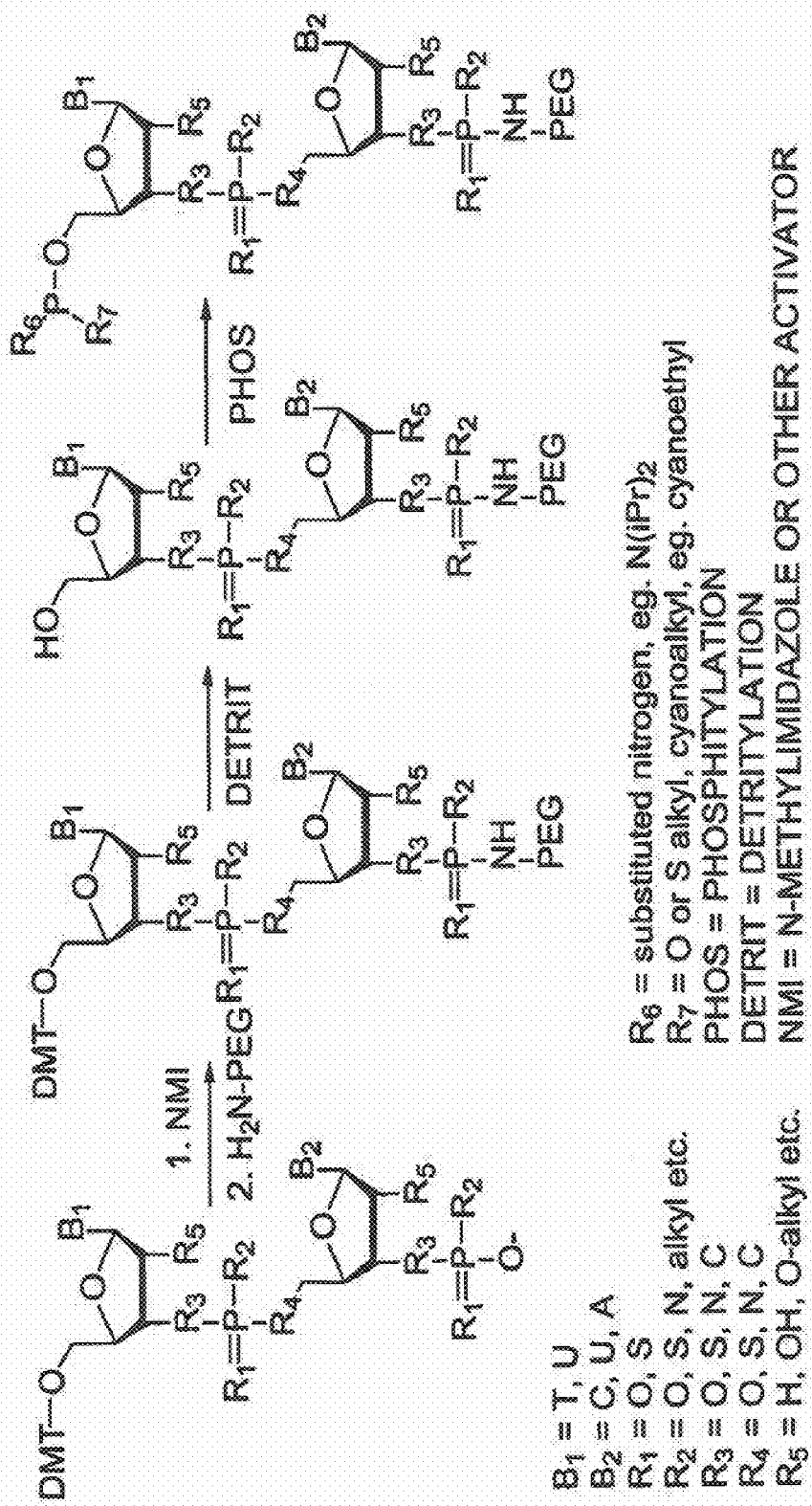
*Figure 26a: PEG with cleavable linker*

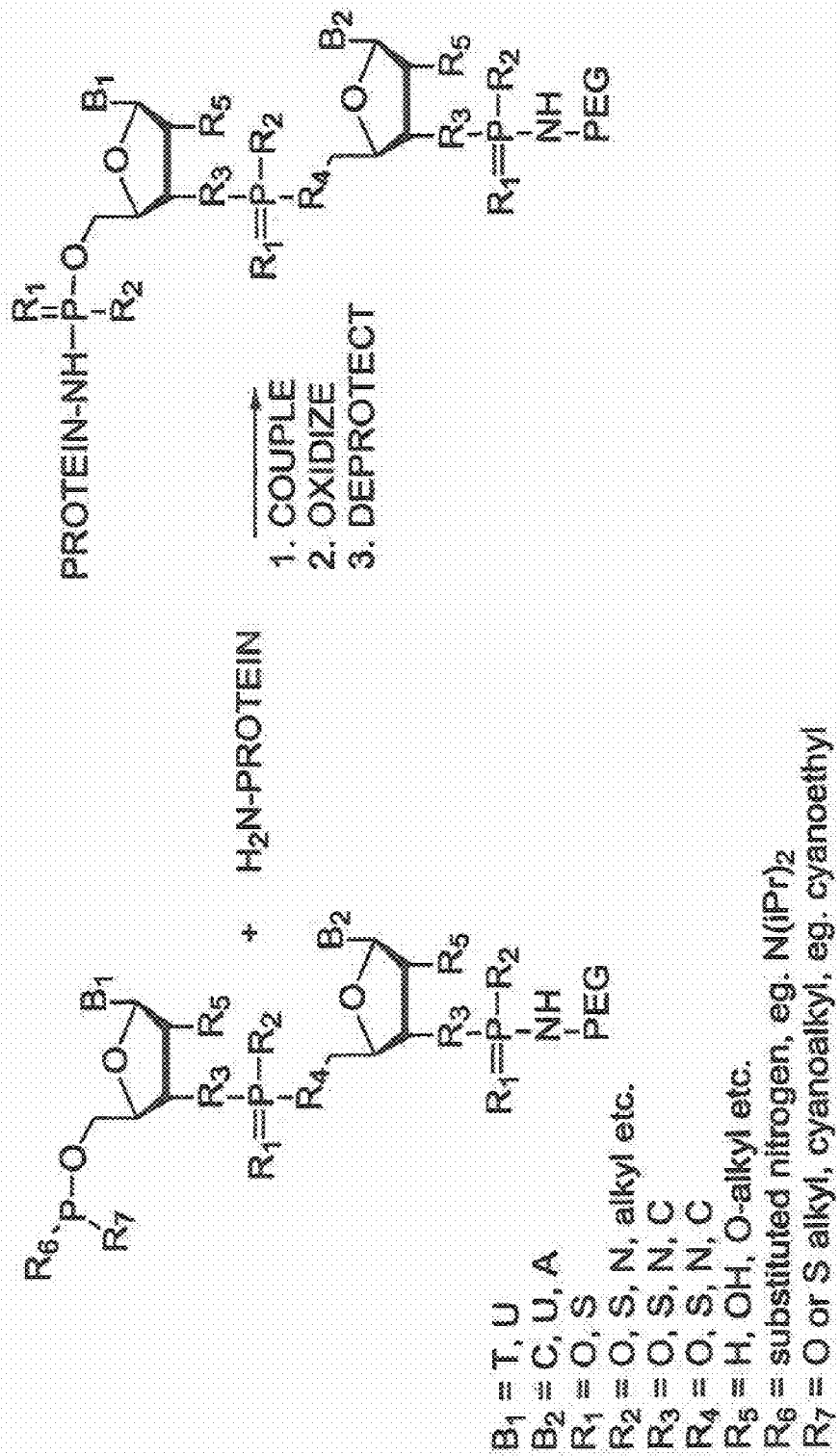
Figure 26b: Protein PEG conjugate with cleavable linker

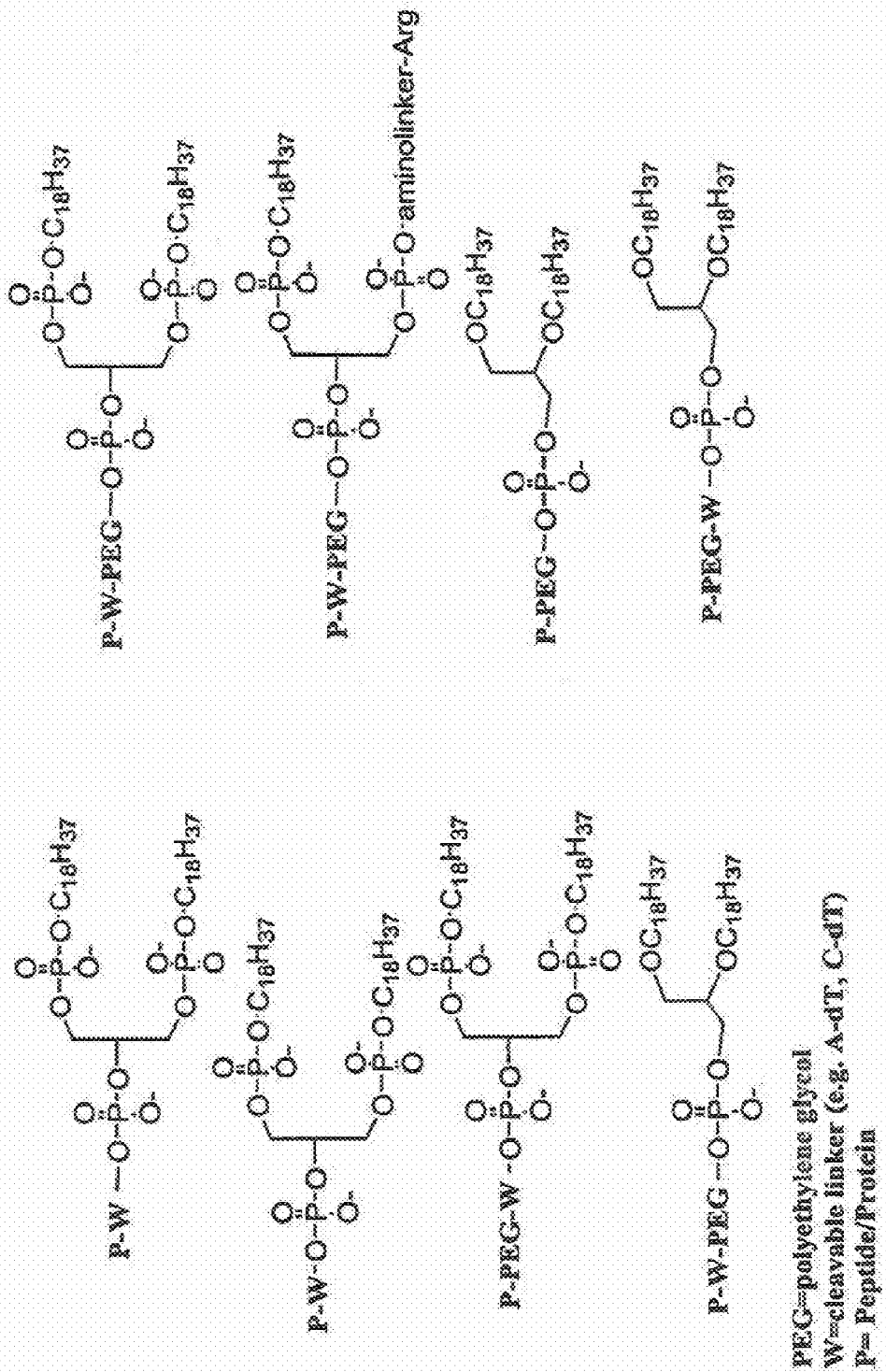

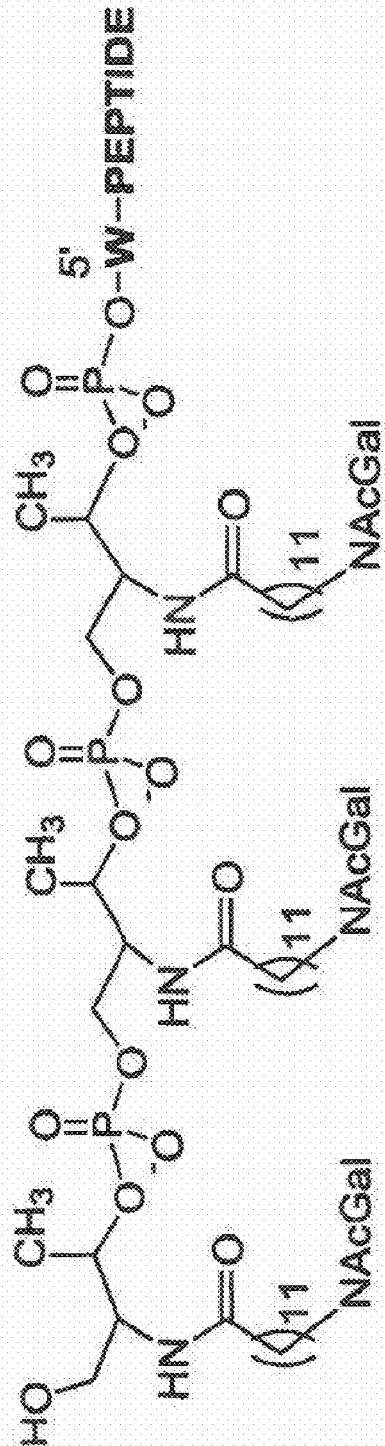
Figure 28: Conjugation of targeting ligands to a peptide or protein
N-acetyl-D-galactosamine conjugate
W = cleavable linker (eg. A-dT, C-dT dimer)

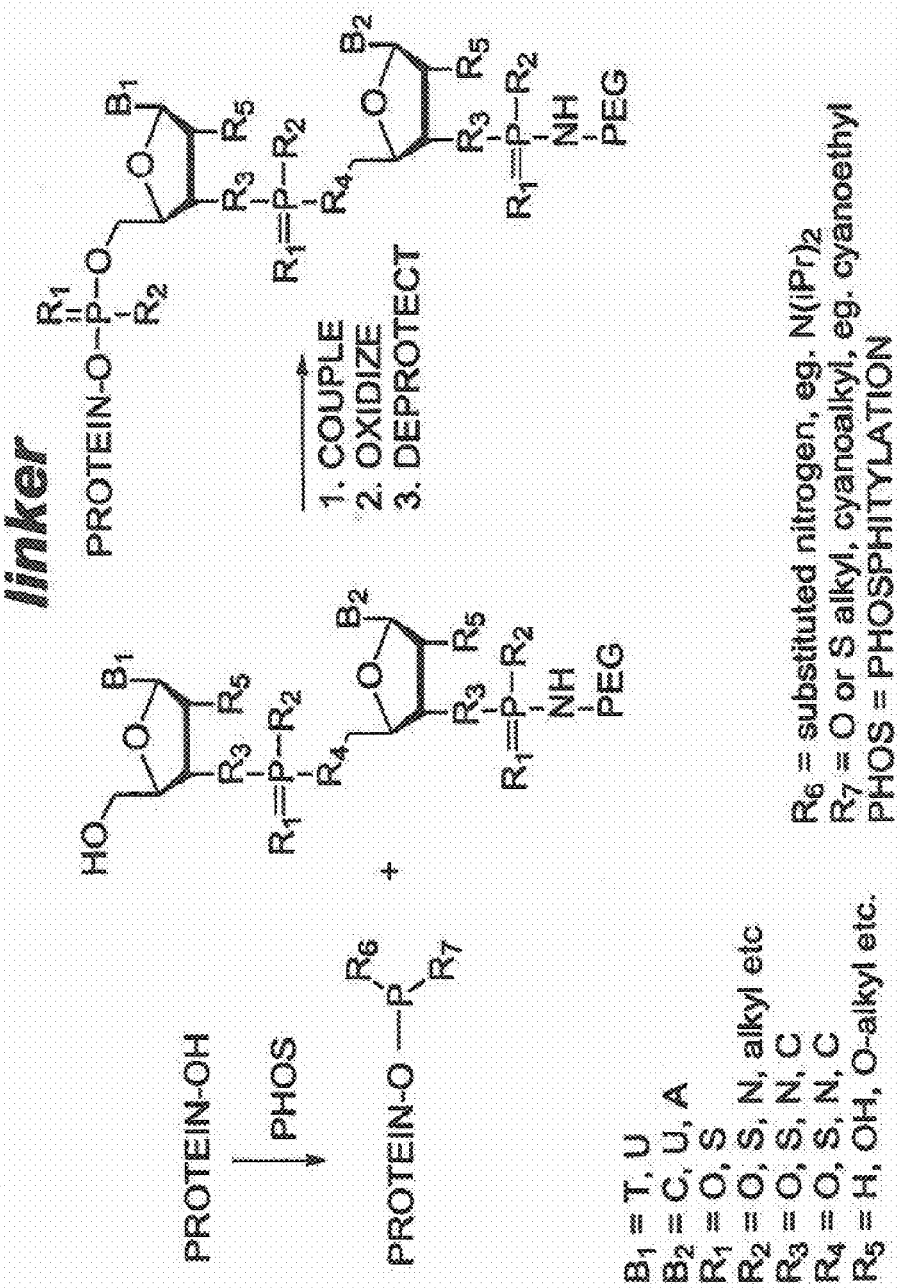
Figure 29: Protein/PEG conjugate with cleavable linker

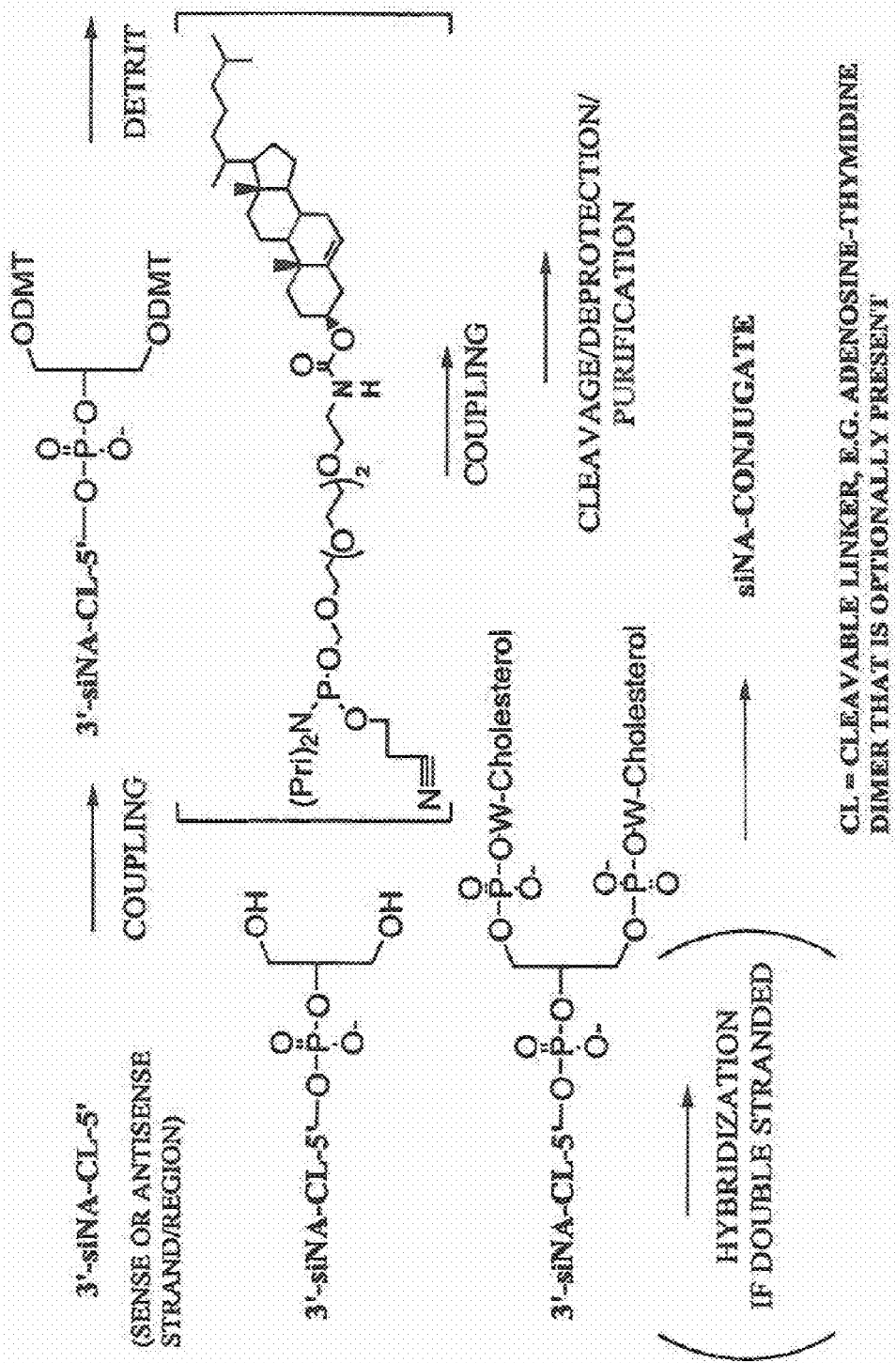

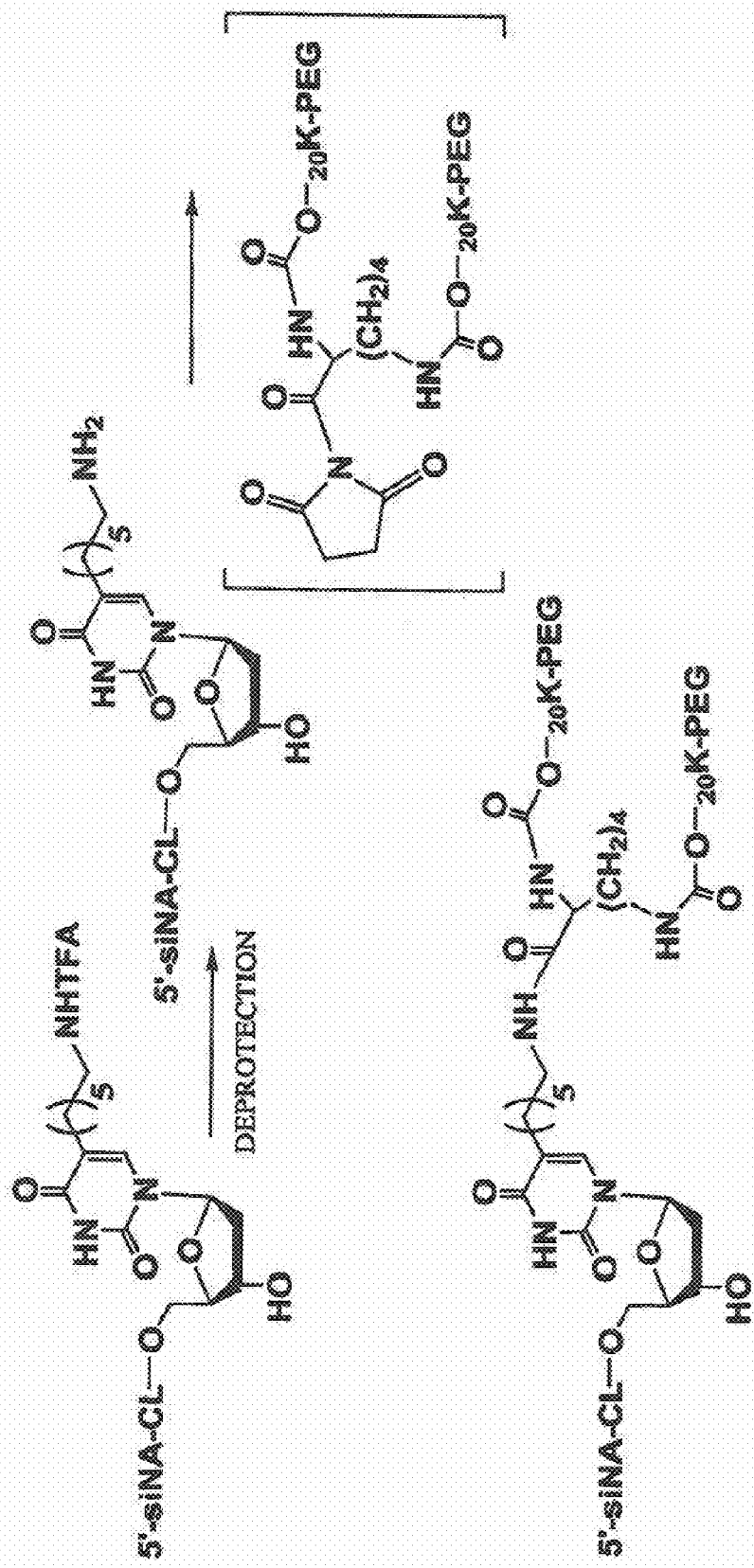
Figure 31: siNA 3'-PEG Conjugate
CL = CLEAVABLE LINKER, E.G. ADENOSINE-THYMIDINE DIMER THAT IS OPTIONALLY PRESENT

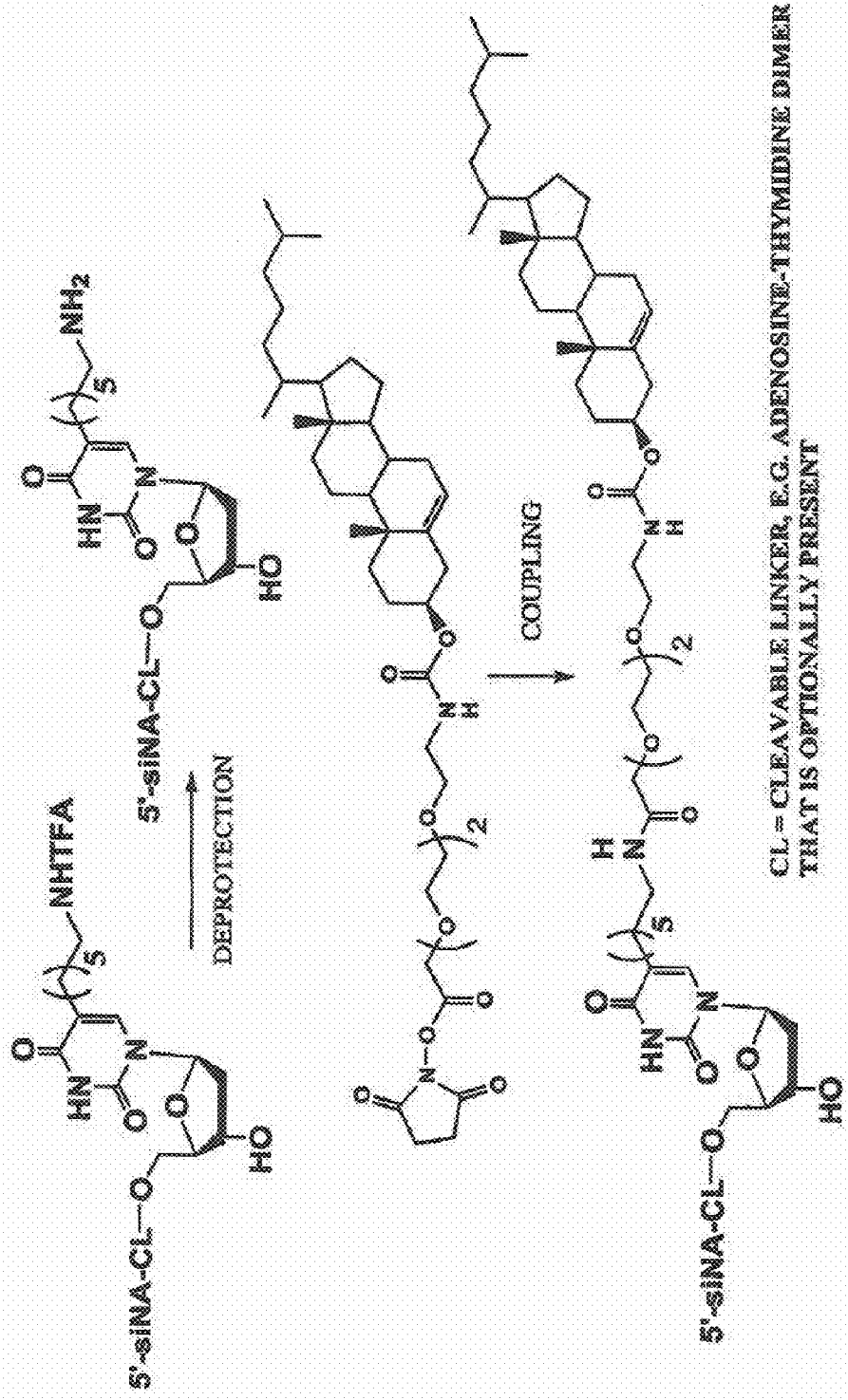
Figure 32: siNA 3'-Cholesterol Conjugate

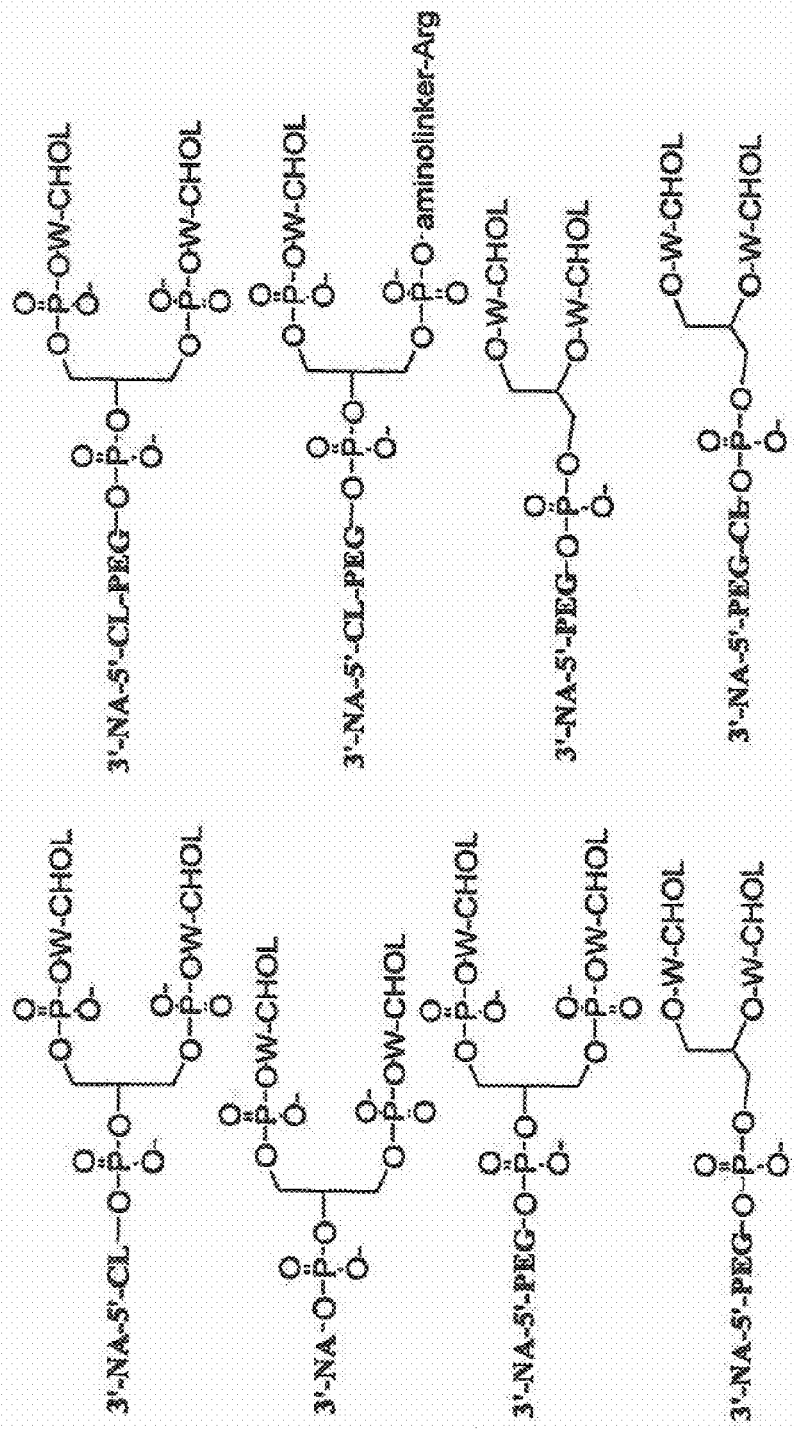

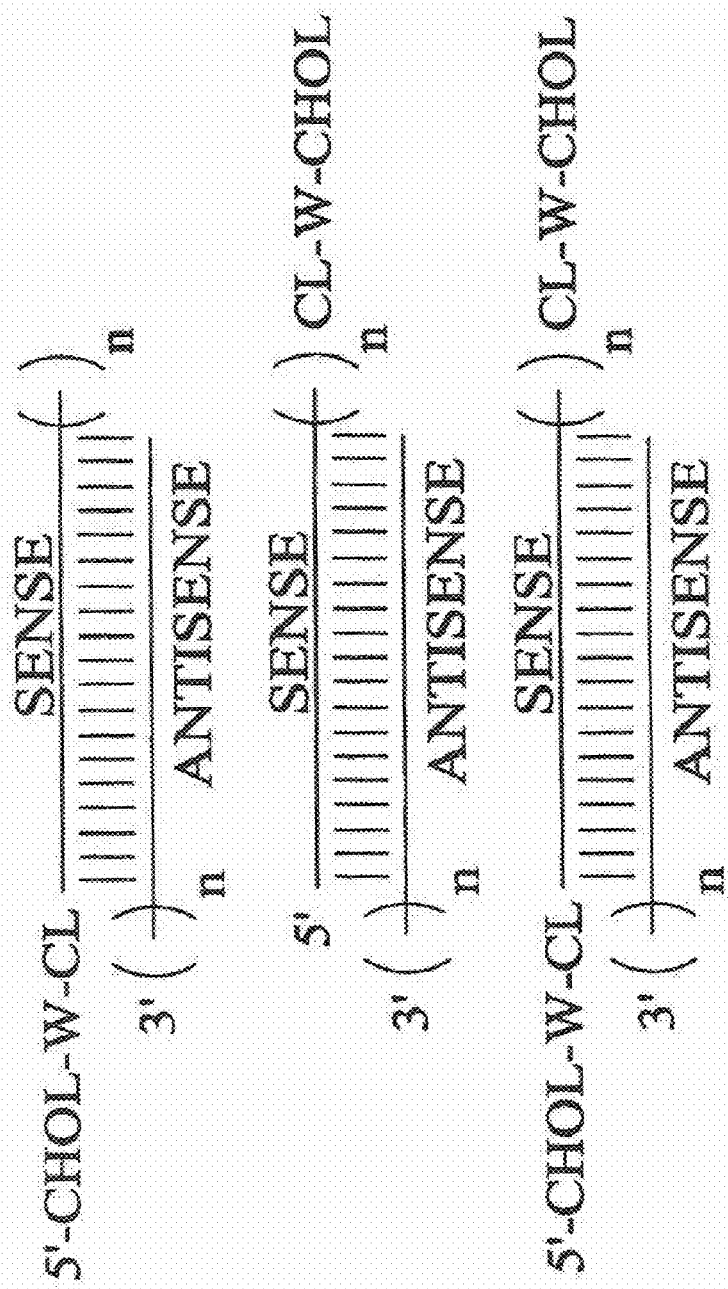
Figure 34: siNA Cholesterol Conjugates

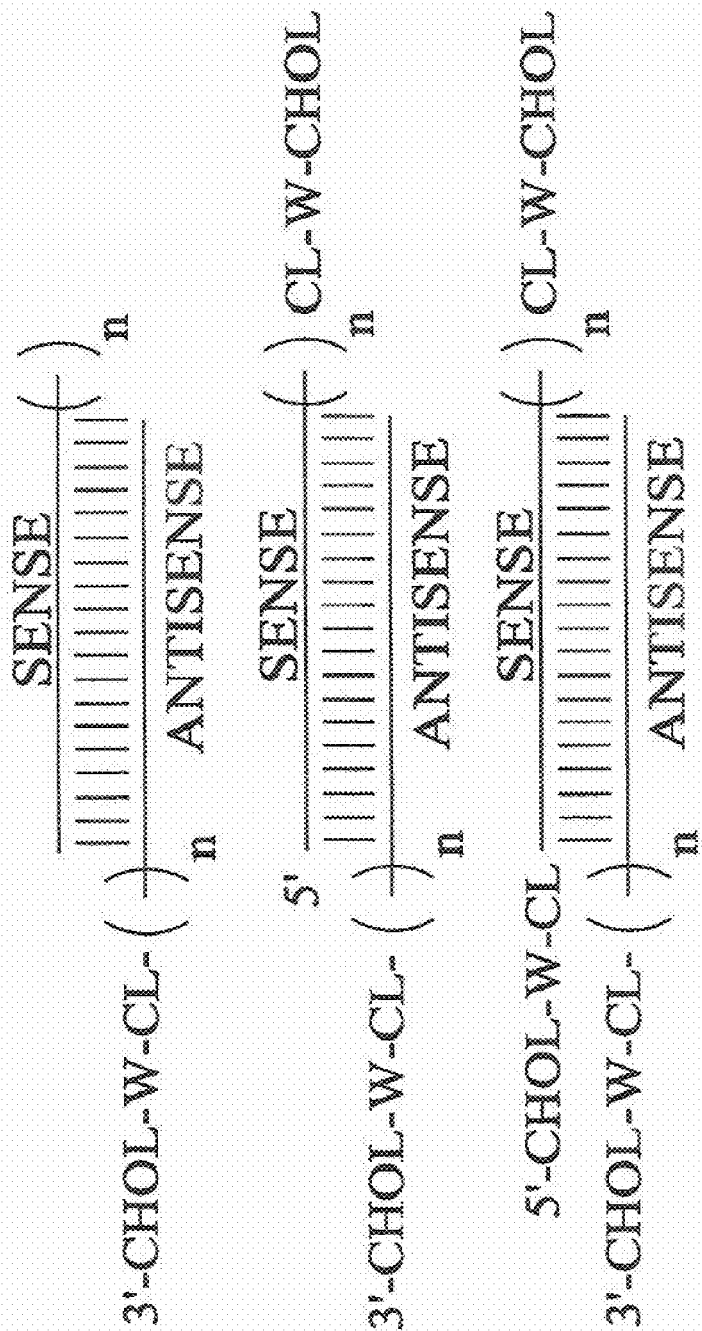
Figure 35: siNA Cholesterol Conjugates

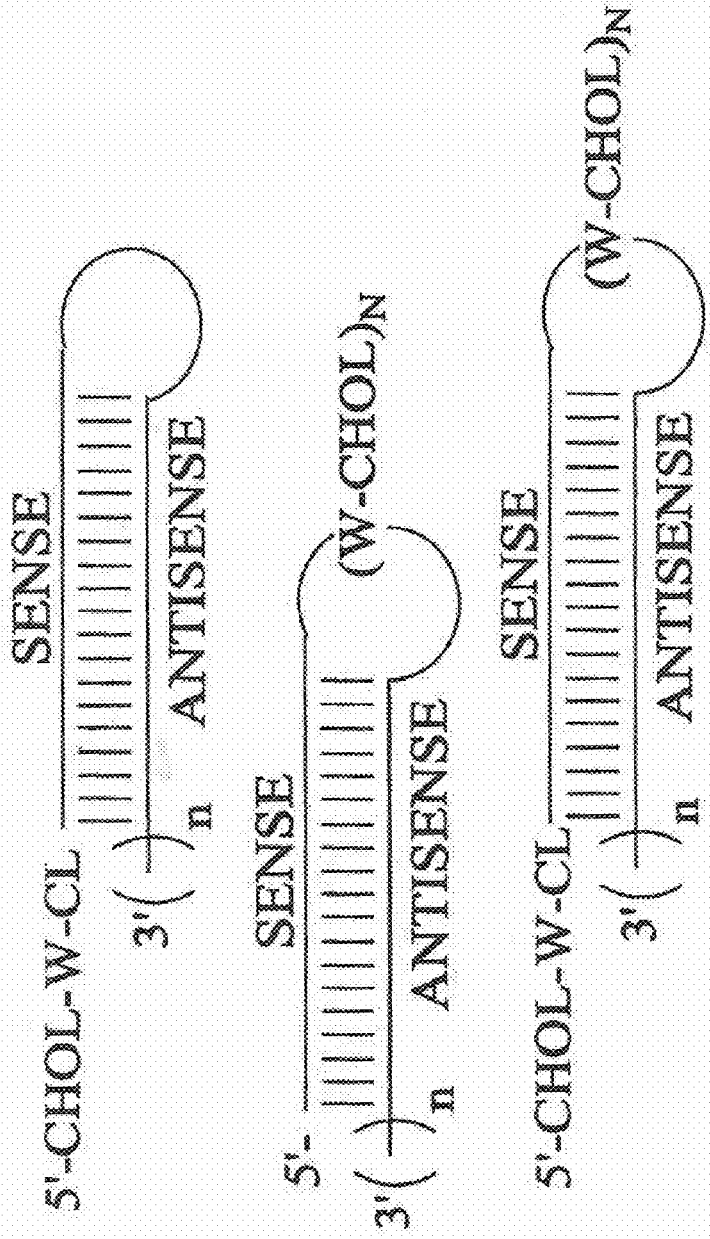
Figure 36: siNA Cholesterol Conjugates

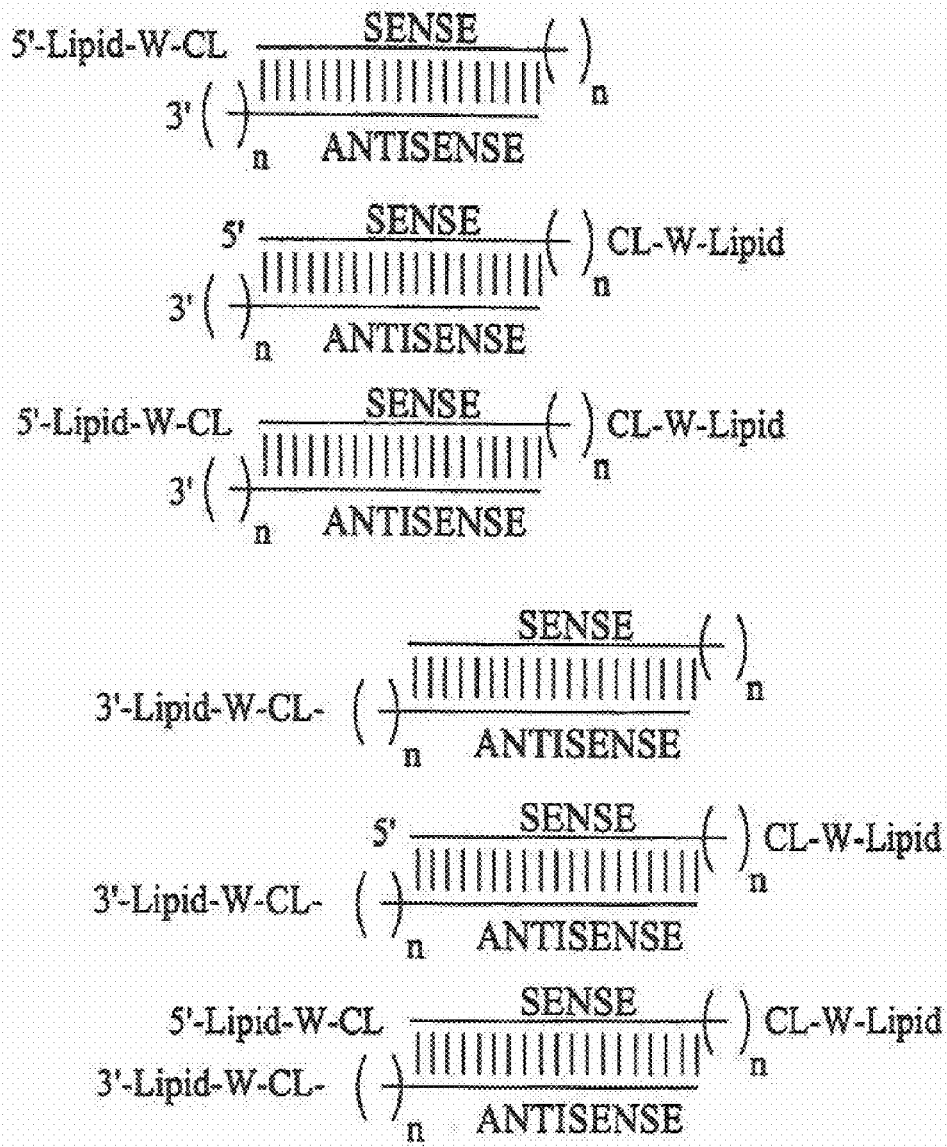
Figure 37: siNA Lipid Conjugates

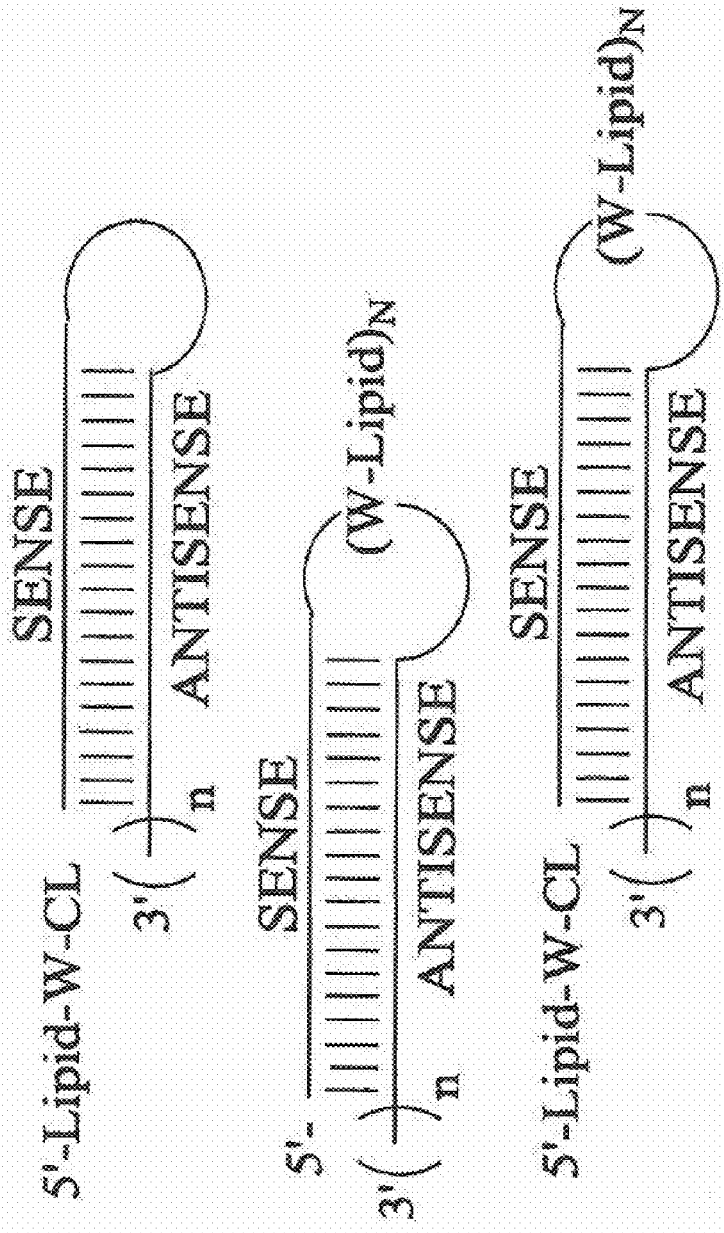

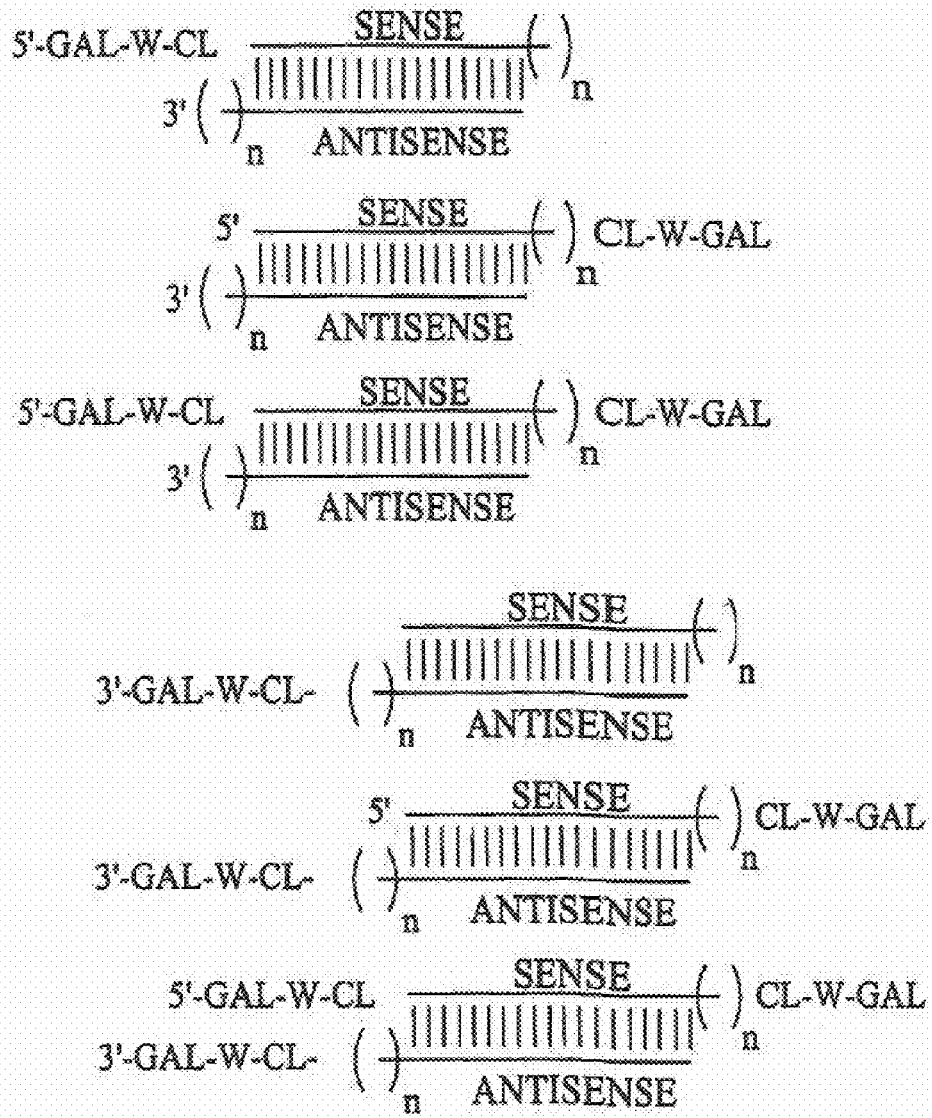
*Figure 39: siNA Galactosamine Conjugates*
CL=cleavable linker (e.g. A-dT, C-dT) that is optionally present
GAL=GALACTOSAMINE; e.g. compounds having Formulae 51-56, 86, 92, 99, 100, 103, 105, 106
W= linker molecule (see for example Formulae 102 or 103)
n = integer, e.g. 1, 2, or 3

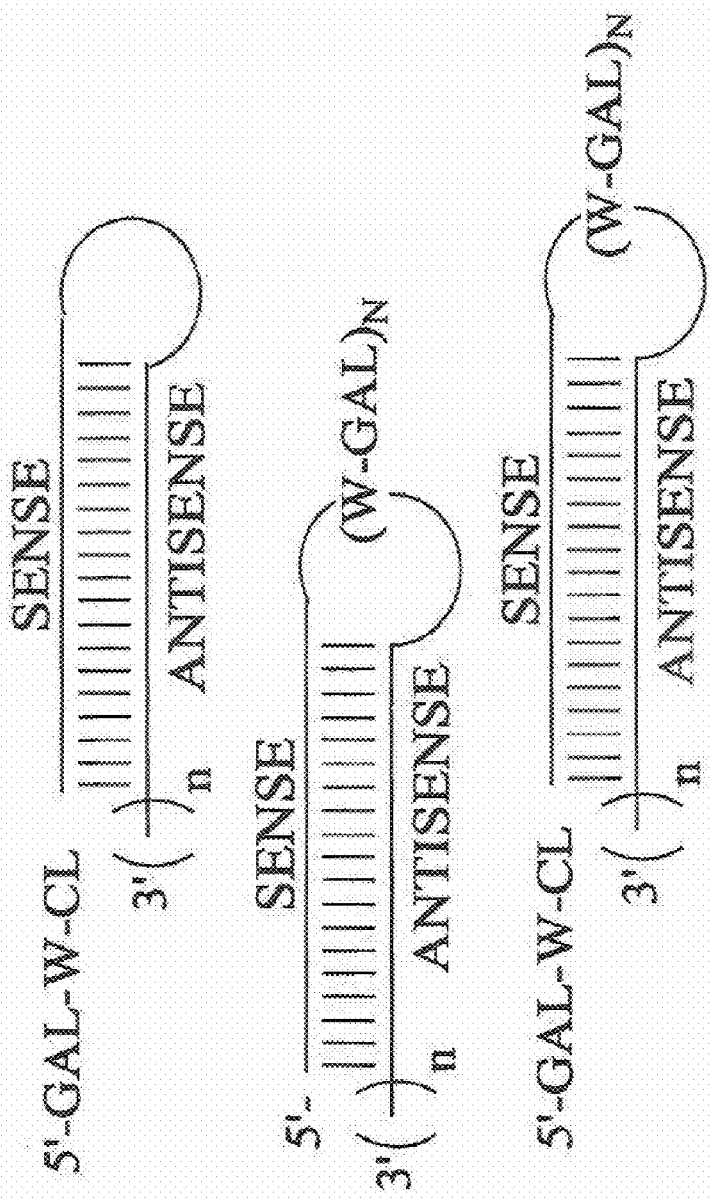

Figure 41: Generalized siNA Conjugate Design
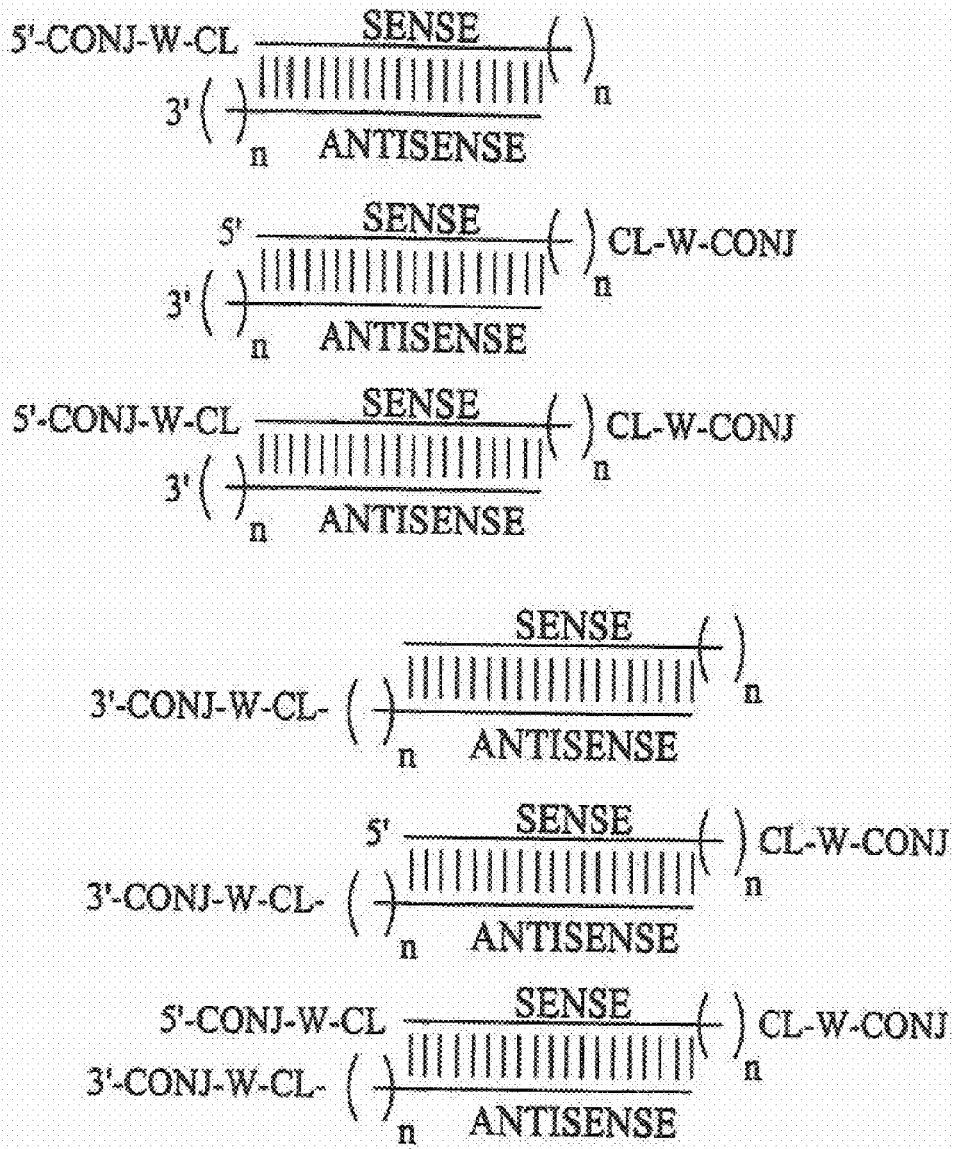
CONJ=any biologically active molecule or conjugate as described herein
CL=cleavable linker (e.g. A-dT, C-dT) that is optionally present
W= linker molecule
n = integer, e.g. 1, 2, or 3

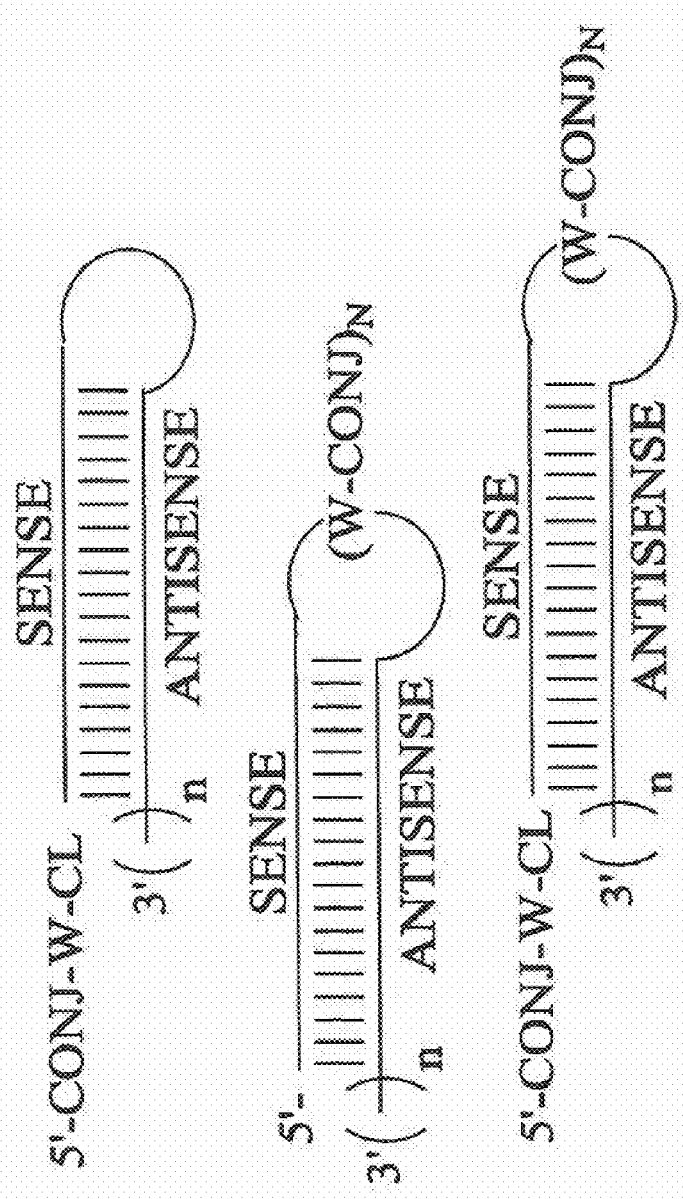
*Figure 42: Generalized siNA Conjugate design*

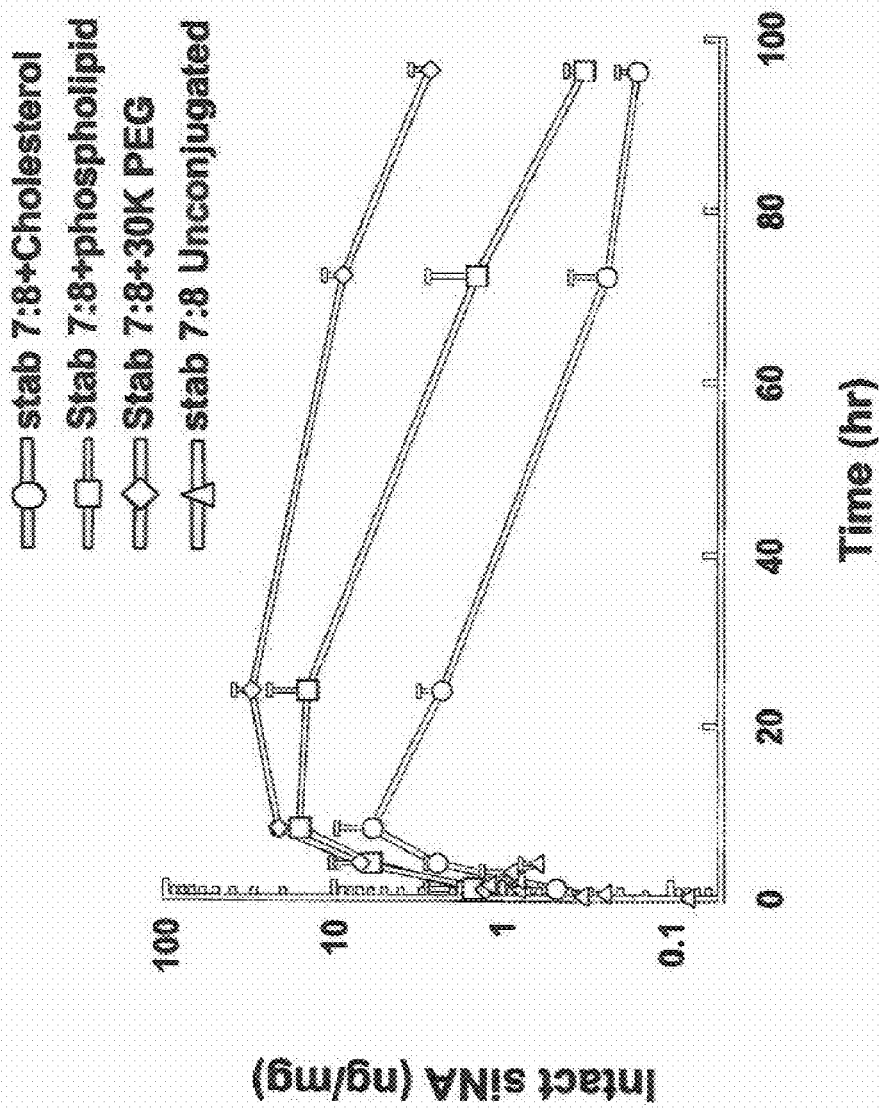

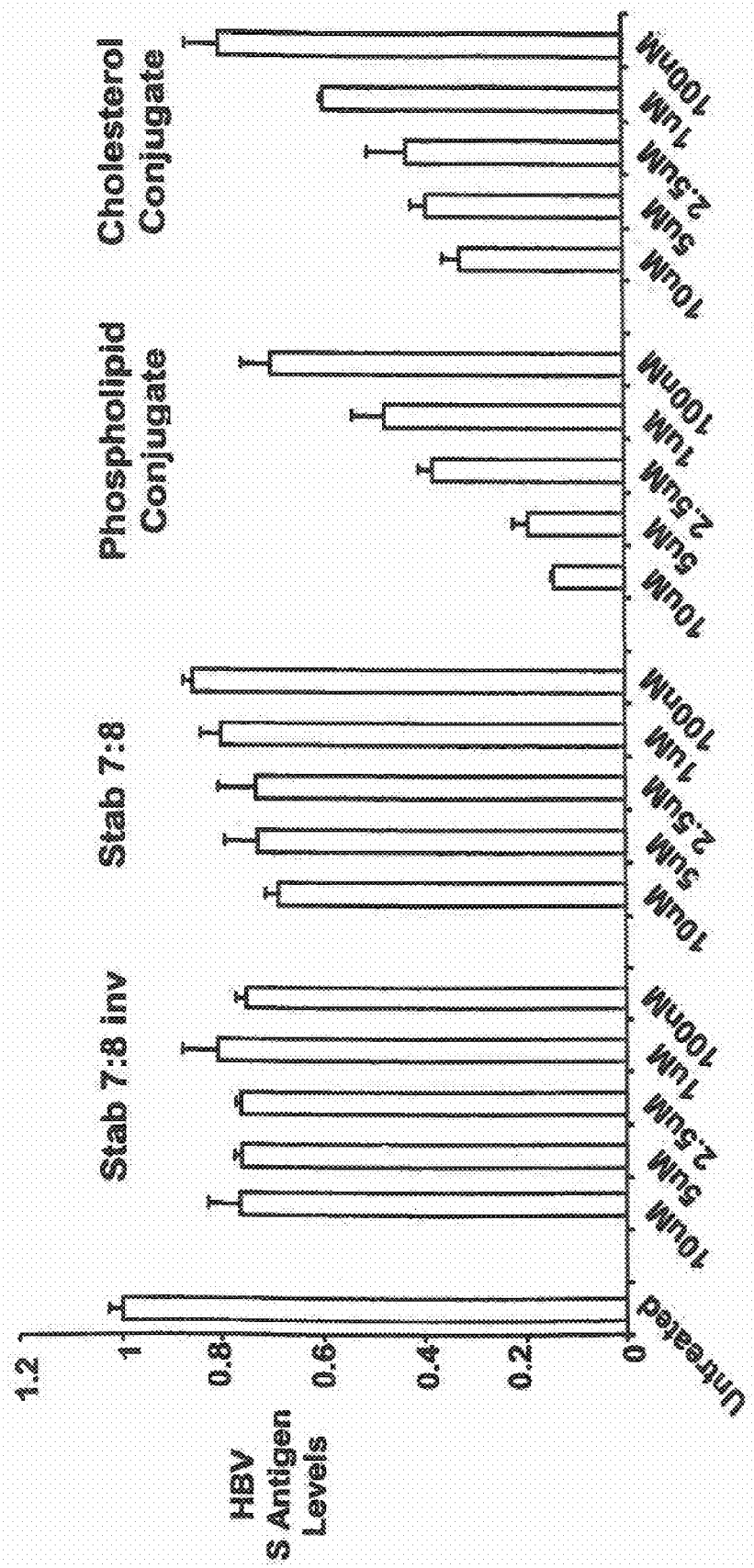
Figure 44: Lipid Free Delivery of HBV siNA Conjugates in Cell Culture

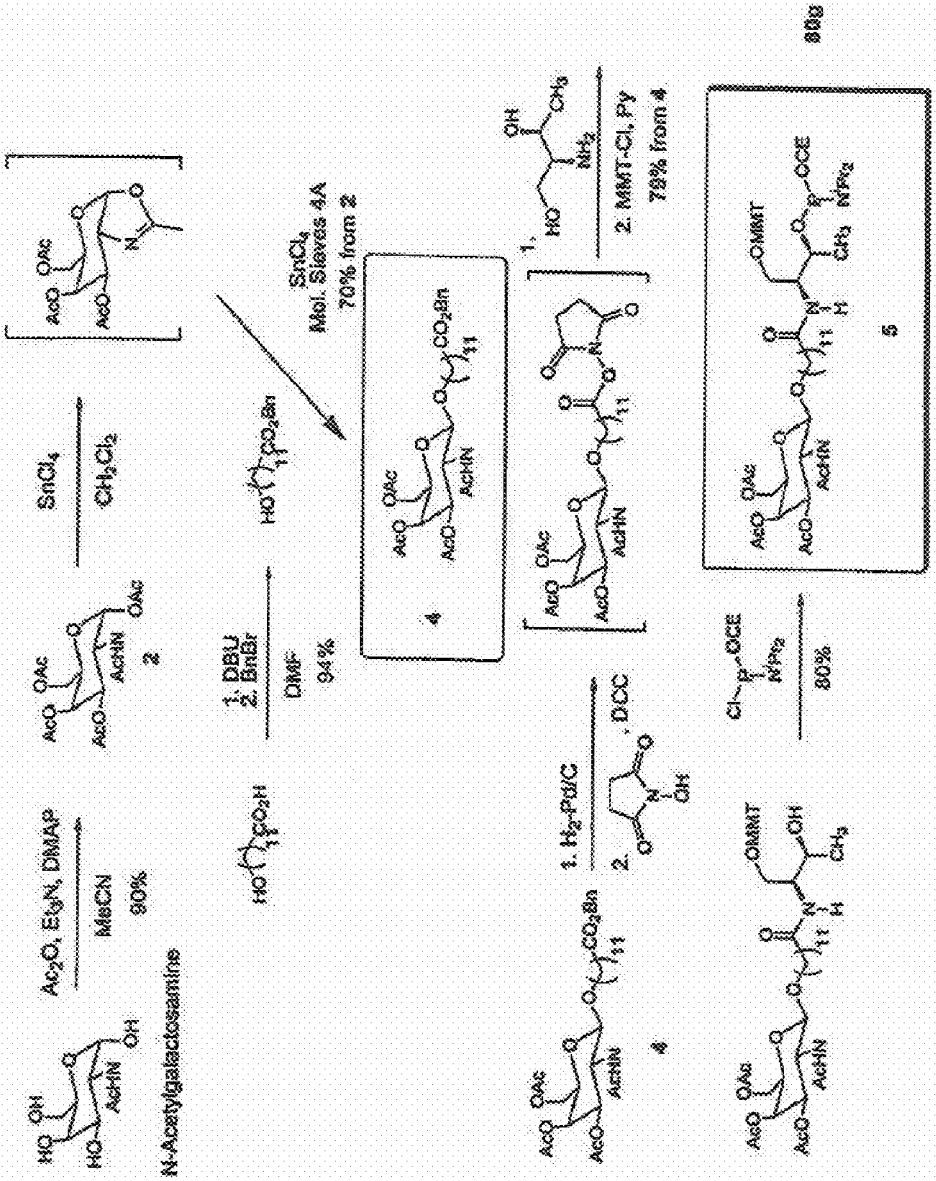
Figure 45: Scale-up of "mono" Galactosamine phosphoramidite

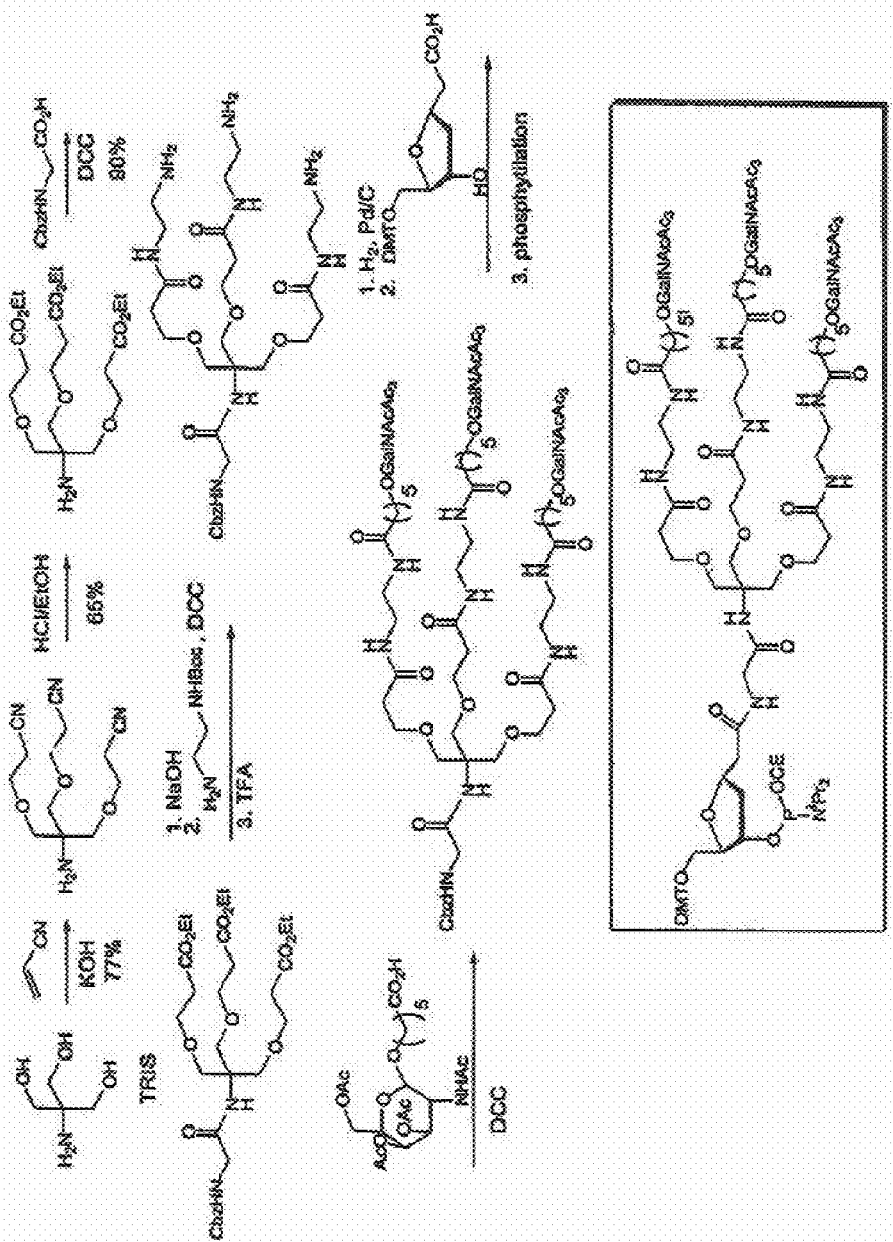
*Figure 46: Synthesis of "tri" Galactosamine phosphoramidite*

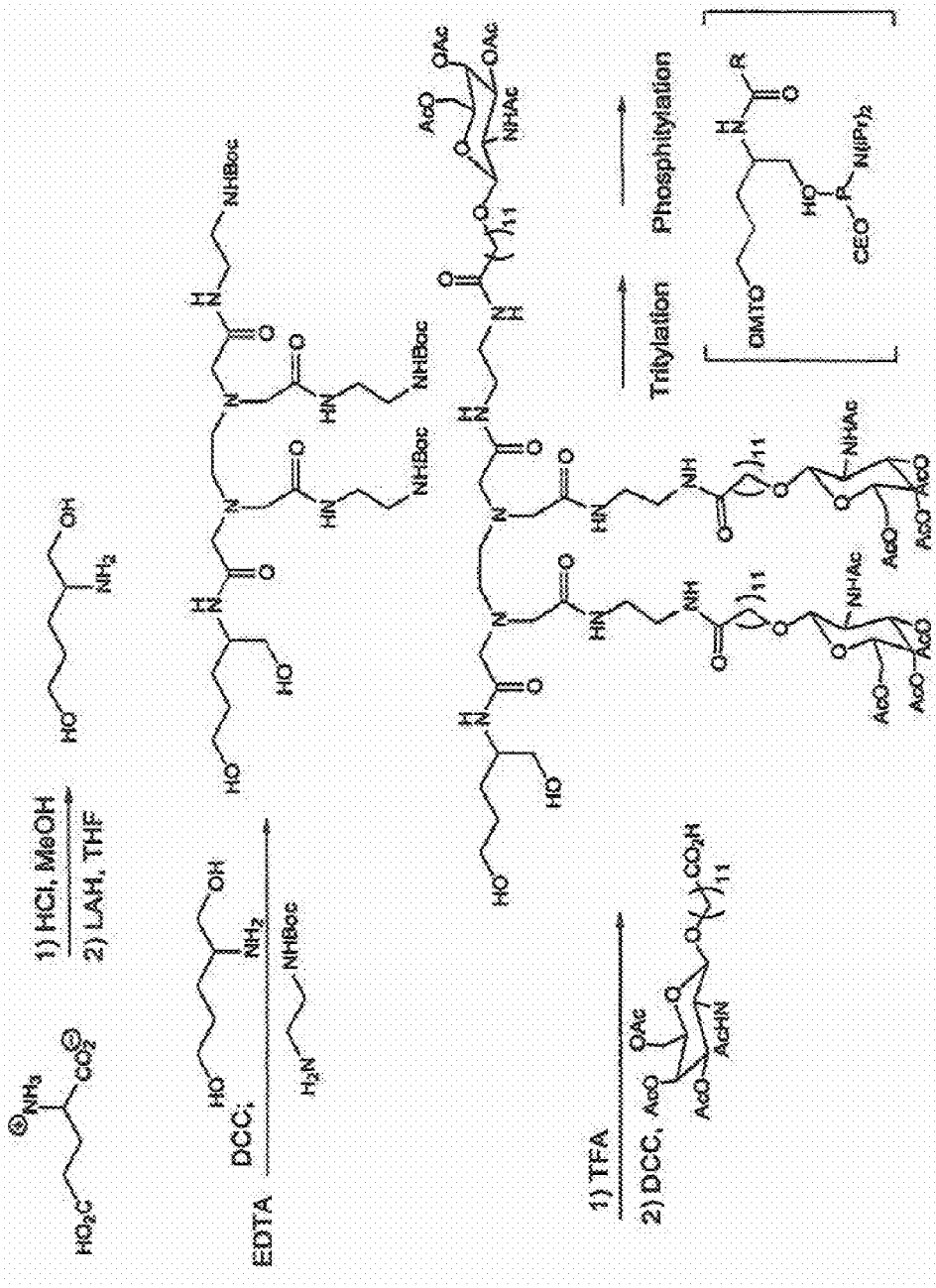
Figure 47: Synthesis of another Tri-Galactosamine Conjugate

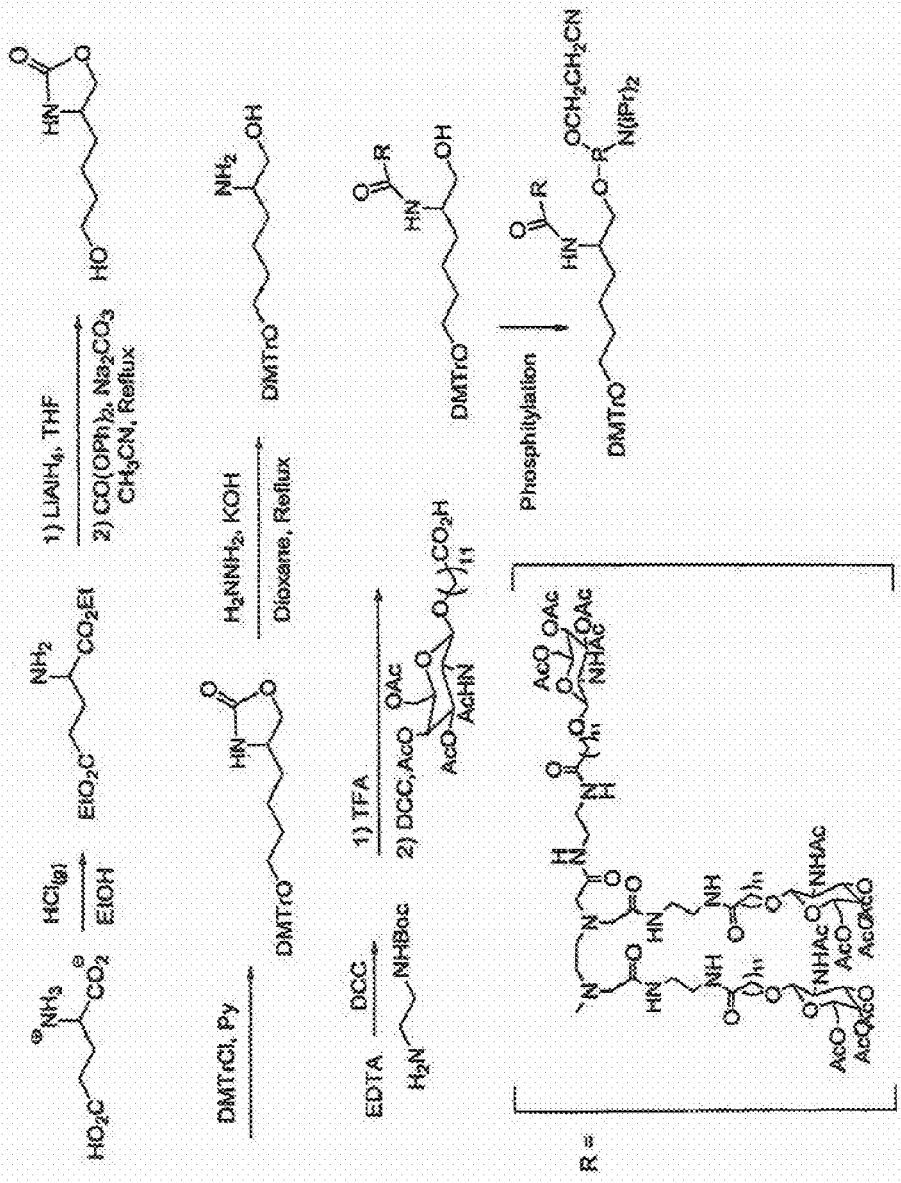
Figure 48: Alternate Synthesis of Tri-Galactosamine Conjugate

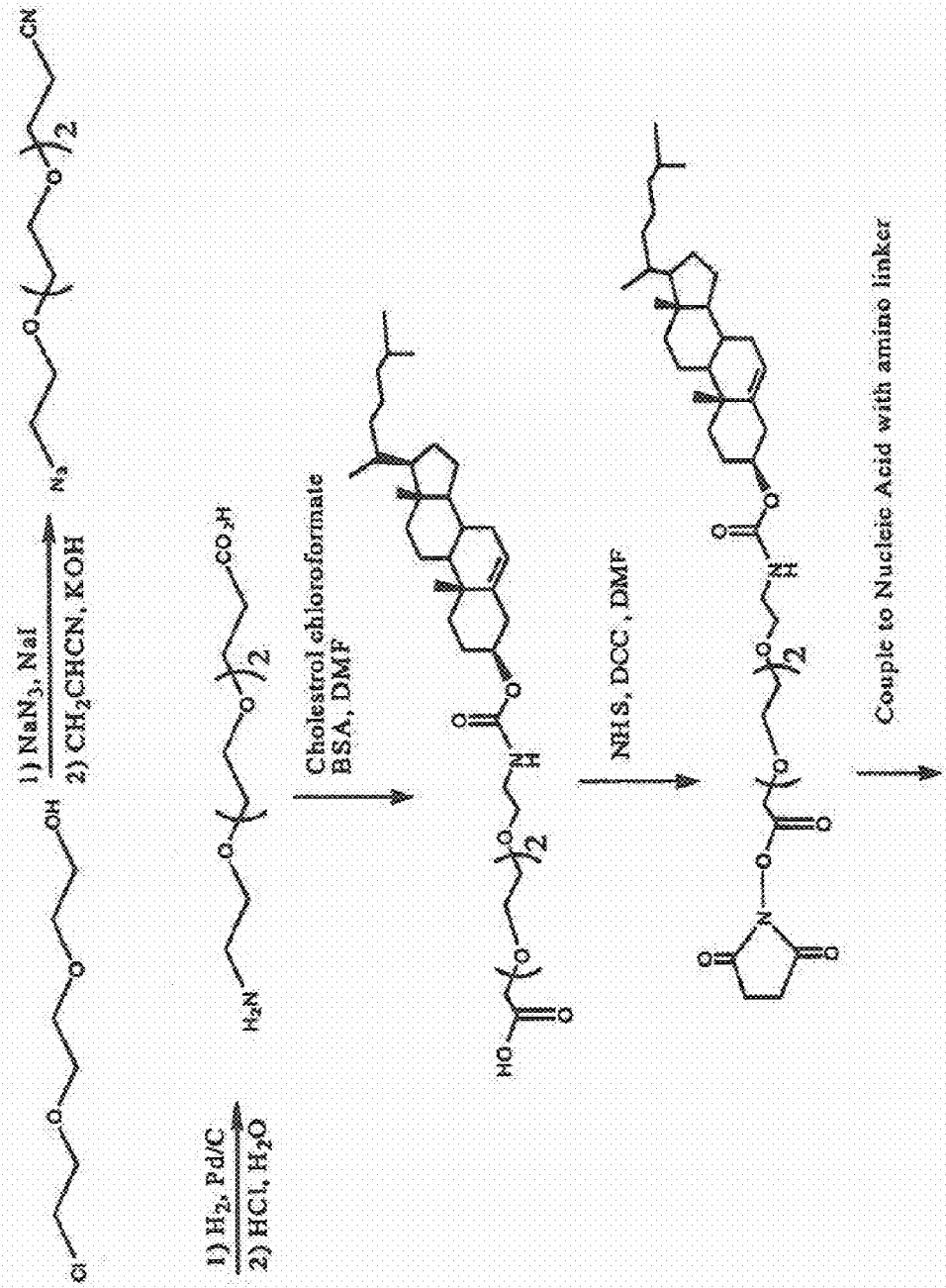
Figure 49: Synthesis of NHS Cholesterol Conjugate

US 7,964,578 B2

CONJUGATES AND COMPOSITIONS FOR CELLULAR DELIVERY

This patent application is a continuation of U.S. patent application Ser. No. 10/780,447, filed on Feb. 13, 2004, which is a continuation-in-part of U.S. patent application Ser. No. 10/427,160, filed Apr. 30, 2003, which is a continuation-in-part of International Patent Application No. PCT/US02/15876, filed May 17, 2002, that claims the benefit of U.S. Provisional Application No. 60/292,217, filed May 18, 2001, U.S. Provisional Application No. 60/362,016, filed Mar. 6, 2002, U.S. Provisional Application No. 60/306,883, filed Jul. 20, 2001, and U.S. Provisional Application No. 60/311,865, filed Aug. 13, 2001; and parent U.S. patent application Ser. No. 10/780,447 is also a continuation-in-part of International Patent Application No. PCT/US03/05346, filed Feb. 20, 2003, and International Patent Application No. PCT/US03/05028, filed Feb. 20, 2003, both of which claim the benefit of U.S. Provisional Application No. 60/358,580, filed Feb. 20, 2002, U.S. Provisional Application No. 60/363,124, filed Mar. 11, 2002, of U.S. Provisional Application No. 60/386,782, filed Jun. 6, 2002, U.S. Provisional Application No. 60/406,784, filed Aug. 29, 2002, U.S. Provisional Application No. 60/408,378, filed Sep. 5, 2002, U.S. Provisional Application No. 60/409,293, filed Sep. 9, 2002, and U.S. Provisional Application No. 60/440,129, filed Jan. 15, 2003. These applications are hereby incorporated by reference herein in their entirety including the drawings.

SEQUENCE LISTING

The sequence listing submitted via EFS, in compliance with 37 CFR §1.52(e)(5), is incorporated herein by reference. The sequence listing text file submitted via EFS contains the file "SequenceListingUpdated12May 20093USCNT2," created on May 12, 2009, which is 10,658 bytes in size.

BACKGROUND OF THE INVENTION

The present invention relates to conjugates, compositions, methods of synthesis, and applications thereof. The discussion is provided only for understanding of the invention that follows. This summary is not an admission that any of the work described below is prior art to the claimed invention.

The cellular delivery of various therapeutic compounds, such as antiviral and chemotherapeutic agents, is usually compromised by two limitations. First the selectivity of therapeutic agents is often low, resulting in high toxicity to normal tissues. Secondly, the trafficking of many compounds into living cells is highly restricted by the complex membrane systems of the cell. Specific transporters allow the selective entry of nutrients or regulatory molecules, while excluding most exogenous molecules such as nucleic acids and proteins. Various strategies can be used to improve transport of compounds into cells, including the use of lipid carriers and various conjugate systems. Conjugates are often selected based on the ability of certain molecules to be selectively transported into specific cells, for example via receptor mediated endocytosis. By attaching a compound of interest to molecules that are actively transported across the cellular membranes, the effective transfer of that compound into cells or specific cellular organelles can be realized. Alternately, molecules that are able to penetrate cellular membranes without active transport mechanisms, for example, various lipophilic molecules, can be used to deliver compounds of interest. Examples of molecules that can be utilized as conjugates include but are not limited to peptides, hormones, fatty acids, vitamins, flavonoids, sugars, reporter molecules, reporter enzymes, chelators, porphyrins, intercalcators, and other molecules that are capable of penetrating cellular membranes, either by active transport or passive transport.

The delivery of compounds to specific cell types, for example, cancer cells or cells specific to particular tissues and organs, can be accomplished by utilizing receptors associated with specific cell types. Particular receptors are overexpressed in certain cancerous cells, including the high affinity folic acid receptor. For example, the high affinity folate receptor is a tumor marker that is overexpressed in a variety of neoplastic tissues, including breast, ovarian, cervical, colorectal, renal, and nasoparyngeal tumors, but is expressed to a very limited extent in normal tissues. The use of folic acid based conjugates to transport exogenous compounds across cell membranes can provide a targeted delivery approach to the treatment and diagnosis of disease and can provide a reduction in the required dose of therapeutic compounds. Furthermore, therapeutic bioavialability, pharmacodynamics, and pharmacokinetic parameters can be modulated through the use of bioconjugates, including folate bioconjugates. Godwin et al., 1972, *J. Biol. Chem.*, 247, 2266-2271, report the synthesis of biologically active pteroyloligo-L-glutamates. Habus et al., 1998, *Bioconjugate Chem.*, 9, 283-291, describe a method for the solid phase synthesis of certain oligonucleotide-folate conjugates. Cook, U.S. Pat. No. 6,721,208, describes certain oligonucleotides modified with specific conjugate groups. The use of biotin and folate conjugates to enhance transmembrane transport of exogenous molecules, including specific oligonucleotides has been reported by Low et al., U.S. Pat. Nos. 5,416,016, 5,108,921, and International PCT publication No. WO 90/12096. Manoharan et al., International PCT publication No. WO 99/66063 describe certain folate conjugates, including specific nucleic acid folate conjugates with a phosphoramidite moiety attached to the nucleic acid component of the conjugate, and methods for the synthesis of these folate conjugates. Nomura et al., 2000, *J. Org. Chem.*, 65, 5016-5021, describe the synthesis of an intermediate, alpha-[2-(trimethylsilyl)ethoxycarbonl]folic acid, useful in the synthesis of certain types of folate-nucleoside conjugates. Guzaev et al., U.S. Pat. No. 6,335,434, describes the synthesis of certain folate oligonucleotide conjugates.

The delivery of compounds to other cell types can be accomplished by utilizing receptors associated with a certain type of cell, such as hepatocytes. For example, drug delivery systems utilizing receptor-mediated endocytosis have been employed to achieve drug targeting as well as drug-uptake enhancement. The asialoglycoprotein receptor (ASGPr) (see for example Wu and Wu, 1987, *J. Biol. Chem.* 262, 4429-4432) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987, *Glycoconjugate J.*, 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose and galactosamine based conjugates to transport exogenous compounds across cell membranes can provide a targeted delivery approach to the treatment of liver disease such as HBV and HCV infection or hepatocellular carcinoma. The use of bioconjugates can also provide a reduction in the required dose of therapeutic compounds required for treatment. Furthermore, therapeutic bioavialability, pharmacodynamics, and pharmacokinetic parameters can be modulated through the use of bioconjugates.

A number of peptide based cellular transporters have been developed by several research groups. These peptides are capable of crossing cellular membranes in vitro and in vivo with high efficiency. Examples of such fusogenic peptides include a 16-amino acid fragment of the homeodomain of ANTENNAPEDIA, a Drosophila transcription factor (Wang et al., 1995, *PNAS USA.*, 92, 3318-3322); a 17-mer fragment representing the hydrophobic region of the signal sequence of Kaposi fibroblast growth factor with or without NLS domain (Antopolsky et al., 1999, *Bioconj. Chem.*, 10, 598-606); a 17-mer signal peptide sequence of caiman crocodylus Ig(5) light chain (Chaloin et al., 1997, *Biochem. Biophys. Res. Comm.*, 243, 601-608); a 17-amino acid fusion sequence of HIV envelope glycoprotein gp4114, (Morris et al., 1997, *Nucleic Acids Res.*, 25, 2730-2736); the HIV-1 Tat49-57 fragment (Schwarze et al., 1999, *Science*, 285, 1569-1572); a transportan A—achimeric 27-mer consisting of N-terminal fragment of neuropeptide galanine and membrane interacting wasp venom peptide mastoporan (Lindgren et al., 2000, *Bioconjugate Chem.*, 11, 619-626); and a 24-mer derived from influenza virus hemagglutinin envelop glycoprotein (Bongartz et al., 1994, *Nucleic Acids Res.*, 22, 4681-4688).

These peptides were successfully used as part of an antisense oligonucleotide-peptide conjugate for cell culture transfection without lipids. In a number of cases, such conjugates demonstrated better cell culture efficacy then parent oligonucleotides transfected using lipid delivery. In addition, use of phage display techniques has identified several organ targeting and tumor targeting peptides in vivo (Ruoslahti, 1996, *Ann. Rev. Cell Dev. Biol.*, 12, 697-715). Conjugation of tumor targeting peptides to doxorubicin has been shown to significantly improve the toxicity profile and has demonstrated enhanced efficacy of doxorubicin in the in vivo murine cancer model MDA-MB-435 breast carcinoma (Arap et al., 1998, *Science*, 279, 377-380).

Hudson et al., 1999, *Int. J. Pharm.*, 182, 49-58, describes the cellular delivery of specific hammerhead ribozymes conjugated to a transferrin receptor antibody. Janjic et al., U.S. Pat. No. 6,168,778, describes specific VEGF nucleic acid ligand complexes for targeted drug delivery. Bonora et al., 1999, *Nucleosides Nucleotides*, 18, 1723-1725, describes the biological properties of specific antisense oligonucleotides conjugated to certain polyethylene glycols. Davis and Bishop, International PCT publication No. WO 99/17120 and Jaeschke et al., 1993, *Tetrahedron Lett.*, 34, 301-4 describe specific methods of preparing polyethylene glycol conjugates. Tullis, International PCT Publication No. WO 88/09810; Jaschke, 1997, *ACS Sympl Ser.*, 680, 265-283; Jaschke et al., 1994, *Nucleic Acids Res.*, 22, 4810-17; Efimov et al., 1993, *Bioorg. Khim.*, 19, 800-4; and Bonora et al., 1997, *Bioconjugate Chem.*, 8, 793-797, describe specific oligonucleotide polyethylene glycol conjugates. Manoharan, International PCT Publication No. WO 00/76554, describes the preparation of specific ligand-conjugated oligodeoxyribonucleotides with certain cellular, serum, or vascular proteins. Defrancq and Lhomme, 2001, *Bioorg Med Chem. Lett.*, 11, 931-933; Cebon et al., 2000, *Aust. J. Chem.*, 53, 333-339; and Salo et al., 1999, *Bioconjugate Chem.*, 10, 815-823 describe specific aminooxy peptide oligonucleotide conjugates.

SUMMARY OF THE INVENTION

The present invention features compositions and conjugates to facilitate delivery of molecules into a biological system, such as cells. The conjugates provided by the instant invention can impart therapeutic activity by transferring therapeutic compounds across cellular membranes. The present invention encompasses the design and synthesis of novel agents for the delivery of molecules, including but not limited to small molecules, lipids, nucleosides, nucleotides, nucleic acids, polynucleotides, oligonucleotides, antibodies, toxins, negatively charged polymers and other polymers, for example proteins, peptides, hormones, carbohydrates, or polyamines, across cellular membranes. In general, the transporters described are designed to be used either individually or as part of a multi-component system, with or without degradable linkers. The compounds of the invention generally shown in the Formulae below are expected to improve delivery of molecules into a number of cell types originating from different tissues, in the presence or absence of serum.

The present invention features a compound having the Formula 1:

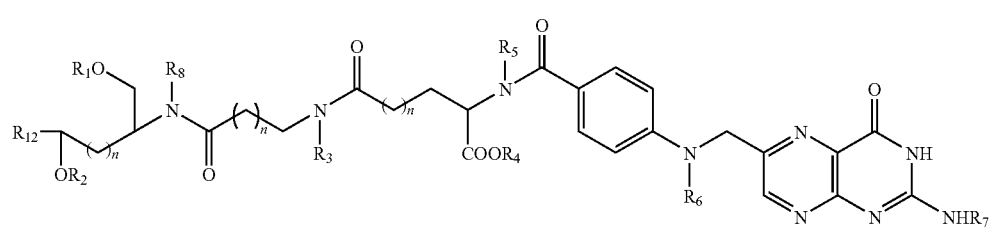

wherein each $R_1$, $R_3$, $R_4$, $R_5$, $R_6$, $R_7$ and $R_8$ is independently hydrogen, alkyl substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof, or a solid support comprising a linker.

The present invention features a compound having the Formula 2:

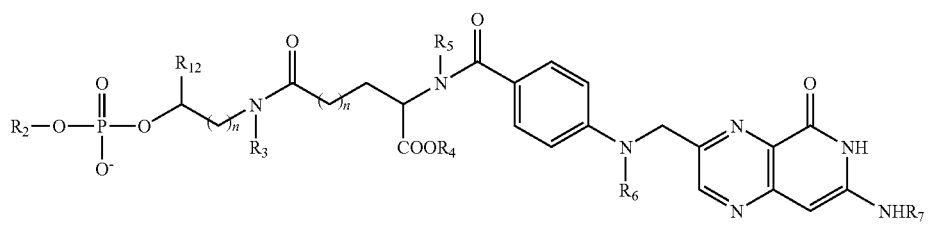

wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof, or a solid support comprising a linker.

The present invention features a compound having the Formula 3:

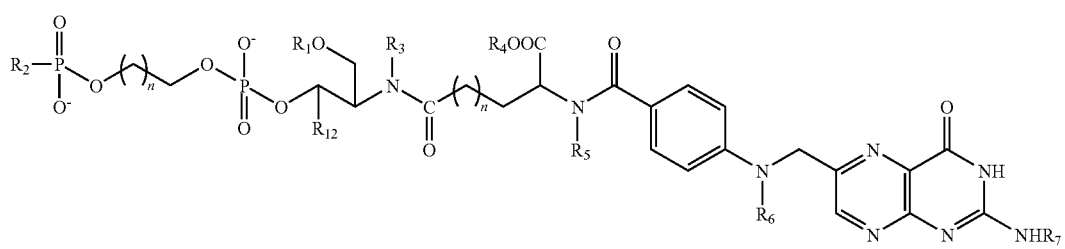

wherein each $R_1$, $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, or nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof.

The present invention features a compound having the Formula 4:

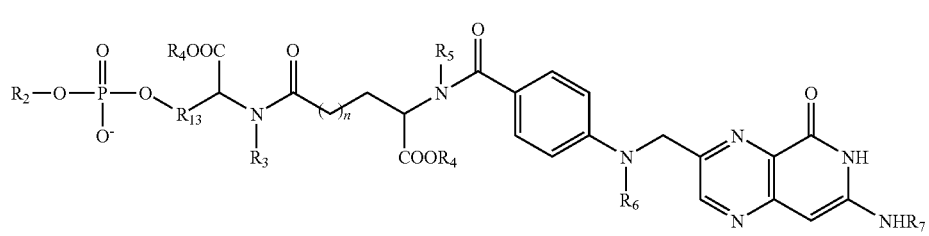

wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_2$ is a phosphorus containing group, nucleoside, nucleotide, small molecule, nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof, or a solid support comprising a linker, and $R_{13}$ is an amino acid side chain.

The present invention features a compound having the Formula 5:

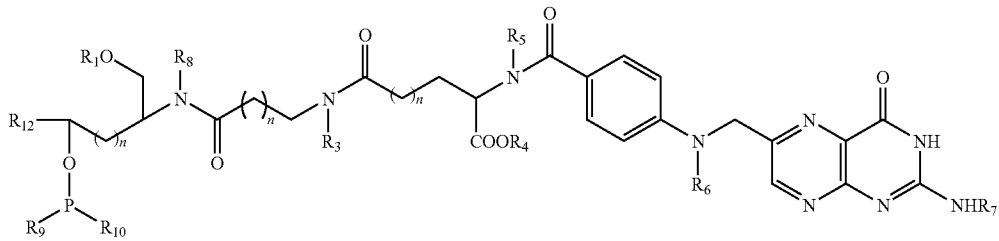

wherein each $R_1$ and $R_4$ is independently a protecting group or hydrogen, each $R_3$, $R_5$, $R_6$, $R_7$ and $R_8$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

The present invention features a compound having the Formula 6:

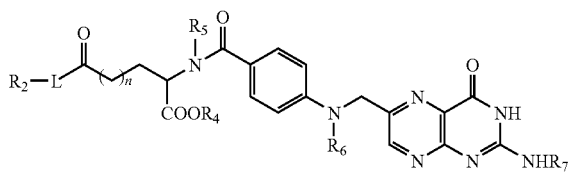

wherein each $R_4$, $R_5$, $R_6$ and $R_7$ is independently hydrogen, alkyl, substituted alkyl, aryl, substituted aryl, or a protecting group, $R_2$ is a phosphorus containing group, nucleoside, nucleotide, small molecule, nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof, or a solid support comprising a linker, each "n" is independently an integer from 0 to about 200, and L is a degradable linker.

The present invention features a compound having the Formula 7:

7 wherein each $R_1$, $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, polynucleotide, or oligonucleotide such as an enzymatic nucleic acid, allozyme, antisense nucleic acid, 2,5-A chimera, decoy, aptamer or triplex forming oligonucleotide, siNA or a portion thereof, or a solid support comprising a linker.

The present invention features a compound having the Formula 8:

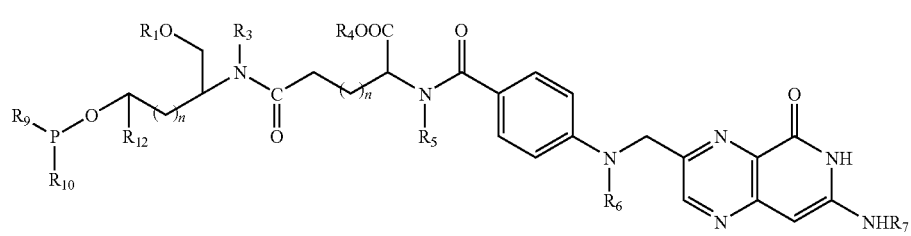

wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

The present invention features a method for synthesizing a compound having Formula 5:

5

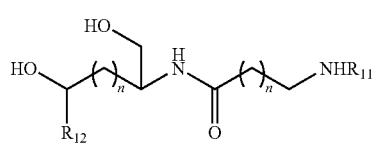

wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group, comprising: coupling a bis-hydroxy aminoalkyl derivative, for example D-threoninol, with a N-protected aminoalkanoic acid to yield a compound of Formula 9;

9

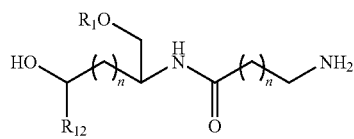

wherein $R_{11}$ is an amino protecting group, $R_{12}$ is a straight or branched chain alkyl, substituted alkyl, aryl, or substituted aryl, and each "n" is independently an integer from 0 to about 200; introducing primary hydroxy protection $R_1$ followed by amino deprotection of $R_{11}$ to yield a compound of Formula 10;

10

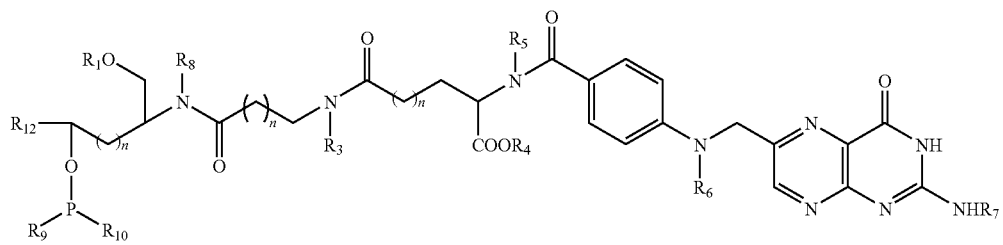

wherein $R_1$ is a protecting group, $R_{12}$ is a straight or branched chain alkyl, substituted alkyl, aryl, or substituted aryl, and each "n" is independently an integer from 0 to about 200; coupling the deprotected amine of Formula 10 with a protected amino acid, for example glutamic acid, to yield a compound of Formula 11;

11

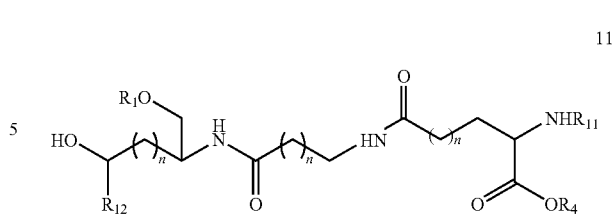

wherein each $R_1$ and $R_4$ is independently a protecting group or hydrogen, each "n" is independently an integer from 0 to about 200, $R_{11}$ is an amino protecting group, and $R_{12}$ is a straight or branched chain alkyl, substituted alkyl, aryl, or substituted aryl; deprotecting the amine $R_{11}$ of the conjugated glutamic acid of Formula XI to yield a compound of Formula 12;

12

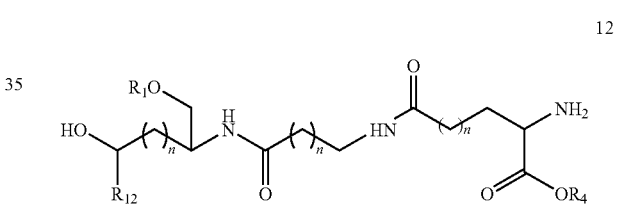

wherein each $R_1$ and $R_4$ is independently a protecting group or hydrogen, each "n" is independently an integer from 0 to about 200, $R_1$ is an amino protecting group, and $R_{12}$ is a straight or branched chain alkyl, substituted alkyl, aryl, or substituted aryl; coupling the deprotected amine of Formula 12 with an amino protected pteroic acid to yield a compound of Formula 13;

13

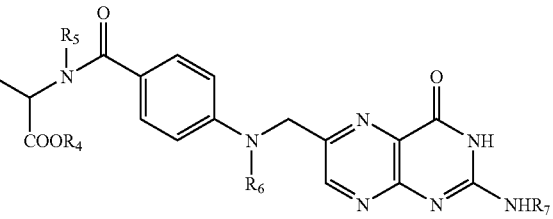

wherein each $R_1$ and $R_4$ is independently a protecting group or hydrogen, each $R_3$, $R_5$, $R_6$ and $R_7$ is independently hydrogen, alkyl or nitrogen protecting group, $R_{12}$ is a straight or branched chain alkyl, substituted alkyl, aryl, or substituted aryl, and each "n" is independently an integer from 0 to about 200; and introducing a phosphorus containing group at the secondary hydroxyl of Formula 13 to yield a compound of Formula 5.

The present invention features a method for synthesizing a compound having Formula 8:

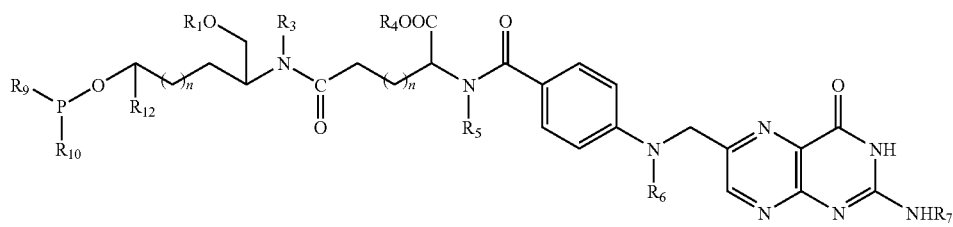

8 wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, each $R_9$ and $R_{10}$ is independently a nitrogen containing group, cyanoalkoxy, alkoxy, aryloxy, or alkyl group, and $R_{12}$ is a straight or branched chain alkyl, substituted alkyl, aryl, or substituted aryl, comprising; coupling a bis-hydroxy aminoalkyl derivative, for example D-threoninol, with a protected amino acid, for example glutamic acid, to yield a compound of Formula 14;

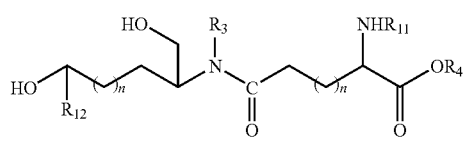

14 wherein $R_{11}$ is an amino protecting group, each "n" is independently an integer from 0 to about 200, $R_4$ is independently a protecting group, and $R_{12}$ is a straight or branched chain alkyl, substituted alkyl, aryl, or substituted aryl; introducing primary hydroxy protection $R_1$ followed by amino deprotection of $R_{11}$ of Formula 14 to yield a compound of Formula 15;

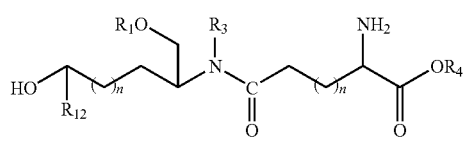

15 wherein each $R_1$ and $R_4$ is independently a protecting group or hydrogen, $R_{12}$ is a straight or branched chain alkyl, substituted alkyl, aryl, or substituted aryl, and each "n" is independently an integer from 0 to about 200; coupling the deprotected amine of Formula 15 with an amino protected pteroic acid to yield a compound of Formula 16;

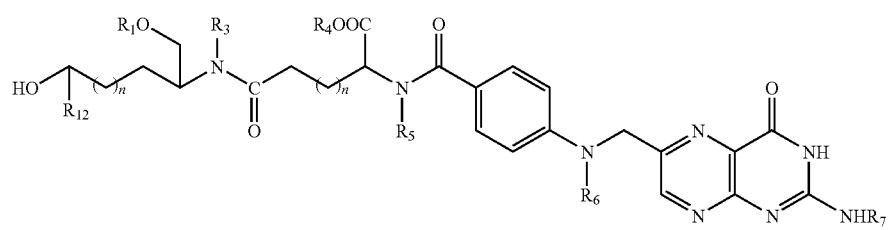

16 wherein each $R_1$ and $R_4$ is independently a protecting group or hydrogen, each $R_3$, $R_5$, $R_6$ and $R_7$ is independently hydrogen, alkyl or nitrogen protecting group, $R_{12}$ is a straight or branched chain alkyl, substituted alkyl, aryl, or substituted aryl, and each "n" is independently an integer from 0 to about 200; and introducing a phosphorus containing group at the secondary hydroxyl of Formula 16 to yield a compound of Formula 8.

In one embodiment, $R_2$ of a compound of the invention comprises a phosphorus containing group.

In another embodiment, $R_2$ of a compound of the invention comprises a nucleoside, for example, a nucleoside with beneficial activity such as anticancer or antiviral activity.

In yet another embodiment, $R_2$ of a compound of the invention comprises a nucleotide, for example, a nucleotide with beneficial activity such as anticancer or antiviral activity.

In a further embodiment, $R_2$ of a compound of the invention comprises a small molecule, for example, a small molecule with beneficial activity such as anticancer or antiviral activity.

In another embodiment, $R_2$ of a compound of the invention comprises a nucleic acid, polynucleotide, or oligonucleotide, for example, a nucleic acid, polynucleotide, or oligonucleotide with beneficial activity such as anticancer or antiviral activity. Non-limiting examples of nucleic acid, polynucleotide, and oligonucleotide compounds include enzymatic nucleic acid molecules, antisense molecules, aptamers, triplex forming oligonucleotides, decoys, 2,5-A chimera molecules, and siNA or a portion thereof.

In one embodiment, $R_2$ of a compound of the invention comprises a solid support comprising a linker.

In another embodiment, a nucleoside ($R_2$) of the invention comprises a nucleoside with anticancer activity.

In another embodiment, a nucleoside ($R_2$) of the invention comprises a nucleoside with antiviral activity.

In another embodiment, the nucleoside ($R_2$) of the invention comprises fludarabine, lamivudine (3TC), 5-fluoro uridine, AZT, ara-adenosine, ara-adenosine monophosphate, a dideoxy nucleoside analog, carbodeoxyguanosine, ribavirin, fialuridine, lobucavir, a pyrophosphate nucleoside analog, an acyclic nucleoside analog, acyclovir, gangciclovir, penciclovir, famciclovir, an L-nucleoside analog, FTC, L-FMAU, L-ddC, L-FddC, L-d4C, L-Fd4C, an L-dideoxypurine nucleoside analog, cytallene, bis-POM PMEA (GS-840), BMS-200,475, carbovir or abacavir.

In one embodiment, $R_{13}$ of a compound of the invention comprises an alkylamino or an alkoxy group, for example, —$CH_2O$— or —$CH(CH_2)CH_2O$—.

In another embodiment, $R_{12}$ of a compound of the invention is an alkylhyrdroxyl, for example, —$(CH_2)_nOH$, where n comprises an integer from about 1 to about 10.

In another embodiment, L of Formula 6 of the invention comprises serine, threonine, or a photolabile linkage.

In one embodiment, $R_9$ of a compound of the invention comprises a phosphorus protecting group, for example —$OCH_2CH_2CN$ (oxyethylcyano).

In one embodiment, $R_{10}$ of a compound of the invention comprises a nitrogen containing group, for example, —$N(R_{14})$ wherein $R_{14}$ is a straight or branched chain alkyl having from about 1 to about 10 carbons.

In another embodiment, $R_{10}$ of a compound of the invention comprises a heterocycloalkyl or heterocycloalkenyl ring containing from about 4 to about 7 atoms, and having from about 1 to about 3 heteroatoms comprising oxygen, nitrogen, or sulfur.

In another embodiment, $R_1$ of a compound of the invention comprises an acid labile protecting group, such as a trityl or substituted trityl group, for example, a dimethoxytrityl or mono-methoxytrityl group.

In another embodiment, $R_4$ of a compound of the invention comprises a tert-butyl, Fm (fluorenyl-methoxy), or allyl group.

In one embodiment, $R_6$ of a compound of the invention comprises a TFA (trifluoracetyl) group.

In another embodiment, $R_3$, $R_5$, $R_7$ and $R_8$ of a compound of the invention are independently hydrogen.

In one embodiment, $R_7$ of a compound of the invention is independently isobutyryl, dimethylformamide, or hydrogen.

In another embodiment, $R_{12}$ of a compound of the invention comprises a methyl group or ethyl group.

In one embodiment, a nucleic acid of the invention comprises a siNA molecule or a portion thereof.

In one embodiment, a nucleic acid of the invention comprises an enzymatic nucleic acid, for example a hammerhead, Inozyme, DNAzyme, G-cleaver, Zinzyme, Amberzyme, or allozyme or a portion thereof.

In another embodiment, a nucleic acid of the invention comprises an antisense nucleic acid, 2-5A nucleic acid chimera, or decoy nucleic acid or a portion thereof.

In another embodiment, the solid support having a linker of the invention comprises a structure of Formula 17:

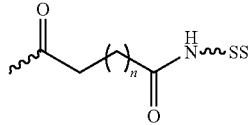

17 wherein SS is a solid support, and each "n" is independently an integer from about 1 to about 200.

In another embodiment, the solid support of the instant invention is controlled pore glass (CPG) or polystyrene, and can be used in the synthesis of a nucleic acid, polynucleotide, or oligonucleotide or the invention, such as an enzymatic nucleic acid, allozyme, antisense nucleic acid, 2,5-A chimera, decoy, aptamer, triplex forming oligonucleotide, siNA or a portion thereof.

In one embodiment, the invention features a pharmaceutical composition comprising a compound of the invention and a pharmaceutically acceptable carrier.

In another embodiment, the invention features a method of treating a cancer patient, comprising contacting cells of the patient with a pharmaceutical composition of the invention under conditions suitable for the treatment. This treatment can comprise the use of one or more other drug therapies under conditions suitable for the treatment. The cancers contemplated by the instant invention include but are not limited to breast cancer, lung cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancers.

In one embodiment, the invention features a method of treating a patient infected with a virus, comprising contacting cells of the patient with a pharmaceutical composition of the invention, under conditions suitable for the treatment. This treatment can comprise the use of one or more other drug therapies under conditions suitable for the treatment. The viruses contemplated by the instant invention include but are not limited to HIV, HBV, HCV, CMV, RSV, HSV, poliovirus, influenza, rhinovirus, west nile virus, Ebola virus, foot and mouth virus, and papilloma virus.

In one embodiment, the invention features a kit for detecting the presence of a nucleic acid molecule or other target molecule in a sample, for example, a gene in a cancer cell, comprising a compound of the instant invention.

In one embodiment, the invention features a kit for detecting the presence of a nucleic acid molecule, or other target molecule in a sample, for example, a gene in a virus-infected cell, comprising a compound of the instant invention.

In another embodiment, the invention features a compound of the instant invention comprising a modified phosphate group, for example, a phosphoramidite, phosphodiester, phosphoramidate, phosphorothioate, phosphorodithioate, alkylphosphonate, arylphosphonate, monophosphate, diphosphate, triphosphate, or pyrophosphate.

In one embodiment, the invention features a method for synthesizing a compound having Formula 18:

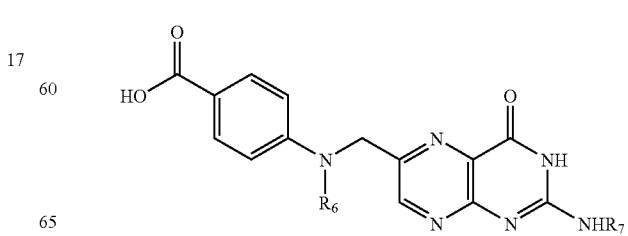

18 wherein each $R_6$ and $R_7$ is independently hydrogen, alkyl or nitrogen protecting group, comprising: reacting folic acid with a carboxypeptidase to yield a compound of Formula 19;

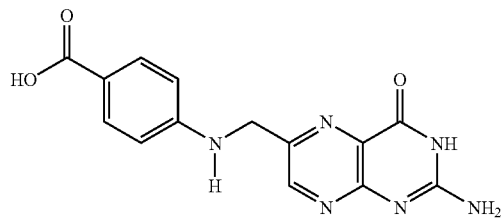

19 introducing a protecting group $R_6$ on the secondary amine of Formula 19 to yield a compound of Formula 20;

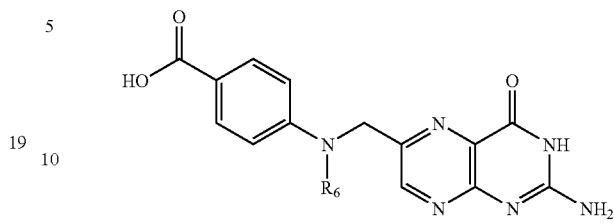

20 wherein $R_6$ is a nitrogen protecting group; and introducing a protecting group $R_7$ on the primary amine of Formula 20 to yield a compound of Formula 18.

In another embodiment, the amino protected pteroic acid of the invention is a compound of Formula 18.

In one embodiment, the invention encompasses a compound of Formula 1 having Formula 21:

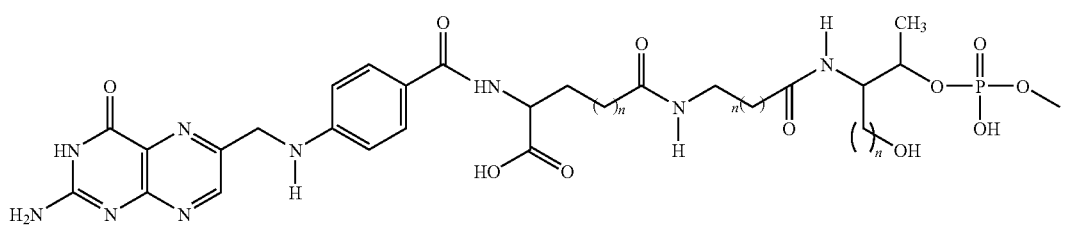

21

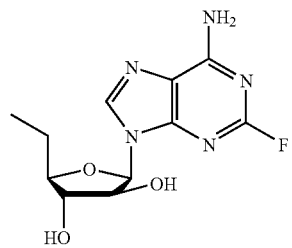

wherein each "n" is independently an integer from 0 to about 200.

In another embodiment, the invention encompasses a compound of Formula 7 having Formula 22:

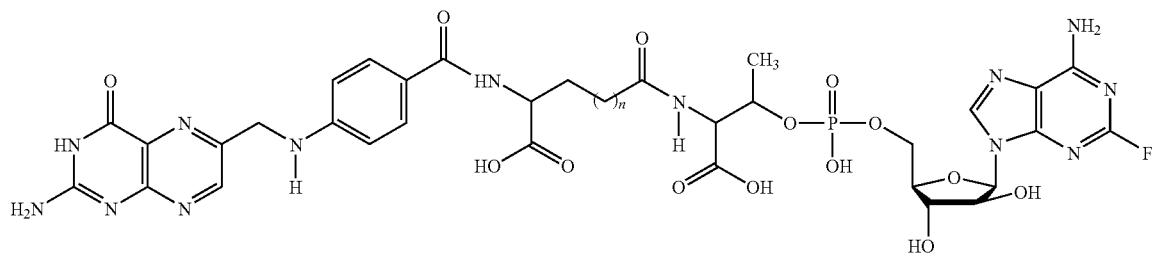

22 wherein each "n" is independently an integer from 0 to about 200.

In another embodiment, the invention encompasses a compound of Formula 4 having Formula 23:

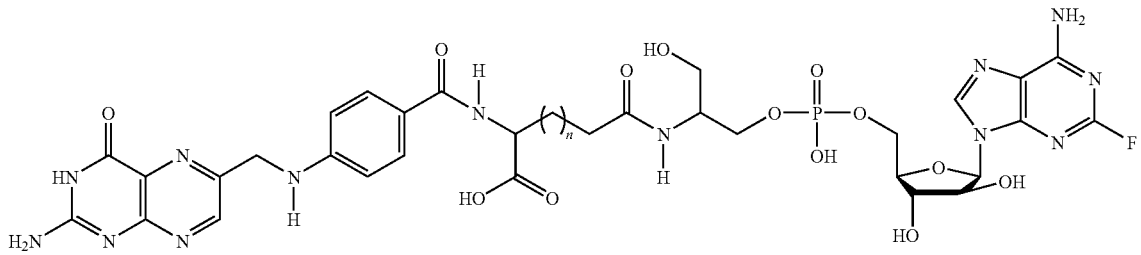

23 wherein "n" is an integer from 0 to about 200.

In another embodiment, the invention encompasses a compound of Formula 4 having Formula 24:

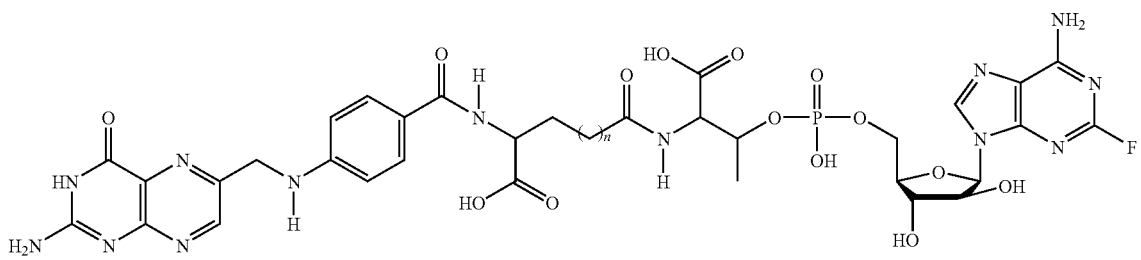

24 wherein "n" is an integer from 0 to about 200.

In another embodiment, the invention features a compound having Formula 25:

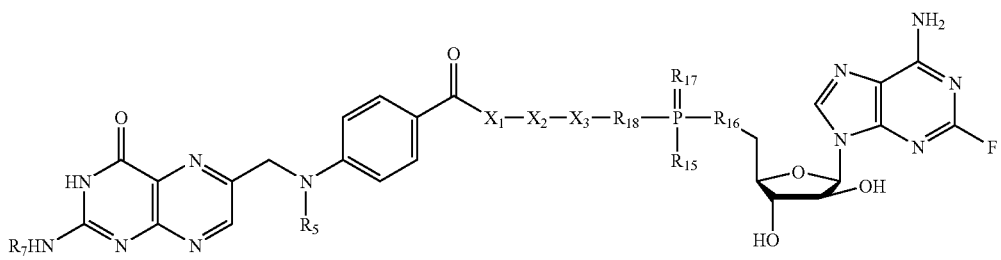

25 wherein each $R_5$ and $R_7$ is independently hydrogen, alkyl or a nitrogen protecting group, each $R_{15}$, $R_{16}$, $R_{17}$, and $R_{18}$ is independently O, S, alkyl, substituted alkyl, aryl, substituted aryl, or halogen, $X_1$ is —CH($X_{1'}$) or a group of Formula 38:

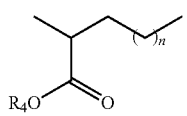

38 wherein $R_4$ is a protecting group and "n" is an integer from 0 to about 200;
$X_{1'}$ is the protected or unprotected side chain of a naturally occurring or non-naturally-occurring amino acid, $X_2$ is amide, alkyl, or carbonyl containing linker or a bond, and $X_3$ is a degradable linker which is optionally absent.

In another embodiment, the $X_3$ group of Formula 25 comprises a group of Formula 26:

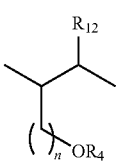

26 wherein $R_4$ is hydrogen or a protecting group, "n" is an integer from 0 to about 200 and $R_{12}$ is a straight or branched chain alkyl, substituted alkyl, aryl, or substituted aryl.

In yet another embodiment, $R_4$ of Formula 26 is hydrogen and $R_{12}$ is methyl or hydrogen.

In still another embodiment, the invention features a compound having Formula 27:

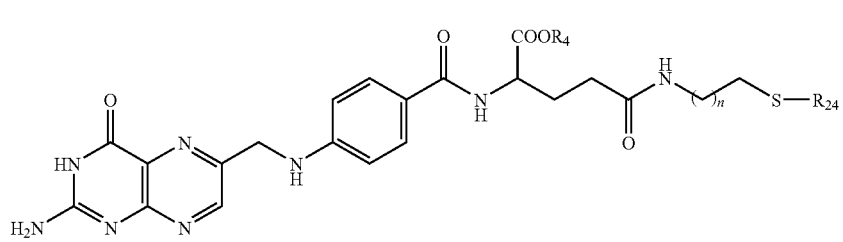
27 wherein "n" is an integer from about 0 to about 20, $R_4$ is H or a cationic salt, and $R_{24}$ is a sulfur containing leaving group, for example a group comprising:

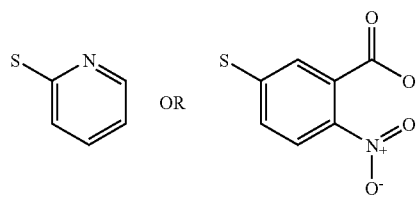

In another embodiment, the invention features a method for synthesizing a compound having Formula 27 comprising:
(a) selective tritylation of the thiol of cysteamine under conditions suitable to yield a compound having Formula 28:

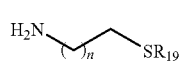
28 wherein "n" is an integer from about 0 to about 20 and $R_{19}$ is a thiol protecting group;
(b) peptide coupling of the product of (a) with a compound having Formula 29:

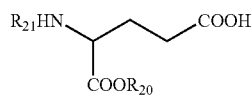
29 wherein $R_{20}$ is a carboxylic acid protecting group and $R_{21}$ an amino protecting group, under conditions suitable to yield a compound having Formula 30:

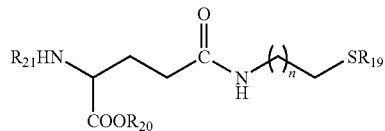
30 wherein "n" is an integer from about 0 to about 20, $R_{19}$ is a thiol protecting group, $R_{20}$ is a carboxylic acid protecting group and $R_{21}$ is an amino protecting group;
(c) removing the amino protecting group $R_{21}$ of the product of (b) under conditions suitable to yield a compound having Formula 31:

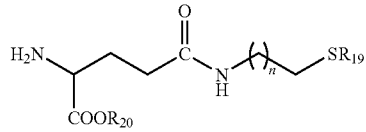
31 wherein "n" is an integer from about 0 to about 20 and $R_{19}$ and $R_{20}$ are as described in (b);
(d) condensation of the product of (c) with a compound having Formula 32:

32 wherein $R_{22}$ is an amino protecting group, under conditions suitable to yield a compound having Formula 33:

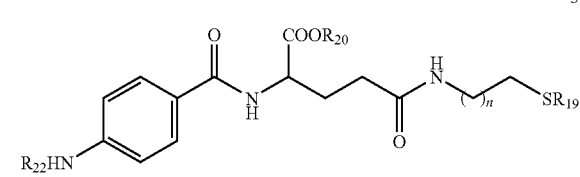
33 wherein "n" is an integer from about 0 to about 20 and $R_{19}$ and $R_{20}$ are as described in (b) and $R_{22}$ is as described in (d);
(e) selective cleavage of $R_{22}$ from the product of (d) under conditions suitable to yield a compound having Formula 34:

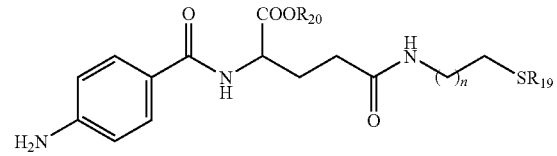
34 wherein "n" is an integer from about 0 to about 20 and $R_{19}$ and $R_{20}$ are as described in (b);
(f) coupling the product of (e) with a compound having Formula 35:

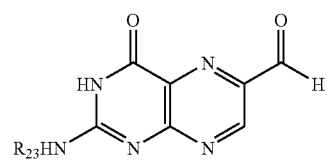
35 wherein $R_{23}$ is an amino protecting group under conditions suitable to yield a compound having Formula 36:

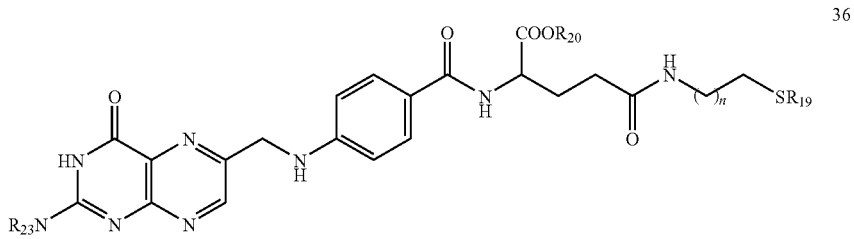

wherein $R_{23}$ is an amino protecting group, "n" is an integer from about 0 to about 20 and $R_{19}$ and $R_{20}$ are as described in (b);
(g) deprotecting the product of (f) under conditions suitable to yield a compound having Formula 37.

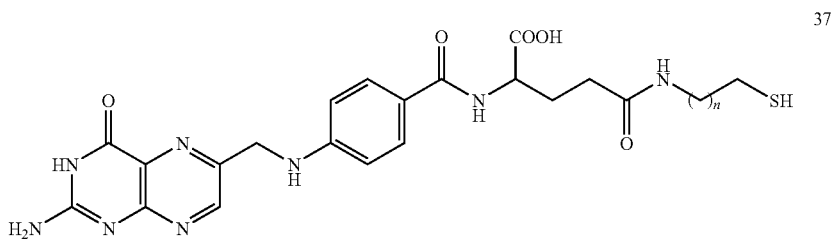

wherein "n" is an integer from about 0 to about 20; and
(h) introducing a disulphide-based leaving group to the product of (g) under conditions suitable to yield a compound having Formula 27.

In one embodiment, the invention features a compound having Formula 39:

wherein "n" is an integer from about 0 to about 20, X is a nucleic acid, polynucleotide, or oligonucleotide such as an enzymatic nucleic acid, allozyme, antisense nucleic acid, siNA, 2,5-A chimera, decoy, aptamer or triplex forming oligonucleotide, and P is a phosphorus containing group. In another embodiment, X comprises a siNA molecule or a portion thereof.

In another embodiment, the invention features a method for synthesizing a compound having Formula 39, comprising:
(a) coupling a thiol containing linker to a nucleic acid, polynucleotide or oligonucleotide under conditions suitable to yield a compound having Formula 40:

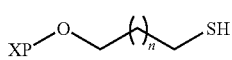

wherein "n" is an integer from about 0 to about 20, X is a nucleic acid, polynucleotide, or oligonucleotide, and P is a phosphorus containing group; and
(b) coupling the product of (a) with a compound having Formula 37 under conditions suitable to yield a compound having Formula 39.

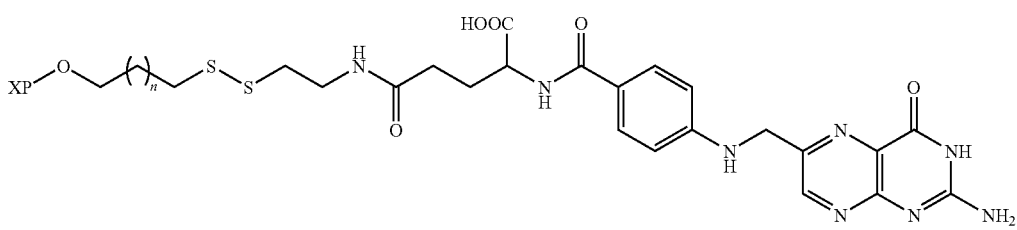

In another embodiment, the thiol containing linker of the invention is a compound having Formula 41:

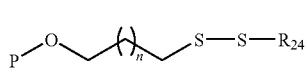

wherein "n" is an integer from about 0 to about 20, P is a phosphorus containing group, for example a phosphine, phosphite, or phosphate, and $R_{24}$ is any alkyl, substituted alkyl, alkoxy, aryl, substituted aryl, alkenyl, substituted alkenyl, alkynyl, or substituted alkynyl group with or without additional protecting groups.

In another embodiment, the conditions suitable to yield a compound having Formula 40 comprises reduction, for example using dithiothreitol (DTT) or any equivalent disulphide reducing agent, of the disulfide bond of a compound having Formula 42:

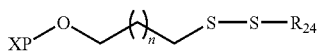

wherein "n" is an integer from about 0 to about 20, X is a nucleic acid, polynucleotide, or oligonucleotide, P is a phosphorus containing group, and $R_{24}$ is any alkyl, substituted alkyl, alkoxy, aryl, substituted aryl, alkenyl, substituted alkenyl, alkynyl, or substituted alkynyl group with or without additional protecting groups. In another embodiment, X comprises a siNA molecule or a portion thereof.

In one embodiment, the invention features a compound having Formula 43:

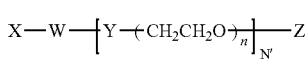

wherein X comprises a biologically active molecule; W comprises a degradable nucleic acid linker; Y comprises a linker molecule or amino acid that can be present or absent; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; n is an integer from about 1 to about 100; and N' is an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 44:

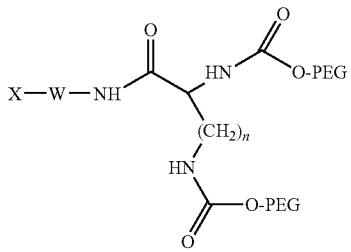

wherein X comprises a biologically active molecule; W comprises a linker molecule or chemical linkage that can be present or absent; n is an integer from about 1 to about 50, and PEG represents a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 46:

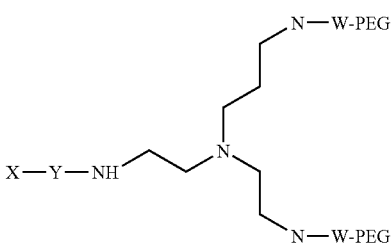

wherein X comprises a biologically active molecule; each W independently comprises linker molecule or chemical linkage that can be present or absent, Y comprises a linker molecule or chemical linkage that can be present or absent; and PEG represents a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 47:

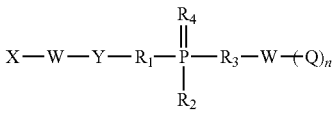

wherein X comprises a biologically active molecule; each W independently comprises a linker molecule or chemical linkage that can be the same or different and can be present or absent, Y comprises a linker molecule that can be present or absent; each Q independently comprises a hydrophobic group or phospholipid; each R1, R2, R3, and R4 independently comprises O, OH, H, alkyl, alkylhalo, O-alkyl, O-alkylcyano, S, S-alkyl, S-alkylcyano, N or substituted N, and n is an integer from about 1 to about 10. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 48:

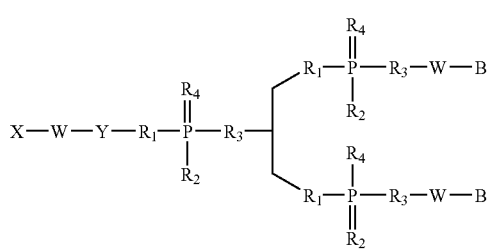

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and B represents a lipophilic group, for example a saturated or unsaturated linear, branched, or cyclic alkyl group, cholesterol, or a derivative thereof. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 49:

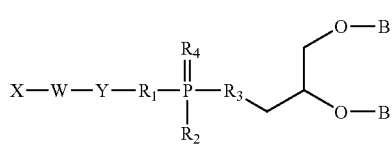

wherein X comprises a biologically active molecule; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and B represents a lipophilic group, for example a saturated or unsaturated linear, branched, or cyclic alkyl group, cholesterol, or a derivative thereof. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 50:

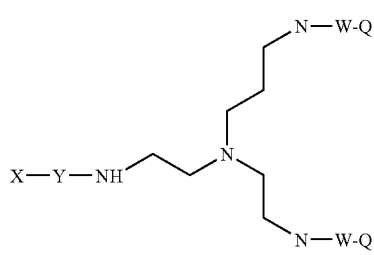

wherein X comprises a biologically active molecule; W comprises a linker molecule or chemical linkage that can be present or absent, Y comprises a linker molecule or chemical linkage that can be present or absent; and each Q independently comprises a hydrophobic group or phospholipid. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 51:

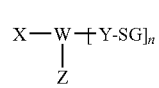

wherein X comprises a biologically active molecule; W comprises a linker molecule or chemical linkage that can be present or absent; Y comprises a linker molecule or amino acid that can be present or absent; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; SG comprises a sugar, for example galactose, galactosamine, N-acetyl-galactosamine, glucose, mannose, fructose, or fucose and the respective D or L, alpha or beta isomers, and n is an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 52:

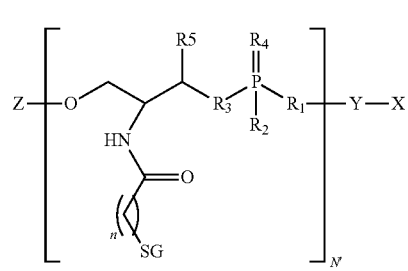

wherein X comprises a biologically active molecule; Y comprises a linker molecule or chemical linkage that can be present or absent; each R1, R2, R3, R4, and R5 independently comprises O, OH, H, alkyl, alkylhalo, O-alkyl, O-alkylcyano, S, S-alkyl, S-alkylcyano, N or substituted N; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; SG comprises a sugar, for example galactose, galactosamine, N-acetyl-galactosamine, glucose, mannose, fructose, or fucose and the respective D or L, alpha or beta isomers, n is an integer from about 1 to about 20; and N' is an integer from about 1 to about 20. In another embodiment, X comprises a siNA molecule or a portion thereof. In another embodiment, Y is selected from the group consisting of amide, phosphate, phosphate ester, phosphoramidate, or thiophosphate ester linkage.

In another embodiment, the invention features a compound having Formula 53:

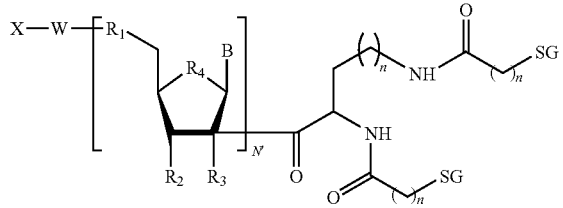

53 wherein B comprises H, a nucleoside base, or a non-nucleosidic base with or without protecting groups; each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises N or O—N, each R4 independently comprises O, CH$_2$, S, sulfone, or sulfoxy; X comprises H, a removable protecting group, amino, substituted amino, nucleotide, nucleoside, nucleic acid, oligonucleotide, enzymatic nucleic acid, siNA or a portion thereof, amino acid, peptide, protein, lipid, phospholipid, or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 10. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 54:

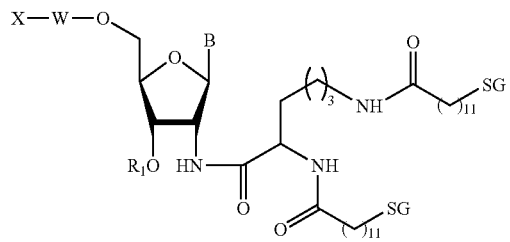

54 wherein B comprises H, a nucleoside base, or a non-nucleosidic base with or without protecting groups; each R1 independently comprises O, OH, H, alkyl, alkylhalo, O-alkyl, O-alkylhalo, S, N, substituted N, or a phosphorus containing group; X comprises H, a removable protecting group, amino, substituted amino, nucleotide, nucleoside, nucleic acid, oligonucleotide, enzymatic nucleic acid, siNA or a portion thereof, amino acid, peptide, protein, lipid, phospholipid, or label; W comprises a linker molecule or chemical linkage that can be present or absent; and SG comprises a sugar, for example galactose, galactosamine, N-acetyl-galactosamine, glucose, mannose, fructose, or fucose and the respective D or L, alpha or beta isomers. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 55:

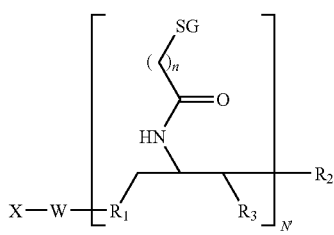

55 wherein each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises H, OH, alkyl, substituted alkyl, or halo; X comprises H, a removable protecting group, amino, substituted amino, nucleotide, nucleoside, nucleic acid, oligonucleotide such as an enzymatic nucleic acid, allozyme, antisense nucleic acid, siNA or a portion thereof, 2,5-A chimera, decoy, aptamer or triplex forming oligonucleotide, amino acid, peptide, protein, lipid, phospholipid, biologically active molecule or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 100. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 56:

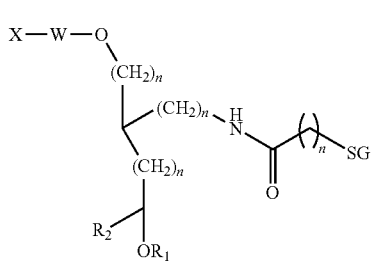

56 wherein R1 comprises H, alkyl, alkylhalo, N, substituted N, or a phosphorus containing group; R2 comprises H, O, OH, alkyl, alkylhalo, halo, S, N, substituted N, or a phosphorus containing group; X comprises H, a removable protecting group, amino, substituted amino, nucleotide, nucleoside, nucleic acid, oligonucleotide such as an enzymatic nucleic acid, allozyme, antisense nucleic acid, 2,5-A chimera, decoy, aptamer or triplex forming oligonucleotide, siNA or a portion thereof, amino acid, peptide, protein, lipid, phospholipid, biologically active molecule or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, and each n is independently an integer from about 0 to about 20. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 57:

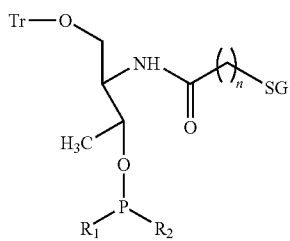

57 wherein R1 can include the groups:

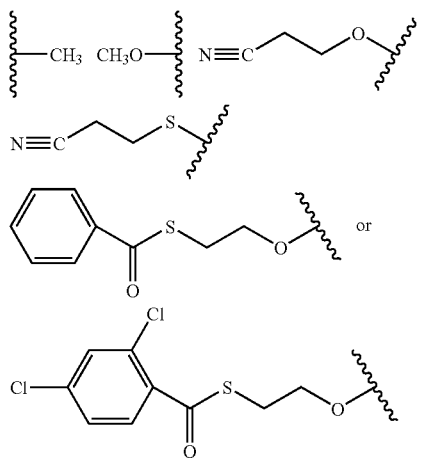

and wherein R2 can include the groups:

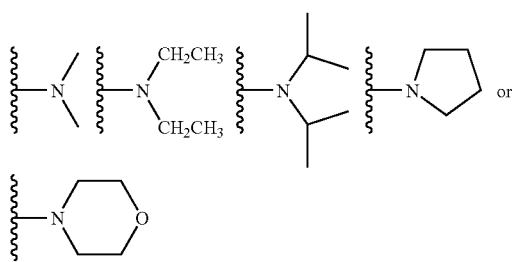

and wherein Tr is a removable protecting group, for example a trityl, monomethoxytrityl, or dimethoxytrityl; SG comprises a sugar, for example galactose, galactosamine, N-acetyl-galactosamine, glucose, mannose, fructose, or fucose and the respective D or L, alpha or beta isomers, and n is an integer from about 1 to about 20.

In one embodiment, compounds having Formula 52, 53, 54, 55, 56, and 57 are featured wherein each nitrogen adjacent to a carbonyl can independently be substituted for a carbonyl adjacent to a nitrogen or each carbonyl adjacent to a nitrogen can be substituted for a nitrogen adjacent to a carbonyl.

In another embodiment, the invention features a compound having Formula 58:

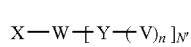

58 wherein X comprises a biologically active molecule; W comprises a linker molecule or chemical linkage that can be present or absent; Y comprises a linker molecule or amino acid that can be present or absent; V comprises a signal protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; each n is independently an integer from about 1 to about 50; and N' is an integer from about 1 to about 100. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 59:

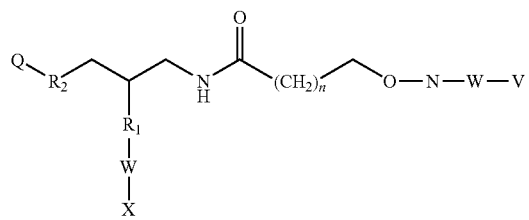

59 wherein each R1 independently comprises O, S, N, substituted N, or a phosphorus containing group; each R2 independently comprises O, S, or N; X comprises H, amino, substituted amino, nucleotide, nucleoside, nucleic acid, oligonucleotide, or enzymatic nucleic acid or other biologically active molecule; n is an integer from about 1 to about 50, Q comprises H or a removable protecting group which can be optionally absent, each W independently comprises a linker molecule or chemical linkage that can be present or absent, and V comprises a signal protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide, or a compound having Formula 45

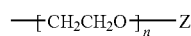

45 wherein Z comprises H, OH, O-alkyl, SH, S-alkyl, alkyl, substituted alkyl, aryl, substituted aryl, amino, substituted amino, nucleotide, nucleoside, nucleic acid, oligonucleotide such as an enzymatic nucleic acid, allozyme, antisense nucleic acid, siNA, 2,5-A chimera, decoy, aptamer or triplex forming oligonucleotide, amino acid, peptide, protein, lipid, phospholipid, or label; and n is an integer from about 1 to about 100. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 60:

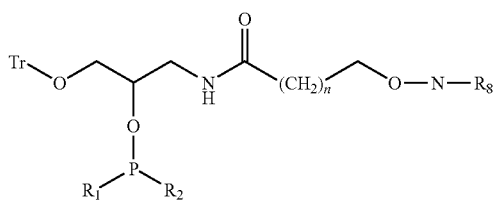
60 wherein R1 can include the groups:

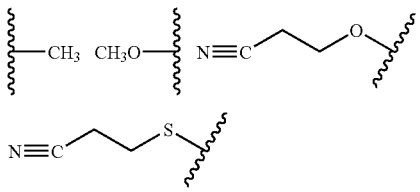

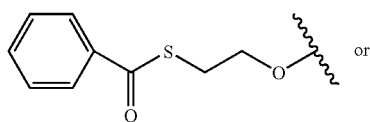

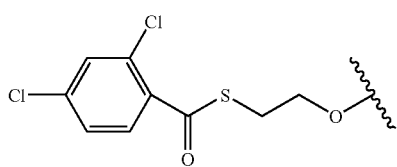 or and wherein R2 can include the groups:

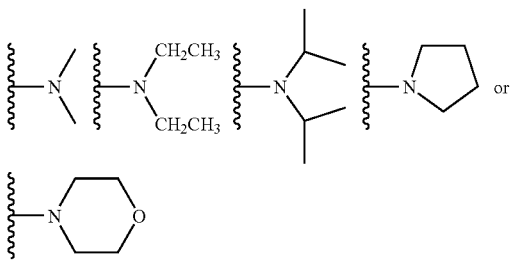

and wherein Tr is a removable protecting group, for example a trityl, monomethoxytrityl, or dimethoxytrityl; n is an integer from about 1 to about 50; and R8 is a nitrogen protecting group, for example a phthaloyl, trifluoroacetyl, FMOC, or monomethoxytrityl group.

In another embodiment, the invention features a compound having Formula 61:

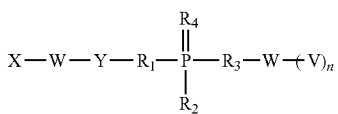
61 wherein X comprises a biologically active molecule; each W independently comprises a linker molecule or chemical linkage that can be the same or different and can be present or absent, Y comprises a linker molecule that can be present or absent; each 5 independently comprises a signal protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; each R1, R2, R3, and R4 independently comprises O, OH, H, alkyl, alkylhalo, O-alkyl, O-alkylcyano, S, S-alkyl, S-alkylcyano, N or substituted N, and n is an integer from about 1 to about 10. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 62:

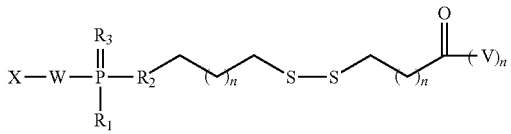
62 wherein X comprises a biologically active molecule; each 5 independently comprises a signal protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; W comprises a linker molecule or chemical linkage that can be present or absent; each R1, R2, and R3 independently comprises O, OH, H, alkyl, alkylhalo, O-alkyl, O-alkylcyano, S, S-alkyl, S-alkylcyano, N or substituted N, and each n is independently an integer from about 1 to about 10. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 63:

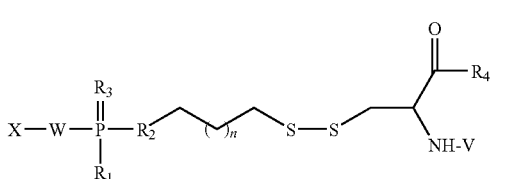
63 wherein X comprises a biologically active molecule; V comprises a signal protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; W comprises a linker molecule or chemical linkage that can be present or absent; each R1, R2, R3 independently comprises O, OH, H, alkyl, alkylhalo, O-alkyl, O-alkylcyano, S, S-alkyl, S-alkylcyano, N or substituted N, R4 represents an ester, amide, or protecting group, and each n is independently an integer from about 1 to about 10. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 64:

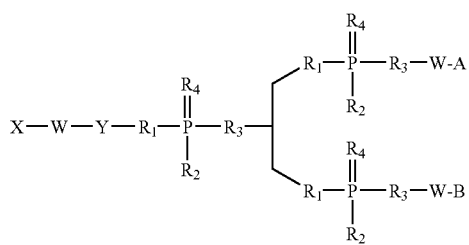

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, A comprises a nitrogen containing group, and B comprises a lipophilic group. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 65:

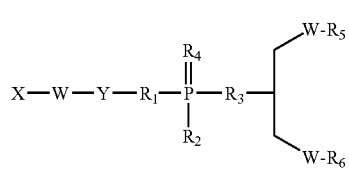

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, RV comprises the lipid or phospholipid component of any of Formulae 47-50, and R6 comprises a nitrogen containing group. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 92:

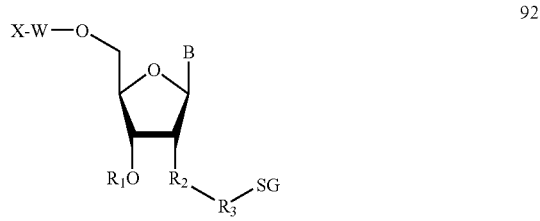

wherein B comprises H, a nucleoside base, or a non-nucleosidic base with or without protecting groups; each R1 independently comprises O, OH, H, alkyl, alkylhalo, O-alkyl, O-alkylhalo, S, N, substituted N, or a phosphorus containing group; X comprises H, a removable protecting group, amino, substituted amino, nucleotide, nucleoside, nucleic acid, oligonucleotide, enzymatic nucleic acid, amino acid, peptide, protein, lipid, phospholipid, biologically active molecule or label; W comprises a linker molecule or chemical linkage that can be present or absent; R2 comprises O, NH, S, CO, COO, ON=C, or alkyl; R3 comprises alkyl, akloxy, or an aminoacyl side chain; and SG comprises a sugar, for example galactose, galactosamine, N-acetyl-galactosamine, glucose, mannose, fructose, or fucose and the respective D or L, alpha or beta isomers. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 86:

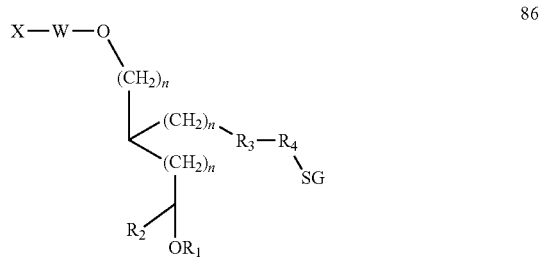

wherein R1 comprises H, alkyl, alkylhalo, N, substituted N, or a phosphorus containing group; R2 comprises H, O, OH, alkyl, alkylhalo, halo, S, N, substituted N, or a phosphorus containing group; X comprises H, a removable protecting group, amino, substituted amino, nucleotide, nucleoside, nucleic acid, oligonucleotide, enzymatic nucleic acid, amino acid, peptide, protein, lipid, phospholipid, biologically active molecule or label; W comprises a linker molecule or chemical linkage that can be present or absent; R3 comprises O, NH, S, CO, COO, ON=C, or alkyl; R4 comprises alkyl, akloxy, or an aminoacyl side chain; and SG comprises a sugar, for example galactose, galactosamine, N-acetyl-galactosamine, glucose, mannose, fructose, or fucose and the respective D or L, alpha or beta isomers, and each n is independently an integer from about 0 to about 20. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 87:

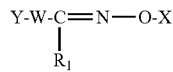

wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent; and Y comprises a biologically active molecule, for example an enzymatic nucleic acid, allozyme, antisense nucleic acid, siNA, 2,5-A chimera, decoy, aptamer or triplex forming oligonucleotide, peptide, protein, or antibody; R1 comprises H, alkyl, or substituted alkyl. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 88:

wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent, and Y comprises a biologically active molecule, for example an enzymatic nucleic acid, allozyme, antisense nucleic acid, siNA, 2,5-A chimera, decoy, aptamer or triplex forming oligonucleotide, peptide, protein, or antibody. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 99:

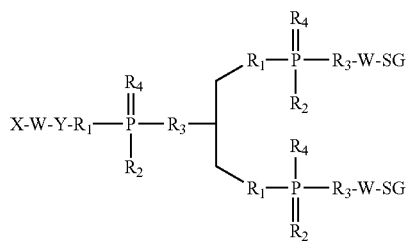

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and SG comprises a sugar, for example galactose, galactosamine, N-acetyl-galactosamine or branched derivative thereof, glucose, mannose, fructose, or fucose and the respective D or L, alpha or beta isomers. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 100:

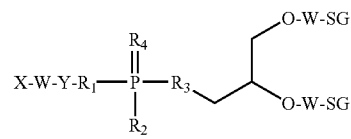

wherein X comprises a biologically active molecule; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and SG comprises a sugar, for example galactose, galactosamine, N-acetyl-galactosamine or branched derivative thereof, glucose, mannose, fructose, or fucose and the respective D or L, alpha or beta isomers. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the SG component of any compound having Formulae 99 or 100 comprises a compound having Formula 101:

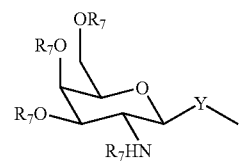

wherein Y comprises a linker molecule or chemical linkage that can be present or absent and each R7 independently is hydrogen or an acyl group, for example an acetyl group.

In one embodiment, the W-SG component of a compound having Formulae 99 comprises a compound having Formula 102:

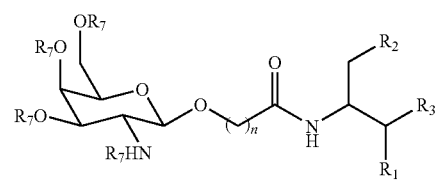

wherein R2 comprises O, OH, H, alkyl, alkylhalo, O-alkyl, O-alkylhalo, S, N, substituted N, a protecting group, or another compound having Formula 102; R1 independently H, OH, alkyl, substituted alkyl, or halo and each R7 independently is hydrogen or an acyl group, for example an acetyl group, and R3 comprises O or R3 in Formula 99, and n is an integer from about 1 to about 20.

In one embodiment, the W-SG component of a compound having Formulae 99 comprises a compound having Formula 103:

wherein R1 can include the groups:

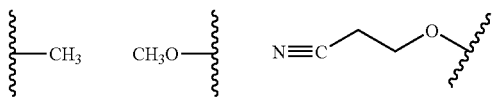

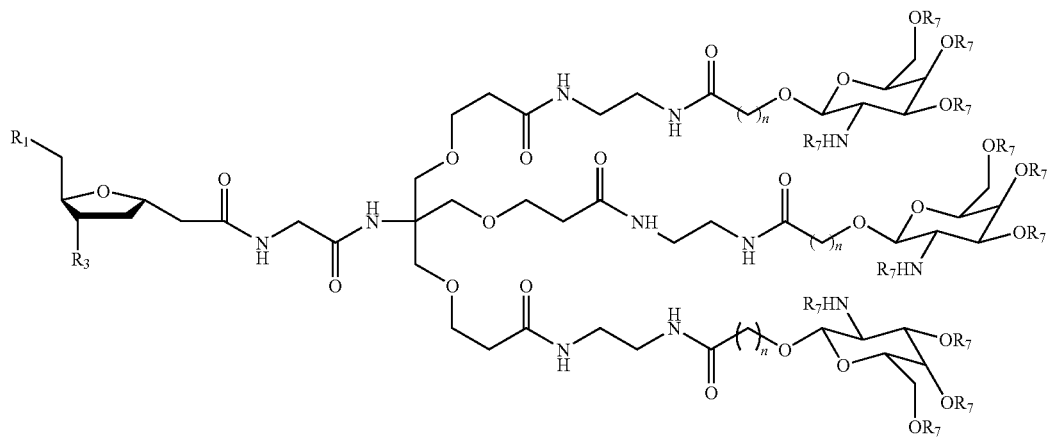

wherein R1 comprises H, alkyl, alkylhalo, O-alkyl, O-alkylhalo, S, N, substituted N, a protecting group, or another compound having Formula 103; each R7 independently is hydrogen or an acyl group, for example an acetyl group, and R3 comprises H or R3 in Formula 99, and each n is independently an integer from about 1 to about 20.

In one embodiment, the invention features a compound having Formula 104:

-continued $$N{\equiv}C\text{-CH}_2\text{CH}_2\text{-S-}\xi$$

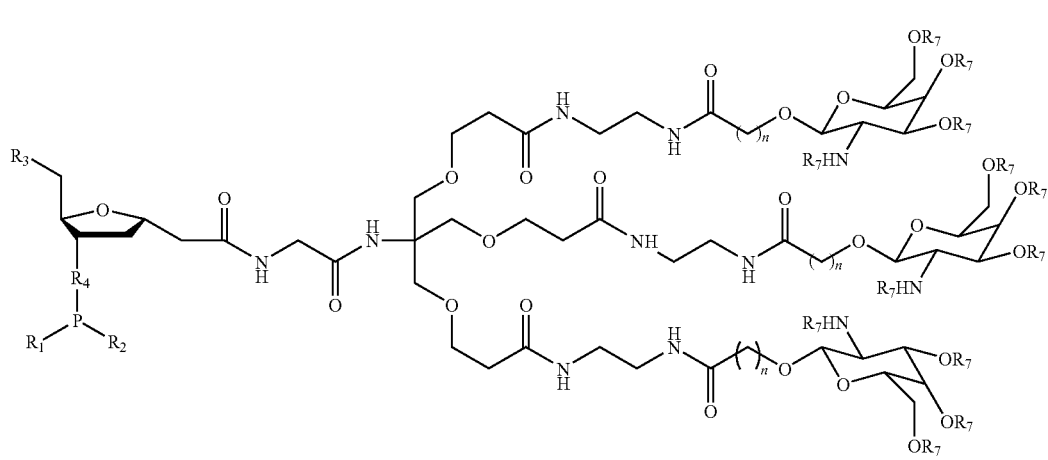

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently is hydrogen or an acyl group, for example an acetyl group, and each n is independently an integer from about 1 to about 20, and -continued

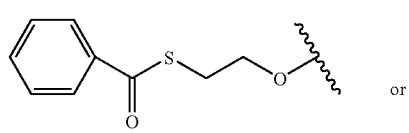

or

-continued

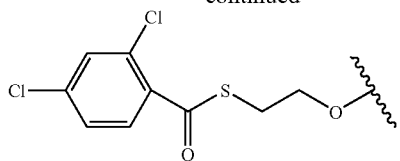

and wherein R2 can include the groups:

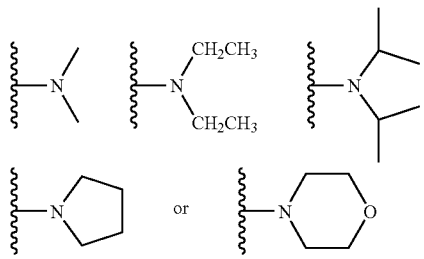

In one embodiment, the invention features a compound having Formula 105:

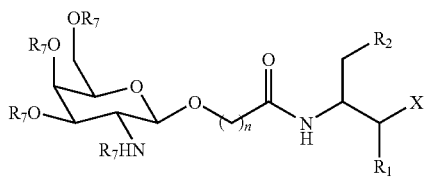

wherein X comprises a nucleotide, polynucleotide, or oligonucleotide or a portion thereof, R2 comprises O, OH, H, alkyl, alkylhalo, O-alkyl, O-alkylhalo, S, N, substituted N, a protecting group, or a nucleotide, polynucleotide, or oligonucleotide or a portion thereof; R1 independently H, OH, alkyl, substituted alkyl, or halo and each R7 independently is hydrogen or an acyl group, for example an acetyl group, and n is an integer from about 1 to about 20. In another embodiment, X comprises a siNA molecule or a portion thereof.

In one embodiment, the invention features a compound having Formula 106:

wherein X comprises a nucleotide, polynucleotide, or oligonucleotide or a portion thereof, R1 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, each R7 independently is hydrogen or an acyl group, for example an acetyl group, and each n is independently an integer from about 1 to about 20. In another embodiment, X comprises a siNA molecule or a portion thereof.

In another embodiment, the invention features a compound having Formula 107:

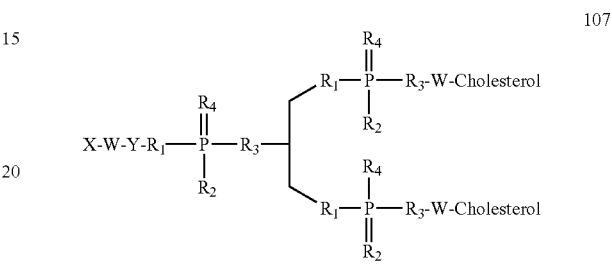

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and Cholesterol comprises cholesterol or an analog, derivative, or metabolite thereof. In another embodiment, X comprises a siNA molecule or a portion thereof. In another embodiment, W is selected from the group consisting of amide, phosphate, phosphate ester, phosphoramidate, or thiophosphate ester linkage.

In another embodiment, the invention features a compound having Formula 108:

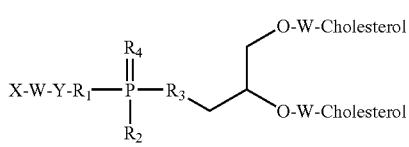

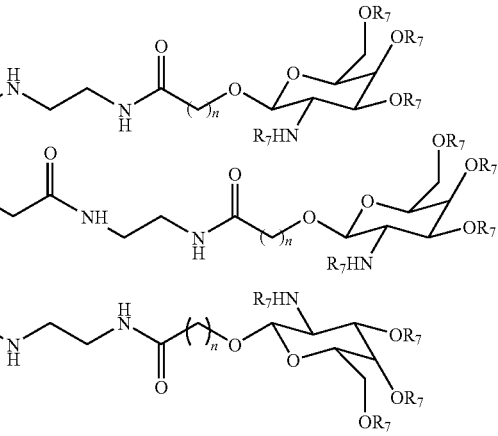

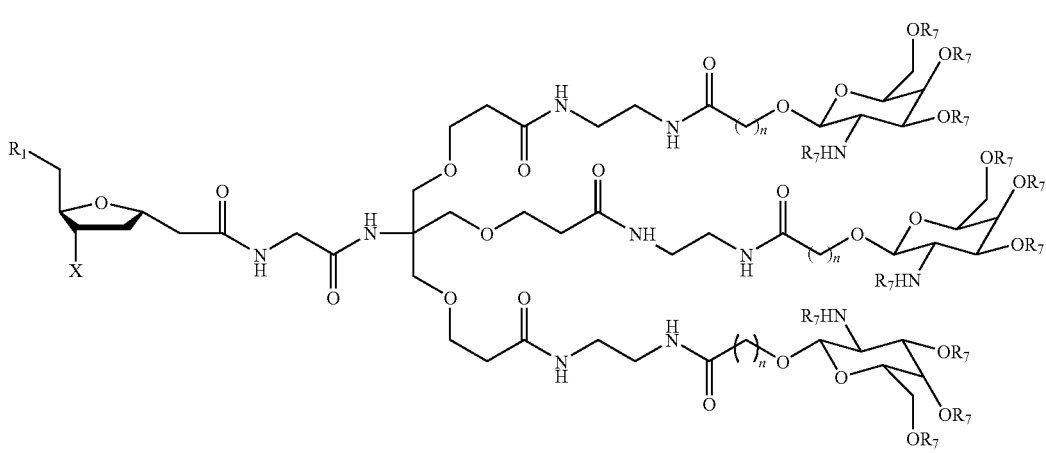

wherein X comprises a biologically active molecule; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and Cholesterol comprises cholesterol or an analog, derivative, or metabolite thereof. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the W-Cholesterol component of a compound having Formula 107 comprises a compound having Formula 109:

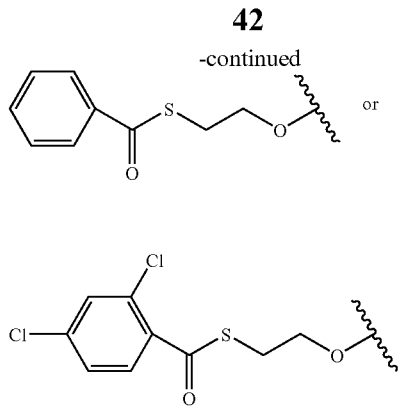

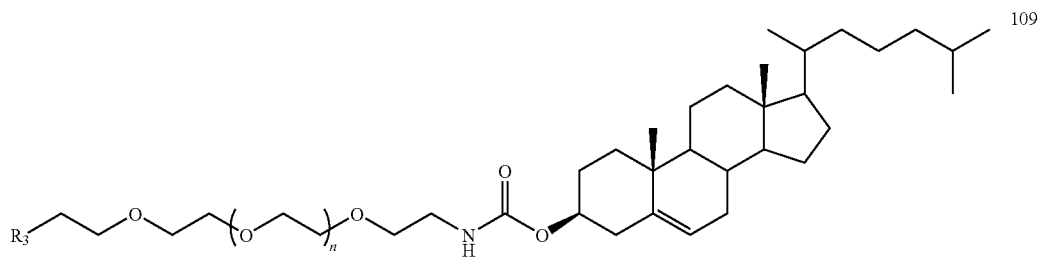

wherein R3 comprises R3 as described in Formula 107, and n is independently an integer from about 1 to about 20.

In one embodiment, the invention features a compound having Formula 110:

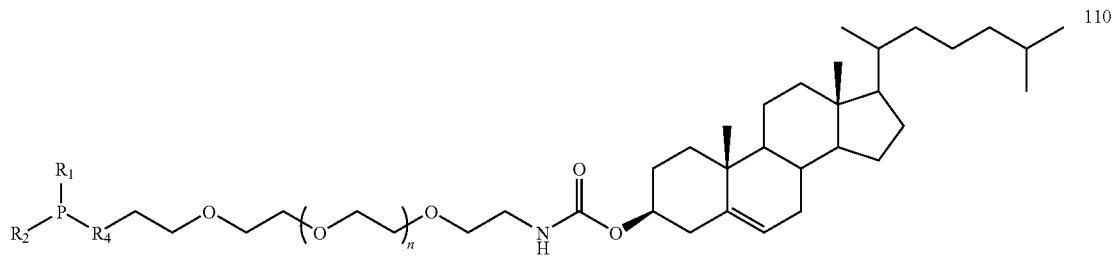

wherein R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

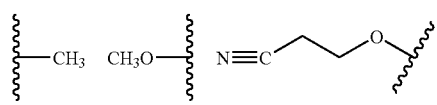

and wherein R2 can include the groups:

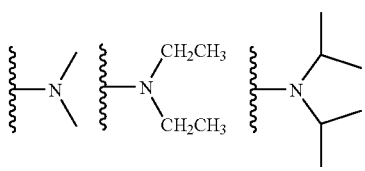

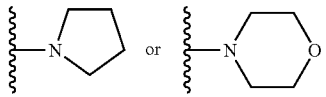

In one embodiment, the invention features a compound having Formula 111:

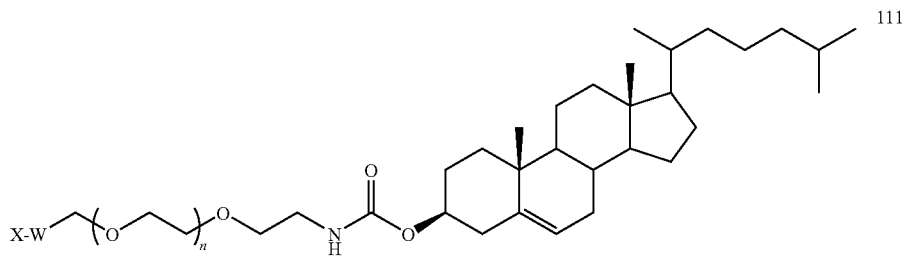

wherein X comprises a biologically active molecule; W comprises a linker molecule or chemical linkage that can be present or absent, and n is an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 112:

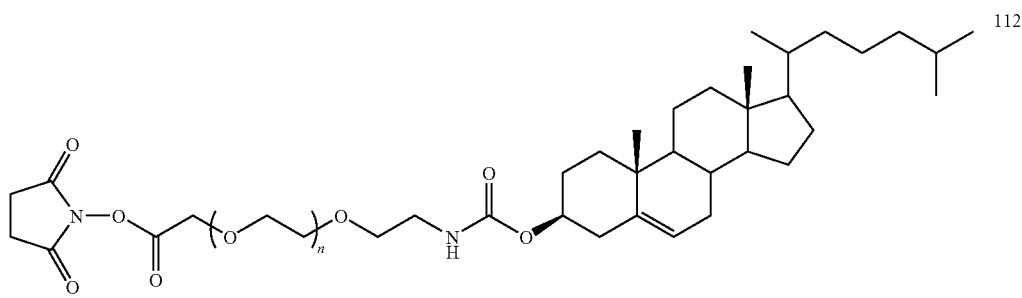

wherein n is an integer from about 1 to about 20. In another embodiment, a compound having Formula 112 is used to generate a compound having Formula 111 via NHS ester mediated coupling with a biologically active molecule, such as a siNA molecule or a portion thereof. In a non-limiting example, the NHS ester coupling can be effectuated via attachment to a free amine present in the siNA molecule, such as an amino linker molecule present on a nucleic acid sugar (e.g. 2'-amino linker) or base (e.g., C5 alkyl amine linker) component of the siNA molecule.

In one embodiment, the invention features a compound having Formula 113:

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

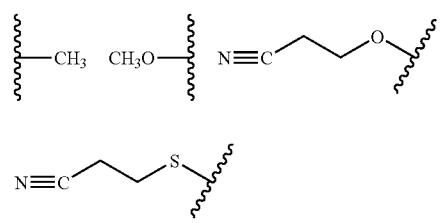

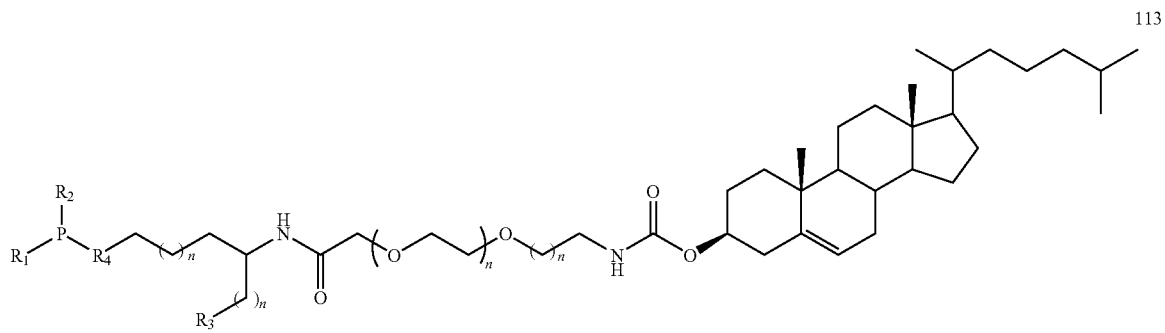

-continued

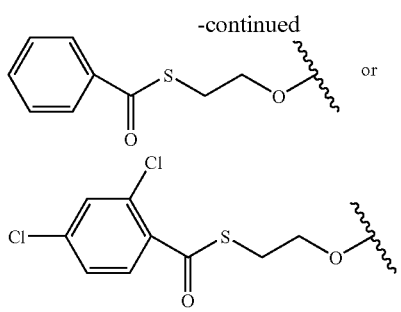

and wherein R2 can include the groups:

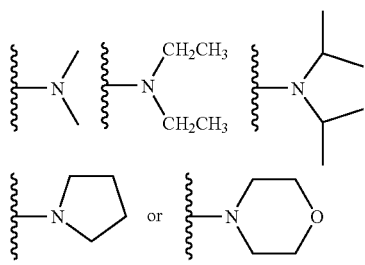

In another embodiment, a compound having Formula 113 is used to generate a compound having Formula 111 via phosphoramidite mediated coupling with a biologically active molecule, such as a siNA molecule or a portion thereof.

In one embodiment, the invention features a compound having Formula 114:

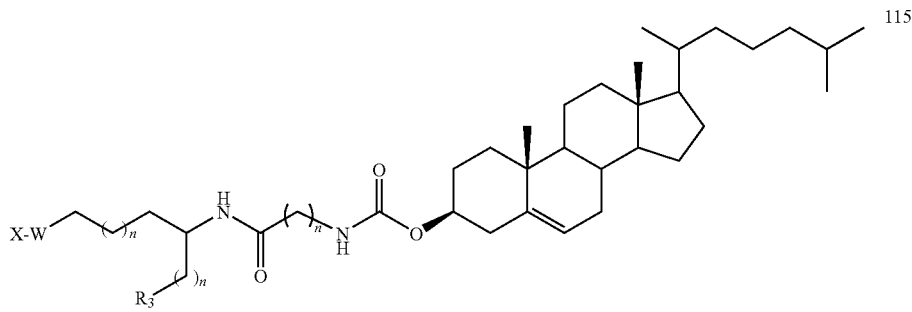

wherein X comprises a biologically active molecule; W comprises a linker molecule or chemical linkage that can be present or absent, and n is an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 115:

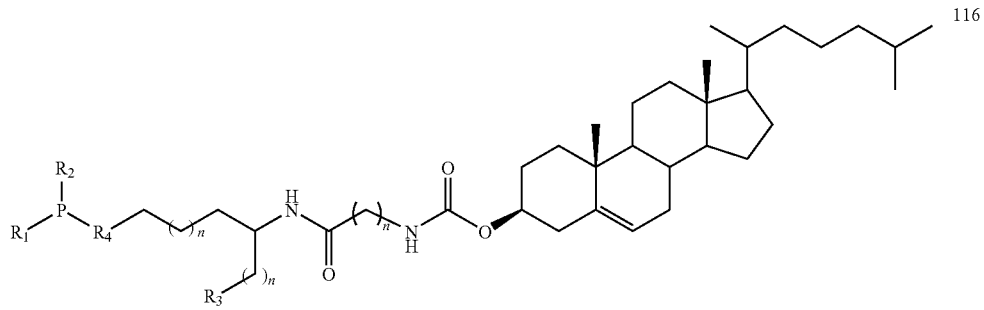

wherein X comprises a biologically active molecule; W comprises a linker molecule or chemical linkage that can be present or absent, R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, and each n is independently an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 116:

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

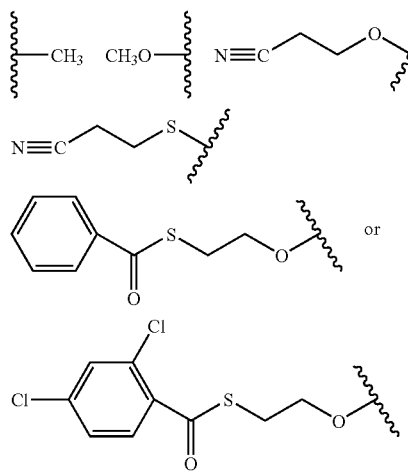

and wherein R2 can include the groups:

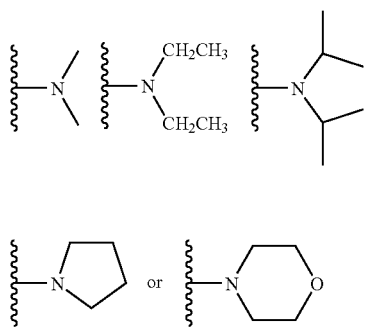

In another embodiment, a compound having Formula 116 is used to generate a compound having Formula 114 or 115 via phosphoramidite mediated coupling with a biologically active molecule, such as a siNA molecule or a portion thereof.

In one embodiment, the invention features a compound having Formula 117:

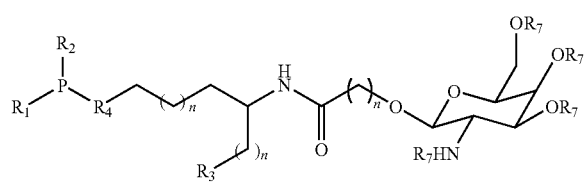

117 wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently is hydrogen or an acyl group, for example an acetyl group, each n is independently an integer from about 1 to about 20, and wherein R1 can include the groups:

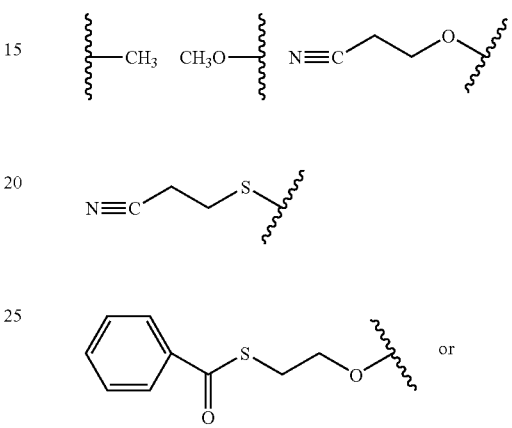

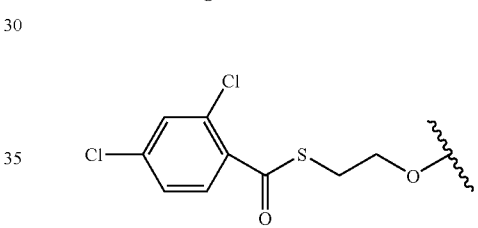

and wherein R2 can include the groups:

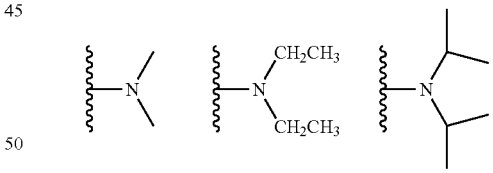

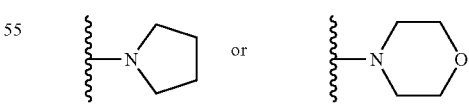

In another embodiment, a compound having Formula 117 is used to generate a compound having Formula 105 via phosphoramidite mediated coupling with a biologically active molecule, such as a siNA molecule or a portion thereof.

In one embodiment, the invention features a compound having Formula 118:

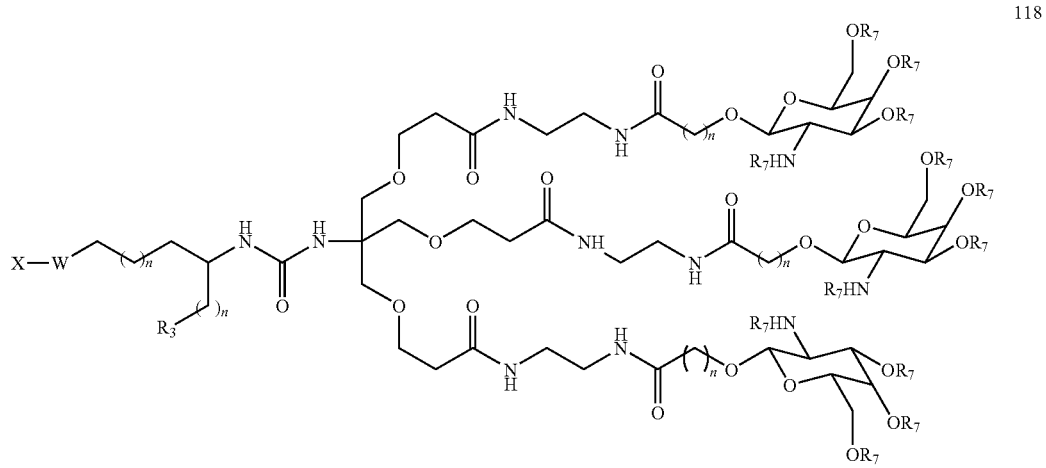

118 wherein X comprises a biologically active molecule; W comprises a linker molecule or chemical linkage that can be present or absent, R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, each R7 independently is hydrogen or an acyl group, for example an acetyl group, and each n is independently an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 119:

wherein X comprises a biologically active molecule; W comprises a linker molecule or chemical linkage that can be present or absent, each R7 independently is hydrogen or an acyl group, for example an acetyl group, and each n is independently an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

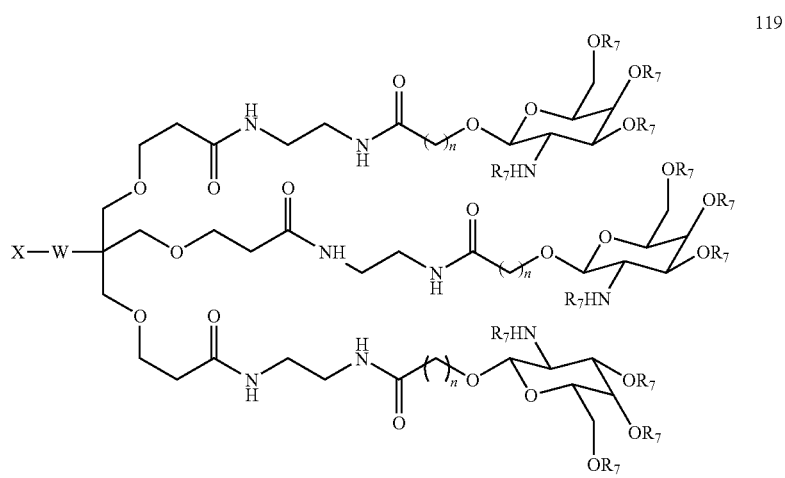

119

In one embodiment, the invention features a compound having Formula 120:

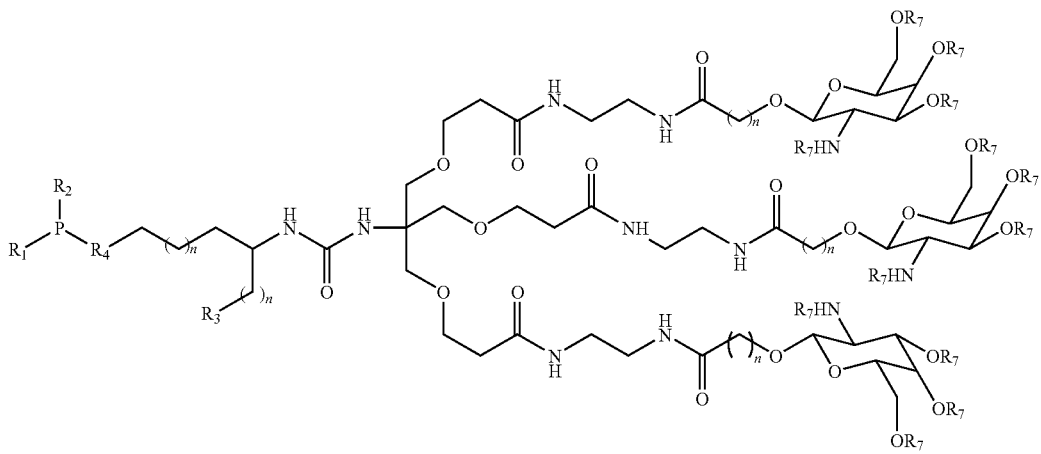

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently is hydrogen or an acyl group, for example an acetyl group, each n is independently an integer from about 1 to about 20, and wherein R1 can include the groups:

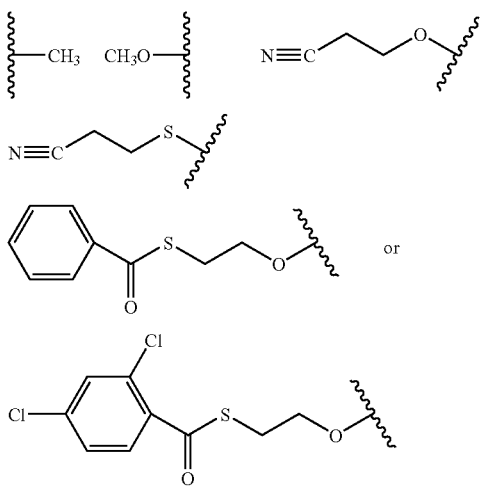

and wherein R2 can include the groups:

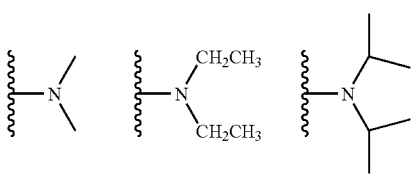

-continued

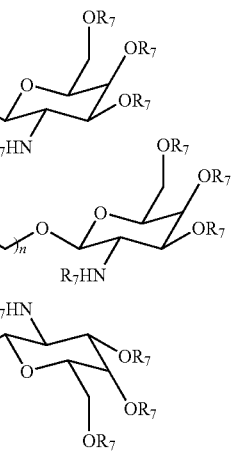

In another embodiment, a compound having Formula 120 is used to generate a compound having Formula 118 or 119 via phosphoramidite mediated coupling with a biologically active molecule, such as a siNA molecule or a portion thereof.

In one embodiment, the invention features a compound having Formula 121:

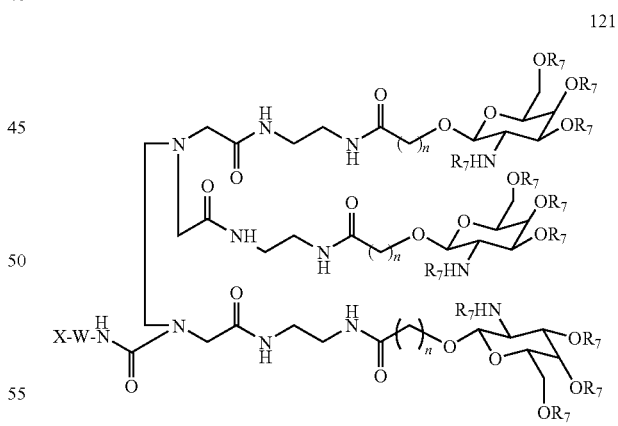

wherein X comprises a biologically active molecule; W comprises a linker molecule or chemical linkage that can be present or absent, each R7 independently is hydrogen or an acyl group, for example an acetyl group, and each n is independently an integer from about 1 to about 20. In another embodiment, X comprises a siNA molecule or a portion thereof. In another embodiment, W is selected from the group consisting of amide, phosphate, phosphate ester, phosphoramidate, or thiophosphate ester linkage.

In one embodiment, the invention features a compound having Formula 122:

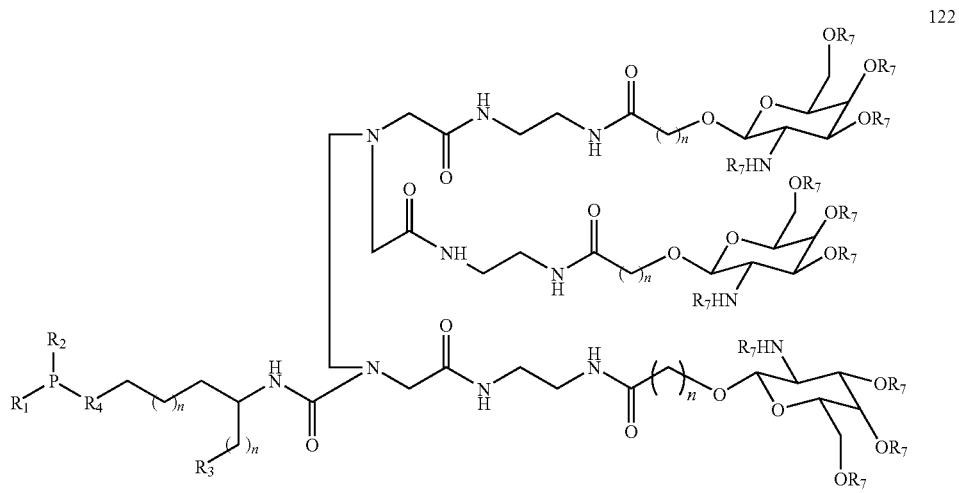

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently is hydrogen or an acyl group, for example an acetyl group, each n is independently an integer from about 1 to about 20, and wherein R1 can include the groups:

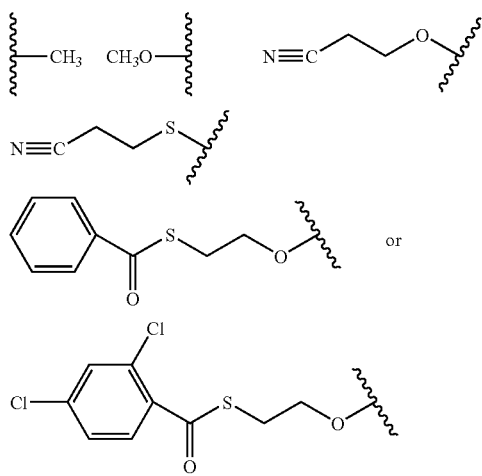

and wherein R2 can include the groups:

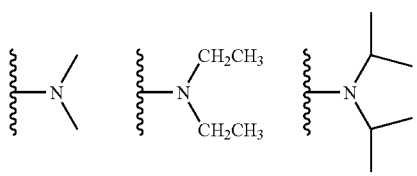

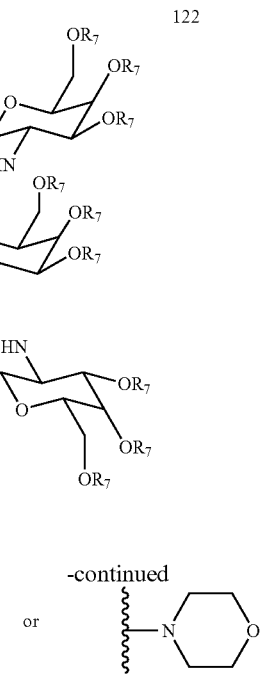

-continued

In another embodiment, a compound having Formula 122 is used to generate a compound having Formula 121 via phosphoramidite mediated coupling with a biologically active molecule, such as a siNA molecule or a portion thereof.

In one embodiment, the invention features a method for the synthesis of a compound having Formula 48:

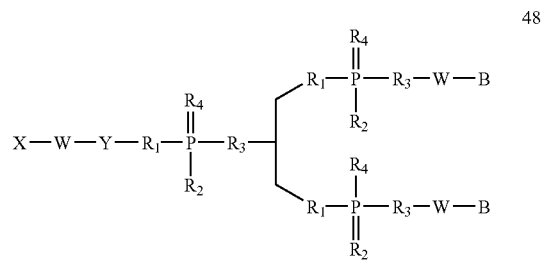

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N; and each B independently represents a lipophilic group, for example a saturated or unsaturated linear, branched, or cyclic alkyl group, comprising: (a) introducing a compound having Formula 66:

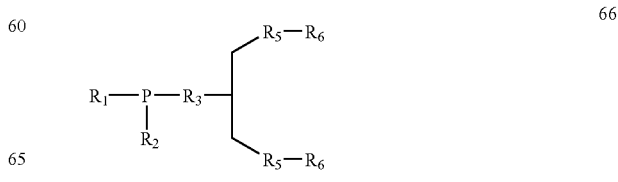

wherein R1 is defined as in Formula 48 and can include the groups:

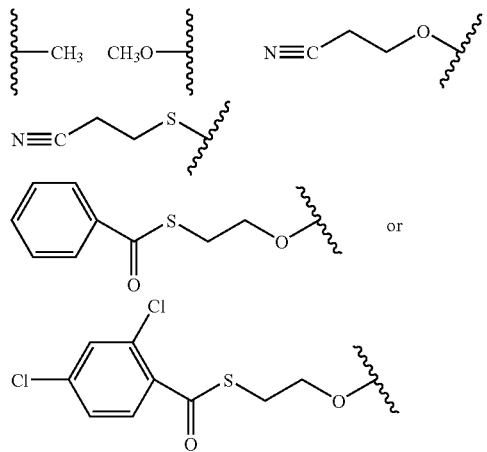

and wherein R2 is defined as in Formula 48 and can include the groups:

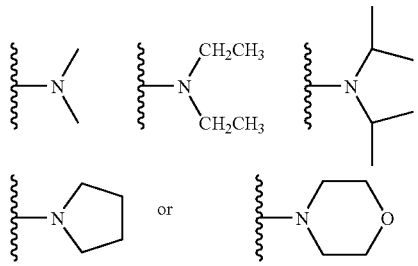

and wherein each R5 independently comprises O, N, or S and each R6 independently comprises a removable protecting group, for example a trityl, monomethoxytrityl, or dimethoxytrityl group, to a compound having Formula 67:

X—W—Y  67 wherein X comprises a biologically active molecule; W comprises a linker molecule or chemical linkage that can be present or absent, and Y comprises a linker molecule that can be present or absent, under conditions suitable for the formation of a compound having Formula 68:

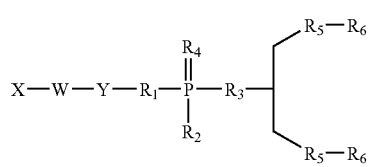

wherein X comprises a biologically active molecule; W comprises a linker molecule or chemical linkage that can be present or absent, Y comprises a linker molecule that can be present or absent; and each R1, R2, R3, and R4 independently comprises O, OH, H, alkyl, alkylhalo, O-alkyl, O-alkylcyano, S, S-alkyl, S-alkylcyano, N or substituted N comprising, each R5 independently comprises O, S, or N; and each R6 is independently a removable protecting group, for example a trityl, monomethoxytrityl, or dimethoxytrityl group; (b) removing R6 from the compound having Formula 26 and (c) introducing a compound having Formula 69:

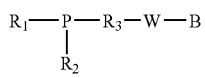

wherein R1 is defined as in Formula 48 and can include the groups:

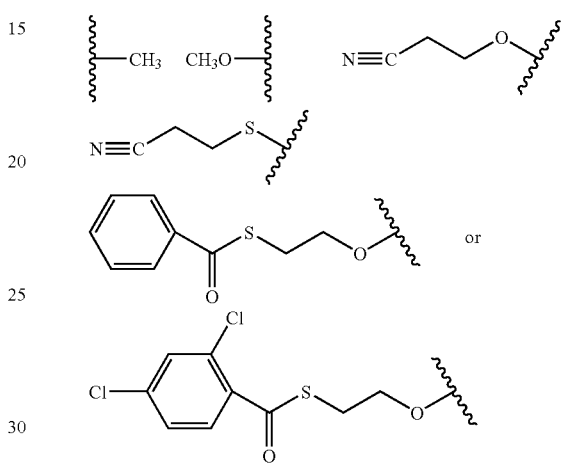

and wherein R2 is defined as in Formula 48 and can include the groups:

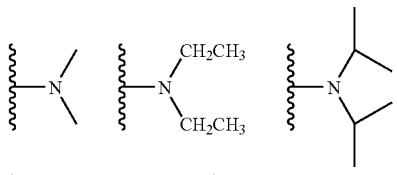

and wherein W and B are defined as in Formula 48, to the compound having Formula 68 under conditions suitable for the formation of a compound having Formula 48.

In another embodiment, the invention features a method for the synthesis of a compound having Formula 49:

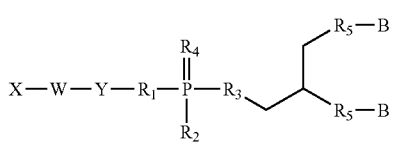

wherein X comprises a biologically active molecule; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N; each R5 independently comprises O, S, or N; and each B independently comprises a lipophilic group, for example a saturated or unsaturated linear, branched, or cyclic alkyl group, comprising: (a) coupling a compound having Formula 70:

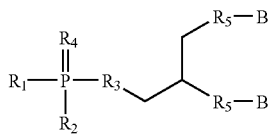
70 wherein R1 is defined as in Formula 49 and can include the groups:

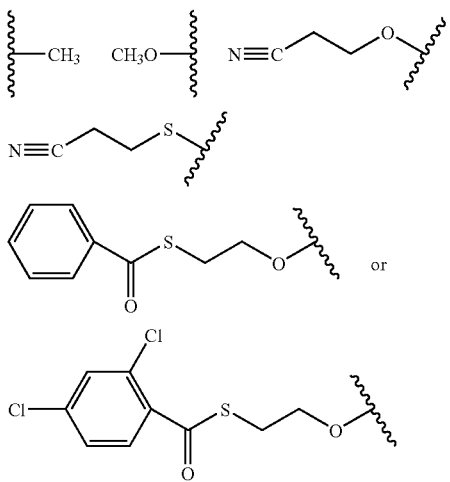

and wherein R2 is defined as in Formula 49 and can include the groups:

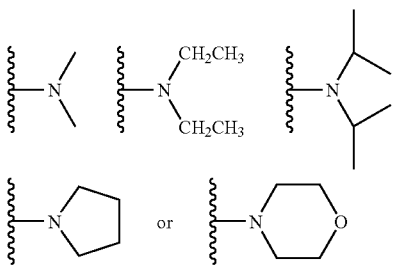

and wherein each R5 independently comprises O, S, or N, and wherein each B independently comprises a lipophilic group, for example a saturated or unsaturated linear, branched, or cyclic alkyl group, with a compound having Formula 67:

X—W—Y    67 wherein X comprises a biologically active molecule; W comprises a linker molecule or chemical linkage that can be present or absent, and Y comprises a linker molecule that can be present or absent, under conditions suitable for the formation of a compound having Formula 49.

In another embodiment, the invention features a method for the synthesis of a compound having Formula 52:

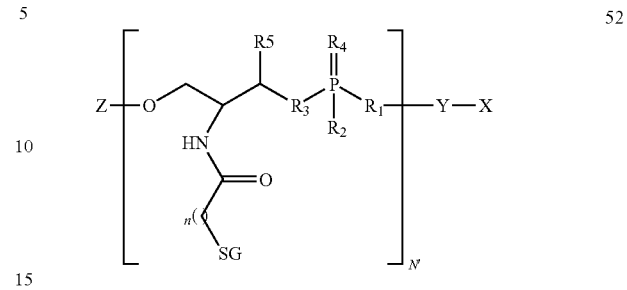
52 wherein X comprises a biologically active molecule; Y comprises a linker molecule or chemical linkage that can be present or absent; each R1, R2, R3, and R4 independently comprises 0, OH, H, alkyl, alkylhalo, O-alkyl, O-alkylcyano, S, S-alkyl, S-alkylcyano, N or substituted N; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; SG comprises a sugar, for example galactose, galactosamine, N-acetyl-galactosamine, glucose, mannose, fructose, or fucose and the respective D or L, alpha or beta isomers, n is an integer from about 1 to about 20; and N' is an integer from about 1 to about 20, comprising: (a) coupling a compound having Formula 71:

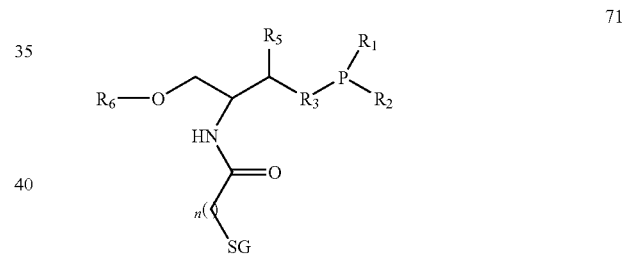
71 wherein R1, R2, R3, R5, SG, and n is as defined in Formula 52, and wherein R1 can include the groups:

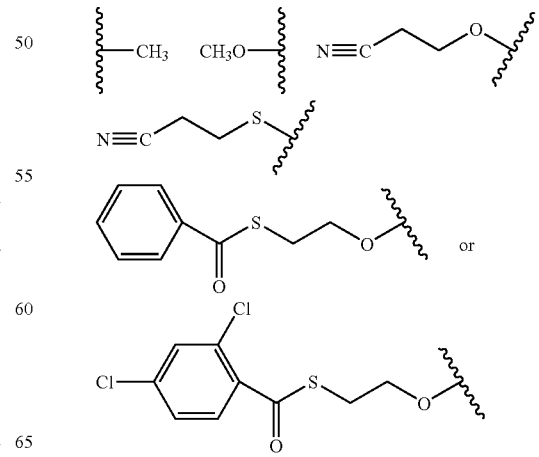

and wherein R2 can include the groups:

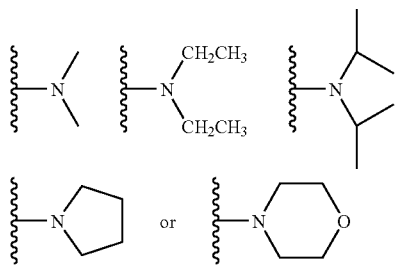

and R6 comprises a removable protecting group, for example a trityl, monomethoxytrityl, or dimethoxytrityl group; with a compound having Formula 72:

X—Y  (72)

wherein X comprises a biologically active molecule and Y comprises a linker molecule that can be present or absent, under conditions suitable for the formation of a compound having Formula 95:

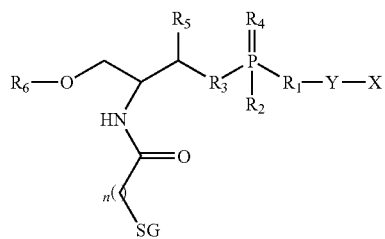

(b) removing R6 from the compound having Formula 95 and (c) optionally coupling a nucleotide, nucleoside, nucleic acid, oligonucleotide, amino acid, peptide, protein, lipid, phospholipid, or label, or optionally; coupling a compound having Formula 71 under and optionally repeating (b) and (c) under conditions suitable for the formation of a compound having Formula 52.

In another embodiment, the invention features a method for synthesizing a compound having Formula 53:

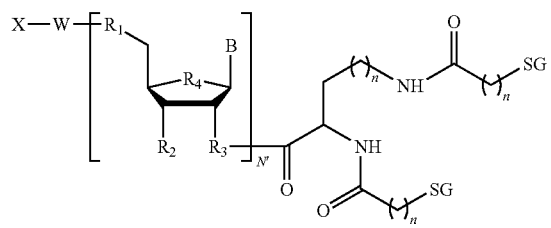

wherein B comprises H, a nucleoside base, or a non-nucleosidic base with or without protecting groups; each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises N or O—N, each R4 independently comprises O, $CH_2$, S, sulfone, or sulfoxy; X comprises H, a removable protecting group, amino, substituted amino, nucleotide, nucleoside, nucleic acid, oligonucleotide, enzymatic nucleic acid, amino acid, peptide, protein, lipid, phospholipid, or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 10, comprising: coupling a compound having Formula 73:

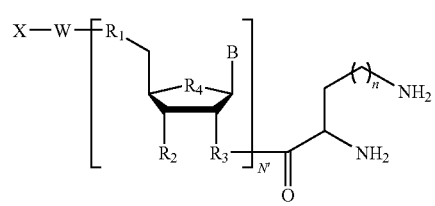

wherein R1, R2, R3, R4, X, W, B, N' and n are as defined in Formula 53, with a sugar, for example a compound having Formula 74:

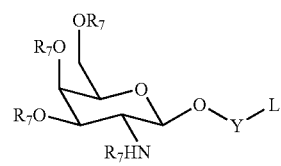

wherein Y comprises a linker molecule or chemical linkage that can be present or absent; L represents a reactive chemical group, for example a NHS ester, and each R7 independently is hydrogen or an acyl group, for example an acetyl group; under conditions suitable for the formation of a compound having Formula 53.

In another embodiment, the invention features a method for the synthesis of a compound having Formula 54:

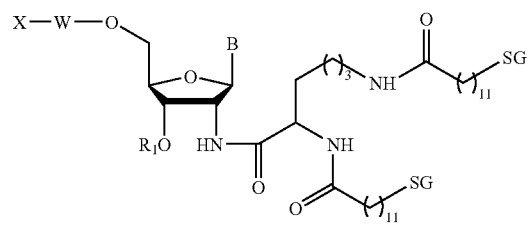

wherein B comprises H, a nucleoside base, or a non-nucleosidic base with or without protecting groups; each R1 independently comprises O, OH, H, alkyl, alkylhalo, O-alkyl, O-alkylhalo, S, N, substituted N, or a phosphorus containing group; X comprises H, a removable protecting group, amino, substituted amino, nucleotide, nucleoside, nucleic acid, oligonucleotide, enzymatic nucleic acid, amino acid, peptide, protein, lipid, phospholipid, biologically active molecule or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, comprising (a) coupling a compound having Formula 75:

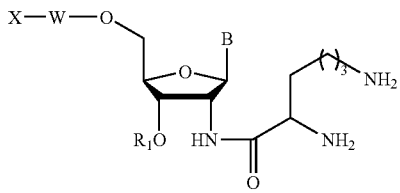

75 wherein R1, R2, R3, R4, X, W, and B are as defined in Formula 53, with a sugar, for example a compound having Formula 74.

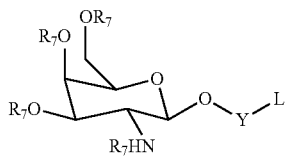

74 wherein Y comprises a C11 alkyl linker molecule; L represents a reactive chemical group, for example a NHS ester, and each R7 independently is hydrogen or an acyl group, for example an acetyl group; under conditions suitable for the formation of a compound having Formula 54.

In another embodiment, the invention features a method for the synthesis of a compound having Formula 55:

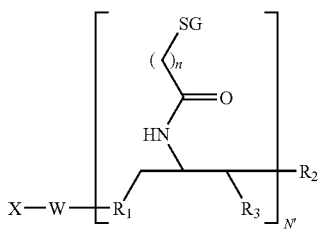

55 wherein each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises H, OH, alkyl, substituted alkyl, or halo; X comprises H, a removable protecting group, nucleotide, nucleoside, nucleic acid, oligonucleotide, or enzymatic nucleic acid or biologically active molecule; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 100, comprising: (a) coupling a compound having Formula 76:

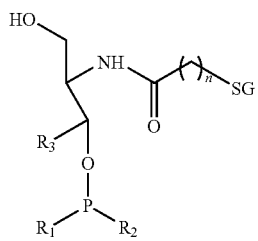

76 wherein R1 can include the groups:

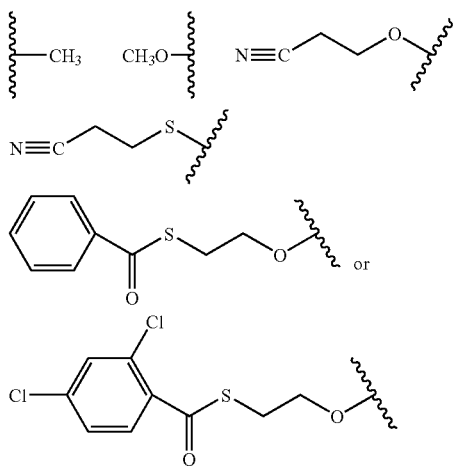

and wherein R2 can include the groups:

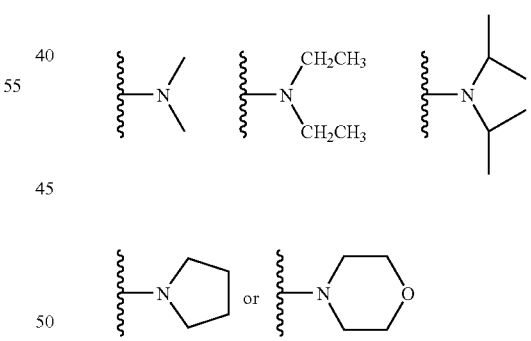

and wherein each R3 independently comprises H, OH, alkyl, substituted alkyl, or halo; SG comprises a sugar, for example galactose, galactosamine, N-acetyl-galactosamine, glucose, mannose, fructose, or fucose and the respective D or L, alpha or beta isomers, and n is an integer from about 1 to about 20, to a compound X—W, wherein X comprises a nucleotide, nucleoside, nucleic acid, oligonucleotide, enzymatic nucleic acid, amino acid, peptide, protein, lipid, phospholipid, biologically active molecule or label, and W comprises a linker molecule or chemical linkage that can be present or absent; and (b) optionally repeating step (a) under conditions suitable for the formation of a compound having Formula 55.

In another embodiment, the invention features a method for the synthesis of a compound having Formula 56:

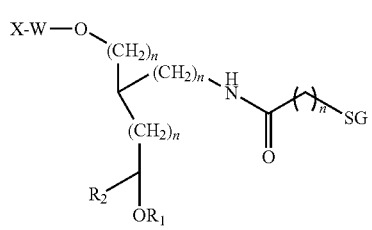

wherein R1 comprises H, alkyl, alkylhalo, N, substituted N, or a phosphorus containing group; R2 comprises H, O, OH, alkyl, alkylhalo, halo, S, N, substituted N, or a phosphorus containing group; X comprises H, a removable protecting group, amino, substituted amino, nucleotide, nucleoside, nucleic acid, oligonucleotide, enzymatic nucleic acid, amino acid, peptide, protein, lipid, phospholipid, biologically active molecule or label; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, and each n is independently an integer from about 0 to about 20, comprising: (a) coupling a compound having Formula 77:

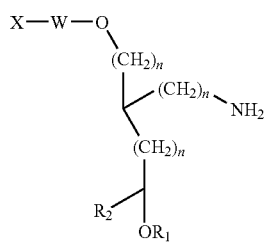

wherein each R1, X, W, and n are as defined in Formula 56, to a sugar, for example a compound having Formula 74:

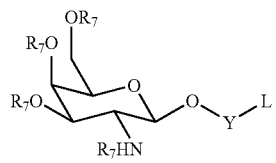

wherein Y comprises an alkyl linker molecule of length n, where n is an integer from about 1 to about 20; L represents a reactive chemical group, for example a NHS ester, and each R7 independently is hydrogen or an acyl group, for example an acetyl group; and (b) optionally coupling X—W, wherein X comprises a removable protecting group, amino, substituted amino, nucleotide, nucleoside, nucleic acid, oligonucleotide, enzymatic nucleic acid, amino acid, peptide, protein, lipid, phospholipid, or label and W comprises a linker molecule or chemical linkage that can be present or absent, under conditions suitable for the formation of a compound having Formula 56.

In another embodiment, the invention features method for synthesizing a compound having Formula 57:

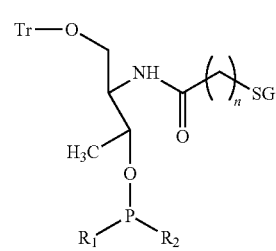

wherein R1 can include the groups:

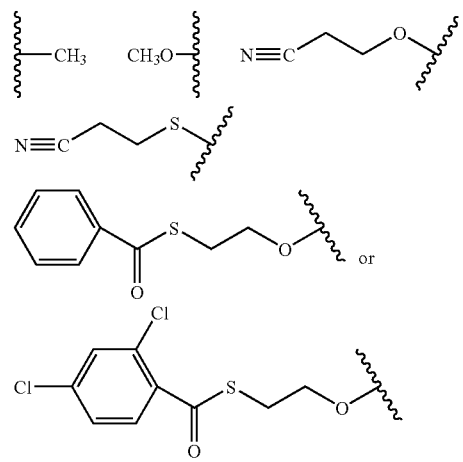

and wherein R2 can include the groups:

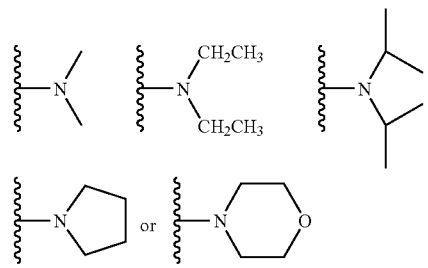

and wherein Tr is a removable protecting group, for example a trityl, monomethoxytrityl, or dimethoxytrityl; SG comprises a sugar, for example galactose, galactosamine, N-acetyl-galactosamine, glucose, mannose, fructose, or fucose and the respective D or L, alpha or beta isomers, and n is an integer from about 1 to about 20, comprising: (a) coupling a compound having Formula 77:

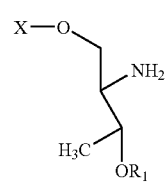

wherein R1 and X comprise H, to a sugar, for example a compound having Formula 74:

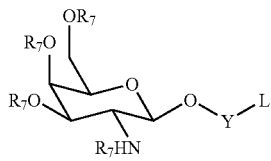

74 wherein Y comprises an alkyl linker molecule of length n, where n is an integer from about 1 to about 20; L represents a reactive chemical group, for example a NHS ester, and each R7 independently is hydrogen or an acyl group, for example an acetyl group; and (b) introducing a trityl group, for example a dimethoxytrityl, monomethoxytrityl, or trityl group to the primary hydroxyl of the product of (a) and (c) introducing a phosphorus containing group having Formula 78:

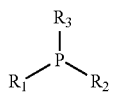

78 wherein R1 can include the groups:

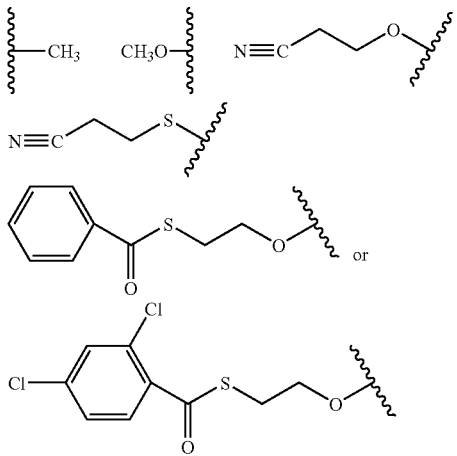

and wherein each R2 and R3 independently can include the groups:

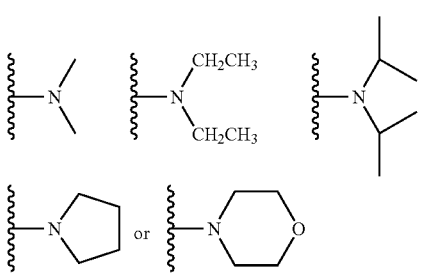

to the secondary hydroxyl of the product of (b) under conditions suitable for the formation of a compound having Formula 57.

In another embodiment, the invention features a method for synthesizing a compound having Formula 60:

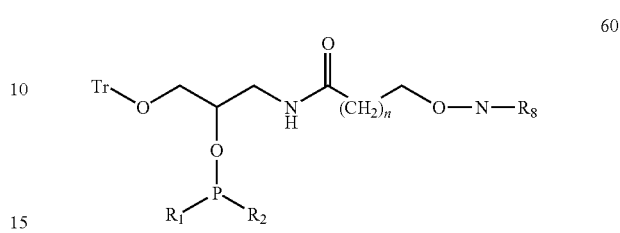

60 wherein R1 can include the groups:

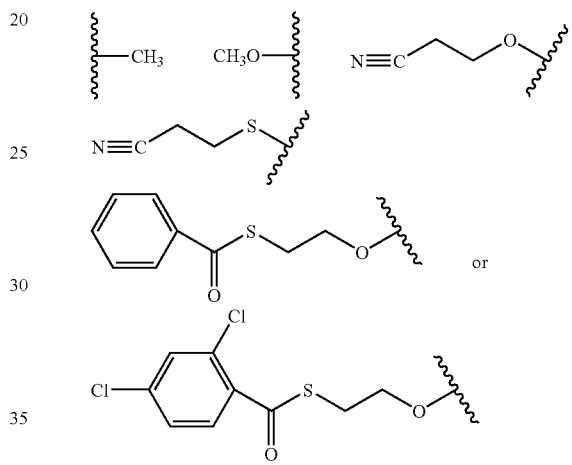

and wherein R2 can include the groups:

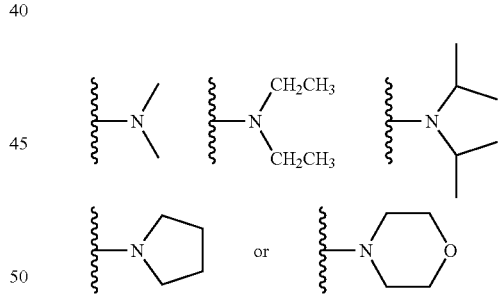

and wherein Tr is a removable protecting group, for example a trityl, monomethoxytrityl, or dimethoxytrityl; n is an integer from about 1 to about 50; and R8 is a nitrogen protecting group, for example a phthaloyl, trifluoroacetyl, FMOC, or monomethoxytrityl group, comprising: (a) introducing carboxy protection to a compound having Formula 79:

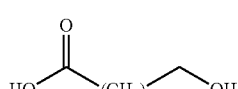

79 wherein n is an integer from about 1 to about 50, under conditions suitable for the formation of a compound having Formula 80:

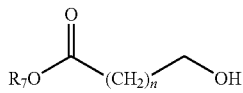

80 wherein n is an integer from about 1 to about 50 and R7 is a carboxylic acid protecting group, for example a benzyl group; (b) introducing a nitrogen containing group to the product of (a) under conditions suitable for the formation of a compound having Formula 81:

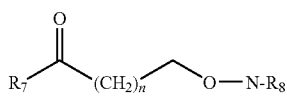

82 wherein n and R7 are as defined in Formula 80 and R8 is a nitrogen protecting group, for example a phthaloyl, trifluoroacetyl, FMOC, or monomethoxytrityl group; (c) removing the carboxylic acid protecting group from the product of (b) and introducing aminopropanediol under conditions suitable for the formation of a compound having Formula 82:

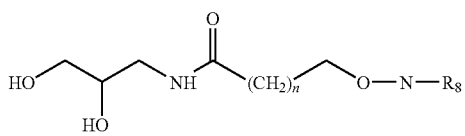

82 wherein n and R8 are as defined in Formula 81; (d) introducing a removable protecting group, for example a trityl, monomethoxytrityl, or dimethoxytrityl to the product of (c) under conditions suitable for the formation of a compound having Formula 83:

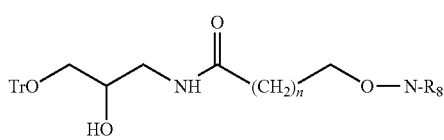

83 wherein Tr, n and R8 are as defined in Formula 60; and (e) introducing a phosphorus containing group having Formula 78:

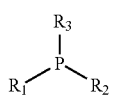

78 wherein R1 can include the groups:

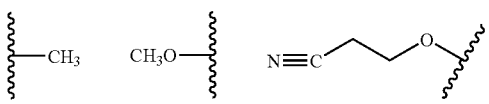

-continued

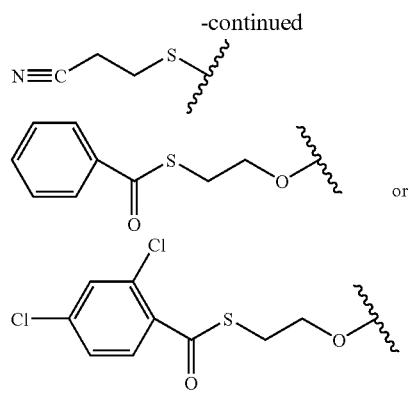

or and wherein each R2 and R3 independently can include the groups:

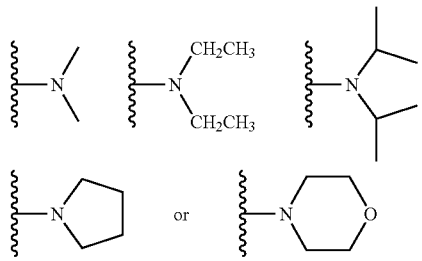

to the product of (d) under conditions suitable for the formation of a compound having Formula 60.

In another embodiment, the invention features a method for the synthesis of a compound having Formula 59:

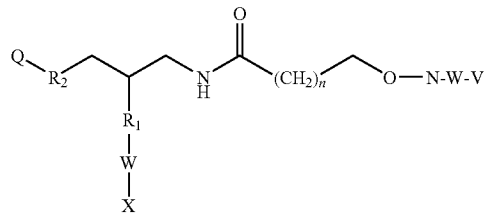

59 wherein each R1 independently comprises O, S, N, substituted N, or a phosphorus containing group; each R2 independently comprises O, S, or N; X comprises H, amino, substituted amino, nucleotide, nucleoside, nucleic acid, oligonucleotide, such as an enzymatic nucleic acid, allozyme, antisense nucleic acid, siNA, 2,5-A chimera, decoy, aptamer or triplex forming oligonucleotide or other biologically active molecule or a portion thereof; n is an integer from about 1 to about 50, Q comprises H or a removable protecting group which can be optionally absent, each W independently comprises a linker molecule or chemical linkage that can be present or absent, and V comprises a protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide, or a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100, comprising: (a) removing R8 from a compound having Formula 84:

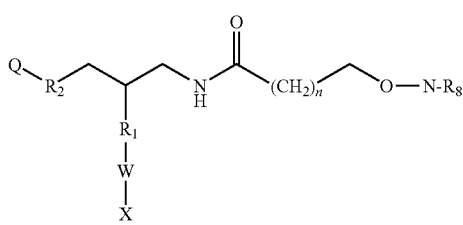

wherein Q, X, W, R1, R2, and n are as defined in Formula 59 and R8 is a nitrogen protecting group, for example a phthaloyl, trifluoroacetyl, FMOC, or monomethoxytrityl group, under conditions suitable for the formation of a compound having Formula 85:

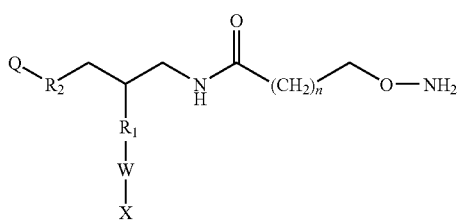

wherein Q, X, W, R1, R2, and n are as defined in Formula 59; (b) introducing a group V to the product of (a) via the formation of an oxime linkage, wherein V comprises a protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide, or a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100, under conditions suitable for the formation of a compound having Formula 59.

In another embodiment, the invention features a method for synthesizing a compound having Formula 64:

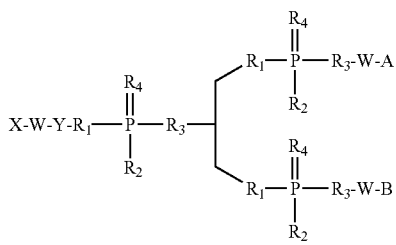

wherein X comprises a biologically active molecule; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, A comprises a nitrogen containing group, and B comprises a lipophilic group, comprising: (a) introducing a compound having Formula 66:

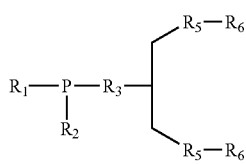

wherein R1 is defined as in Formula 64 and can include the groups:

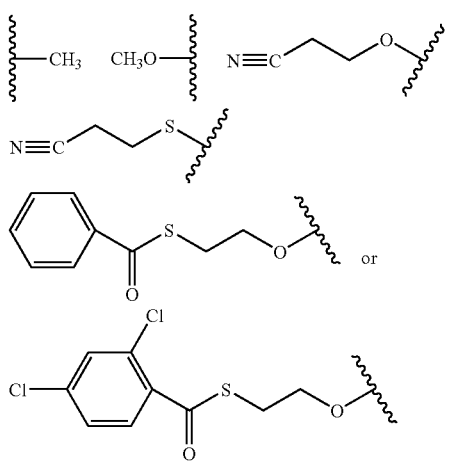

and wherein R2 is defined as in Formula 64 and can include the groups:

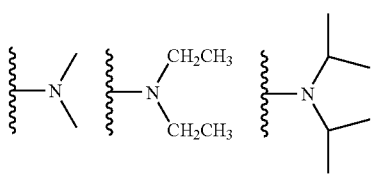

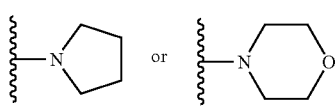 or and wherein each R5 independently comprises O, N, or S and each R6 independently comprises a removable protecting group, for example a trityl, monomethoxytrityl, or dimethoxytrityl group, to a compound having Formula 67:

X—W—Y  (67)

wherein X comprises a biologically active molecule; W comprises a linker molecule or chemical linkage that can be present or absent, and Y comprises a linker molecule that can be present or absent, under conditions suitable for the formation of a compound having Formula 68:

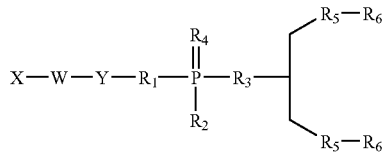  (68)

wherein X comprises a biologically active molecule; W comprises a linker molecule or chemical linkage that can be present or absent, Y comprises a linker molecule that can be present or absent; and each R1, R2, R3, and R4 independently comprises O, OH, H, alkyl, alkylhalo, O-alkyl, O-alkylcyano, S, S-alkyl, S-alkylcyano, N or substituted N comprising, each R5 independently comprises O, S, or N; and each R6 is independently a removable protecting group, for example a trityl, monomethoxytrityl, or dimethoxytrityl group; (b) removing R6 from the compound having Formula 68 and (c) introducing a compound having Formula 69:

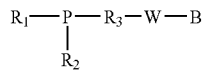  (69)

wherein R1 is defined as in Formula 64 and can include the groups:

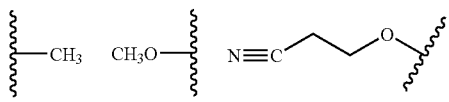

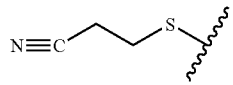

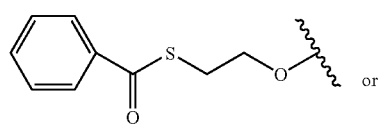 or

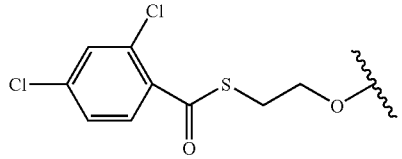

and wherein R2 is defined as in Formula 64 and can include the groups:

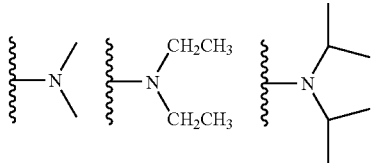

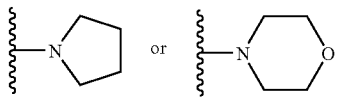 or 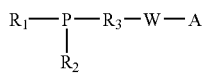

and wherein R3, W and B are defined as in Formula 64; and introducing a compound having Formula 69':

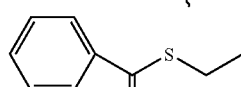  (69')

wherein R1 is defined as in Formula 64 and can include the groups:

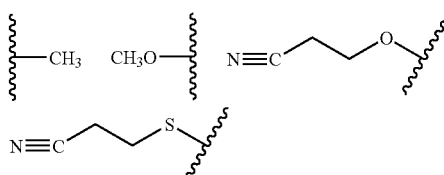

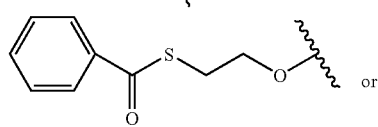

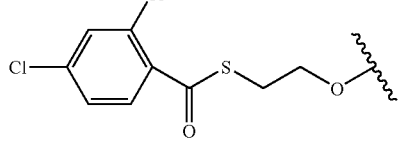

and wherein R2 is defined as in Formula 48 and can include the groups:

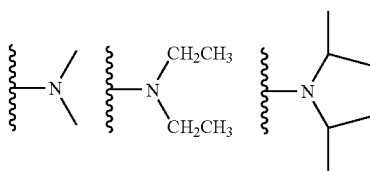

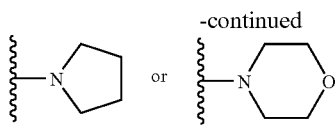

and wherein R3, W and A are defined as in Formula 64; to the compound having Formula 68 under conditions suitable for the formation of a compound having Formula 64.

In another embodiment, the invention features a method for the synthesis of a compound having Formula 62:

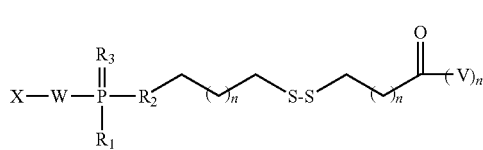

62 wherein X comprises a biologically active molecule; W comprises a linker molecule or chemical linkage that can be present or absent; each 5 independently comprises a protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; each R1, R2, and R3 independently comprises O, OH, H, alkyl, alkylhalo, O-alkyl, O-alkylcyano, S, S-alkyl, S-alkylcyano, N or substituted N, and each n is independently an integer from about 1 to about 10, comprising: (a) introducing a compound having Formula 93:

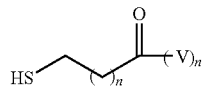

93 wherein V and n are as defined in Formula 62, to a compound having Formula 86:

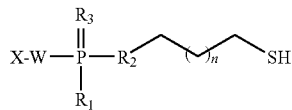

86 wherein X, W, R1, R2, R3, and n are as defined in Formula 62, under conditions suitable for the formation of a compound having Formula 62.

In another embodiment, the invention features a method for the synthesis of a compound having Formula 63:

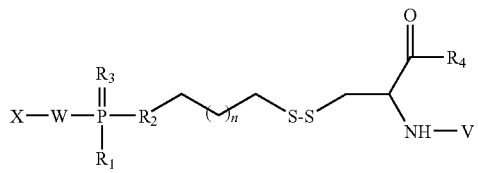

63 wherein X comprises a biologically active molecule; W comprises a linker molecule or chemical linkage that can be present or absent; V comprises a protein or peptide, for example Human serum albumin protein, Antennapedia peptide, Kaposi fibroblast growth factor peptide, Caiman crocodylus Ig(5) light chain peptide, HIV envelope glycoprotein gp41 peptide, HIV-1 Tat peptide, Influenza hemagglutinin envelope glycoprotein peptide, or transportan A peptide; each R1, R2, and R3 independently comprises O, OH, H, alkyl, alkylhalo, O-alkyl, O-alkylcyano, S, S-alkyl, S-alkylcyano, N or substituted N, R4 represents an ester, amide, or protecting group, and each n is independently an integer from about 1 to about 10, comprising: (a) introducing a compound having Formula 96:

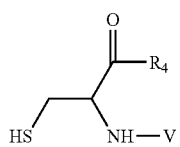

96 wherein V and R4 are as defined in Formula 63, to a compound having Formula 86:

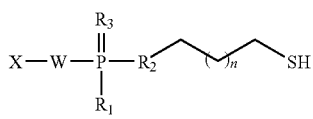

86 wherein X, W, R1, R2, R3, and n are as defined in Formula 63, under conditions suitable for the formation of a compound having Formula 63.

In another embodiment, the invention features a method for the synthesis of a compound having Formula 87:

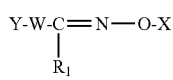

87 wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent; and Y comprises a biologically active molecule, for example an enzymatic nucleic acid, allozyme, antisense nucleic acid, siNA, 2,5-A chimera, decoy, aptamer or triplex forming oligonucleotide, peptide, protein, or antibody; R1 comprises H, alkyl, or substituted alkyl, comprising (a) coupling a compound having Formula 89:

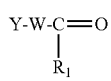

89 wherein Y, W and R are as defined in Formula 87, with a compound having Formula 90:

$$H_2N-O-X \qquad 90$$

wherein X is as defined in Formula 87, under conditions suitable for the formation of a compound having Formula 87, for example by post-synthetic conjugation of a compound having Formula 89 with a compound having Formula 90, wherein X of compound 90 comprises an enzymatic nucleic acid molecule and Y of Formula 89 comprises a peptide.

In another embodiment, the invention features a method for the synthesis of a compound having Formula 88:

$$Y-W-\overset{O}{\underset{\|}{C}}-NH-O-X \qquad 88$$

wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent, and Y comprises a biologically active molecule, for example an enzymatic nucleic acid, allozyme, antisense nucleic acid, siNA, 2,5-A chimera, decoy, aptamer or triplex forming oligonucleotide, peptide, protein, or antibody, comprising (a) coupling a compound having Formula 91:

$$Y-W-\underset{H}{C}=O \qquad 91$$

wherein Y and W are as defined in Formula 88, with a compound having Formula 90:

$$H_2N-O-X \qquad 90$$

wherein X is as defined in Formula 88, under conditions suitable for the formation of a compound having Formula 88, for example by post-synthetic conjugation of a compound having Formula 91 with a compound having Formula 90, wherein X of compound 90 comprises an enzymatic nucleic acid molecule and Y of Formula 91 comprises a peptide.

In one embodiment, the invention features a compound having Formula 94, $$X-Y-W-Y-Z \qquad 94$$

wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; each Y independently comprises a linker or chemical linkage that can be present or absent, W comprises a biodegradable nucleic acid linker molecule, and Z comprises a biologically active molecule, for example an enzymatic nucleic acid, allozyme, antisense nucleic acid, siNA, 2,5-A chimera, decoy, aptamer or triplex forming oligonucleotide, peptide, protein, or antibody.

In another embodiment, W of a compound having Formula 94 of the invention comprises 5'-cytidine-deoxythymidine-3', 5'-deoxythymidine-cytidine-3', 5'-cytidine-deoxyuridine-3', 5'-deoxyuridine-cytidine-3', 5'-uridine-deoxythymidine-3', or 5'-deoxythymidine-uridine-3'.

In yet another embodiment, W of a compound having Formula 94 of the invention comprises 5'-adenosine-deoxythymidine-3', 5'-deoxythymidine-adenosine-3', 5'-adenosine-deoxyuridine-3', or 5'-deoxyuridine-adenosine-3'.

In another embodiment, Y of a compound having Formula 94 of the invention comprises a phosphorus containing linkage, phoshoramidate linkage, phosphodiester linkage, phosphorothioate linkage, amide linkage, ester linkage, carbamate linkage, disulfide linkage, oxime linkage, or morpholino linkage.

In another embodiment, compounds having Formula 89 and 91 of the invention are synthesized by periodate oxidation of an N-terminal Serine or Threonine residue of a peptide or protein.

In one embodiment, X of compounds having Formulae 43, 44, 46-52, 58, 61-65, 85-88, 92, 94, 95, 99, 100, 105-108, 111, 114, 115, 118, 119, or 121 of the invention comprises a siNA molecule or a portion thereof. In one embodiment, the siNA molecule can be conjugated at the 5' end, 3'-end, or both 5' and 3' ends of the sense strand or region of the siNA. In one embodiment, the siNA molecule can be conjugated at the 3'-end of the antisense strand or region of the siNA with a compound of the invention. In one embodiment, both the sense strand and antisense strands or regions of the siNA molecule are conjugated with a compound of the invention. In one embodiment, only the sense strand or region of the siNA is conjugated with a compound of the invention. In one embodiment, only the antisense strand or region of the siNA is conjugated with a compound of the invention.

In one embodiment, X of compounds having Formulae 43, 44, 46-52, 58, 61-65, 85-88, 92, 94, 95, 99, 100, 105-108, 111, 114, 115, 118, 119, or 121 of the invention comprises an enzymatic nucleic acid.

In another embodiment, X of compounds having Formulae 43, 44, 46-52, 58, 61-65, 85-88, 92, 94, 95, 99, 100, 105-108, 111, 114, 115, 118, 119, or 121 of the invention comprises an antibody. In yet another embodiment, X of compounds having Formulae 43, 44, 46-52, 58, 61-65, 85-88, 92, 94, 95, 99, 100, 105-108, 111, 114, 115, 118, 119, or 121 of the invention comprises an interferon.

In another embodiment, X of compounds having Formulae 43, 44, 46-52, 58, 61-65, 85-88, 92, 94, 95, 99, 100, 105-108, 111, 114, 115, 118, 119, or 121 of the invention comprises an antisense nucleic acid, dsRNA, ssRNA, decoy, triplex oligonucleotide, aptamer, or 2,5-A chimera.

In one embodiment, W and/or Y of compounds having Formulae 43, 44, 46-52, 58, 61-65, 85-88, 92, 94, 95, 99, 100, 101, 107, 108, 111, 114, 115, 118, 119, or 121 of the invention comprises a degradable or cleavable linker, for example a nucleic acid sequence comprising ribonucleotides and/or deoxynucleotides, such as a dimer, trimer, or tetramer. A non limiting example of a nucleic acid cleavable linker is an adenosine-deoxythymidine (A-dT) dimer or a cytidine-deoxythymidine (C-dT) dimer. In yet another embodiment, W and/or V of compounds having Formulae 43, 44, 48-51, 58, 63-65, 96, 99, 100, 107, 108, 111, 114, 115, 118, 119, or 121 of the invention comprises a N-hydroxy succinimide (NHS) ester linkage, oxime linkage, disulfide linkage, phosphoramidate, phosphorothioate, phosphorodithioate, phosphodiester linkage, or NHC(O), $CH_3NC(O)$, CONH, $C(O)NCH_3$, S, SO, $SO_2$, O, NH, $NCH_3$ group. In another embodiment, the degradable linker, W and/or Y, of compounds having Formulae Formulae 43, 44, 46-52, 58, 61-65, 85-88, 92, 94, 95, 99, 100, 101, 107, 108, 111, 114, 115, 118, 119, or 121 of the invention comprises a linker that is susceptible to cleavage by carboxypeptidase activity.

In another embodiment, W and/or Y of Formulae Formulae 43, 44, 46-52, 58, 61-65, 85-88, 92, 94, 95, 99, 100, 101, 107, 108, 111, 114, 115, 118, 119, or 121 comprises a polyethylene glycol linker having Formula 45:

45 wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100.

In one embodiment, the nucleic acid conjugates of the instant invention are assembled by solid phase synthesis, for example on an automated peptide synthesizer, for example a Miligen 9050 synthesizer and/or an automated oligonucleotide synthesizer such as an ABI 394, 390Z, or Pharmacia OligoProcess, OligoPilot, OligoMax, or AKTA synthesizer. In another embodiment, the nucleic acid conjugates of the invention are assembled post synthetically, for example, following solid phase oligonucleotide synthesis (see for example FIG. 15).

In another embodiment, V of compounds having Formula 58-63 and 96 comprise peptides having SEQ ID NOS: 14-23 (Table III).

In one embodiment, the nucleic acid conjugates of the instant invention are assembled post synthetically, for example, following solid phase oligonucleotide synthesis.

The present invention provides compositions and conjugates comprising nucleosidic and non-nucleosidic derivatives. The present invention also provides nucleic acid, polynucleotide and oligonucleotide derivatives including RNA, DNA, and PNA based conjugates. The attachment of compounds of the invention to nucleosides, nucleotides, non-nucleosides, and nucleic acid molecules is provided at any position within the molecule, for example, at internucleotide linkages, nucleosidic sugar hydroxyl groups such as 5', 3', and 2'-hydroxyls, and/or at nucleobase positions such as amino and carbonyl groups.

The exemplary conjugates of the invention are described as compounds of the formulae herein, however, other peptide, protein, phospholipid, and poly-alkyl glycol derivatives are provided by the invention, including various analogs of the compounds of formulae 1-122, including but not limited to different isomers of the compounds described herein.

In one embodiment, the present invention features molecules, compositions and conjugates of molecules, for example, non-nucleosidic small molecules, nucleosides, nucleotides, and nucleic acids, such as enzymatic nucleic acid molecules, antisense nucleic acids, 2-5A antisense chimeras, triplex oligonucleotides, decoys, siNA, allozymes, aptamers, and antisense nucleic acids containing RNA cleaving chemical groups.

The exemplary folate conjugates of the invention are described as compounds shown by formulae herein, however, other folate and antifolate derivatives are provided by the invention, including various folate analogs of the formulae of the invention, including dihydrofloates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acids. As used herein, the term "folate" is meant to refer to folate and folate derivatives, including pteroic acid derivatives and analogs.

The present invention features compositions and conjugates to facilitate delivery of molecules into a biological system such as cells. The conjugates provided by the instant invention can impart therapeutic activity by transferring therapeutic compounds across cellular membranes. The present invention encompasses the design and synthesis of novel agents for the delivery of molecules, including but not limited to small molecules, lipids, nucleosides, nucleotides, nucleic acids, negatively charged polymers and other polymers, for example proteins, peptides, carbohydrates, or polyamines. In general, the transporters described are designed to be used either individually or as part of a multi-component system. The compounds of the invention generally shown in Formulae herein are expected to improve delivery of molecules into a number of cell types originating from different tissues, in the presence or absence of serum.

In another embodiment, the present invention features methods to modulate gene expression, for example, genes involved in the progression and/or maintenance of cancer or in a viral infection. For example, in one embodiment, the invention features the use of one or more of the nucleic acid-based molecules and methods independently or in combination to inhibit the expression of the gene(s) encoding proteins associated with cancerous conditions, for example breast cancer, lung cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer associated genes.

In another embodiment, the invention features the use of one or more of the nucleic acid-based molecules and methods independently or in combination to inhibit the expression of the gene(s) encoding viral proteins, for example HIV, HBV, HCV, CMV, RSV, HSV, poliovirus, influenza, rhinovirus, west nile virus, Ebola virus, foot and mouth virus, and papilloma virus associated genes.

In one embodiment, the invention features the use of an enzymatic nucleic acid molecule conjugate comprising compounds of formulae 1-122, preferably in the hammerhead, NCH, G-cleaver, amberzyme, zinzyme and/or DNAzyme motif, to inhibit the expression of cancer and virus associated genes.

In another embodiment, the invention features the use of an enzymatic nucleic acid molecule as a conjugate. These enzymatic nucleic acids can catalyze the hydrolysis of RNA phosphodiester bonds in trans (and thus can cleave other RNA molecules) under physiological conditions. Table I summarizes some of the characteristics of these enzymatic nucleic acids. Without being bound by any particular theory, in general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA destroys its ability to direct synthesis of an encoded protein. After an enzymatic nucleic acid has bound and cleaved its RNA target, it is released from that RNA to search for another target and can repeatedly bind and cleave new targets. Thus, a single enzymatic nucleic acid molecule is able to cleave many molecules of target RNA. In addition, the enzymatic nucleic acid is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of an enzymatic nucleic acid.

In one embodiment of the invention described herein, the enzymatic nucleic acid molecule component of the conjugate is formed in a hammerhead or hairpin motif, but can also be formed in the motif of a hepatitis delta virus, group I intron, group II intron or RNase P RNA (in association with an RNA guide sequence), Neurospora VS RNA, DNAzymes, NCH cleaving motifs, or G-cleavers. Examples of such hammerhead motifs are described by Dreyfus, supra, Rossi et al., 1992, AIDS Research and Human Retroviruses 8, 183; of hairpin motifs by Hampel et al., EP0360257, Hampel and Tritz, 1989 Biochemistry 28, 4929, Feldstein et al., 1989, Gene 82, 53, Haseloff and Gerlach, 1989, Gene, 82, 43, and Hampel et al., 1990 Nucleic Acids Res. 18, 299; Chowrira & McSwiggen, U.S. Pat. No. 5,631,359; of the hepatitis delta virus motif is described by Perrotta and Been, 1992 Biochemistry 31, 16; of the RNase P motif by Guerrier-Takada et al., 1983 Cell 35, 849; Forster and Altman, 1990, Science 249, 783; Li and Altman, 1996, Nucleic Acids Res. 24, 835; Neurospora VS RNA ribozyme motif is described by Collins (Saville and Collins, 1990 Cell 61, 685-696; Saville and Collins, 1991 Proc. Natl. Acad. Sci. USA 88, 8826-8830; Collins and Olive, 1993 Biochemistry 32, 2795-2799; Guo and Collins, 1995, EMBO. J. 14, 363); Group II introns are described by Griffin et al., 1995, Chem. Biol. 2, 761; Michels and Pyle, 1995, Biochemistry 34, 2965; Pyle et al., International PCT Publication No. WO 96/22689; of the Group I intron by Cech et al., U.S. Pat. No. 4,987,071 and of DNAzymes by Usman et al., International PCT Publication No. WO 95/11304; Chartrand et al., 1995, NAR 23, 4092; Breaker et al., 1995, Chem. Bio. 2, 655; Santoro et al., 1997, PNAS 94, 4262, and Beigelman et al., International PCT publication No. WO 99/55857. NCH cleaving motifs are described in Ludwig & Sproat, International PCT Publication No. WO 98/58058; and G-cleavers are described in Kore et al., 1998, Nucleic Acids Research 26, 4116-4120 and Eckstein et al., International PCT Publication No. WO 99/16871. Additional motifs such as the Aptazyme (Breaker et al., WO 98/43993), Amberzyme (Class I motif; FIG. 3; Beigelman et al., U.S. Ser. No. 09/301,511) and Zinzyme (FIG. 4) (Beigelman et al., U.S. Ser. No. 09/301,511), all incorporated by reference herein including drawings, can also be used in the present invention. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule (Cech et al., U.S. Pat. No. 4,987,071).

In one embodiment of the present invention, a nucleic acid molecule component of a conjugate of the instant invention can be about 12 to about 100 nucleotides in length. For example, enzymatic nucleic acid molecules of the invention are preferably about 15 to about 50 nucleotides in length, more preferably about 25 to about 40 nucleotides in length, e.g., 34, 36, or 38 nucleotides in length (for example see Jarvis et al., 1996, J. Biol. Chem., 271, 29107-29112). Exemplary DNAzymes of the invention are preferably about 15 to about 40 nucleotides in length, more preferably about 25 to about 35 nucleotides in length, e.g., 29, 30, 31, or 32 nucleotides in length (see for example Santoro et al., 1998, Biochemistry, 37, 13330-13342; Chartrand et al., 1995, Nucleic Acids Research, 23, 4092-4096). Exemplary antisense molecules of the invention are preferably about 15 to about 75 nucleotides in length, more preferably about 20 to about 35 nucleotides in length, e.g., 25, 26, 27, or 28 nucleotides in length (see, for example, Woolf et al., 1992, PNAS., 89, 7305-7309; Milner et al., 1997, Nature Biotechnology, 15, 537-541). Exemplary triplex forming oligonucleotide molecules of the invention are preferably about 10 to about 40 nucleotides in length, more preferably about 12 to about 25 nucleotides in length, e.g., 18, 19, 20, or 21 nucleotides in length (see for example Maher et al., 1990, Biochemistry, 29, 8820-8826; Strobel and Dervan, 1990, Science, 249, 73-75). Exemplary double stranded siNA molecules of the invention comprise about 19 to about 25 nucleotides in length, e.g., about 19, 20, 21, 22, 23, 24, or 25 nucleotides in length, for each strand of the siNA molecule. Exemplary single stranded siNA molecules of the invention are about 38 to about 50 nucleotides in length, e.g., about 38, 39, 40, 41, 42, 43, 44, 45, 46, 47, 48, 49, or 50 nucleotides in length. The length of the nucleic acid molecules described and exemplified herein are not limiting within the general size ranges stated.

The conjugates of the invention are added directly, or can be complexed with cationic lipids, packaged within liposomes, or otherwise delivered to target cells or tissues. The conjugates and/or conjugate complexes can be locally administered to relevant tissues ex vivo, or in vivo through injection or infusion pump, with or without their incorporation in biopolymers. The compositions and conjugates of the instant invention, individually, or in combination or in conjunction with other drugs, can be used to treat diseases or conditions discussed above. For example, to treat a disease or condition associated with the levels of a pathogenic protein, the patient can be treated, or other appropriate cells can be treated, as is evident to those skilled in the art, individually or in combination with one or more drugs under conditions suitable for the treatment.

In a further embodiment, the described molecules can be used in combination with other known treatments to treat conditions or diseases discussed above. For example, the described molecules can be used in combination with one or more known therapeutic agents to treat breast, lung, prostate, colorectal, brain, esophageal, bladder, pancreatic, cervical, head and neck, and ovarian cancer, melanoma, lymphoma, glioma, multidrug resistant cancers, and/or HIV, HBV, HCV, CMV, RSV, HSV, poliovirus, influenza, rhinovirus, west nile virus, Ebola virus, foot and mouth virus, and papilloma virus infection.

Included in another embodiment are a series of multidomain cellular transport vehicles (MCTV) including one or more compounds of Formulae 1-122 herein that enhance the cellular uptake and transmembrane permeability of negatively charged molecules in a variety of cell types. The compounds of the invention are used either alone or in combination with other compounds with a neutral or a negative charge including but not limited to neutral lipid and/or targeting components, to improve the effectiveness of the formulation or conjugate in delivering and targeting the predetermined compound or molecule to cells. Another embodiment of the invention encompasses the utility of these compounds for increasing the transport of other impermeable and/or lipophilic compounds into cells. Targeting components include ligands for cell surface receptors including, peptides and proteins, glycolipids, lipids, carbohydrates, and their synthetic variants, for example folate receptors.

In another embodiment, the compounds of the invention are provided as a surface component of a lipid aggregate, such as a liposome encapsulated with the predetermined molecule to be delivered. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm.

In one embodiment the invention features a lipid aggregate formulation of the compounds described herein, including phosphatidylcholine (of varying chain length; e.g., egg yolk phosphatidylcholine), cholesterol, a cationic lipid, and 1,2-distearoyl-sn-glycero-3-phosphoethanolamine-polythyleneglycol-2000 (DSPE-PEG2000). The cationic lipid component of this lipid aggregate can be any cationic lipid known in the art such as dioleoyl 1,2,-diacyl-3-trimethylammonium-propane (DOTAP). In another embodiment this cationic lipid aggregate comprises a covalently bound compound described in any of the Formulae herein.

In another embodiment, polyethylene glycol (PEG) is covalently attached to the compounds of the present invention. The attached PEG can be any molecular weight but is preferably between 2000-50,000 daltons.

The compounds and methods of the present invention are useful for introducing nucleotides, nucleosides, nucleic acid molecules, lipids, peptides, proteins, and/or non-nucleosidic small molecules into a cell. For example, the invention can be used for nucleotide, nucleoside, nucleic acid, lipids, peptides, proteins, and/or non-nucleosidic small molecule delivery where the corresponding target site of action exists intracellularly.

In one embodiment, the compounds of the instant invention provide conjugates of molecules that can interact with cellular receptors, such as high affinity folate receptors and ASGPr receptors, and provide a number of features that allow the efficient delivery and subsequent release of conjugated compounds across biological membranes. The compounds utilize chemical linkages between the receptor ligand and the compound to be delivered of length that can interact preferentially with cellular receptors. Furthermore, the chemical linkages between the ligand and the compound to be delivered can be designed as degradable linkages, for example by utilizing a phosphate linkage that is proximal to a nucleophile, such as a hydroxyl group. Deprotonation of the hydroxyl group or an equivalent group, as a result of pH or interaction with a nuclease, can result in nucleophilic attack of the phosphate resulting in a cyclic phosphate intermediate that can be hydrolyzed. This cleavage mechanism is analogous RNA cleavage in the presence of a base or RNA nuclease. Alternately, other degradable linkages can be selected that respond to various factors such as UV irradiation, cellular nucleases, pH, temperature etc. The use of degradable linkages allows the delivered compound to be released in a predetermined system, for example in the cytoplasm of a cell, or in a particular cellular organelle.

The present invention also provides ligand derived phosphoramidites that are readily conjugated to compounds and molecules of interest. Phosphoramidite compounds of the invention permit the direct attachment of conjugates to molecules of interest without the need for using nucleic acid phosphoramidite species as scaffolds. As such, the used of phosphoramidite chemistry can be used directly in coupling the compounds of the invention to a compound of interest, without the need for other condensation reactions, such as condensation of the ligand to an amino group on the nucleic acid, for example at the N6 position of adenosine or a 2'-deoxy-2'-amino function. Additionally, compounds of the invention can be used to introduce non-nucleic acid based conjugated linkages into oligonucleotides that can provide more efficient coupling during oligonucleotide synthesis than the use of nucleic acid-based phosphoramidites. This improved coupling can take into account improved steric considerations of abasic or non-nucleosidic scaffolds bearing pendant alkyl linkages.

Compounds of the invention utilizing triphosphate groups can be utilized in the enzymatic incorporation of conjugate molecules into oligonucleotides. Such enzymatic incorporation is useful when conjugates are used in post-synthetic enzymatic conjugation or selection reactions, (see for example Matulic-Adamic et al., 2000, *Bioorg. Med. Chem. Lett.*, 10, 1299-1302; Lee et al., 2001, *NAR.*, 29, 1565-1573; Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; Kuwabara et al., 2000, *Curr. Opin. Chem. Biol.*, 4, 669).

Compounds of the invention can be used to detect the presence of a target molecule in a biological system, such as tissue, cell or cell lysate. Examples of target molecules include nucleic acids, proteins, peptides, antibodies, polysaccharides, lipids, hormones, sugars, metals, microbial or cellular metabolites, analytes, pharmaceuticals, and other organic and inorganic molecules or other biomolecules in a sample. The compounds of the instant invention can be conjugated to a predetermined compound or molecule that is capable of interacting with the target molecule in the system and providing a detectable signal or response. Various compounds and molecules known in the art that can be used in these applications include but are not limited to antibodies, labeled antibodies, allozymes, aptamers, labeled nucleic acid probes, molecular beacons, fluorescent molecules, radioisotopes, polysaccharides, and any other compound capable of interacting with the target molecule and generating a detectable signal upon target interaction. For example, such compounds are described in Application entitled "NUCLEIC ACID SENSOR MOLECULES", U.S. Ser. No. 09/800,594 filed on Mar. 6, 2001 with inventors Nassim Usman and James A. McSwiggen, which is incorporated by reference in its entirety, including the drawings.

The term "biodegradable nucleic acid linker molecule" as used herein, refers to a nucleic acid molecule that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example 2'-O-methyl, 2'-fluoro, 2'-amino, 2'-O-amino, 2'-O-allyl, 2'-O-allyl, and other 2'-modified or base modified nucleotides. The biodegradable nucleic acid linker molecule can be a dimer, trimer, tetramer or longer nucleic acid molecule, for example an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active molecules contemplated by the instant invention include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus containing group and saturated or unsaturated alkyl group, optionally substituted with OH, COOH, oxo, amine, or substituted or unsubstituted aryl groups.

The term "nitrogen containing group" as used herein refers to any chemical group or moiety comprising a nitrogen or substituted nitrogen. Non-limiting examples of nitrogen containing groups include amines, substituted amines, amides, alkylamines, amino acids such as arginine or lysine, polyamines such as spermine or spermidine, cyclic amines such as pyridines, pyrimidines including uracil, thymine, and cytosine, morpholines, phthalimides, and heterocyclic amines such as purines, including guanine and adenine.

The term "target molecule" as used herein, refers to nucleic acid molecules, proteins, peptides, antibodies, polysaccharides, lipids, sugars, metals, microbial or cellular metabolites, analytes, pharmaceuticals, and other organic and inorganic molecules that are present in a system.

By "inhibit" or "down-regulate" it is meant that the expression of the gene, or level of RNAs or equivalent RNAs encoding one or more protein subunits, or activity of one or more protein subunits, such as pathogenic protein, viral protein or cancer related protein subunit(s), is reduced below that observed in the absence of the compounds or combination of compounds of the invention. In one embodiment, inhibition or down-regulation with an enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of viral or oncogenic RNA, protein, or protein subunits with a compound of the instant invention is greater in the presence of the compound than in its absence.

By "up-regulate" is meant that the expression of the gene, or level of RNAs or equivalent RNAs encoding one or more protein subunits, or activity of one or more protein subunits, such as viral or oncogenic protein subunit(s), is greater than that observed in the absence of the compounds or combination of compounds of the invention. For example, the expression of a gene, such as a viral or cancer related gene, can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more protein subunits, or activity of one or more protein subunit(s) of a protein, for example a viral or cancer related protein is up-regulated or down-regulated, such that the expression, level, or activity is greater than or less than that observed in the absence of the compounds or combination of compounds of the invention.

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

The term "nucleic acid molecule" as used herein, refers to a molecule having nucleotides. The nucleic acid can be single, double, or multiple stranded and can comprise modified or unmodified nucleotides or non-nucleotides or various mixtures and combinations thereof.

The term "enzymatic portion" or "catalytic domain" as used herein refers to that portion/region of the enzymatic nucleic acid molecule essential for cleavage of a nucleic acid substrate (for example see FIG. 1).

The term "substrate binding arm" or "substrate binding domain" as used herein refers to that portion/region of a enzymatic nucleic acid which is able to interact, for example via complementarity (i.e., able to base-pair with), with a portion of its substrate. Preferably, such complementarity is 100%, but can be less if desired. For example, as few as 10 bases out of 14 can be base-paired (see for example Werner and Uhlenbeck, 1995, Nucleic Acids Research, 23, 2092-2096; Hammann et al., 1999, Antisense and Nucleic Acid Drug Dev., 9, 25-31). Examples of such arms are shown generally in FIGS. 1-4. That is, these arms contain sequences within a enzymatic nucleic acid which are intended to bring enzymatic nucleic acid and target RNA together through complementary base-pairing interactions. The enzymatic nucleic acid of the invention can have binding arms that are contiguous or non-contiguous and can be of varying lengths. The length of the binding arm(s) are preferably greater than or equal to four nucleotides and of sufficient length to stably interact with the target RNA; preferably 12-100 nucleotides; more preferably 14-24 nucleotides long (see for example Werner and Uhlenbeck, supra; Hamman et al., supra; Hampel et al., EP0360257; Berzal-Herrance et al., 1993, EMBO J., 12, 2567-73). If two binding arms are chosen, the design is such that the length of the binding arms are symmetrical (i.e., each of the binding arms is of the same length; e.g., five and five nucleotides, or six and six nucleotides, or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

The term "Inozyme" or "NCH" motif as used herein, refers to an enzymatic nucleic acid molecule comprising a motif as is generally described as NCH Rz in FIG. 1. Inozymes possess endonuclease activity to cleave RNA substrates having a cleavage triplet NCH/, where N is a nucleotide, C is cytidine and H is adenosine, uridine or cytidine, and/represents the cleavage site. H is used interchangeably with X. Inozymes can also possess endonuclease activity to cleave RNA substrates having a cleavage triplet NCN/, where N is a nucleotide, C is cytidine, and/represents the cleavage site. "I" in FIG. 2 represents an Inosine nucleotide, preferably a ribo-Inosine or xylo-Inosine nucleoside.

The term "G-cleaver" motif as used herein, refers to an enzymatic nucleic acid molecule comprising a motif as is generally described as G-cleaver Rz in FIG. 1. G-cleavers possess endonuclease activity to cleave RNA substrates having a cleavage triplet NYN/, where N is a nucleotide, Y is uridine or cytidine and/represents the cleavage site. G-cleavers can be chemically modified as is generally shown in FIG. 2.

The term "amberzyme" motif as used herein, refers to an enzymatic nucleic acid molecule comprising a motif as is generally described in FIG. 2. Amberzymes possess endonuclease activity to cleave RNA substrates having a cleavage triplet NG/N, where N is a nucleotide, G is guanosine, and/represents the cleavage site. Amberzymes can be chemically modified to increase nuclease stability through substitutions as are generally shown in FIG. 3. In addition, differing nucleoside and/or non-nucleoside linkers can be used to substitute the 5'-gaaa-3' loops shown in the figure. Amberzymes represent a non-limiting example of an enzymatic nucleic acid molecule that does not require a ribonucleotide (2'-OH) group within its own nucleic acid sequence for activity.

The term "zinzyme" motif as used herein, refers to an enzymatic nucleic acid molecule comprising a motif as is generally described in FIG. 3. Zinzymes possess endonuclease activity to cleave RNA substrates having a cleavage triplet including but not limited to YG/Y, where Y is uridine or cytidine, and G is guanosine and/represents the cleavage site. Zinzymes can be chemically modified to increase nuclease stability through substitutions as are generally shown in FIG. 3, including substituting 2'-O-methyl guanosine nucleotides for guanosine nucleotides. In addition, differing nucleotide and/or non-nucleotide linkers can be used to substitute the 5'-gaaa-2' loop shown in the figure. Zinzymes represent a non-limiting example of an enzymatic nucleic acid molecule that does not require a ribonucleotide (2'-OH) group within its own nucleic acid sequence for activity.

The term 'DNAzyme' as used herein, refers to an enzymatic nucleic acid molecule that does not require the presence of a 2'-OH group for its activity. In particular embodiments the enzymatic nucleic acid molecule can have an attached linker(s) or other attached or associated groups, moieties, or chains containing one or more nucleotides with 2'-OH groups. DNAzymes can be synthesized chemically or expressed endogenously in vivo, by means of a single stranded DNA vector or equivalent thereof. An example of a DNAzyme is shown in FIG. 4 and is generally reviewed in Usman et al., International PCT Publication No. WO 95/11304; Chartrand et al., 1995, NAR 23, 4092; Breaker et al., 1995, Chem. Bio. 2, 655; Santoro et al., 1997, PNAS 94, 4262; Breaker, 1999, Nature Biotechnology, 17, 422-423; and Santoro et. al., 2000, J. Am. Chem. Soc., 122, 2433-39. Additional DNAzyme motifs can be selected for using techniques similar to those described in these references, and hence, are within the scope of the present invention.

The term "sufficient length" as used herein, refers to an oligonucleotide of length great enough to provide the intended function under the expected condition, i.e., greater than or equal to 3 nucleotides. For example, for binding arms of enzymatic nucleic acid "sufficient length" means that the binding arm sequence is long enough to provide stable binding to a target site under the expected binding conditions. Preferably, the binding arms are not so long as to prevent useful turnover of the nucleic acid molecule.

The term "stably interact" as used herein, refers to interaction of the oligonucleotides with target nucleic acid (e.g., by forming hydrogen bonds with complementary nucleotides in the target under physiological conditions) that is sufficient to the intended purpose (e.g., cleavage of target RNA by an enzyme).

The term "homology" as used herein, refers to the nucleotide sequence of two or more nucleic acid molecules is partially or completely identical.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989, 912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothioate substitutions; more specifically, 4-11 of the nucleotides are phosphorothioate substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease which, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113).

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206).

The term "gene" it as used herein, refers to a nucleic acid that encodes an RNA, for example, nucleic acid sequences including but not limited to structural genes encoding a polypeptide.

The term "pathogenic protein" as used herein, refers to endogenous or exongenous proteins that are associated with a disease state or condition, for example a particular cancer or viral infection.

The term "complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

The term "RNA" as used herein, refers to a molecule comprising at least one ribonucleotide residue. By "ribonucleotide" or "2'-OH" is meant a nucleotide with a hydroxyl group at the 2' position of a β-D-ribo-furanose moiety.

The term "decoy RNA" as used herein, refers to a RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, Cell, 63, 601-608). This is but a specific example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628. Similarly, a decoy RNA can be designed to bind to a receptor and block the binding of an effector molecule or a decoy RNA can be designed to bind to receptor of interest and prevent interaction with the receptor.

The term "single stranded RNA" (ssRNA) as used herein refers to a naturally occurring or synthetic ribonucleic acid molecule comprising a linear single strand, for example a ssRNA can be a messenger RNA (mRNA), transfer RNA (tRNA), ribosomal RNA (rRNA) etc. of a gene.

The term "single stranded DNA" (ssDNA) as used herein refers to a naturally occurring or synthetic deoxyribonucleic acid molecule comprising a linear single strand, for example, a ssDNA can be a sense or antisense gene sequence or EST (Expressed Sequence Tag).

The term "double stranded RNA" or "dsRNA" as used herein refers to a double stranded RNA molecule capable of RNA interference, including short interfering RNA (siNA).

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Non limiting examples of siNA molecules of the invention are described in Haeberli et al., PCT/US03/05346 and McSwiggen et al., PCT/US03/05028, both incorporated by reference herein in their entirety including the drawings, and in FIGS. 34-42 herein. Chemical modifications described in Haeberli et al., PCT/US03/05346 and McSwiggen et al., PCT/US03/05028 and/or shown in Table IV can be applied to any siNA sequence of the invention. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate. In certain embodiment, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. In addition, as used herein, the term RNAi is meant to be equivalent to other terms used to describe sequence specific RNA interference, such as post transcriptional gene silencing, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

The term "allozyme" as used herein refers to an allosteric enzymatic nucleic acid molecule, see for example see for example George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

The term "cell" as used herein, refers to its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "highly conserved sequence region" as used herein, refers to a nucleotide sequence of one or more regions in a target gene does not vary significantly from one generation to the other or from one biological system to the other.

The term "non-nucleotide" as used herein, refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "nucleoside" as used herein, refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguano sine, N6-methyladeno sine, 7-methylguano sine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "cap structure" as used herein, refers to chemical modifications, which have been incorporated at either terminus of the oligonucleotide (see for example Wincott et al., WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

The term "abasic" as used herein, refers to sugar moieties lacking a base or having other chemical groups in place of a base at the 1' position, for example a 3',3'-linked or 5',5'-linked deoxyabasic ribose derivative (for more details see Wincott et al., International PCT publication No. WO 97/26270).

The term "unmodified nucleoside" as used herein, refers to one of the bases adenine, cytosine, guanine, thymine, uracil joined to the 1' carbon of β-D-ribo-furanose.

The term "modified nucleoside" as used herein, refers to any nucleotide base which contains a modification in the chemical structure of an unmodified nucleotide base, sugar and/or phosphate.

The term "consists essentially of" as used herein, is meant that the active nucleic acid molecule of the invention, for example, an enzymatic nucleic acid molecule, contains an enzymatic center or core equivalent to those in the examples, and binding arms able to bind RNA such that cleavage at the target site occurs. Other sequences can be present which do not interfere with such cleavage. Thus, a core region can, for example, include one or more loop, stem-loop structure, or linker which does not prevent enzymatic activity. For example, a core sequence for a hammerhead enzymatic nucleic acid can comprise a conserved sequence, such as 5'-CUGAUGAG-3' and 5'-CGAA-3' connected by "X", where X is 5'-GCCGUUAGGC-3' (SEQ ID NO 1), or any other Stem II region known in the art, or a nucleotide and/or non-nucleotide linker. Similarly, for other nucleic acid molecules of the instant invention, such as Inozyme, G-cleaver, amberzyme, zinzyme, DNAzyme, antisense, 2-5A antisense, triplex forming nucleic acid, and decoy nucleic acids, other sequences or non-nucleotide linkers can be present that do not interfere with the function of the nucleic acid molecule.

Sequence X can be a linker of >2 nucleotides in length, preferably 3, 4, 5, 6, 7, 8, 9, 10, 15, 20, 26, 30, where the nucleotides can preferably be internally base-paired to form a stem of preferably >2 base pairs. In yet another embodiment, the nucleotide linker X can be a nucleic acid aptamer, such as an ATP aptamer, HIV Rev aptamer (RRE), HIV Tat aptamer (TAR) and others (for a review see Gold et al., 1995, Annu. Rev. Biochem., 64, 763; and Szostak & Ellington, 1993, in The RNA World, ed. Gesteland and Atkins, pp. 511, CSH Laboratory Press). A "nucleic acid aptamer" as used herein is meant to indicate a nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

Alternatively or in addition, sequence X can be a non-nucleotide linker. Non-nucleotides can include abasic nucleotide, polyether, polyamine, polyamide, peptide, carbohydrate, lipid, or polyhydrocarbon compounds. Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, all hereby incorporated by reference herein. A "non-nucleotide" further means any group or compound which can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine. Thus, in a preferred embodiment, the invention features an enzymatic nucleic acid molecule having one or more non-nucleotide moieties, and having enzymatic activity to cleave an RNA or DNA molecule.

The term "patient" as used herein, refers to an organism, which is a donor or recipient of explanted cells or the cells themselves. "Patient" also refers to an organism to which the nucleic acid molecules of the invention can be administered. Preferably, a patient is a mammal or mammalian cells. More preferably, a patient is a human or human cells.

The term "enhanced enzymatic activity" as used herein, includes activity measured in cells and/or in vivo where the activity is a reflection of both the catalytic activity and the stability of the nucleic acid molecules of the invention. In this invention, the product of these properties can be increased in vivo compared to an all RNA enzymatic nucleic acid or all DNA enzyme. In some cases, the activity or stability of the nucleic acid molecule can be decreased (i.e., less than tenfold), but the overall activity of the nucleic acid molecule is enhanced, in vivo.

By "comprising" is meant including, but not limited to, whatever follows the word "comprising". Thus, use of the term "comprising" indicates that the listed elements are required or mandatory, but that other elements are optional and can or can not be present. By "consisting of" is meant including, and limited to, whatever follows the phrase "consisting of". Thus, the phrase "consisting of" indicates that the listed elements are required or mandatory, and that no other elements can be present.

The term "negatively charged molecules" as used herein, refers to molecules such as nucleic acid molecules (e.g., RNA, DNA, oligonucleotides, mixed polymers, peptide nucleic acid, and the like), peptides (e.g., polyaminoacids, polypeptides, proteins and the like), nucleotides, pharmaceutical and biological compositions, that have negatively charged groups that can ion-pair with the positively charged head group of the cationic lipids of the invention.

The term "coupling" as used herein, refers to a reaction, either chemical or enzymatic, in which one atom, moiety, group, compound or molecule is joined to another atom, moiety, group, compound or molecule.

The terms "deprotection" or "deprotecting" as used herein, refers to the removal of a protecting group.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Preferably, the alkyl group has 1 to 12 carbons. More preferably it is a lower alkyl of from about 1 to about 7 carbons, more preferably about 1 to about 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has about 2 to about 12 carbons. More preferably it is a lower alkenyl of from about 2 to about 7 carbons, more preferably about 2 to about 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has about 2 to about 12 carbons. More preferably it is a lower alkynyl of from about 2 to about 7 carbons, more preferably about 2 to about 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to about 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example, methoxyethyl or ethoxymethyl.

The term "alkyl-thio-alkyl" as used herein refers to an alkyl-S-alkyl thioether, for example, methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example, an acyl or amide group.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3-C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3-C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3-C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein, refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1-C6 hydrocarbyl" as used herein refers to straight, branched, or cyclic alkyl groups having 1-6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1-C6 hydrocarbyl containing one or two double or triple bonds it is understood that at least two carbons are present in the alkyl for one double or triple bond, and at least four carbons for two double or triple bonds.

The term "protecting group" as used herein, refers to groups known in the art that are readily introduced and removed from an atom, for example O, N, P, or S. Protecting groups are used to prevent undesirable reactions from taking place that can compete with the formation of a specific compound or intermediate of interest. See also "Protective Groups in Organic Synthesis", 3rd Ed., 1999, Greene, T. W. and related publications.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 3rd Ed., 1999, Greene, T. W. and related publications.

The term "hydroxy protecting group," or "hydroxy protection" as used herein, refers to groups known in the art that are readily introduced on to and removed from an oxygen, specifically an —OH group. Examples of hyroxy protecting groups include trityl or substituted trityl groups, such as monomethoxytrityl and dimethoxytrityl, or substituted silyl groups, such as tert-butyldimethyl, trimethylsilyl, or tert-butyldiphenyl silyl groups. See also "Protective Groups in Organic Synthesis", 3rd Ed., 1999, Greene, T. W. and related publications.

The term "acyl" as used herein refers to —C(O)R groups, wherein R is an alkyl or aryl.

The term "phosphorus containing group" as used herein, refers to a chemical group containing a phosphorus atom. The phosphorus atom can be trivalent or pentavalent, and can be substituted with O, H, N, S, C or halogen atoms. Examples of phosphorus containing groups of the instant invention include but are not limited to phosphorus atoms substituted with O, H, N, S, C or halogen atoms, comprising phosphonate, alkylphosphonate, phosphate, diphosphate, triphosphate, pyrophosphate, phosphorothioate, phosphorodithioate, phosphoramidate, phosphoramidite groups, nucleotides and nucleic acid molecules.

The term "phosphine" or "phosphite" as used herein refers to a trivalent phosphorus species, for example compounds having Formula 97:

wherein R can include the groups:

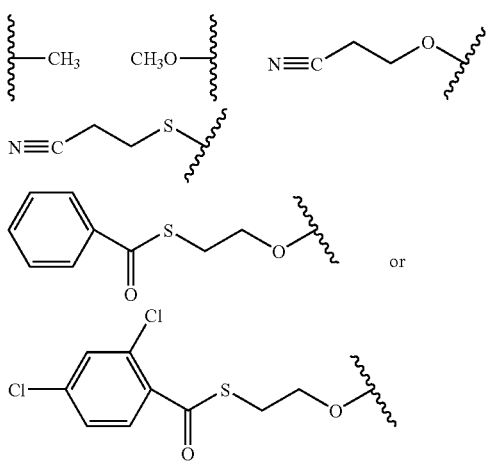

and wherein S and T independently include the groups:

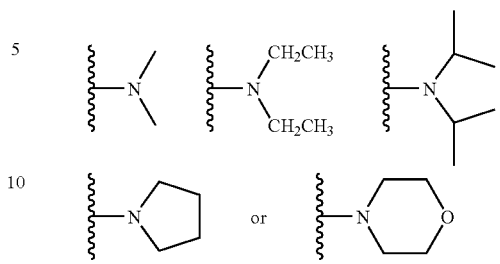

The term "phosphate" as used herein refers to a pentavalent phosphorus species, for example a compound having Formula 98:

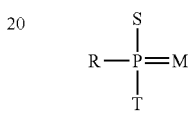

wherein R includes the groups:

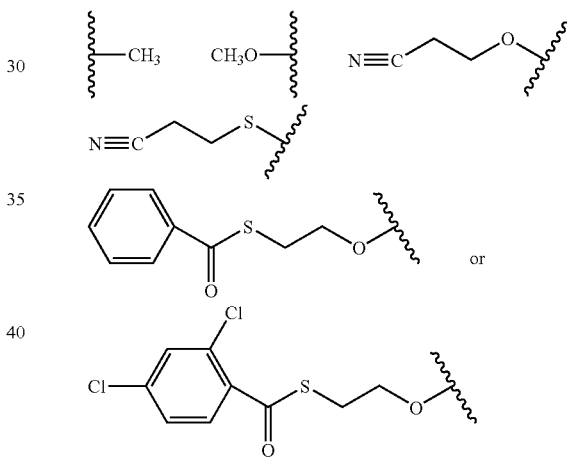

and wherein S and T each independently can be a sulfur or oxygen atom or a group which can include:

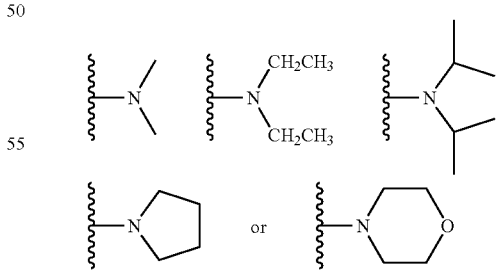

and wherein M comprises a sulfur or oxygen atom. The phosphate of the invention can comprise a nucleotide phosphate, wherein any R, S, or T in Formula 98 comprises a linkage to a nucleic acid or nucleoside.

The term "cationic salt" as used herein refers to any organic or inorganic salt having a net positive charge, for example a triethylammonium (TEA) salt.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage.

The term "photolabile linker" as used herein, refers to linker moieties as are known in the art, that are selectively cleaved under particular UV wavelengths. Compounds of the invention containing photolabile linkers can be used to deliver compounds to a target cell or tissue of interest, and can be subsequently released in the presence of a UV source.

The term "nucleic acid conjugates" as used herein, refers to nucleoside, nucleotide and oligonucleotide conjugates.

The term "lipid" as used herein, refers to any lipophilic compound. Non-limiting examples of lipid compounds include fatty acids and their derivatives, including straight chain, branched chain, saturated and unsaturated fatty acids, carotenoids, terpenes, bile acids, and steroids, including cholesterol and derivatives or analogs thereof.

The term "folate" as used herein, refers to analogs and derivatives of folic acid, for example antifolates, dihydrofloates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives.

The term "compounds with neutral charge" as used herein, refers to compositions which are neutral or uncharged at neutral or physiological pH. Examples of such compounds are cholesterol and other steroids, cholesteryl hemisuccinate (CHEMS), dioleoyl phosphatidyl choline, distearoylphosphotidyl choline (DSPC), fatty acids such as oleic acid, phosphatidic acid and its derivatives, phosphatidyl serine, polyethylene glycol-conjugated phosphatidylamine, phosphatidylcholine, phosphatidylethanolamine and related variants, prenylated compounds including farnesol, polyprenols, tocopherol, and their modified forms, diacylsuccinyl glycerols, fusogenic or pore forming peptides, dioleoylphosphotidylethanolamine (DOPE), ceramide and the like.

The term "lipid aggregate" as used herein refers to a lipid-containing composition wherein the lipid is in the form of a liposome, micelle (non-lamellar phase) or other aggregates with one or more lipids.

The term "biological system" as used herein, refers to a eukaryotic system or a prokaryotic system, can be a bacterial cell, plant cell or a mammalian cell, or can be of plant origin, mammalian origin, yeast origin, Drosophila origin, or archebacterial origin.

The term "systemic administration" as used herein refers to the in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as the cancer cells.

The term "pharmacological composition" or "pharmaceutical formulation" refers to a composition or formulation in a form suitable for administration, for example, systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is targeted).

Other features and advantages of the invention will be apparent from the following description of the preferred embodiments thereof, and from the claims.

DESCRIPTION OF THE PREFERRED EMBODIMENTS

The drawings will be first described briefly.

DRAWINGS

FIG. 1 shows examples of chemically stabilized ribozyme motifs. HH Rz, represents hammerhead ribozyme motif (Usman et al., 1996, Curr. Op. Struct. Bio., 1, 527); NCH Rz represents the NCH ribozyme motif (Ludwig & Sproat, International PCT Publication No. WO 98/58058); G-Cleaver, represents G-cleaver ribozyme motif (Kore et al., 1998, Nucleic Acids Research 26, 4116-4120, Eckstein et al., International PCT publication No. WO 99/16871). N or n, represent independently a nucleotide which can be same or different and have complementarity to each other; rI, represents ribo-Inosine nucleotide; arrow indicates the site of cleavage within the target. Position 4 of the HH Rz and the NCH Rz is shown as having 2'-C-allyl modification, but those skilled in the art will recognize that this position can be modified with other modifications well known in the art, so long as such modifications do not significantly inhibit the activity of the ribozyme.

FIG. 12 shows an alternative synthetic scheme for post-synthetic modification of a nucleic acid molecule to produce a folate conjugate.

FIG. 13 shows a non-limiting example of a synthetic scheme for the synthesis of a N-acetyl-D-galactosamine-2'-aminouridine phosphoramidite conjugate of the invention.

FIG. 14 shows a non-limiting example of a synthetic scheme for the synthesis of a N-acetyl-D-galactosamine-D-threoninol phosphoramidite conjugate of the invention.

Figure 1:
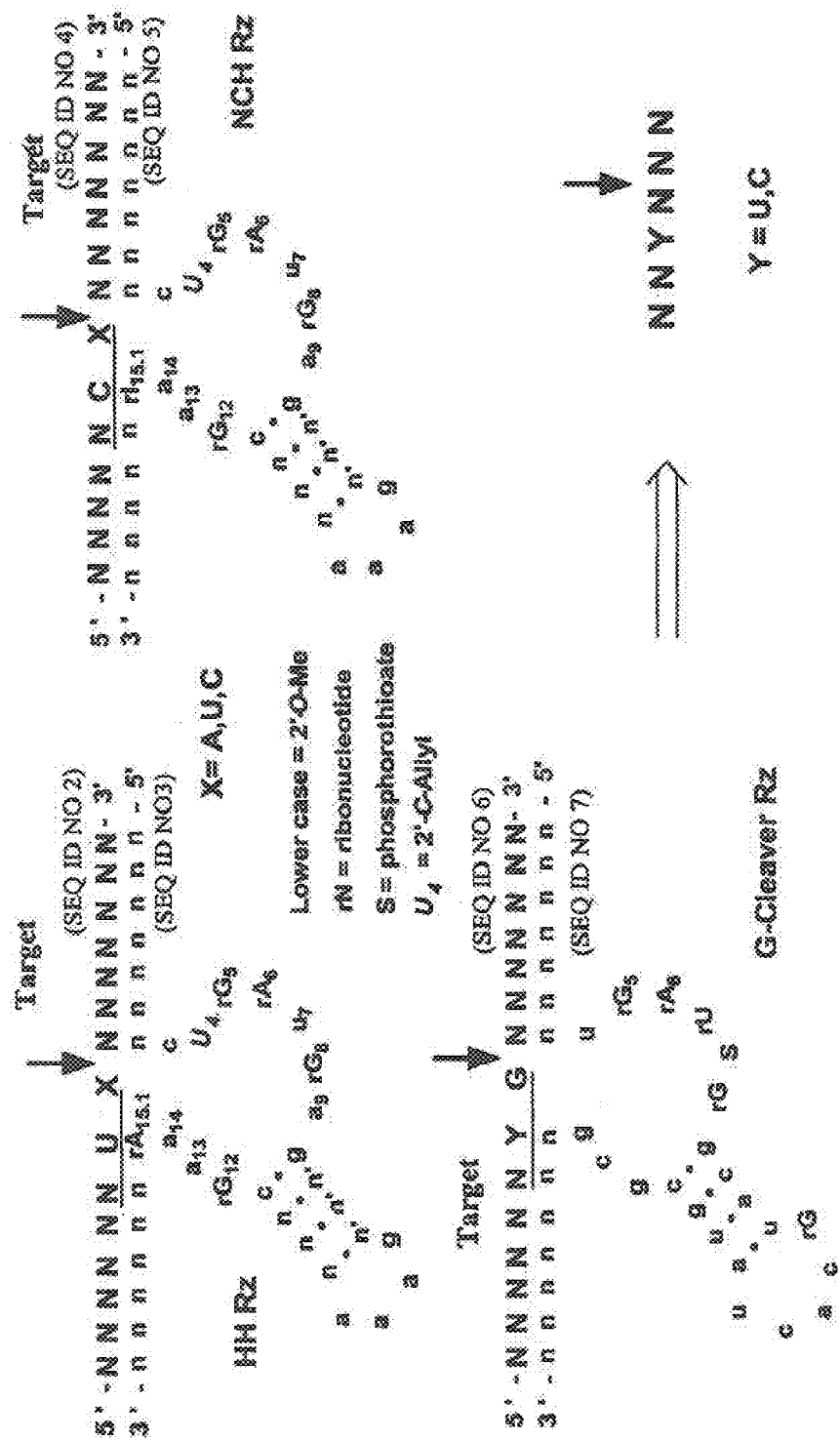
Figure 2:
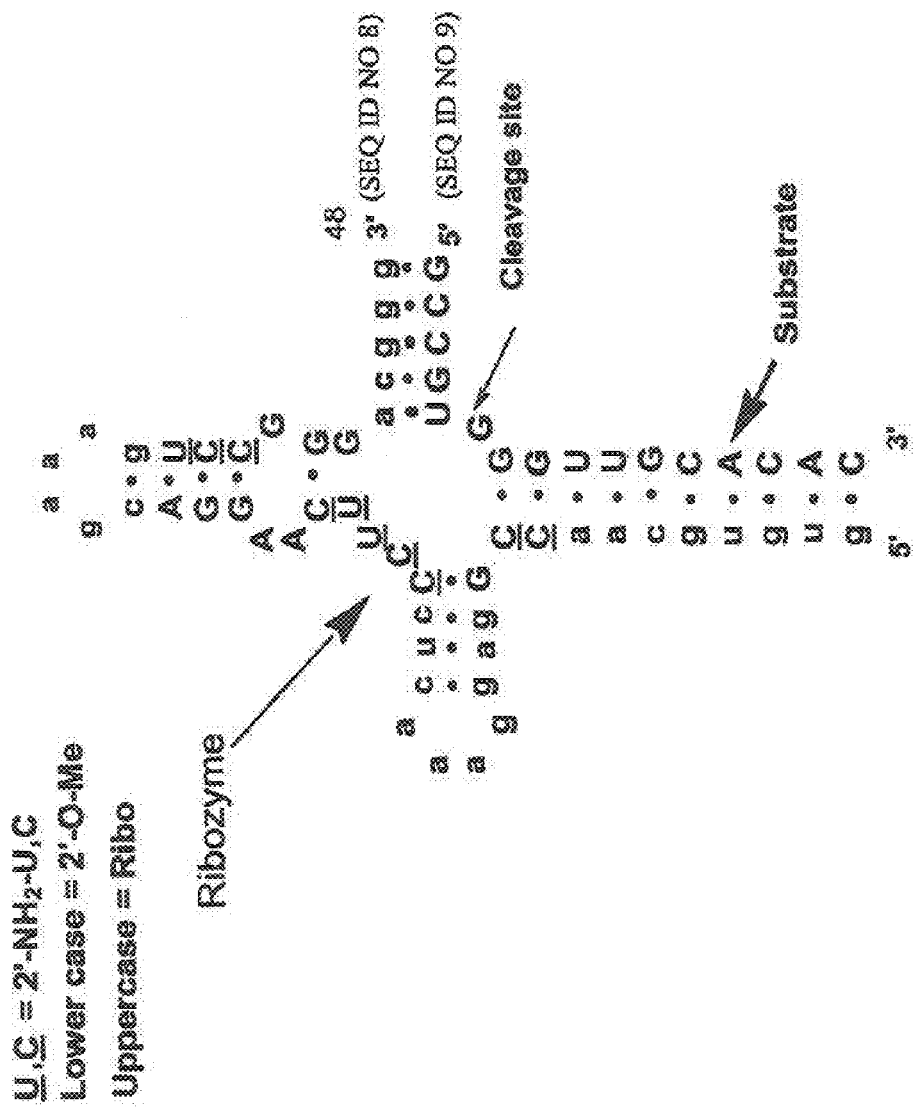
FIG. 2 shows an example of the Amberzyme ribozyme motif that is chemically stabilized (see for example Beigelman et al., International PCT publication No. WO 99/55857).
Figure 3:
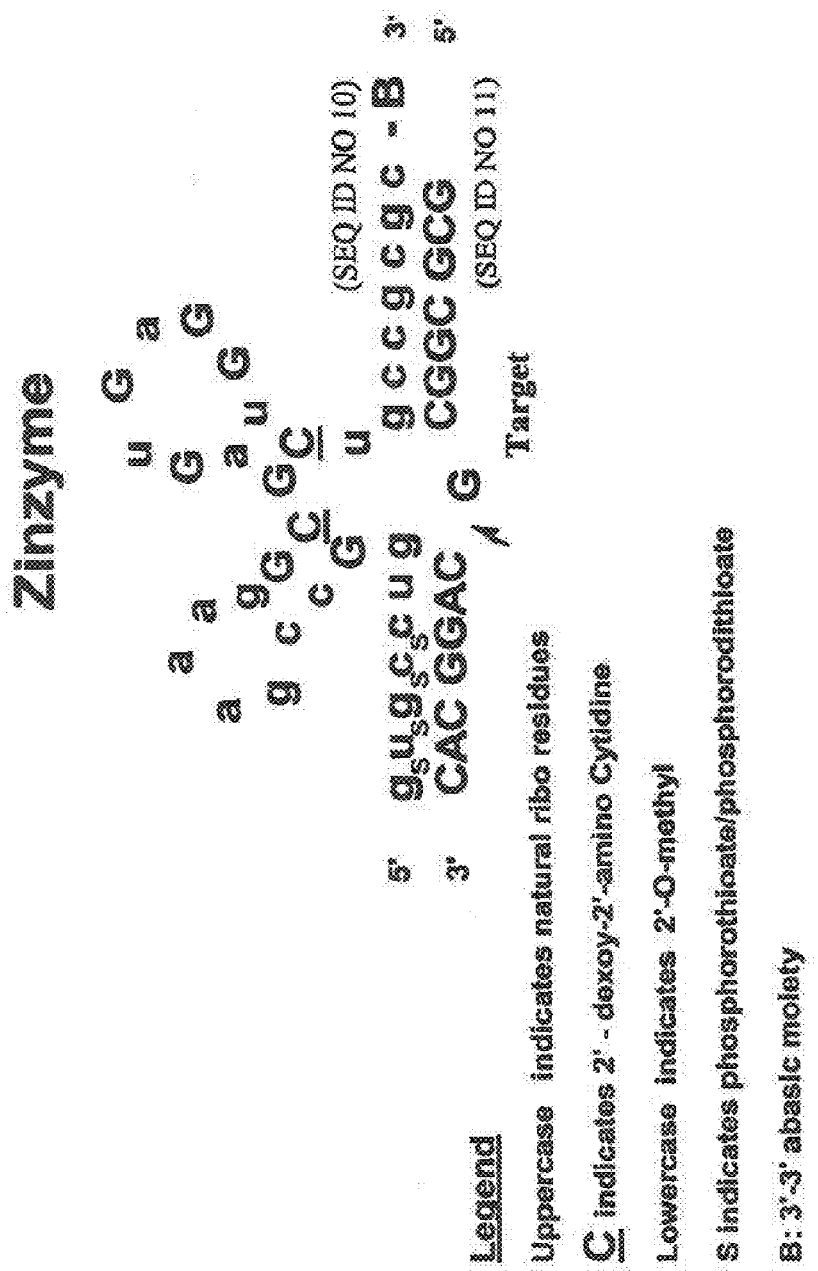
FIG. 3 shows an example of the Zinzyme A ribozyme motif that is chemically stabilized (see for example Beigelman et al., Beigelman et al., International PCT publication No. WO 99/55857).
Figure 4:
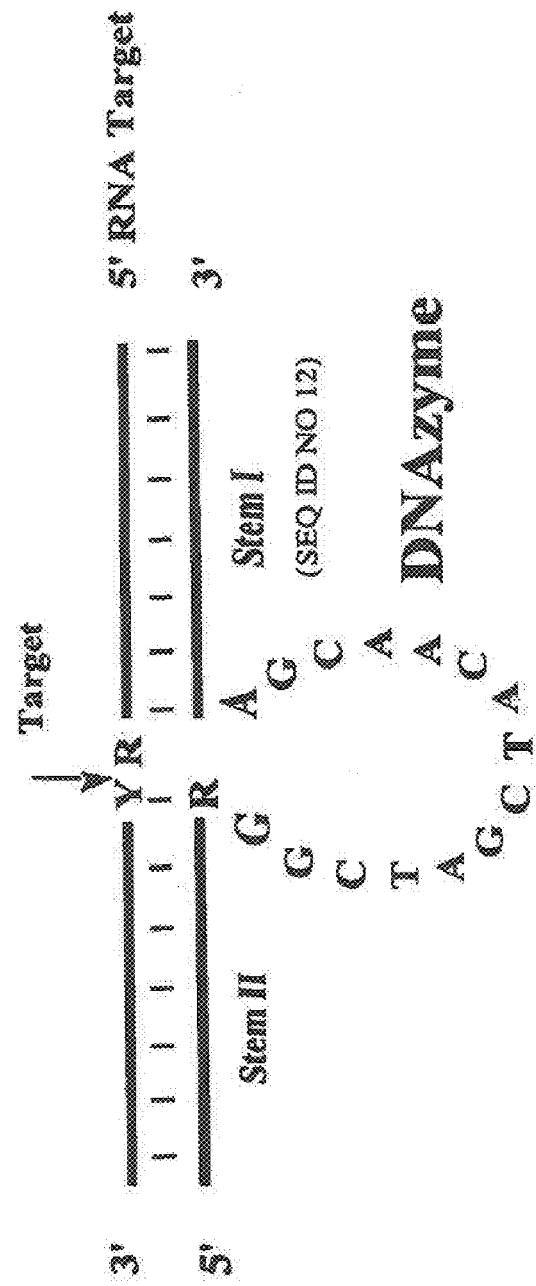
FIG. 4 shows an example of a DNAzyme motif described by Santoro et al., 1997, PNAS, 94, 4262.

FIG. 15 shows a non-limiting example of a N-acetyl-D-galactosamine siNA nucleic acid conjugate and a N-acetyl-D-galactosamine enzymatic nucleic acid conjugate of the invention. W shown in the example refers to a biodegradable linker, for example a nucleic acid dimer, trimer, or tetramer comprising ribonucleotides and/or deoxyribonucleotides. The siNA can be conjugated at the 3', 5' or both 3' and 5' ends of the sense strand of a double stranded siNA and/or the 3'-end of the antisense strand of the siNA. A single stranded siNA molecule can be conjugated at the 3'-end of the siNA.

FIG. 16 shows a non-limiting example of a synthetic scheme for the synthesis of a dodecanoic acid derived conjugate linker of the invention.

FIG. 17 shows a non-limiting example of a synthetic scheme for the synthesis of an oxime linked nucleic acid/peptide conjugate of the invention.

FIG. 18 shows non-limiting examples of phospholipid derived nucleic acid conjugates of the invention. W shown in the examples refers to a biodegradable linker, for example a nucleic acid dimer, trimer, or tetramer comprising ribonucleotides and/or deoxyribonucleotides. The siNA can be conjugated at the 3', 5' or both 3' and 5' ends of the sense strand of a double stranded siNA and/or the 3'-end of the antisense strand of the siNA. A single stranded siNA molecule can be conjugated at the 3'-end of the siNA.

FIG. 19 shows a non-limiting example of a synthetic scheme for preparing a phospholipid derived siNA conjugates of the invention.

FIG. 20 shows a non-limiting example of a synthetic scheme for preparing a polyethylene glycol (PEG) derived enzymatic nucleic acid conjugates of the invention.

FIG. 21 shows PK data of a 40K PEG conjugated enzymatic nucleic acid molecule compared to the corresponding non-conjugated enzymatic nucleic acid molecule. The graph is a time course of serum concentration in mice dosed with 30 mg/kg of Angiozyme™ or 40-kDa-PEG-Angiozyme™. The hybridization method was used to quantitate Angiozyme™ levels.

FIG. 22 shows PK data of a phospholipid conjugated enzymatic nucleic acid molecule compared to the corresponding non-conjugated enzymatic nucleic acid molecule.

FIG. 23 shows a non-limiting example of a synthetic scheme for preparing a poly-N-acetyl-D-galactosamine nucleic acid conjugate of the invention.

FIG. 24a-b shows a non-limiting example of a synthetic approach for synthesizing peptide or protein conjugates to PEG utilizing a biodegradable linker using oxime and morpholino linkages.

FIG. 25 shows a non-limiting example of a synthetic approach for synthesizing peptide or protein conjugates to PEG utilizing a biodegradable linker using oxime and phosphoramidate linkages.

FIG. 26a-b shows a non-limiting example of a synthetic approach for synthesizing peptide or protein conjugates to PEG utilizing a biodegradable linker using phosphoramidate linkages.

FIG. 27 shows non-limiting examples of phospholipid derived protein/peptide conjugates of the invention. W shown in the examples refers to a biodegradable linker, for example a nucleic acid dimer, trimer, or tetramer comprising ribonucleotides and/or deoxyribonucleotides.

FIG. 28 shows a non-limiting example of an N-acetyl-D-galactosamine peptide/protein conjugate of the invention, the example shown is with a peptide. W shown in the example refers to a biodegradable linker, for example a nucleic acid dimer, trimer, or tetramer comprising ribonucleotides and/or deoxyribonucleotides.

FIG. 29 shows a non-limiting example of a synthetic approach for synthesizing peptide or protein conjugates to PEG utilizing a biodegradable linker using phosphoramidate linkages via coupling a protein phosphoramidite to a PEG conjugated nucleic acid linker.

FIG. 30 shows a non-limiting example of the synthesis of siNA cholesterol conjugates of the invention using a phosphoramidite approach.

FIG. 31 shows a non-limiting example of the synthesis of siNA PEG conjugates of the invention using NHS ester coupling.

FIG. 32 shows a non-limiting example of the synthesis of siNA cholesterol conjugates of the invention using NHS ester coupling.

FIG. 33 shows a non-limiting example of various siNA cholesterol conjugates of the invention.

FIG. 34 shows a non-limiting example of various siNA cholesterol conjugates of the invention in which various linker chemistries and/or cleavable linkers can be utilized at different positions of a double stranded siNA molecule.

FIG. 35 shows a non-limiting example of various siNA cholesterol conjugates of the invention in which various linker chemistries and/or cleavable linkers can be utilized at different positions of a double stranded siNA molecule.

FIG. 36 shows a non-limiting example of various siNA cholesterol conjugates of the invention in which various linker chemistries and/or cleavable linkers can be utilized at different positions of a single stranded siNA molecule.

FIG. 37 shows a non-limiting example of various siNA phospholipid conjugates of the invention in which various linker chemistries and/or cleavable linkers can be utilized at different positions of a double stranded siNA molecule.

FIG. 38 shows a non-limiting example of various siNA phospholipid conjugates of the invention in which various linker chemistries and/or cleavable linkers can be utilized at different positions of a single stranded siNA molecule.

FIG. 39 shows a non-limiting example of various siNA galactosamine conjugates of the invention in which various linker chemistries and/or cleavable linkers can be utilized at different positions of a double stranded siNA molecule.

FIG. 40 shows a non-limiting example of various siNA galactosamine conjugates of the invention in which various linker chemistries and/or cleavable linkers can be utilized at different positions of a single stranded siNA molecule.

FIG. 41 shows a non-limiting example of various generalized siNA conjugates of the invention in which various linker chemistries and/or cleavable linkers can be utilized at different positions of a double stranded siNA molecule. CONJ in the figure refers to any biologically active compound or any other conjugate compound as described herein and in the Formulae herein.

FIG. 42 shows a non-limiting example of various generalized siNA conjugates of the invention in which various linker chemistries and/or cleavable linkers can be utilized at different positions of a single stranded siNA molecule. CONJ in the figure refers to any biologically active compound or any other conjugate compound as described herein and in the Formulae herein.

FIG. 43 shows a non-limiting example of the pharmacokinetic distribution of intact siNA in liver after administration of conjugated or unconjugated siNA molecules in mice.

FIG. 44 shows a non-limiting example of the activity of conjugated siNA constructs compared to matched chemistry unconjugated siNA constructs in an HBV cell culture system without the use of transfection lipid. As shown in the Figure, siNA conjugates provide efficacy in cell culture without the need for transfection reagent.

FIG. 45 shows a non-limiting example of a scheme for the synthesis of a mono-galactosamine phosphoramidite of the invention that can be used to generate galactosamine conjugated nucleic acid molecules.

FIG. 46 shows a non-limiting example of a scheme for the synthesis of a tri-galactosamine phosphoramidite of the invention that can be used to generate tri-galactosamine conjugated nucleic acid molecules.

FIG. 47 shows a non-limiting example of a scheme for the synthesis of another tri-galactosamine phosphoramidite of the invention that can be used to generate tri-galactosamine conjugated nucleic acid molecules.

FIG. 48 shows a non-limiting example of an alternate scheme for the synthesis of a tri-galactosamine phosphoramidite of the invention that can be used to generate tri-galactosamine conjugated nucleic acid molecules.

FIG. 49 shows a non-limiting example of a scheme for the synthesis of a cholesterol NHS ester of the invention that can be used to generate cholesterol conjugated nucleic acid molecules.

METHOD OF USE

The compositions and conjugates of the instant invention can be used to administer pharmaceutical agents. Pharmaceutical agents prevent, inhibit the occurrence, or treat (alleviate a symptom to some extent, preferably all of the symptoms) of a disease state in a patient.

Generally, the compounds of the instant invention are introduced by any standard means, with or without stabilizers, buffers, and the like, to form a pharmaceutical composition. For use of a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the like.

The present invention also includes pharmaceutically acceptable formulations of the compounds described above, preferably in combination with the molecule(s) to be delivered. These formulations include salts of the above compounds, e.g., acid addition salts, for example, salts of hydrochloric, hydrobromic, acetic acid, and benzene sulfonic acid.

In one embodiment, the invention features the use of the compounds of the invention in a composition comprising surface-modified liposomes containing poly (ethylene glycol) lipids (PEG-modified, or long-circulating liposomes or stealth liposomes). In another embodiment, the invention features the use of compounds of the invention covalently attached to polyethylene glycol. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such compositions have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating compositions enhance the pharmacokinetics and pharmacodynamics of therapeutic compounds, such as DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating compositions are also likely to protect drugs from nuclease degradation to a greater extent compared to cationic liposomes, based on their ability to avoid accumulation in metabolically aggressive MPS tissues such as the liver and spleen.

The present invention also includes a composition(s) prepared for storage or administration that includes a pharmaceutically effective amount of the desired compound(s) in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be included in the composition. Examples of such agents include but are not limited to sodium benzoate, sorbic acid and esters of p-hydroxybenzoic acid. In addition, antioxidants and suspending agents can be included in the composition.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. Furthermore, the compounds of the invention and formulations thereof can be administered to a fetus via administration to the mother of a fetus.

The compounds of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The compounds of the present invention can also be administered to a patient in combination with other therapeutic compounds to increase the overall therapeutic effect. The use of multiple compounds to treat an indication can increase the beneficial effects while reducing the presence of side effects.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs less than about 100 nucleotides in length, preferably less than about 80 nucleotides in length, and more preferably less than about 50 nucleotides in length; e.g., antisense oligonucleotides, hammerhead or the NCH ribozymes are preferably used for exogenous delivery. The simple structure of these molecules increases the ability of the nucleic acid to invade targeted regions of RNA structure. Exemplary molecules of the instant invention are chemically synthesized, and others can similarly be synthesized.

Oligonucleotides (eg; antisense GeneBlocs) are synthesized using protocols known in the art as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.*, 74, 59, Brennan et al., 1998, *Biotechnol Bioeng.*, 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 sec coupling step for 2'-deoxy nucleotides. Table II outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. In a non-limiting example, a 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. In a non-limiting example, a 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer includebut are not limited to; detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the antisense oligonucleotides is performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. Standard drying or lyophilization methods known to those skilled in the art can be used.

The method of synthesis used for normal RNA including certain enzymatic nucleic acid molecules follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677-2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH: MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA.3HF (0.1 mL) is added and the vial is heated at 65° C. for 15 min. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

Inactive hammerhead ribozymes or binding attenuated control ((BAC) oligonucleotides) are synthesized by substituting a U for $G_5$ and a U for $A_{14}$ (numbering from Hertel, K. J., et al., 1992, Nucleic Acids Res., 20, 3252). Similarly, one or more nucleotide substitutions can be introduced in other enzymatic nucleic acid molecules to inactivate the molecule and such molecules can serve as a negative control.

The average stepwise coupling yields are typically >98% (Wincott et al., 1995 Nucleic Acids Res. 23, 2677-2684). Those of ordinary skill in the art will recognize that the scale of synthesis can be adapted to be larger or smaller than the example described above including, but not limited to, 96 well format, with the ratio of chemicals used in the reaction being adjusted accordingly.

Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

The nucleic acid molecules of the present invention are modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163). Nucleic acid conjugates of the invention can purified by gel electrophoresis using general methods or are purified by high pressure liquid chromatography (HPLC; See Wincott et al., Supra, the totality of which is hereby incorporated herein by reference) or hydrophobic interaction chromatography and are re-suspended in water.

Optimizing Activity of the Nucleic Acid Molecule of the Invention.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic acid Sciences), 48, 39-55; Verma and Eckstein, 1998, Annu. Rev. Biochem., 67, 99-134; and Burlina et al., 1997, Bioorg. Med. Chem., 5, 1999-2010; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications may cause some toxicity. Therefore, when designing nucleic acid molecules the amount of these internucleotide linkages should be minimized. Without being bound by any particular theory, the reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity can not be significantly lowered. Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. The nucleic acid molecules should be resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above.

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules can also include combinations of different types of nucleic acid molecules.

In another embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid can not be significantly lowered. As exemplified herein such enzymatic nucleic acids are useful in a cell and/or in vivo even if activity over all is reduced 10 fold (Burgin et al., 1996, *Biochemistry*, 35, 14090). Such enzymatic nucleic acids herein are said to "maintain" the enzymatic activity of an all RNA ribozyme or all DNA DNAzyme.

In another aspect the nucleic acid molecules comprise a 5' and/or a 3'-cap structure.

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods*, VCH, 331-417, and Mesmaeker et al., 1994, *Novel Backbone Replacements for Oligonucleotides*, in *Carbohydrate Modifications in Antisense Research*, ACS, 24-39. These references are hereby incorporated by reference herein.

In connection with 2'-modified nucleotides as described for the invention, by "amino" is meant 2'-NH$_2$ or 2'-O—NH$_2$, which can be modified or unmodified. Such modified groups are described, for example, in Eckstein et al., U.S. Pat. No. 5,672,695 and Matulic-Adamic et al., WO 98/28317, respectively, which are both incorporated by reference in their entireties.

Various modifications to nucleic acid (e.g., antisense and ribozyme) structure can be made to enhance the utility of these molecules. For example, such modifications can enhance shelf-life, half-life in vitro, stability, and ease of introduction of such oligonucleotides to the target site, including e.g., enhancing penetration of cellular membranes and conferring the ability to recognize and bind to targeted cells.

Use of these molecules can lead to better treatment of disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecule motifs) and/or other chemical or biological molecules). The treatment of patients with nucleic acid molecules can also include combinations of different types of nucleic acid molecules. Therapies can be devised which include a mixture of enzymatic nucleic acid molecules (including different enzymatic nucleic acid molecule motifs), antisense and/or 2-5A chimera molecules to one or more targets to alleviate symptoms of a disease.

Indications

Particular disease states that can be treated using compounds and compositions of the invention include, but are not limited to, cancers and cancerous conditions such as breast, lung, prostate, colorectal, brain, esophageal, stomach, bladder, pancreatic, cervical, hepatocellular, head and neck, and ovarian cancer, melanoma, lymphoma, glioma, multidrug resistant cancers; ocular conditions such as macular degeneration and diabetic retinopathy, and/or viral infections including HIV, HBV, HCV, CMV, RSV, HSV, poliovirus, influenza, rhinovirus, west nile virus, severe acute respiratory syndrome (SARS) virus, Ebola virus, foot and mouth virus, and papilloma virus infection.

The molecules of the invention can be used in conjunction with other known methods, therapies, or drugs. For example, the use of monoclonal antibodies (eg; mAb IMC C225, mAB ABX-EGF) treatment, tyrosine kinase inhibitors (TKIs), for example OSI-774 and ZD1839, chemotherapy, and/or radiation therapy, are all non-limiting examples of a methods that can be combined with or used in conjunction with the compounds of the instant invention. Common chemotherapies that can be combined with nucleic acid molecules of the instant invention include various combinations of cytotoxic drugs to kill the cancer cells. These drugs include, but are not limited to, paclitaxel (Taxol), docetaxel, cisplatin, methotrexate, cyclophosphamide, doxorubin, fluorouracil carboplatin, edatrexate, gemcitabine, vinorelbine etc. Those skilled in the art will recognize that other drug compounds and therapies can be similarly be readily combined with the compounds of the instant invention are hence within the scope of the instant invention.

Diagnostic Uses

The compounds of this invention, for example, nucleic acid conjugate molecules, can be used as diagnostic tools to examine genetic drift and mutations within diseased cells or to detect the presence of a disease related RNA in a cell. The close relationship between, for example, enzymatic nucleic acid molecule activity and the structure of the target RNA allows the detection of mutations in any region of the molecule which alters the base-pairing and three-dimensional structure of the target RNA. By using multiple enzymatic nucleic acid molecules conjugates of the invention, one can map nucleotide changes which are important to RNA structure and function in vitro, as well as in cells and tissues. Cleavage of target RNAs with enzymatic nucleic acid molecules can be used to inhibit gene expression and define the role (essentially) of specified gene products in the progression of disease. In this manner, other genetic targets can be defined as important mediators of the disease. These experiments can lead to better treatment of the disease progression by affording the possibility of combinational therapies (e.g., multiple enzymatic nucleic acid molecules targeted to different genes, enzymatic nucleic acid molecules coupled with known small molecule inhibitors, or intermittent treatment with combinations of enzymatic nucleic acid molecules and/or other chemical or biological molecules). Other in vitro uses of enzymatic nucleic acid molecules of this invention are well known in the art, and include detection of the presence of mRNAs associated with a disease-related condition. Such RNA is detected by determining the presence of a cleavage product after treatment with an enzymatic nucleic acid molecule using standard methodology.

In a specific example, enzymatic nucleic acid molecules that are delivered to cells as conjugates and which cleave only wild-type or mutant forms of the target RNA are used for the assay. The first enzymatic nucleic acid molecule is used to identify wild-type RNA present in the sample and the second enzymatic nucleic acid molecule is used to identify mutant RNA in the sample. As reaction controls, synthetic substrates of both wild-type and mutant RNA are cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates also serve to generate size markers for the analysis of wild-type and mutant RNAs in the sample population. Thus each analysis requires two enzymatic nucleic acid molecules, two substrates and one unknown sample which is combined into six reactions. The presence of cleavage products is determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios are correlated with higher risk whether RNA levels are compared qualitatively or quantitatively. The use of enzymatic nucleic acid molecules in diagnostic applications contemplated by the instant invention is more fully described in George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

Additional Uses

Potential uses of sequence-specific enzymatic nucleic acid molecules of the instant invention that are delivered to cells as conjugates can have many of the same applications for the study of RNA that DNA restriction endonucleases have for the study of DNA (Nathans et al., 1975 Ann. Rev. Biochem. 44:273). For example, the pattern of restriction fragments can be used to establish sequence relationships between two related RNAs, and large RNAs can be specifically cleaved to fragments of a size more useful for study. The ability to engineer sequence specificity of the enzymatic nucleic acid molecule is ideal for cleavage of RNAs of unknown sequence. Applicant has described the use of nucleic acid molecules to down-regulate gene expression of target genes in bacterial, microbial, fungal, viral, and eukaryotic systems including plant, or mammalian cells.

Example 1

Figure 5:
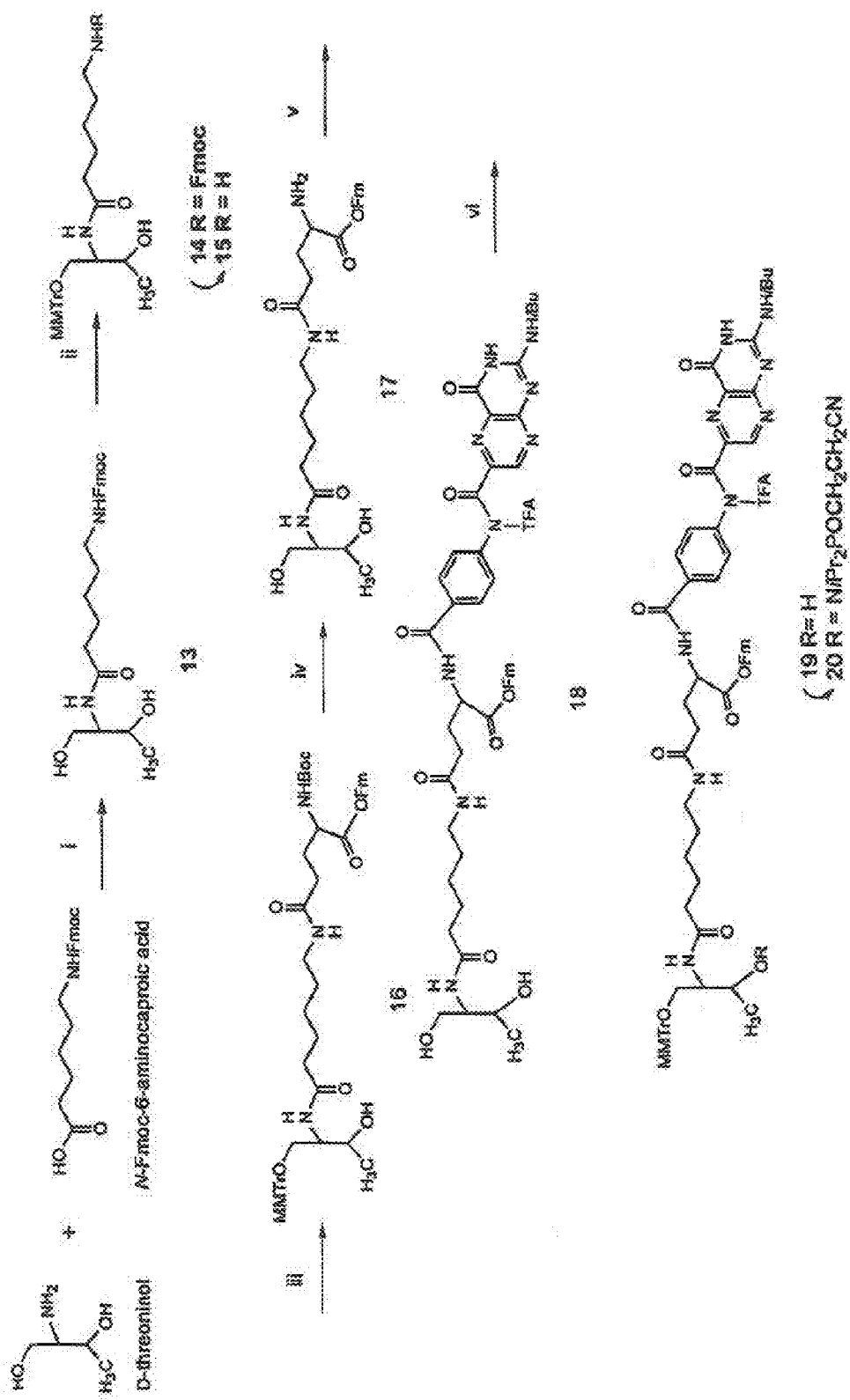
FIG. 5 shows a synthetic scheme for the synthesis of a folate conjugate of the instant invention.
Figure 6:
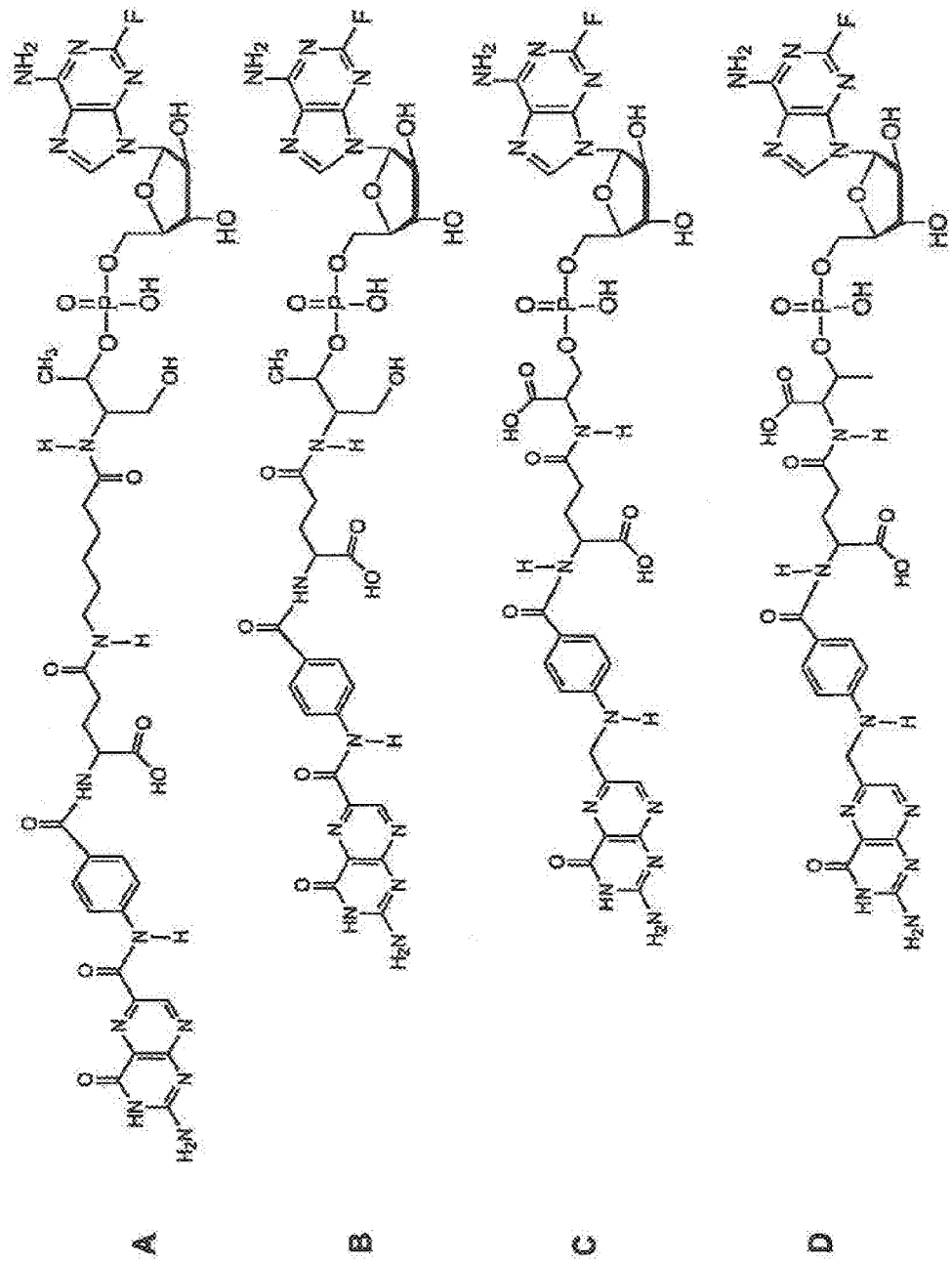
FIG. 6 shows representative examples of fludarabine-folate conjugate molecules of the invention.
Figure 7:
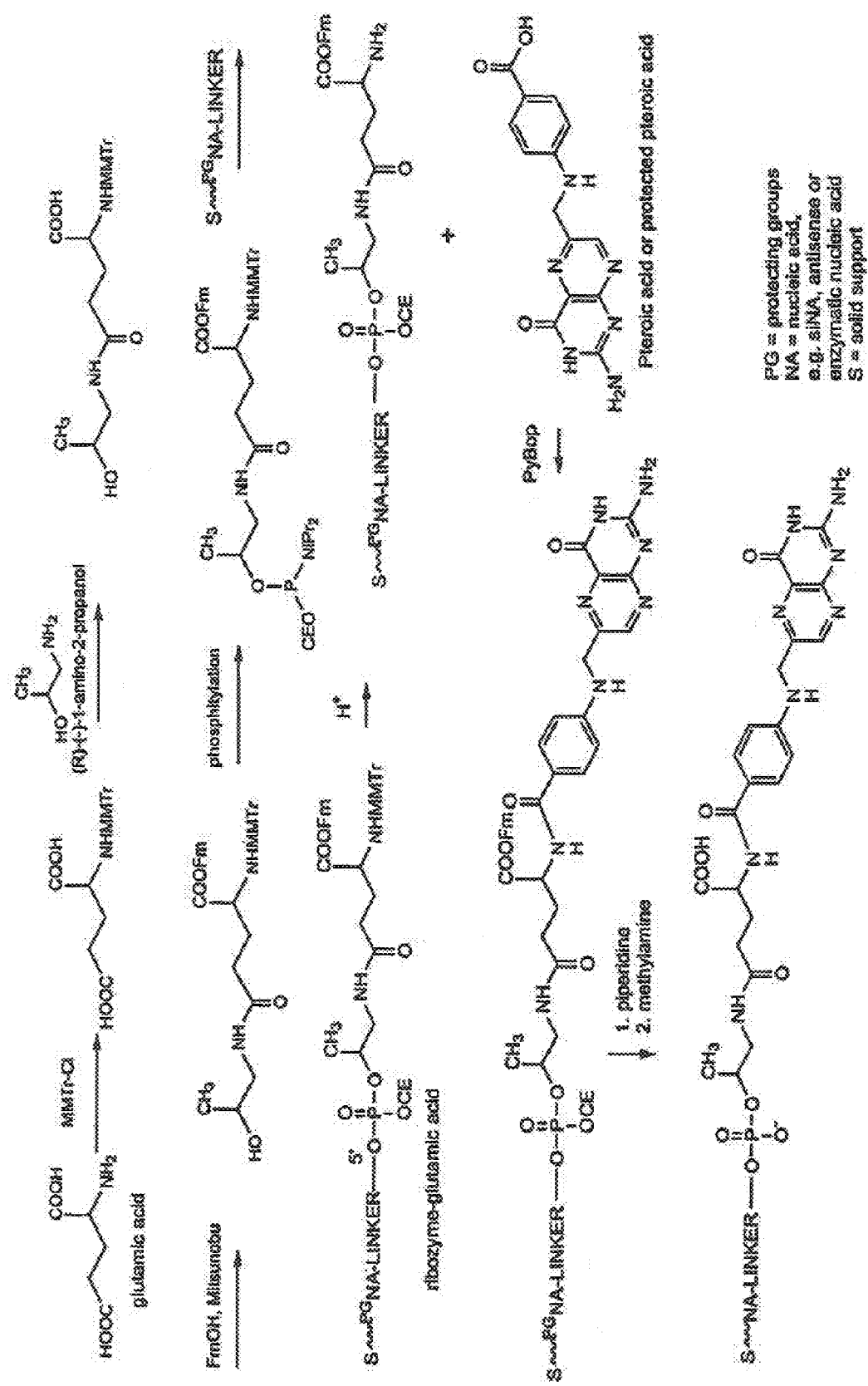
FIG. 7 shows a synthetic scheme for post-synthetic modification of a nucleic acid molecule to produce a folate conjugate.
Figure 8:
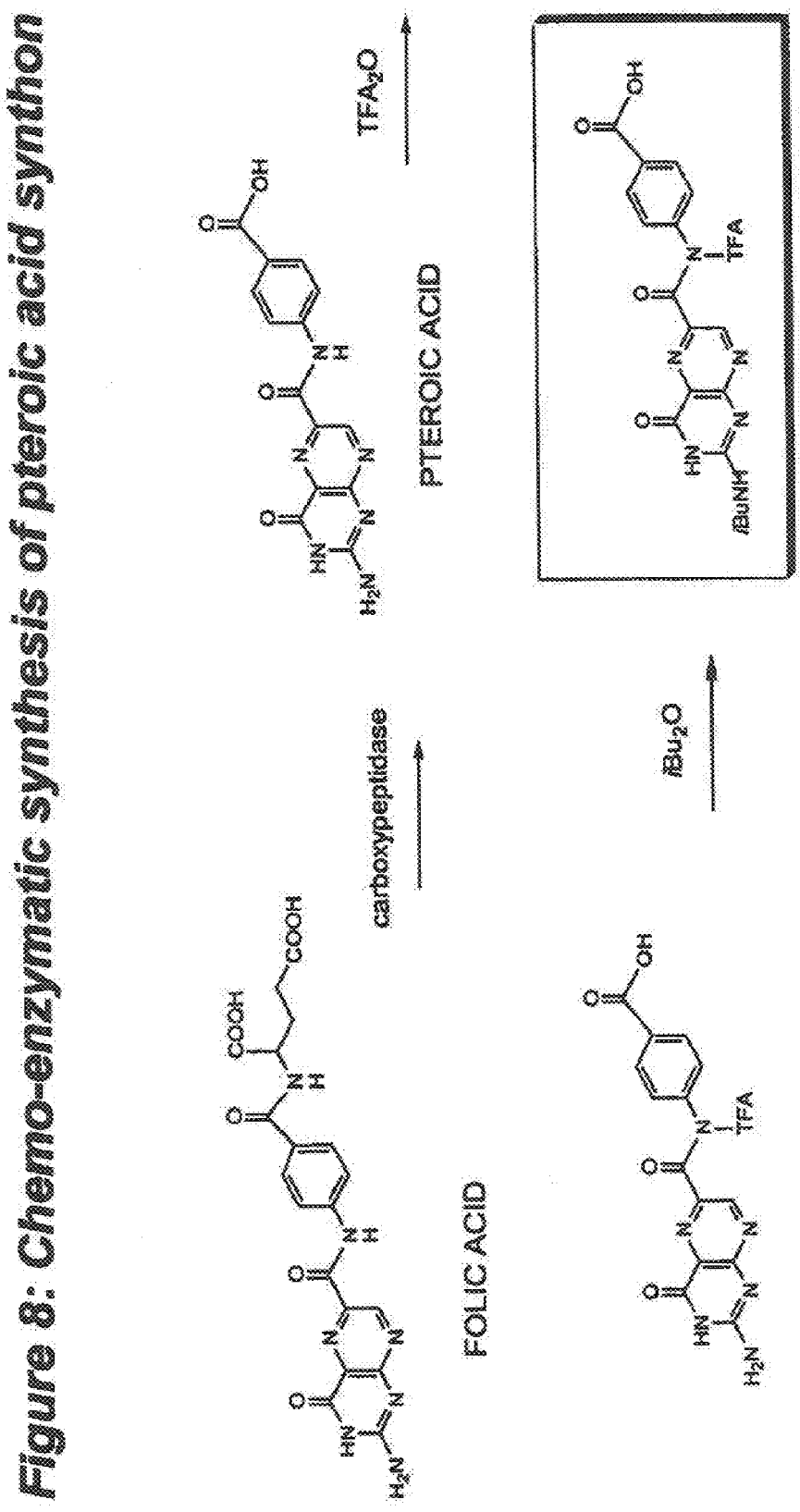
FIG. 8 shows a synthetic scheme for generating a protected pteroic acid synthon of the invention.

Synthesis of $O^1$-(4-monomethoxytrityl)-N-(6-(N-(α-OFm-L-glutamyl)aminocaproyl))-D-threoninol-$N^2$-iBu-$N^{10}$-TFA-pteroic acid conjugate 3'-O-(2-cyanoethyl-N,N-diisopropylphosphor-amidite) (20) (FIG. 5)

General. All reactions were carried out under a positive pressure of argon in anhydrous solvents. Commercially available reagents and anhydrous solvents were used without further purification. $^1$H (400.035 MHz) and $^{31}$P (161.947 MHz) NMR spectra were recorded in $CDCl_3$, unless stated otherwise, and chemical shifts in ppm refer to TMS and $H_3PO_4$, respectively. Analytical thin-layer chromatography (TLC) was performed with Merck Art.5554 Kieselgel 60 $F_{254}$ plates and flash column chromatography using Merck 0.040-0.063 mm silica gel 60.

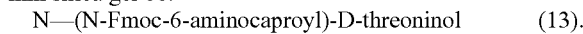

N—(N-Fmoc-6-aminocaproyl)-D-threoninol (13). N-Fmoc-6-aminocaproic acid (10 g, 28.30 mmol) was dissolved in DMF (50 ml) and N-hydroxysuccinimide (3.26 g, 28.30 mmol) and 1,3-dicyclohexylcarbodiimide (5.84 g, 28.3 mmol) were added to the solution. The reaction mixture was stirred at RT (about 23° C.) overnight and the precipitated 1,3-dicyclohexylurea filtered off. To the filtrate D-threoninol (2.98 g, 28.30 mmol) was added and the reaction mixture stirred at RT overnight. The solution was reduced to ca half the volume in vacuo, the residue diluted with about m ml of ethyl acetate and extracted with about x ml of 5% $NaHCO_3$, followed by washing with brine. The organic layer was dried ($Na_2SO_4$), evaporated to a syrup and chromatographed by silica gel column chromatography using 1-10% gradient of methanol in ethyl acetate. Fractions containing the product were pooled and evaporated to a white solid (9.94 g, 80%). $^1$H-NMR (DMSO-$d_6$-$D_2O$) δ7.97-7.30 (m, 8H, aromatic), 4.34 (d, J=6.80, 2H, Fm), 4.26 (t, J=6.80, 1H, Fm), 3.9 (m, 1H, H3 Thr), 3.69 (m, 1H, H2 Thr), 3.49 (dd, J=10.6, J=7.0, 1H, H1 Thr), 3.35 (dd, J=10.6, J=6.2, 1H, H1' Thr), 3.01 (m, 2H, $CH_2CO$ Acp), 2.17 (m, 2H, $CH_2NH$ Acp), 1.54 (m, 2H, $CH_2$ Acp), 1.45 (m, 2H, $CH_2$ Acp), 1.27 (m, 2H, $CH_2$ Acp), 1.04 (d, J=6.4, 3H, $CH_3$). MS/ESI$^+$ m/z 441.0 $(M+H)^+$.

$O^1$-(4-Monomethoxytrityl)-N—(N-Fmoc-6-aminocaproyl)-D-threoninol (14). To the solution of 13 (6 g, 13.62 mmol) in dry pyridine (80 ml) p-anisylchlorodiphenyl-methane (6 g, 19.43 mmol) was added and the reaction mixture stirred at RT overnight. Methanol was added (20 ml) and the solution concentrated in vacuo. The residual syrup was partitioned between about x ml of dichloromethane and about x ml of 5% $NaHCO_3$, the organic layer was washed with brine, dried ($Na_2SO_4$) and evaporated to dryness. Flash column chromatography using 1-3% gradient of methanol in dichloromethane afforded 14 as a white foam (6 g, 62%). $^1$H-NMR (DMSO) δ7.97-6.94 (m, 22H, aromatic), 4.58 (d, 1H, J=5.2, OH), 4.35 (d, J=6.8, 2H, Fm), 4.27 (t, J=6.8, 1H, Fm), 3.97 (m, 2H, H2, H3 Thr), 3.80 (s, 3H, $OCH_3$), 3.13 (dd, J=8.4, J=5.6, 1H, H1 Thr), 3.01 (m, 2H, $CH_2CO$ Acp), 2.92 (m, dd, J=8.4, J=6.4, 1H, H1' Thr), 2.21 (m, 2H, $CH_2NH$ Acp), 1.57 (m, 2H, $CH_2$ Acp), 1.46 (m, 2H, $CH_2$ Acp), 1.30 (m, 2H, $CH_2$ Acp), 1.02 (d, J=5.6, 3H, $CH_3$). MS/ESI$^+$ m/z 735.5 $(M+Na)^+$.

$O^1$-(4-Monomethoxytrityl)-N-(6-aminocaproyl)-D-threoninol (15). 14 (9.1 g, 12.77 mmol) was dissolved in DMF (100 ml) containing piperidine (10 ml) and the reaction mixture was kept at RT for about 1 hour. The solvents were removed in vacuo and the residue purified by silica gel column chromatography using 1-10% gradient of methanol in dichloromethane to afford 15 as a syrup (4.46 g, 71%). $^1$H-NMR δ7.48-6.92 (m, 14H, aromatic), 6.16 (d, J=8.8, 1H, NH), 4.17 (m, 1H, H3 Thr), 4.02 (m, 1H, H2 Thr), 3.86 (s, 3H, $OCH_3$), 3.50 (dd, J=9.7, J=4.4, 1H, H1 Thr), 3.37 (dd, J=9.7, J=3.4, 1H, H1' Thr), 2.78 (t, J=6.8, 2H, $CH_2CO$ Acp), 2.33 (t, J=7.6, 2H, $CH_2NH$ Acp), 1.76 (m, 2H, $CH_2$ Acp), 1.56 (m, 2H, $CH_2$ Acp), 1.50 (m, 2H, $CH_2$ Acp), 1.21 (d, J=6.4, 3H, $CH_3$). MS/ESI$^+$ m/z 491.5 $(M+H)^+$.

$O^1$-(4-Monomethoxytrityl)-N-(6-(N—(N-Boc-α-OFm-L-glutamyl)aminocaproyl))-D-threoninol (16). To the solution of N-Boc-α-OFm-glutamic acid (Bachem) (1.91 g, 4.48 mmol) in DMF (10 ml) N-hydroxysuccinimide (518 mg, 4.50 mmol) and 1,3-dicyclohexylcarbodiimide (928 mg, 4.50 mmol) was added and the reaction mixture was stirred at RT overnight. 1,3-Dicyclohexylurea was filtered off and to the filtrate 15 (2 g, 4.08 mmol) and pyridine (2 ml) were added. The reaction mixture was stirred at RT for 3 hours and than concentrated in vacuo. The residue was partitioned between ethyl acetate and 5% $Na_2HCO_3$, the organic layer extracted with brine as previously described, dried ($Na_2SO_4$) and evaporated to a syrup. Column chromatography using 2-10% gradient of methanol in dichlotomethane afforded 16 as a white foam (3.4 g, 93%). $^1$H-NMR δ7.86-6.91 (m, 22H, aromatic), 6.13 (d, J=8.8, 1H, NH), 5.93 (br s, 1H, NH), 5.43 (d, J=8.4, 1H, NH), 4.63 (dd, J=10.6, J=6.4, 1H, Fm), 4.54 (dd, J=10.6, J=6.4, 1H, Fm), 4.38 (m, 1H, Glu), 4.3 (t, J=6.4, 1H, Fm), 4.18 (m, 1H, H3 Thr), 4.01 (m, 1H, H2 Thr), 3.88 (s, 3H, $OCH_3$), 3.49 (dd, J=9.5, J=4.4, 1H, H1 Thr), 3.37 (dd, J=9.5, J=3.8, 1H, H1' Thr), 3.32 (m, 2H, $CH_2CO$ Acp), 3.09 (br s, 1H, OH), 2.32 (m, 2H, $CH_2NH$ Acp), 2.17 (m, 3H, Glu), 1.97 (m, 1H, Glu), 1.77 (m, 2H, $CH_2$ Acp), 1.61 (m, 2H, $CH_2$ Acp), 1.52 (s, 9H, t-Bu), 1.21 (d, J=6.4, 3H, $CH_3$). MS/ESI$^+$ m/z 920.5 (M+Na)$^+$.

N-(6-(N-α-OFm-L-glutamyl)aminocaproyl))-D-threoninol hydrochloride (17). 16 (2 g, 2.23 mmol) was dissolved in methanol (30 ml) containing anisole (10 ml) and to this solution x ml of 4M HCl in dioxane was added. The reaction mixture was stirred for 3 hours at RT and then concentrated in vacuo. The residue was dissolved in ethanol and the product precipitated by addition of x ml of ether. The precipitate was washed with ether and dried to give 17 as a colorless foam (1 g, 80%). $^1$H-NMR (DMSO-$d_6$-$D_2O$) δ7.97-7.40 (m, 8H, aromatic), 4.70 (m, 1H, Fm), 4.55 (m, 1H, Fm), 4.40 (t, J=6.4, 1H, Fm), 4.14 (t, J=6.6, 1H, Glu), 3.90 (dd, J=2.8, J=6.4, 1H, H3 Thr), 3.68 (m, 1H, H2 Thr), 3.49 (dd, J=10.6, J=7.0, 1H, H1 Thr), 3.36 (dd, J=10.6, J=6.2, 1H, H1' Thr), 3.07 (m, 2H, $CH_2CO$ Acp), 2.17 m, 3H), 1.93 (m, 2H), 1.45 (m, 2H), 1.27 (m, 2H), 1.04 (d, J=6.4, 3H Thr). MS/ESI$^+$ m/z 526.5 (M+H)$^+$.

N-(6-(N-α-OFm-L-glutamyl)aminocaproyl))-D-threoninol-$N^2$-iBu-$N^{10}$-TFA-pteroic acid conjugate (18). To the solution of $N^2$-iBu-$N^{10}$-TFA-pteroic acid$^1$ (480 mg, 1 mmol) in DMF (5 ml) 1-hydroxybenzotriazole (203 mg, 1.50 mmol), EDCI (288 mg, 1.50 mmol) and 17 (free base, 631 mg, 1.2 mmol) are added. The reaction mixture is stirred at RT for 2 hours, then concentrated to ca 3 ml and loaded on the column of silica gel. Elution with dichloromethane, followed by 1-20% gradient of methanol in dichloromethane afforded 18 (0.5 g, 51%). $^1$H-NMR (DMSO-$d_6$-$D_2O$) δ 9.09 (d, J=6.8, 1H, NH) 8.96 (s, 1H, H7 pteroic acid), 8.02-7.19 (m, 13H, aromatic, NH), 5.30 (s, 2H, pteroic acid), 4.50 (m, 1H, Glu), 4.41 (d, J=6.8, 2H, Fm), 4.29 (t, J=6.8, 1H, Fm), 3.89 (dd, J=6.2, J=2.8, 1H, H3 Thr), 3.68 (m, 1H, H2 Thr), 3.48 (dd, J=10.4, J=7.0, 1H, H1 Thr), 3.36 (dd, J=10.4, J=6.2, 1H H1' Thr), 3.06 (m, 2H, $CH_2CO$ Acp), 2.84 (m, 1H, iBu), 2.25 (m, 2H, $CH_2NH$ Acp), 2.16 (m, 3H, Glu), 1.99 (m, 1H, Glu), 1.52 (m, 2H Acp), 1.42 (m, 2H Acp), 1.27 (m, 2H Acp), 1.20 (s, 3H iBu), 1.19 (s, 3H, iBu), 1.03 (d, J=6.2, 3H Thr). MS/ESI$^-$ m/z 984.5 (M–H)$^-$.

$O^1$-(4-monomethoxytrityl)-N-(6-(N-α-OFm-L-glutamyl) aminocaproyl))-D-threoninol-$N^2$-iBu-$N^{10}$-TFA-pteroic acid conjugate (19). To the solution of conjugate 18 (1 g, 1.01 mmol) in dry pyridine (15 ml) p-anisylchlorodiphenylmethane (405 mg) was added and the reaction mixture was stirred, protected from moisture, at RT overnight. Methanol (3 ml) was added and the reaction mixture concentrated to a syrup in vacuo. The residue was partitioned between dichloromethane and 5% $NaHCO_3$, the organic layer washed with brine, dried ($Na_2SO_4$) and evaporated to dryness. Column chromatography using 0.5-10% gradient of methanol in dichloromethane afforded 19 as a colorless foam (0.5 g, 39%. $^1$H-NMR (DMSO-$d_6$-$D_2O$ δ9.09 (d, J=6.8, 1H, NH) 8.94 (s, 1H, H7 pteroic acid), 8.00-6.93 (m, 27H, aromatic, NH), 5.30 (s, 2H, pteroic acid), 4.50 (m, 1H, Glu), 4.40 (d, J=6.8, 2H, Fm), 4.29 (t, J=6.8, 1H, Fm), 3.94 (m, 2H, H3, H2 Thr), 3.79 (s, 3H, $OCH_3$) 3.11 (dd, J=8.6, J=5.8, 1H, H1 Thr), 3.04 (m, 2H, $CH_2CO$ Acp), 2.91 (dd, J=8.6, J=6.4, 1H, H1' Thr), 2.85 (m, 1H, iBu), 2.25 (m, 2H, $CH_2NH$ Acp), 2.19 (m, 2H, Glu), 2.13 (m, 1H, Glu), 1.98 (m, 1H, Glu), 1.55 (m, 2H Acp), 1.42 (m, 2H Acp), 1.29 (m, 2H Acp), 1.20 (s, 3H iBu), 1.18 (s, 3H, iBu), 1.00 (d, J=6.4, 3H Thr). MS/ESI$^-$ m/z 1257.0 (M–H)$^-$.

$O^1$-(4-monomethoxytrityl)-N-(6-(N-α-OFm-L-glutamyl) aminocaproyl))-D-threoninol-$N^2$-iBu-$N^{10}$-TFA-pteroic acid conjugate 3'-O-(2-cyanoethyl-N,N-diisopropylphosphoramidite) (20). To the solution of 19 (500 mg, 0.40 mmol) in dichloromethane (2 ml) 2-cyanoethyl tetraisopropylphosphordiamidite (152 μL, 0.48 mmol) was added followed by pyridinium trifluoroacetate (93 mg, 0.48 mmol). The reaction mixture was stirred at RT for 1 hour and than loaded on the column of silica gel in hexanes. Elution using ethyl acetate-hexanes 1:1, followed by ethyl acetate and ethyl acetate-acetone 1:1 in the presence of 1% pyridine afforded 20 as a colorless foam (480 mg, 83%). $^{31}$P NMR δ 149.4 (s), 149.0 (s).

Example 2

Figure 9:
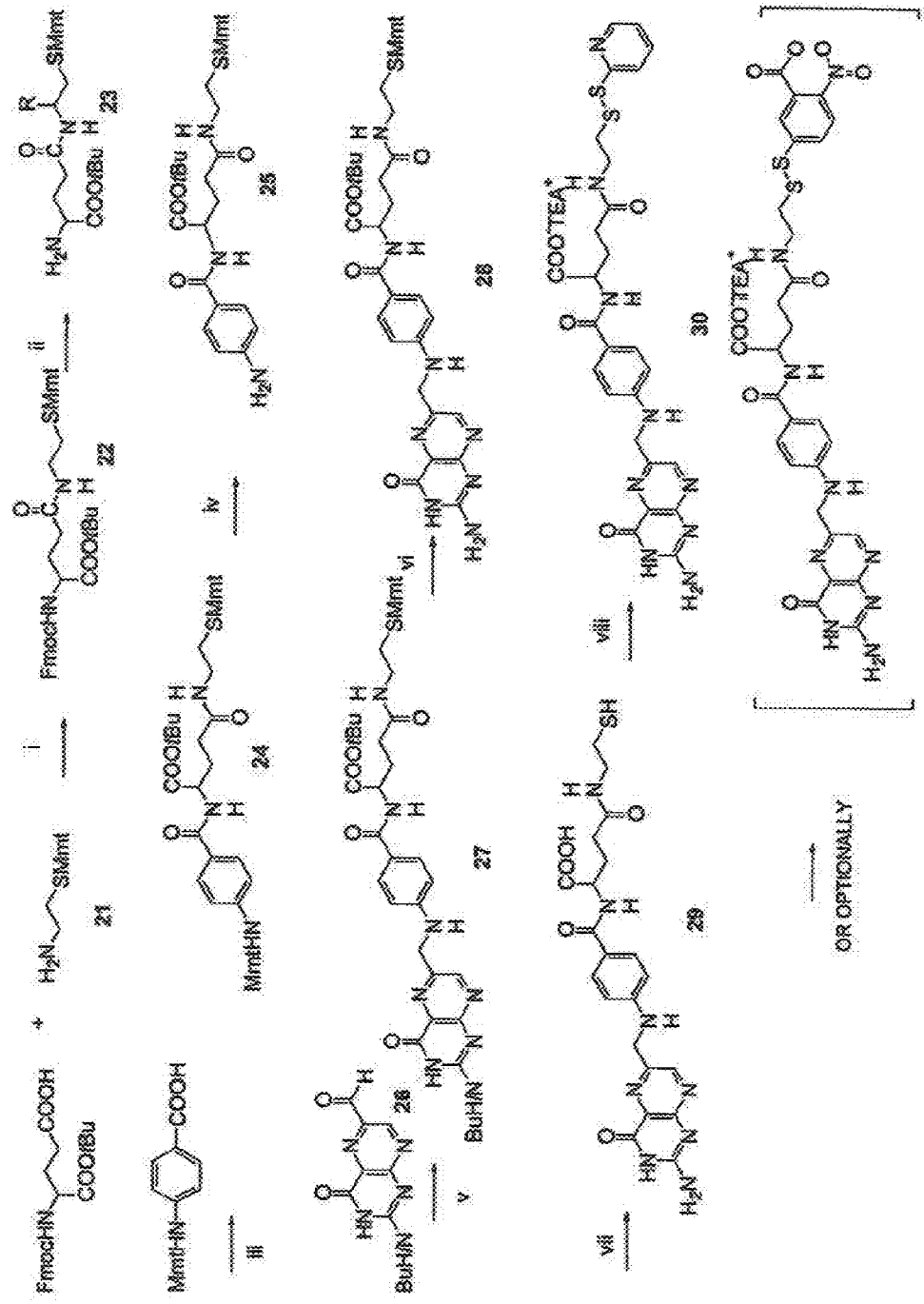
FIG. 9 shows a synthetic scheme for generating a 2-dithiopyridyl activated folic acid synthon of the invention.

Synthesis of 2-dithiopyridyl activated folic acid (30) (FIG. 9)

Synthesis of the cysteamine modified folate 30 is presented in FIG. 9. Monomethoxytrityl cysteamine 21 was prepared by selective tritylation of the thiol group of cysteamine with 4-methoxytrityl alcohol in trifluoroacetic acid. Peptide coupling of 21 with Fmoc-Glu-OtBu (Bachem Bioscience Inc., King of Prussia, Pa.) in the presence of PyBOP yielded 22 in a high yield. N-Fmoc group was removed smoothly with piperidine to give 23. Condensation of 23 with p-(4-methoxytrityl)aminobenzoic acid, prepared by reaction of p-aminobenzoic acid with 4-methoxytrityl chloride in pyridine, afforded the fully protected conjugate 24. Selective cleavage of N-MMTr group with acetic acid afforded 25 in quantitative yield. Shiff base formation between 25 and $N^2$-iBu-6-formylpterin 26,[9] followed by reduction with borane-pyridine complex proceeded with a good yield to give fully protected cysteamine-folate adduct 27.[12] The consecutive cleavage of protecting groups of 27 with base and acid yielded thiol derivative 29. The thiol exchange reaction of 29 with 2,2-dipyridyl disulfide afforded the desired S-pyridyl activated synthon 30 as a yellow powder; Isolated as a TEA$^+$+ salt: $^1$H NMR spectrum for 10 in $D_2O$: δ8.68 (s, 1H, H-7), 8.10 (d, J=3.6, 1H, pyr), 7.61 (d, J=8.8, 2H, PABA), 7.43 (m, 1H, pyr), 7.04 (d, J=7.6, 1H, pyr), 6.93 (m, 1H, pyr), 6.82 (d, J=8.8, 1H, PABA), 4.60 (s, 2H, 6-$CH_2$), 4.28 (m, 1H, Glu), 3.30-3.08 (m, 2H, cysteamine), 3.05 (m, 6H, TEA), 2.37 (m, 2H, cysteamine), 2.10 (m, 4H, Glu), 1.20 (m, 9H, TEA). MS/ESI$^-$ m/z 608.02 [M–H]$^-$. It is worth noting that the isolation of 30 as its TEA$^+$ or Na$^+$ salt made it soluble in DMSO and/or water, which is an important requirement for its use in conjugation reactions.

Example 3

Figure 10:
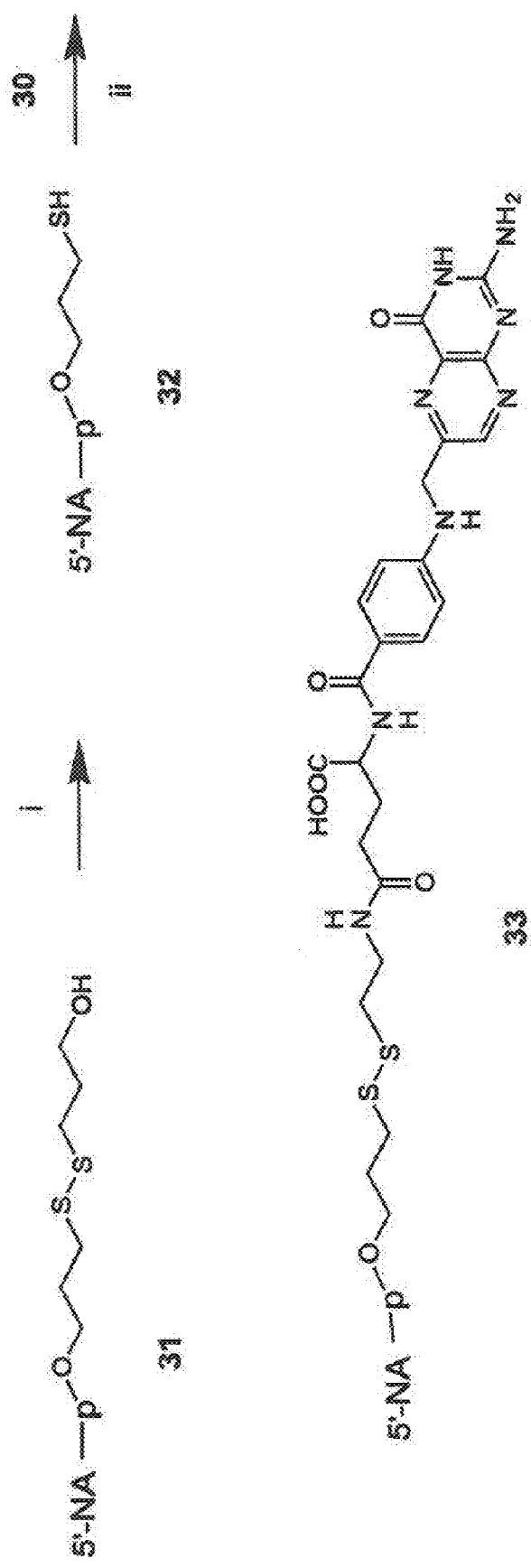
FIG. 10 shows a synthetic scheme for generating an oligonucleotide or nucleic acid-folate conjugate.

Post Synthetic Conjugation of Enzymatic Nucleic Acid to Form Nucleic Acid-Folate Conjugate (33) (FIG. 10)

Figure 11:
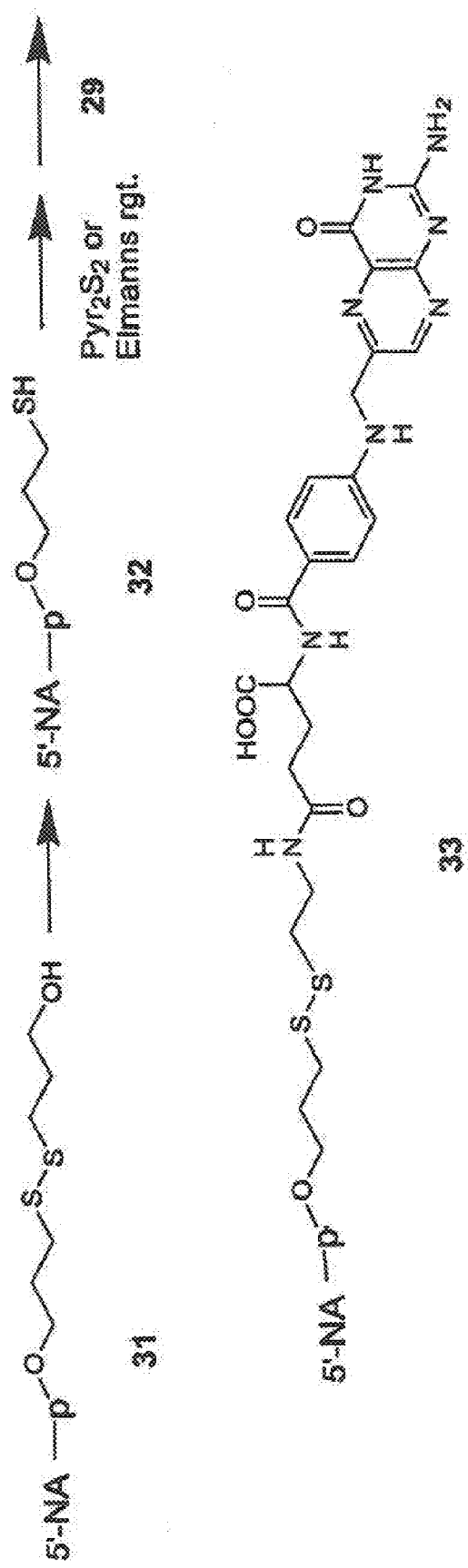
FIG. 11 shows an alternative synthetic scheme for generating an oligonucleotide or nucleic acid-folate conjugate.

Oligonucleotide synthesis, deprotection and purification was performed as described herein. 5'-Thiol-Modifier C6 (Glen Research, Sterling, Va.) was coupled as the last phosphoramidite to the 5'-end of a growing oligonucleotide chain. After cleavage from the solid support and base deprotection, the disulfide modified enzymatic nucleic acid molecule 31 (FIG. 10) was purified using ion exchange chromatography. The thiol group was unmasked by reduction with dithiothreitol (DTT) to afford 32 which was purified by gel filtration and immediately conjugated with 30. The resulting conjugate 33 was separated from the excess folate by gel filtration and then purified by RP HPLC using gradient of acetonitrile in 50 mM triethylammonium acetate (TEAA). Desalting was performed by RP HPLC. Reactions were conducted on 400 mg of disulfide modified enzymatic nucleic acid molecule 31 to afford 200-250 mg (50-60% yield) of conjugate 33. MALDI TOF MS confirmed the structure: 13 [M–H]$^-$ 12084.74 (calc. 12083.82). An alternative approach to this synthesis is shown in FIG. 11.

As shown in Examples 2 and 3, a folate-cysteamine adduct can be prepared by a scaleable solution phase synthesis in a good overall yield. Disulfide conjugation of this novel targeting ligand to the thiol-modified oligonucleotide is suitable for the multi-gram scale synthesis. The 9-atom spacer provides a useful spatial separation between folate and attached oligonucleotide cargo. Importantly, conjugation of folate to the oligonucleotide through a disulfide bond should permit intermolecular separation which was suggested to be required for the functional cytosolic entry of a protein drug.

Example 4

Synthesis of Galactose and N-acetyl-Galactosamine Conjugates (FIGS. 13, 14, and 15)

Applicant has designed both nucleoside and non-nucleoside-N-acetyl-D-galactosamine conjugates suitable for incorporation at any desired position of an oligonucleotide. Multiple incorporations of these monomers could result in a "glycoside cluster effect".

All reactions were carried out under a positive pressure of argon in anhydrous solvents. Commercially available reagents and anhydrous solvents were used without further purification. N-acetyl-D-galactosamine was purchased from Pfanstiel (Waukegan, Ill.), folic acid from Sigma (St. Louis, Mo.), D-threoninol from Aldrich (Milwaukee, Wis.) and N-Boc-α-OFm glutamic acid from Bachem. $^1$H (400.035 MHz) and $^{31}$P (161.947 MHz) NMR spectra were recorded in CDCl$_3$, unless stated otherwise, and chemical shifts in ppm refer to TMS and H3PO4, respectively. Analytical thin-layer chromatography (TLC) was performed with Merck Art.5554 Kieselgel 60 F$_{254}$ plates and flash column chromatography using Merck 0.040-0.063 mm silica gel 60. The general procedures for RNA synthesis, deprotection and purification are described herein. MALDI-TOF mass spectra were determined on PerSeptive Biosystems Voyager spectrometer. Electrospray mass spectrometry was run on the PE/Sciex API365 instrument.

2'-(N-L-lysyl)amino-5'-O-4,4'-dimethoxytrityl-2'-deoxyuridine (2). 2'-(N-α,ε-bis-Fmoc-L-lysyl)amino-5'-O-4,4'-dimethoxytrityl-2'-deoxyuridine (1) (4 g, 3.58 mmol) was dissolved in anhydrous DMF (30 ml) and diethylamine (4 ml) was added. The reaction mixture was stirred at rt for 5 hours and than concentrated (oil pump) to a syrup. The residue was dissolved in ethanol and ether was added to precipitate the product (1.8 g, 75%). $^1$H-NMR (DMSO-d$_6$-D$_2$O) $_\delta$ 7.70 (d, $J_{6,5}$=8.4, 1H, H6), 7.48-6.95 (m, 13H, aromatic), 5.93 (d, $J_{1',2'}$=8.4, 1H, H1'), 5.41 (d, $J_{5,6}$=8.4, 1H, H5), 4.62 (m, 1H, H2'), 4.19 (d, 1H, $J_{3',2'}$=6.0, H3'), 3.81 (s, 6H, 2×OMe), 3.30 (m, 4H, 2H5', CH$_2$), 1.60-1.20 (m, 6H, 3×CH$_2$). MS/ESI$^+$ m/z 674.0 (M+H)$^+$.

N-Acetyl-1,4,6-tri-O-acetyl-2-amino-2-deoxy-β-D-galactospyranose (3). N-Acetyl-D-galac-tosamine (6.77 g, 30.60 mmol) was suspended in acetonitrile (200 ml) and triethylamine (50 ml, 359 mmol) was added. The mixture was cooled in an ice-bath and acetic anhydride (50 ml, 530 mmol)) was added dropwise under cooling. The suspension slowly cleared and was then stirred at rt for 2 hours. It was than cooled in an ice-bath and methanol (60 ml) was added and the stirring continued for 15 min. The mixture was concentrated under reduced pressure and the residue partitioned between dichloromethane and 1 N HCl. Organic layer was washed twice with 5% NaHCO$_3$, followed by brine, dried (Na$_2$SO$_4$) and evaporated to dryness to afford 10 g (84%) of 3 as a colorless foam. $^1$H NMR was in agreement with published data (Findeis, 1994, *Int. J. Peptide Protein Res.*, 43, 477-485.

2-Acetamido-3,4,6-tetra-O-acetyl-1-chloro-D-galactospyranose (4). This compound was prepared from 3 as described by Findeis supra.

Benzyl 12-Hydroxydodecanoate (5). To a cooled (0° C.) and stirred solution of 12-hydroxydodecanoic acid (10.65 g, 49.2 mmol) in DMF (70 ml) DBU (8.2 ml, 54.1 mmol) was added, followed by benzyl bromide (6.44 ml, 54.1 mmol). The mixture was left overnight at rt, than concentrated under reduced pressure and partitioned between 1 N HCl and ether. Organic phase was washed with saturated NaHCO$_3$, dried over Na$_2$SO$_4$ and evaporated. Flash chromatography using 20-30% gradient of ethyl acetate in hexanes afforded benzyl ester as a white powder (14.1 g, 93.4%). $^1$H-NMR spectral data were in accordance with the published values.[33]

12'-Benzyl hydroxydodecanoyl-2-acetamido-3,4,6-tri-O-acetyl-2-deoxy-β-D-galactopyrano-se (6). 1-Chloro sugar 4 (4.26 g, 11.67 mmol) and benzyl 12-hydroxydodecanoate (5) (4.3 g, 13.03 mmol) were dissolved in nitromethane-toluene 1:1 (122 ml) under argon and Hg(CN)$_2$ (3.51 g, 13.89 mmol) and powdered molecular sieves 4A (1.26 g) were added. The mixture was stirred at rt for 24 h, filtered and the filtrate concentrated under reduced pressure. The residue was partitioned between dichloromethane and brine, organic layer was washed with brine, followed by 0.5 M KBr, dried (Na$_2$SO$_4$) and evaporated to a syrup. Flash silica gel column chromatography using 15-30% gradient of acetone in hexanes yielded product 6 as a colorless foam (6 g, 81%). $^1$H-NMR $_\delta$ 7.43 (m, $_{5H}$, phenyl), 5.60 (d, 1H, J$_{NH,2}$=8.8, NH), 5.44 (d, J$_{4,3}$=3.2, 1H, H4), 5.40 (dd, $_{J3,4}$=3.2, J$_{3,2}$=10.8, 1H, H3), 5.19 (s, 2H, CH$_2$Ph), 4.80 (d, J$_{1,2}$=8.0, 1H, H1), 4.23 (m, 2H, CH$_2$), 3.99 (m, 3H, H2, H6), 3.56 (m, 1H, H5), 2.43 (t, J=7.2, 2H, CH$_2$), 2.22 (s, 3H, Ac), 2.12 (s, 3H, Ac), 2.08 (s, 3H, Ac), 2.03 (s, 3H, Ac), 1.64 (m, 4H, 2×CH$_2$), 1.33 (br m, 14H, 7×CH$_2$). MS/ESI$^-$ m/z 634.5 (M–H)$^-$.

12'-Hydroxydodecanoyl-2-acetamido-3,4,6-tri-O-acetyl-2-deoxy-β-D-galactopyranose (7).

Conjugate 6 (2 g, 3.14 mmol)) was dissolved in ethanol (50 ml) and 5% Pd—C (0.3 g) was added. The reaction mixture was hydrogenated overnight at 45 psi H$_2$, the catalyst was filtered off and the filtrate evaporated to dryness to afford pure 7 (1.7 g, quantitative) as a white foam. $^1$H-NMR $_\delta$ 5.73 (d, 1H, $J_{NH,2}$=8.4, NH), 5.44 (d, $J_{4,3}$=3.0, 1H, H4), 5.40 (dd, $J_{3,4}$=3.0, $J_{3,2}$=11.2, 1H, H3), 4.78 (d, $J_{1,2}$=8.8, 1H, H1), 4.21 (m, 2H, CH$_2$), 4.02 (m, 3H, H2, H6), 3.55 (m, 1H, H5), 2.42 (m, 2H, CH$_2$), 2.23 (s, 3H, Ac), 2.13 (s, 3H, Ac), 2.09 (s, 3H, Ac), 2.04 (s, 3H, Ac), 1.69 (m, 4H, 2×CH$_2$), 1.36 (br m, 14H, 7×CH$_2$). MS/ESI⁻ m/z 544.0 (M−H)⁻.

2'-(N-α-bis-(12'-Hydroxydodecanoyl-2-acetamido-3,4,6-tri-O-acetyl-2-deoxy-β-D-galac-topyranose)-L-lysyl) amino-2'-deoxy-5'-O-4,4'-dimethoxytrityl uridine (9). 7 (1.05 g, 1.92 mmol) was dissolved in anhydrous THF and N-hydroxysuccinimide (0.27 g, 2.35 mmol) and 1,3-dicyclohexylcarbodiimide (0.55 g, 2.67 mmol) were added. The reaction mixture was stirred at rt overnight, then filtered through Celite pad and the filtrate concentrated under reduced pressure. The crude NHSu ester 8 was dissolved in dry DMF (13 ml) containing diisopropylethylamine (0.67 ml, 3.85 mmol) and to this solution nucleoside 2 (0.64 g, 0.95 mmol was added). The reaction mixture was stirred at rt overnight and than concentrated under reduced pressure. The residue was partitioned between water and dichloromethane, the aqueous layer extracted with dichloromethane, the organic layers combined, dried (Na$_2$SO$_4$) and evaporated to a syrup. Flash silica gel column chromatography using 2-3% gradient of methanol in ethyl acetate yielded 9 as a colorless foam (1.04 g, 63%). ¹H-NMR $_δ$ 7.42 (d, $J_{6,5}$=8.4, 1H, H6 Urd), 7.53-6.97 (m, 13H, aromatic), 6.12 (d, $J_{1,2}$=8.0, 1H, H-1'), 5.41 (m, 3H, H5 Urd, H4 NAcGal), 5.15 (dd, $J_{3,4}$=3.6, $J_{3,2}$=11.2, 2H, H$_3$NAcGal), 4.87 (dd, $J_{2',3'}$=5.6, $J_{2',1}$=8.0, 1H, H2'), 4.63 (d, $J_{1,2}$=8.0, 2H, H1 NAcGal), 4.42 (d, $J_{3',2'}$=5.6, 1H, H3'), 4.29-4.04 (m, 9H, H4', H$_2$NAcGal, H$_5$NacGal, CH$_2$), 3.95-3.82 (m, 8H, H6 NAcGal, 2×OMe), 3.62-3.42 (m, 4H, H5', H$_6$NAcGal), 3.26 (m, 2H, CH$_2$), 2.40-1.97 (m, 28H, CH$_2$, Ac), 1.95-1.30 (m, 50H, CH$_2$). MS/ESI⁻ m/z 1727.0 (M−H)⁻.

2'-(N-α-bis-(12'-Hydroxydodecanoyl-2-acetamido-3,4,6-tri-O-acetyl-2-deoxy-β-D-galac-topyranose)-L-lysyl) amino-2'-deoxy-5'-O-4,4'-dimethoxytrityl uridine 3'-O-(2-cyanoethyl N,N-diisopropylphosphoramidite) (10). Conjugate 9 (0.87 g, 0.50 mmol) was dissolved in dry dichloromethane (10 ml) under argon and diisopropylethylamine (0.36 ml, 2.07 mmol) and 1-methylimidazole (21 μL, 0.26 mmol) were added. The solution was cooled to 0° C. and 2-cyanoethyl diisopropylchlorophosphoramidite (0.19 ml, 0.85 mmol) was added. The reaction mixture was stirred at rt for 1 hour, than cooled to 0° C. and quenched with anhydrous ethanol (0.5 ml). After stirring for 10 min the solution was concentrated under reduced pressure (40° C.) and the residue dissolved in dichloromethane and chromatographed on the column of silica gel using hexanes-ethyl acetate 1:1, followed by ethyl acetate and finally ethyl acetate-acetone 1:1 (1% triethylamine was added to solvents) to afford the phosphoramidite 10 (680 mg, 69%). ³¹P-NMR $_δ$ 152.0 (s), 149.3 (s). MS/ESI⁻ m/z 1928.0 (M−H)⁻.

N-(12'-Hydroxydodecanoyl-2-acetamido-3,4,6-tri-O-acetyl-2-deoxy-β-D-galactopyranose)-D-threoninol (11). 12'-Hydroxydodecanoyl-2-acetamido-3,4,6-tri-O-acetyl-2-deoxy-β-D-galac-topyranose 7 (850 mg, 1.56 mmol) was dissolved in DMF (5 ml) and to the solution N-hydroxysuccinimide (215 mg, 1.87 mmol) and 1,3-dicyclohexylcarbodiimide (386 mg, 1.87 mmol) were added. The reaction mixture was stirred at rt overnight, the precipitate was filtered off and to the filtrate D-threoninol (197 mg, 1.87 mmol) was added. The mixture was stirred at rt overnight and concentrated in vacuo. The residue was partitioned between dichloromethane and 5% NaHCO$_3$, the organic layer was washed with brine, dried (Na$_2$SO$_4$) and evaporated to a syrup. Silica gel column chromatography using 1-10% gradient of methanol in dichloromethane afforded 11 as a colorless oil (0.7 g, 71%). ¹H-NMR δ6.35 (d, J=7.6, 1H, NH), 5.77 (d, J=8.0, 1H, NH), 5.44 (d, $J_{4,3}$=3.6, 1H, H4), 5.37 (dd, $J_{3,4}$=3.6, $J_{3,2}$=11.2, 1H, H3), 4.77 (d, $J_{1,2}$=8.0, 1H, H1), 4.28-4.18 (m, 3H, CH$_2$, CH), 4.07-3.87 (m, 6H), 3.55 (m, 1H, H5), 3.09 (d, J=3.2, 1H, OH), 3.02 (t, J=4.6, 1H, OH), 2.34 (t, J=7.4 2H, CH$_2$), 2.23 (s, 3H, Ac), 2.10 (s, 3H, Ac), 2.04 (s, 3H, Ac), 1.76-1.61 (m, 2×CH$_2$), 1.35 (m, 14H, 7×CH$_2$), 1.29 (d, J=6.4, 3H, CH$_3$). MS/ESI⁻ m/z (M−H)⁻.

1-O-(4-Monomethoxytrityl)-N-(12'-hydroxydodecanoyl-2-acetamido-3,4,6-tri-O-acetyl-2-deoxy-β-D-galactopyranose)-D-threoninol (12). To the solution of 11 (680 mg, 1.1 mmol) in dry pyridine (10 ml) p-anisylchlorotriphenylmethane (430 mg, 1.39 mmol) was added and the reaction mixture was stirred, protected from moisture, overnight. Methanol (3 ml) was added and the solution stirred for 15 min and evaporated in vacuo. The residue was partitioned between dichloromethane and 5% NaHCO$_3$, the organic layer was washed with brine, dried (Na$_2$SO$_4$) and evaporated to a syrup. Silica gel column chromatography using 1-3% gradient of methanol in dichloromethane afforded 12 as a white foam (0.75 g, 77%). ¹H-NMR δ7.48-6.92 (m, 14H, aromatic), 6.15 (d, J=8.8, 1H, NH), 5.56 (d, J=8.0, 1H, NH), 5.45 (d, $J_{4,3}$=3.2, 1H, H4), 5.40 (dd, $J_{3,4}$=3.2, $J_{3,2}$=11.2, 1H, H3), 4.80 (d, $J_{1,2}$=8.0, 1H, H1), 4.3-4.13 (m, 3H, CH$_2$, CH), 4.25-3.92 (m, 4H, H6, H2, CH), 3.89 (s, 3H, OMe), 3.54 (m, 2H, H5, CH), 3.36 (dd, J=3.4, J=9.8, 1H, CH), 3.12 (d, J=2.8, 1H, OH), 2.31 (t, J=7.6, 2H, CH$_2$), 2.22 (s, 3H, Ac), 2.13 (s, 3H, Ac), 2.03 (s, 3H, Ac), 1.80-1.55 (m, 2×CH$_2$), 1.37 (m, 14H, 7×CH$_2$), 1.21 (d, J=6.4, 3H, CH$_3$). MS/ESI⁻ m/z 903.5 (M−H)⁻.

1-O-(4-Monomethoxytrityl)-N-(12'-hydroxydodecanoyl-2-acetamido-3,4,6-tri-O-acetyl-2-deoxy-β-D-galactopyranose)-D-threoninol 3-O-(2-cyanoethyl N,N-diisopropylphosphorami-dite) (13). Conjugate 12 (1.2 g, 1.33 mmol) was dissolved in dry dichloromethane (15 ml) under argon and diisopropylethylamine (0.94 ml, 5.40 mmol) and 1-methylimidazole (55 μL, 0.69 mmol) were added. The solution was cooled to 0° C. and 2-cyanoethyl N,N-diisopropyl-chlorophosphoramidite (0.51 ml, 2.29 mmol) was added. The reaction mixture was stirred at rt for 2 hours, than cooled to 0° C. and quenched with anhydrous ethanol (0.5 ml). After stirring for 10 min. the solution was concentrated under reduced pressure (40° C.) and the residue dissolved in dichloromethane and chromatographed on the column of silica gel using 50-80% gradient of ethyl acetate in hexanes (1% triethylamine) to afford the phosphoramidite 13 (1.2 g, 82%). ³¹P-NMR δ149.41 (s), 149.23 (s).

Oligonucleotide Synthesis

Phosphoramidites 10, and 13, were used along with standard 2'-O-TBDMS and 2'-O-methyl nucleoside phosphoramidites. Synthesis were conducted on a 394 (ABI) synthesizer using modified 2.5 μmol scale protocol with a 5 min coupling step for 2'-O-TBDMS protected nucleotides and 2.5 min coupling step for 2'-O-methyl nucleosides. Coupling efficiency for the phosphoramidite 10 was lower than 50% while coupling efficiencies for phosphoramidite 13 was typically greater than 95% based on the measurement of released trityl cations. Once the synthesis was completed, the oligonucleotides were deprotected. The 5'-trityl groups were left attached to the oligomers to assist purification. Cleavage from the solid support and the removal of the protecting groups was performed as described herein with the exception of using 20% piperidine in DMF for 15 min for the removal of Fm protection prior methylamine treatment. The 5'-tritylated oligomers were separated from shorter (trityl-off) failure sequences using a short column of SEP-PAK C-18 adsorbent. The bound, tritylated oligomers were detritylated on the column by treatment with 1% trifluoroacetic acid, neutralized with triethylammonium acetate buffer, and than eluted. Further purification was achieved by reverse-phase HPLC. An example of a N-acetyl-D-galactosamine conjugate that can be synthesized using phosphoramidite 13 is shown in FIG. 15.

Structures of the ribozyme conjugates were confirmed by MALDI-TOF MS.

Monomer Synthesis

2'-Amino-2'-deoxyuridine-N-acetyl-D-galactosamine conjugate. The bis-Fmoc protected lysine linker was attached to the 2'-amino group of 2'-amino-2'-deoxyuridine using the EEDQ catalyzed peptide coupling. The 5'-OH was protected with 4,4'-dimethoxytrityl group to give 1, followed by the cleavage of N-Fmoc groups with diethylamine to afford synthon 2 in the high overall yield.

2-acetamido-3,4,6-tetra-O-acetyl-1-chloro-D-galactopyranose 4 was synthesized with minor modifications according to the reported procedure (Findeis supra). Mercury salt catalyzed glycosylation of 4 with the benzyl ester of 12-hydroxydodecanoic acid 5 afforded glycoside 6 in 81% yield. Hydrogenolysis of benzyl protecting group yielded 7 in a quantitative yield. The coupling of the sugar derivative with the nucleoside synthon was achieved through preactivation of the carboxylic function of 7 as N-hydroxysuccinimide ester 8, followed by coupling to lysyl-2'-aminouridine conjugate 2. The final conjugate 9 was than phosphitylated under standard conditions to afford the phosphoramidite 10 in 69% yield.

D-Threoninol-N-acetyl-D-galactosamine conjugate Using the similar strategy as described above, D-threoninol was coupled to 7 to afford conjugate 11 in a good yield. Monomethoxytritylation, followed by phosphitylation yielded the desired phosphoramidite 13.

Synthesis of Oxime Linked Nucleic Acid/Peptide Conjugates (FIGS. 16 and 17)

12-Hydroxydodecanoic acid benzyl ester Benzyl bromide (10.28 ml, 86.45 mmol) was added dropwise to a solution of 12-hydroxydodecanoic acid (17 g, 78.59 mmol) and DBU ml, 86.45 mmol) in absolute DMF (120 ml) under vigorous stirring at 0° C. After completion of the addition reaction mixture was warmed to a room temperature and left overnight under stirring. TLC (hexane-ethylacetate 3:1) indicated complete transformation of the starting material. DMF was removed under reduced pressure and the residue was partitioned between ethyl ether and 1N HCl. Organic phase was separated, washed with saturated aq sodium bicarbonate and dried over sodium sulfate. Sodium sulfate was filtered off, filtrate was evaporated to dryness. The residue was crystallized from hexane to give 21.15 g (92%) of the title compound as a white powder.

12-O—N-Phthaloyl-dodecanoic acid benzyl ester (15). Diethylazodicarboxylate (DEAD, 16.96 ml, 107.7 mmol) was added dropwise to the mixture of 12-Hydroxydodecanoic acid benzyl ester (21 g, 71.8 mmol), triphenylphosphine (28.29 g, 107.7 mmol) and N-hydroxyphthalimide (12.88 g, 78.98 mmol) in absolute THF (250 ml) at −20°-−30° C. under stirring. The reaction mixture was stirred at this temperature for additional 2-3 h, after which time TLC (hexane-ethylacetate 3:1) indicated reaction completion. The solvent was removed in vacuo and the residue was treated ether (250 ml). Formed precipitate of triphenylphosphine oxide was filtered off, mother liquor was evaporated to dryness and the residue was dissolved in methylene chloride and purified by flash chromatography on silica gel in hexane-ethyl acetate (7:3). Appropriate fractions were pooled and evaporated to dryness to afford 26.5 g (84.4%) of compound 15.

12-O—N-Phthaloyl-dodecanoic acid (16). Compound 15 (26.2 g, 59.9 mmol) was dissolved in 225 ml of ethanol-ethylacetate (3.5:1) mixture and 10% Pd/C (2.6 g) was added. The reaction mixture was hydrogenated in Parr apparatus for 3 hours. Reaction mixture was filtered through celite and evaporated to dryness. The residue was crystallized from methanol to provide 15.64 g (75%) of compound 16.

12-O—N-Phthaloyl-dodecanoic acid 2,3-di-hydroxy-propylamide (18) The mixture of compound 16 (15.03 g, 44.04 mmol), dicyclohexylcarbodiimide (10.9 g, 52.85 mmol) and N-hydroxysuccinimide (6.08 g, 52.85 mmol) in absolute DMF (150 ml) was stirred at room temperature overnight. TLC (methylene chloride-methanol 9:1) indicated complete conversion of the starting material and formation of NHS ester 17. Then aminopropanediol (4.01 g, 44 mmol) was added and the reaction mixture was stirred at room temperature for another 2 h. The formed precipitate of dicyclohexylurea was removed by filtration, filtrate was evaporated under reduced pressure. The residue was partitioned between ethyl acetate and saturated aq sodium bicarbonate. The whole mixture was filtered to remove any insoluble material and clear layers were separated. Organic phase was concentrated in vacuo until formation of crystalline material. The precipitate was filtered off and washed with cold ethylacetate to produce 10.86 g of compound 17. Combined mother liquor and washings were evaporated to dryness and crystallized from ethylacetate to afford 3.21 g of compound 18. Combined yield— 14.07 g (73.5%).

12-O—N-Phthaloyl-dodecanoic acid 2-hydroxy,3-dimethoxytrityloxy-propylamide (19) Dimethoxytrityl chloride (12.07 g, 35.62 mmol) was added to a stirred solution of compound 18 (14.07 g, 32.38 mmol) in absolute pyridine (130 ml) at 0° C. The reaction solution was kept at 0° C. overnight. Then it was quenched with MeOH (10 ml) and evaporated to dryness. The residue was dissolved in methylene chloride and washed with saturated aq sodium bicarbonate. Organic phase was separated, dried over sodium sulfate and evaporated to dryness. The residue was purified by flash chromatography on silica gel using step gradient of acetone in hexanes (3:7 to 1:1) as an eluent. Appropriate fractions were pooled and evaporated to provide 14.73 g (62%) of compound 19, as a colorless oil.

12-O—N-Phthaloyl-dodecanoic acid 2-O-(cyanoethyl-N, N-diisopropylamino-phosphoramidite),3-dimethoxytrityloxy-propylamide (20). Phosphitylated according to Sanghvi, et al., 2000, *Organic Process Research and Development*, 4, 175-81.

Purified by flash chromatography on silica gel using step gradient of acetone in hexanes (1:4 to 3:7) containing 0.5% of triethylamine. Yield—82%, colourless oil.

Oxidation of Peptides

Peptide (3.3 mg, 3.3 µmol) was dissolved in 10 mM AcONa and 2 eq of sodium periodate (100 mM soln in water) was added. Final reaction volume—0.5 ml. After 10 minutes reaction mixture was purified using analytical HPLC on Phenomenex Jupiter 5u C18 300A (150×4.6 mm) column; solvent A: 50 mM $KH_2PO_4$ (pH 3); solvent B: 30% of solvent A in MeCN; gradient B over 30 min. Appropriate fractions were pooled and concentrated on a SpeedVac to dryness. Yield: quantitative.

Conjugation Reaction of Herzyme-ONH2-1Lnker with N-Glyoxyl Peptide (FIG. 17)

Herzyme (SEQ ID NO: 13) with a 5'-terminal linker (100 OD) was mixed with oxidized peptide (3-5 eq) in 50 mM KH2PO4 (pH3, reaction volume 1 ml) and kept at room temperature for 24-48 h. The reaction mixture was purified using analytical HPLC on a Phenomenex Jupiter 5u C18

300A (150×4.6 mm) column; solvent A: 10 mM TEAA; solvent B: 10 mM TEAA/MeCN. Appropriate fractions were pooled and concentrated on a SpeedVac to dryness to provide desired conjugate. ESMS: calculated: 12699, determined: 12698.

Example 5

Synthesis of Phospholipid Enzymatic Nucleic Acid Conjugates (FIG. 19)

A phospholipid enzymatic nucleic acid conjugate (see FIG. 19) was prepared by coupling a C18H37 phosphoramidite to the 5'-end of an enzymatic nucleic acid molecule (Angiozyme™, SEQ ID NO: 24) during solid phase oligonucleotide synthesis on an ABI 394 synthesizer using standard synthesis chemistry. A 5'-terminal linker comprising 3'-AdT-di-Glycerol-5', where A is Adenosine, dT is 2'-deoxy Thymidine, and di-Glycerol is a di-DMT-Glycerol linker (Chemgenes CAT number CLP-5215), is used to attach two C18H37 phosphoramidites to the enzymatic nucleic acid molecule using standard synthesis chemistry. Additional equivalents of the C18H37 phosphoramidite were used for the bis-coupling. Similarly, other nucleic acid conjugates as shown in FIG. 18 can be prepared according to similar methodology.

Example 6

Synthesis of Peg Enzymatic Nucleic Acid Conjugates (FIG. 20)

A 40K-PEG enzymatic nucleic acid conjugate (see FIG. 20) was prepared by post synthetic N-hydroxysuccinimide ester coupling of a PEG derivative (Shearwater Polymers Inc, CAT number PEG2-NHS) to the 5'-end of an enzymatic nucleic acid molecule (Angiozyme™, SEQ ID NO: 24). A 5'-terminal linker comprising 3'-AdT-C6-amine-5', where A is Adenosine, dT-C6-amine is 2'-deoxy Thymidine with a C5 linked six carbon amine linker (Glen Research CAT number 10-1039-05), is used to attach the PEG derivative to the enzymatic nucleic acid molecule using NHS coupling chemistry.

Angiozyme™ with the C6dT-NH2 at the 5' end was synthesized and deprotected using standard oligonucleotide synthesis procedures as described herein. The crude sample was subsequently loaded onto a reverse phase column and rinsed with sodium chloride solution (0.5 M). The sample was then desalted with water on the column until the concentration of sodium chloride was close to zero. Acetonitrile was used to elute the sample from the column. The crude product was then concentrated and lyophilized to dryness.

The crude material (Angiozyme™) with 5'-amino linker (50 mg) was dissolved in sodium borate buffer (1.0 mL, pH 9.0). The PEG NHS ester (200 mg) was dissolved in anhydrous DMF (1.0 mL). The Angiozyme™ buffer solution was then added to the PEG NHS ester solution. The mixture was immediately vortexed for 5 minutes. Sodium acetate buffer solution (5 mL, pH 5.2) was used to quench the reaction. Conjugated material was then purified by ion-exchange and reverse phase chromatography.

Example 7

Phamacokinetics of PEG ribozyme acid conjugate (FIG. 21)

Forty-eight female C57B1/6 mice were given a single subcutaneous (SC) bolus of 30 mg/kg Angiozyme™ and 30 mg/kg Angiozyme™/40K PEG conjugate. Plasma was collected out to 24 hours post ribozyme injection. Plasma samples were analyzed for full length ribozyme by a hybridization assay.

Oligonucleotides complimentary to the 5' and 3' ends of Angiozyme™ were synthesized with biotin at one oligo, and FITC on the other oligo. A biotin oligo and FITC labeled oligo pair are incubated at 1 ug/ml with known concentrations of Angiozyme™ at 75 degrees C. for 5 min. After 10 minutes at RT, the mixture is allowed to bind to streptavidin coated wells of a 96-wll plate for two hours. The plate is washed with Tris-saline and detergent, and peroxidase labeled anti-FITC antibody is added. After one hour, the wells are washed, and the enzymatic reaction is developed, then read on an ELISA plate reader. Results are shown in FIG. 21.

Example 8

Phamacokinetics of Phospholipid Ribozyme Conjugate (FIG. 22)

Seventy-two female C57B1/6 mice were given a single intravenous (4) bolus of 30 mg/kg Angiozyme™ and 30 mg/kg Angiozyme™ conjugated with phospholipid (FIG. 19). Plasma was collected out to 3 hours post ribozyme injection. Plasma samples were analyzed for full length ribozyme by a hybridization assay.

Oligonucleotides complimentary to the 5' and 3' ends of Angiozyme™ were synthesized with biotin at one oligo, and FITC on the other oligo. A biotin oligo and FITC labeled oligo pair are incubated at 1 ug/ml with known concentrations of Angiozyme™ at 75 degrees C. for 5 min. After 10 minutes at RT, the mixture is allowed to bind to streptavidin coated wells of a 96-wll plate for two hours. The plate is washed with Tris-saline and detergent, and peroxidase labeled anti-FITC antibody is added. After one hr, the wells are washed, and the enzymatic reaction is developed, then read on an ELISA plate reader. Results are shown in FIG. 22.

Example 9

Synthesis of Protein or Peptide Conjugates with Biodegradable Linkers (FIGS. 24-26, and 29)

Proteins and peptides can be conjugated with various molecules, including PEG, via biodegradable nucleic acid linker molecules of the invention, using oxime and morpholino linkages. For example, a therapeutic antibody can be conjugated with PEG to improve the FIG. 24 shows a non-limiting example of a synthetic approach for synthesizing peptide or protein conjugates to PEG utilizing a biodegradable linker, the example shown is for a protein conjugate. Other conjugates can be synthesized in a similar manner where the protein or peptide is conjugated to molecules other than PEG, such as small molecules, toxins, radioisotopes, peptides or other proteins. (a) The protein of interest, such as an antibody or interferon, is synthesized with a terminal Serine or Threonine moiety that is oxidized, for example with sodium periodate. The oxidized protein is then coupled to a nucleic acid linker molecule that is designed to be biodegradable, for example a cytidine-deoxythymidine, cytidine-deoxyuridine, adenosine-deoxythymidine, or adenosine-deoxyuridine dimer that contains an oxyamino (O—$NH_2$) function. Other biodegradable nucleic acid linkers can be similarly used, for example other dimers, trimers, tetramers etc. that are designed to be biodegradable. The example shown makes use of a 5'-oxyamino moiety, however, other examples can utilize an oxyamino at other positions within the nucleic acid molecule, for example at the 2'-position, 3'-position, or at a nucleic acid base position. (b) The protein/nucleic acid conjugate is then oxidized to generate a dialdehyde function that is coupled to PEG molecule comprising an amino group ($H_2N$-PEG), for example a PEG molecule with an amino linker. Other amino containing molecules can be conjugated as shown in the figure, for example small molecules, toxins, or radioisotope labeled molecules.

Proteins and peptides can be conjugated with various molecules, including PEG, via biodegradable nucleic acid linker molecules of the invention, using oxime and phosphoramidate linkages. FIG. 25 shows a non-limiting example of a synthetic approach for synthesizing peptide or protein conjugates to PEG utilizing a biodegradable linker, the example shown is for a protein conjugate. Other conjugates can be synthesized in a similar manner where the protein or peptide is conjugated to molecules other than PEG, such as small molecules, toxins, radioisotopes, peptides or other proteins. The protein of interest, such as an antibody or interferon, is synthesized with a terminal Serine or Threonine moiety that is oxidized, for example with sodium periodate. The oxidized protein is then coupled to a nucleic acid linker molecule that is designed to be biodegradable, for example a cytidine-deoxythymidine, cytidine-deoxyuridine, adenosine-deoxythymidine, or adenosine-deoxyuridine dimer that contains an oxyamino (O—$NH_2$) function and a terminal phosphate group. Terminal phosphate groups can be introduced during synthesis of the nucleic acid molecule using chemical phosphorylation reagents, such as Glen Research Cat Nos. 10-1909-02, 10-1913-02, 10-1914-02, and 10-1918-02. Other biodegradable nucleic acid linkers can be similarly used, for example other dimers, trimers, tetramers etc. that are designed to be biodegradable. The example shown makes use of a 5'-oxyamino moiety, however, other examples can utilize an oxyamino at other positions within the nucleic acid molecule, for example at the 2'-position, 3'-position, or at a nucleic acid base position. The protein/nucleic acid conjugate terminal phosphate group is then activated with an activator reagent, such as NMI and/or tetrazole, and coupled a PEG molecule comprising an amino group ($H_2N$-PEG), for example a PEG molecule with an amino linker. Other amino containing molecules can be conjugated as shown in the figure, for example small molecules, toxins, or radioisotope labeled molecules.

Proteins and peptides can be conjugated with various molecules, including PEG, via biodegradable nucleic acid linker molecules of the invention, using phosphoramidate linkages. FIG. 26 shows a non-limiting example of a synthetic approach for synthesizing peptide or protein conjugates to PEG utilizing a biodegradable linker, the example shown is for a protein conjugate. Other conjugates can be synthesized in a similar manner where the protein or peptide is conjugated to molecules other than PEG, such as small molecules, toxins, radioisotopes, peptides or other proteins. (a) A nucleic acid linker molecule that is designed to be biodegradable, for example a cytidine-deoxythymidine, cytidine-deoxyuridine, adenosine-deoxythymidine, or adenosine-deoxyuridine dimer, is synthesized with a terminal phosphate group. Other biodegradable nucleic acid linkers can be similarly used, for example other dimers, trimers, tetramers etc. that are designed to be biodegradable. The protein/nucleic acid conjugate terminal phosphate group is then activated with an activator reagent, such as NMI and/or tetrazole, and coupled a PEG molecule comprising an amino group ($H_2N$-PEG), for example a PEG molecule with an amino linker. Other amino containing molecules can be conjugated as shown in the figure, for example small molecules, toxins, or radioisotope labeled molecules. The terminal protecting group, for example a dimethoxytrityl group, is removed from the conjugate and a terminal phosphite group is introduced with a phosphitylating reagent, such as N,N-diisopropyl-2-cyanoethyl chlorophosphoramidite. (b) The PEG/nucleic acid conjugate is then coupled to a peptide or protein comprising an amino group, such as the amino terminus or amino side chain of a suitably protected peptide or protein or via an amino linker. The conjugate is then oxidized and any protecting groups are removed to yield the protein/PEG conjugate comprising a biodegradable linker.

Proteins and peptides can be conjugated with various molecules, including PEG, via biodegradable nucleic acid linker molecules of the invention, using phosphoramidate linkages from coupling protein-based phosphoramidites. FIG. 29 shows a non-limiting example of a synthetic approach for synthesizing peptide or protein conjugates to PEG utilizing a biodegradable linker, the example shown is for a protein conjugate. Other conjugates can be synthesized in a similar manner where the protein or peptide is conjugated to molecules other than PEG, such as small molecules, toxins, radioisotopes, peptides or other proteins. The protein of interest, such as an antibody or interferon, is synthesized with a terminal Serine, Threonin, or Tyrosine moiety that is phosphitylated, for example with N,N-diisopropyl-2-cyanoethyl chlorophosphoramidite. The phosphitylated protein is then coupled to a nucleic acid linker molecule that is designed to be biodegradable, for example a cytidine-deoxythymidine, cytidine-deoxyuridine, adenosine-deoxythymidine, or adenosine-deoxyuridine dimer that contains conjugated PEG molecule as described in FIG. 18. Other biodegradable nucleic acid linkers can be similarly used, for example other dimers, trimers, tetramers etc. that are designed to be biodegradable.

Example 10

Galactosamine Ribozyme Conjugate Targeting HBV

A nuclease-resistance ribozyme directed against the Hepatitis B viral RNA (HBV) (HepBzyme™) is in early stages of preclinical development. HepBzyme, which targets site 273 of the Hepatitis B viral RNA, has produced statistically significant decreases in serum HBV levels in a HBV transgenic mouse model in a dose-dependent manner (30 and 100 mg/kg/day). In an effort to improve hepatic uptake by targeting the asialoglycoprotein receptor, a series of 5 branched galactosamine residues were attached via phosphate linkages to the 5'-terminus of HepBzyme (Gal-HepBzyme). The affect of the galactosamine conjugation on HepBzyme was assessed by quantitation of $^{32}$P-labeled HepBzyme and Gal-HepBzyme in plasma, liver and kidney of mice following a single SC bolus administration of 30 mg/kg. The plasma disposition of the intact ribozyme was similar between Gal-HepBzyme and HepBzyme. An approximate three-fold increase in the maximum observed concentration of intact ribozyme in liver ($C_{max}$) was observed in liver for Gal-HepBzyme (6.1±1.8 ng/mg) vs. HepBzyme (2.2±0.8 ng/mg) (p<0.05). The area under the curve (AUCall) for Gal-HepBzyme was also increased by approximately two-fold. This was accompanied by a substantial decrease (approximately 40%) in the AUCall for intact ribozyme in kidney. In addition to the significant increase in $C_{max}$ observed for intact Gal-HepBzyme in the liver, there was an increase in the total number of ribozyme equivalents, which may be suggestive of increased affinity of both the intact ribozyme and metabolites for asialoglycoprotein receptor and galactose-specific receptors in the liver. These data demonstrate that conjugation of a ribozyme with galactosamine produces a compound with a more favorable disposition profile, and illustrates the utility of conjugated ribozymes with improved in vivo pharmacokinetics and biodistribution.

Example 11

Synthesis of siNA Conjugates siNA molecules can be designed to interact with various sites in a target RNA message, for example, target sequences within the RNA sequence. The sequence of one strand of the siNA molecule(s) is complementary to the target site sequences. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference herein in their entirety).

In a non-limiting example, RNA oligonucleotides are synthesized in a stepwise fashion using the phosphoramidite chemistry as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphos-phoroamidite groups, and exocyclic amine protecting groups (e.g. N6-benzoyl adenosine, N4 acetyl cytidine, and N2-isobutyryl guanosine). Alternately, 2'-O-Silyl Ethers can be used in conjunction with acid-labile 2'-O-orthoester protecting groups in the synthesis of RNA as described by Scaringe supra. Differing 2' chemistries can require different protecting groups, for example 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Deprotection and purification of the siNA can be performed as is generally described in Usman et al., U.S. Pat. No. 5,831,071, U.S. Pat. No. 6,353,098, U.S. Pat. No. 6,437,117, and Bellon et al., U.S. Pat. No. 6,054,576, U.S. Pat. No. 6,162,909, U.S. Pat. No. 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

The introduction of conjugate moieties is accomplished either during solid phase synthesis using phosphoramidite chemistry described above, or post-synthetically using, for example, N-hydroxysuccinimide (NHS) ester coupling to an amino linker present in the siNA. Typically, a conjugate introduced during solid phase synthesis will be added to the 5'-end of a nucleic acid sequence as the final coupling reaction in the synthesis cycle using the phosphoramidite approach. Coupling conditions can be optimized for high yield coupling, for example by modification of coupling times and reagent concentrations to effectuate efficient coupling. As such, the 5'-end of the sense strand of a siNA molecule is readily conjugated with a conjugate moiety having a reactive phosphorus group available for coupling (e.g., a compound having Formulae 1, 5, 8, 55, 56, 57, 60, 86, 92, 104, 110, 113, 115, 116, 117, 118, 120, or 122) using the phosphoramidite approach, providing a 5'-terminal conjugate (see for example FIG. 41).

Conjugate precursors having a reactive phosphorus group and a protected hydroxyl group can be used to incorporate a conjugate moiety anywhere in the siNA sequence, such as in the loop portion of a single stranded hairpin siNA construct (see for example FIG. 42). For example, using the phosphoramidite approach, a conjugate moiety comprising a phosphoramidite and protected hydroxyl (e.g., a compound having Formulae 86, 92, 104, 113, 115, 116, 117, 118, 120, or 122 herein) is first coupled at the desired position within the siNA sequence using solid phase synthesis phosphoramidite coupling. Second, removal of the protecting group (e.g., dimethoxytrityl) allows coupling of additional nucleotides to the siNA sequence. This approach allows the conjugate moiety to be positioned anywhere within the siNA molecule.

Conjugate derivatives can also be introduced to a siNA molecule post synthetically. Post synthetic conjugation allows a conjugate moiety to be introduced at any position within the siNA molecule where an appropriate functional group is present (e.g., a C5 alkylamine linker present on a nucleotide base or a 2'-alkylamine linker present on a nucleotide sugar can provide a point of attachment for an NHS-conjugate moiety). Generally, a reactive chemical group present in the siNA molecule is unmasked following synthesis, thus allowing post-synthetic coupling of the conjugate to occur. In a non-limiting example, an protected amino linker containing nucleotide (e.g., TFA protected C5 propylamino thymidine) is introduced at a desired position of the siNA during solid phase synthesis. Following cleavage and deprotection of the siNA, the free amine is made available for NHS ester coupling of the conjugate at the desired position within the siNA sequence, such as at the 3'-end of the sense and/or antisense strands, the 3' and/or 5'-end of the sense strand, or within the siNA sequence, such as in the loop portion of a single stranded hairpin siNA sequence.

A conjugate moiety can be introduced at different locations within a siNA molecule using both solid phase synthesis and post-synthetic coupling approaches. For example, solid phase synthesis can be used to introduce a conjugate moiety at the 5'-end of the siNA (e.g. sense strand) and post-synthetic coupling can be used to introduce a conjugate moiety at the 3'-end of the siNA (e.g. sense strand and/or antisense strand). As such, a siNA sense strand having 3' and 5' end conjugates can be synthesized (see for example FIG. 41). Conjugate moieties can also be introduced in other combinations, such as at the 5'-end, 3'-end and/or loop portions of a siNA molecule (see for example FIG. 42).

Example 12

Phamacokinetics of siNA Conjugates (FIG. 43)

Three nuclease resistant siNA molecule targeting site 1580 of hepatitis B virus (HBV) RNA were designed using Stab 7/8 chemistry (see Table IV) and a 5'-terminal conjugate moiety.

One siNA conjugate comprises a branched cholesterol conjugate linked to the sense strand of the siNA. The "cholesterol" siNA conjugate molecule has the structure shown below:

for 2'-fluoro cytidine, a stands for adenosine, and s stands for phosphorothioate linkage.

Another siNA conjugate comprises a branched phospholipid conjugate linked to the sense strand of the siNA. The "phospholipid" siNA conjugate molecule has the structure shown below:

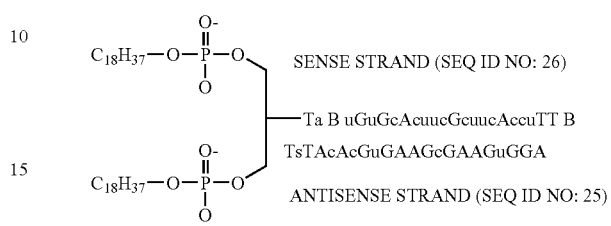

SENSE STRAND (SEQ ID NO: 26)

Ta B uGuGcAcuucGcuucAccuTT B
TsTAcAcGuGAAGcGAAGuGGA

ANTISENSE STRAND (SEQ ID NO: 25)

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands for 2'-fluoro cytidine, a stands for adenosine, and s stands for phosphorothioate linkage.

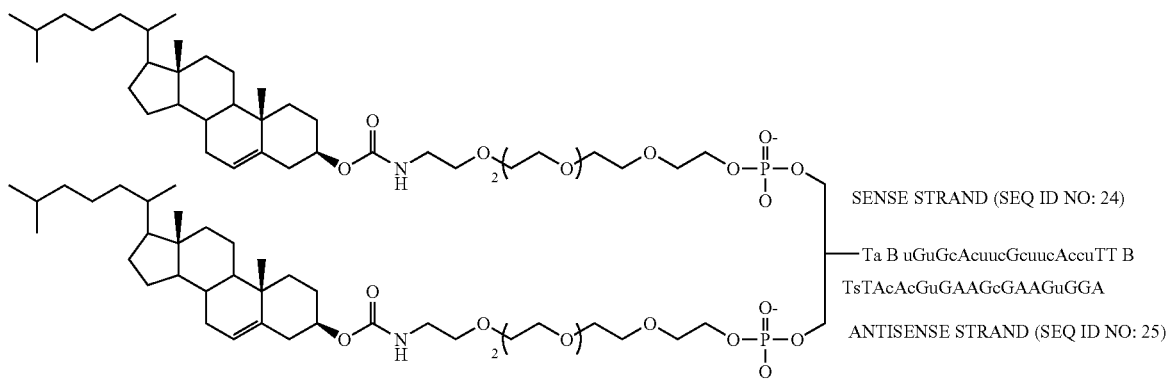

SENSE STRAND (SEQ ID NO: 24)

Ta B uGuGcAcuucGcuucAccuTT B
TsTAcAcGuGAAGcGAAGuGGA

ANTISENSE STRAND (SEQ ID NO: 25)

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands Another siNA conjugate comprises a polyethylene glycol (PEG) conjugate linked to the sense strand of the siNA. The "PEG" siNA conjugate molecule has the structure shown below:

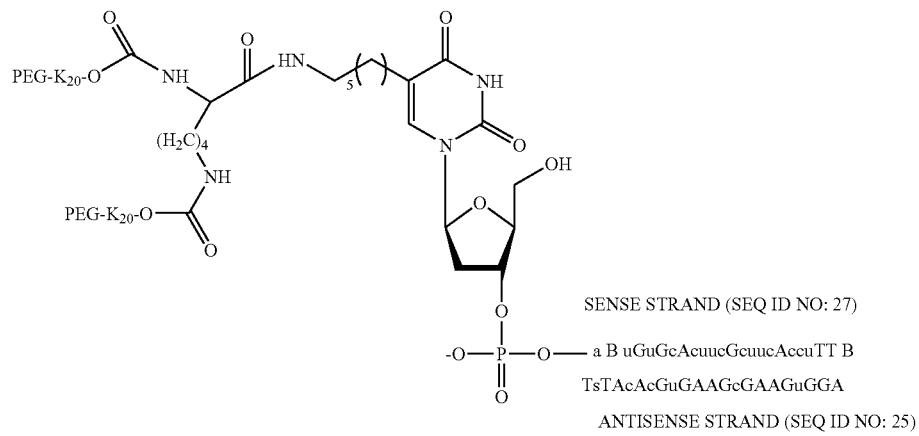

SENSE STRAND (SEQ ID NO: 27)

a B uGuGcAcuucGcuucAccuTT B
TsTAcAcGuGAAGcGAAGuGGA

ANTISENSE STRAND (SEQ ID NO: 25)

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands for 2'-fluoro cytidine, a stands for adenosine, and s stands for phosphorothioate linkage.

The Cholesterol, Phospholipid, and PEG conjugates were evaluated for pharmakokinetic properties in mice compared to a non-conjugated siNA construct having matched chemistry and sequence. This study was conducted in female CD-1 mice approximately 26 g (6-7 weeks of age). Animals were housed in groups of 3. Food and water were provided ad libitum. Temperature and humidity were according to Pharmacology Testing Facility performance standards (SOP's) which are in accordance with the 1996 Guide for the Care and Use of Laboratory Animals (NRC). Animals were acclimated to the facility for at least 3 days prior to experimentation.

Absorbance at 260 nm was used to determine the actual concentration of the stock solution of pre-annealed HBV siNA. An appropriate amount of HBV siNA was diluted in sterile veterinary grade normal saline (0.9%) based on the average body weight of the mice. A small amount of the antisense (Stab 7) strand was internally labeled with gamma 32P-ATP. The 32P-labeled stock was combined with excess sense strand (Stab 8) and annealed. Annealing was confirmed prior to combination with unlabled drug. Each mouse received a subcutaneous bolus of 30 mg/kg (based on duplex) and approximately 10 million cpm (specific activity of approximately 15 cpm/ng).

Three animals per timepoint (1, 4, 8, 24, 72, 96 h) were euthanized by $CO_2$ inhalation followed immediately by exsanguination. Blood was sampled from the heart and collected in heparinized tubes. After exsanguination, animals were perfused with 10-15 mL of sterile veterinary grade saline via the heart. Samples of liver were then collected and frozen.

Tissue samples were homogenized in a digestion buffer prior to compound quantitation. Quantitation of intact compound was determined by scintillation counting followed by PAGE and phosphorimage analysis. Results are shown in FIG. 43. As shown in the figure, the conjugated siNA constructs shown vastly improved liver PK compared to the unconjugated siNA construct.

Example 13

Cell Culture of siNA Conjugates (FIG. 44)

The Cholesterol conjugates and Phospholipid conjugated siNA constructs described in Example 12 above were evaluated for cell culture efficacy in a HBV cell culture system.
Transfection of HepG2 Cells with psHBV-1 and siNA The human hepatocellular carcinoma cell line Hep G2 was grown in Dulbecco's modified Eagle media supplemented with 10% fetal calf serum, 2 mM glutamine, 0.1 mM nonessential amino acids, 1 mM sodium pyruvate, 25 mM Hepes, 100 units penicillin, and 100 µg/ml streptomycin. To generate a replication competent cDNA, prior to transfection the HBV genomic sequences are excised from the bacterial plasmid sequence contained in the psHBV-1 vector. Other methods known in the art can be used to generate a replication competent cDNA. This was done with an EcoRI and Hind III restriction digest. Following completion of the digest, a ligation was performed under dilute conditions (20 µg/ml) to favor intermolecular ligation. The total ligation mixture was then concentrated using Qiagen spin columns.

siNA Activity Screen and Dose Response Assay

Transfection of the human hepatocellular carcinoma cell line, Hep G2, with replication-competent HBV DNA results in the expression of HBV proteins and the production of virions. To test the efficacy of siNA conjugates targeted against HBV RNA, the Cholesterol siNA conjugate and Phospholipid siNA conjugate described in Example 12 were compared to a non-conjugated control siNA (see FIG. 44). An inverted sequence duplex was used as a negative control for the unconjugated siNA. Dose response studies were performed in which HBV genomic DNA was transfected with HBV genomic DNA with lipid at 12.5 ug/ml into Hep G2 cells. 24 hours after transfection with HBV DNA, cell culture media was removed and siNA duplexes were added to cells without lipid at 10 uM, 5, uM, 2.5 uM, 1 uM, and 100 nm and the subsequent levels of secreted HBV surface antigen (HBsAg) were analyzed by ELISA 72 hours post treatment (see FIG. 44). To determine siNA activity, HbsAg levels were measured following transfection with siNA. Immulon 4 (Dynax) microtiter wells were coated overnight at 4° C. with anti-HBsAg Mab (Biostride B88-95-31ad,ay) at 1 µg/ml in Carbonate Buffer (Na2CO3 15 mM, NaHCO3 35 mM, pH 9.5). The wells were then washed 4× with PBST (PBS, 0.05% Tween® 20) and blocked for 1 hr at 37° C. with PBST, 1% BSA. Following washing as above, the wells were dried at 37° C. for 30 min. Biotinylated goat ant-HBsAg (Accurate YVS1807) was diluted 1:1000 in PBST and incubated in the wells for 1 hr. at 37° C. The wells were washed 4× with PBST. Streptavidin/Alkaline Phosphatase Conjugate (Pierce 21324) was diluted to 250 ng/ml in PBST, and incubated in the wells for 1 hr. at 37° C. After washing as above, p-nitrophenyl phosphate substrate (Pierce 37620) was added to the wells, which were then incubated for 1 hour at 37° C. The optical density at 405 nm was then determined. As shown in FIG. 44, the phospholipid and cholesterol conjugates demonstrate marked dose dependent inhibition of HBsAg expression compared to the unconjugated siNA construct when delivered to cells without any transfection agent (lipid).

Example 14

Purification of Nucleic Acid Conjugates

Nucleic acid conjugates of the invention can be purified using, for example, anion exchange, reverse phase, and/or hydrophobic interaction chromoatography. Non-lipophilic nucleic acid conjugates of the invention (e.g., PEG, PEI, polyamine conjugates) are readily purified using anion exchange chromatography as is known in the art. Lipophilic nucleic acid conjugates of the invention (e.g., cholesterol, phospholipid, or alkyl polymer conjugates) can be purified using reverse phase chromatography as is known in the art and/or by hydrophobic interaction chromatography. Hydrophobic interaction chromotography (HIC) allows high efficiency purification of nucleic acid conjugates of the invention without the use of organic solvents.

Hydrophobic interaction chromatography is based on interactions between hydrophobic groups on the molecules to be purified or isolated and the corresponding HIC resin. HIC utilizes such hydrophobic interactions in highly polar nondenaturing buffers. Several different HIC resins can be utilized in purifying hydrophobic polynucleotide conjugates (e.g., siNA conjugates). Examples of HIC resins include but are not limited to ether, phenyl, butyl, or hexyl stationary phases such as Toyopearl.650 S Phenyl, TSK GEL Phenyl-5PW, TSK GEL Ether-5PW, Toyopearl Ether-650, Toyopearl Phenyl-650, Toyopearl Butyl-650, and Toyopearl Hexyl-650 from TosoHaas and Fractogel EMD Phenyl S from Merck. Various conditions that can be altered to achieve highly purified material using HIC include alterations in the concentration of salts in buffers, use of different resins, varying pH and temperature.

In a non-limiting example, HIC was used to purify a Stab 7/8 (Table IV) siNA cholesterol conjugate having SEQ ID NO: 24 (see for example FIG. 30) and a Stab 7/8 (Table IV) siNA phospholipid conjugate having SEQ ID NO: 26 (see for example FIG. 19). The purification buffer reagents used in the HIC purification consisted of Ammonium Sulfate, Sodium Phosphate Monobasic and Dibasic (see Table V) which were purchased from VWR. The material was purified on a Waters LC-2000 preparative system including an LC Controller and pump and a waters 24487 dual wavelength UV Detector. The system is controlled by Millennium software version 4. The buffers and loading material is passed through a heat exchanger, such as a Timberline TL50D (Timberline Instruments (Boulder, Colo.). The Columns used in the development included a Pharmacia HR 5/5, Pharmacia HR 16/10 and a Pharmacia Fineline 35. The columns were packed with Toyopearl Phenyl-650s (Tosoh Bioscience, LLC Montgomeryville, Pa.) to a bed height of 5 cm, 10 cm and 10 cm respectively as the process was scaled up. Further work included the Toyopearl 650 S Phenyl to the Tosoh Bioscience TSK GEL Phenyl-5PW and the Fractogel EMD Phenyl S.

The deprotected cholesterol siNA and phospholipid siNA conjugates were diluted in Milli-Q-water and ammonium sulfate was added to a 2M concentration following filtration and rinsing of the filter with Milli-Q-water. The addition of solid ammonium sulfate as a dry powder resulted in precipitation of the siNA conjugates. This process has been further optimized so that the oligonucleotide is diluted in Milli-Q-water and then the volume is doubled with 2 M ammonium sulfate yielding a solution of 1 M ammonium sulfate with 10 mM Sodium Phosphate.

The purified conjugated siRNA is eluted from the column during step 2 of the gradient (see Table VI). This step also desalts the molecule. The eluate was collected as fractions, which were analyzed by SAX or RP HPLC to determine purity. Fractions containing the conjugated product were pooled and this pool was analyzed by SAX or RP HPLC for purity. The pooled material was stored 2-8° C. until annealed to the complementary strand and desalted.

One skilled in the art would readily appreciate that the present invention is well adapted to carry out the objects and obtain the ends and advantages mentioned, as well as those inherent therein. The methods and compositions described herein are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the following claims.

TABLE I

Characteristics of naturally occurring ribozymes

Group I Introns

Size: ~150 to >1000 nucleotides.
Requires a U in the target sequence immediately 5' of the cleavage site.
Binds 4-6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintenance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [i, ii].
Complete kinetic framework established for one ribozyme [iii, iv, v, vi].
Studies of ribozyme folding and substrate docking underway [vii, viii, ix].
Chemical modification investigation of important residues well established [xxi].
The small (4-6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [xii].

TABLE I-continued

Characteristics of naturally occurring ribozymes

RNAse P RNA (M1 RNA)

Size: ~290 to 400 nucleotides.
RNA portion of a ubiquitous ribonucleoprotein enzyme.
Cleaves tRNA precursors to form mature tRNA [xiii].
Reaction mechanism: possible attack by $M^{2+}$-OH to generate cleavage products
with 3'-OH and 5'-phosphate.
RNAse P is found throughout the prokaryotes and eukaryotes. The RNA subunit
has been sequenced from bacteria, yeast, rodents, and primates.
Recruitment of endogenous RNAse P for therapeutic applications is possible
through hybridization of an External Guide Sequence (EGS) to the target RNA [xiv, xv]
Important phosphate and 2' OH contacts recently identified [xvi, xvii]

Group II Introns

Size: >1000 nucleotides.
Trans cleavage of target RNAs recently demonstrated [xviii, xvix].
Sequence requirements not fully determined.
Reaction mechanism: 2'-OH of an internal adenosine generates cleavage products
with 3'-OH and a "lariat" RNA containing a 3'-5' and a 2'-5' branch point.
Only natural ribozyme with demonstrated participation in DNA cleavage [xx, xxi]
in addition to RNA cleavage and ligation.
Major structural features largely established through phylogenetic comparisons [xxii].
Important 2' OH contacts beginning to be identified [xxiii]
Kinetic framework under development [xxiv]

Neurospora VS RNA

Size: ~144 nucleotides.
Trans cleavage of hairpin target RNAs recently demonstrated [xxv].
Sequence requirements not fully determined.
Reaction mechanism: attack by 2'-OH 5' to the scissile bond to generate cleavage
products with 2',3'-cyclic phosphate and 5'-OH ends.
Binding sites and structural requirements not fully determined.
Only 1 known member of this class. Found in Neurospora VS RNA.

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage
products with 2',3'-cyclic phosphate and 5'-OH ends.
14 known members of this class. Found in a number of plant pathogens (virusoids)
that use RNA as the infectious agent.
Essential structural features largely defined, including 2 crystal structures [xxvi, xxvii]
Minimal ligation activity demonstrated (for engineering through in vitro selection)
[xxviii]
Complete kinetic framework established for two or more ribozymes [xxix].
Chemical modification investigation of important residues well established [xxx].

Hairpin Ribozyme

Size: ~50 nucleotides.
Requires the target sequence GUC immediately 3' of the cleavage site.
Binds 4-6 nucleotides at the 5'-side of the cleavage site and a variable number to
the 3'-side of the cleavage site.
Reaction mechanism: attack by 2'-OH 5' to the scissile bond to generate cleavage
products with 2',3'-cyclic phosphate and 5'-OH ends.
3 known members of this class. Found in three plant pathogen (satellite RNAs of
the tobacco ringspot virus, arabis mosaic virus and chicory yellow mottle virus)
which uses RNA as the infectious agent.
Essential structural features largely defined [xxxi, xxxii, xxxiii, xxxiv]
Ligation activity (in addition to cleavage activity) makes ribozyme amenable to
engineering through in vitro selection [xxxv]
Complete kinetic framework established for one ribozyme [xxxvi].
Chemical modification investigation of important residues begun [xxxvii, xxxviii].

Hepatitis Delta Virus (HDV) Ribozyme

Size: ~60 nucleotides.
Trans cleavage of target RNAs demonstrated [xxxix].
Binding sites and structural requirements not fully determined, although no
sequences 5' of cleavage site are required. Folded ribozyme contains a pseudoknot
structure [xl].
Reaction mechanism: attack by 2'-OH 5' to the scissile bond to generate cleavage
products with 2',3'-cyclic phosphate and 5'-OH ends.
Only 2 known members of this class. Found in human HDV.
Circular form of HDV is active and shows increased nuclease stability [xli]

REFERENCES i. Michel, Francois; Westhof, Eric. Slippery substrates. Nat. Struct. Biol. (1994), 1(1), 5-7.
ii. Lisacek, Frederique; Diaz, Yolande; Michel, Francois. Automatic identification of group I intron cores in genomic DNA sequences. J. Mol. Biol. (1994), 235(4), 1206-17.
iii. Herschlag, Daniel; Cech, Thomas R. Catalysis of RNA cleavage by the Tetrahymena thermophila ribozyme. 1. Kinetic description of the reaction of an RNA substrate complementary to the active site. Biochemistry (1990), 29(44), 10159-71.
iv. Herschlag, Daniel; Cech, Thomas R. Catalysis of RNA cleavage by the Tetrahymena thermophila ribozyme. 2. Kinetic description of the reaction of an RNA substrate that forms a mismatch at the active site. Biochemistry (1990), 29(44), 10172-80.
v. Knitt, Deborah S.; Herschlag, Daniel. pH Dependencies of the Tetrahymena Ribozyme Reveal an Unconventional Origin of an Apparent pKa. Biochemistry (1996), 35(5), 1560-70.
vi. Bevilacqua, Philip C.; Sugimoto, Naoki; Turner, Douglas H. A mechanistic framework for the second step of splicing catalyzed by the Tetrahymena ribozyme. Biochemistry (1996), 35(2), 648-58.
vii. Li, Yi; Bevilacqua, Philip C.; Mathews, David; Turner, Douglas H. Thermodynamic and activation parameters for binding of a pyrene-labeled substrate by the Tetrahymena ribozyme: docking is not diffusion-controlled and is driven by a favorable entropy change. Biochemistry (1995), 34(44), 14394-9.
viii. Banerjee, Aloke Raj; Turner, Douglas H. The time dependence of chemical modification reveals slow steps in the folding of a group I ribozyme. Biochemistry (1995), 34(19), 6504-12.
ix. Zarrinkar, Patrick P.; Williamson, James R. The P9.1-P9.2 peripheral extension helps guide folding of the Tetrahymena ribozyme. Nucleic Acids Res. (1996), 24(5), 854-8.
x. Strobel, Scott A.; Cech, Thomas R. Minor groove recognition of the conserved G.cntdot.U pair at the Tetrahymena ribozyme reaction site. Science (Washington, D.C.) (1995), 267(5198), 675-9.
xi. Strobel, Scott A.; Cech, Thomas R. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201-11.
xii. Sullenger, Bruce A.; Cech, Thomas R. Ribozyme-mediated repair of defective mRNA by targeted trans-splicing. Nature (London) (1994), 371(6498), 619-22.
xiii. Robertson, H. D.; Altman, S.; Smith, J. D. J. Biol. Chem., 247, 5243-5251 (1972).
xiv. Forster, Anthony C.; Altman, Sidney. External guide sequences for an RNA enzyme. Science (Washington, D.C., 1883-) (1990), 249(4970), 783-6.
xv. Yuan, Y.; Hwang, E. S.; Altman, S. Targeted cleavage of mRNA by human RNase P. Proc. Natl. Acad. Sci. USA (1992) 89, 8006-10.
xvi. Harris, Michael E.; Pace, Norman R. Identification of phosphates involved in catalysis by the ribozyme RNase P RNA. RNA (1995), 1(2), 210-18.
xvii. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510-14.
xviii. Pyle, Anna Marie; Green, Justin B. Building a Kinetic Framework for Group II Intron Ribozyme Activity: Quantitation of Interdomain Binding and Reaction Rate. Biochemistry (1994), 33(9), 2716-25.
xix. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965-77.
xx. Zimmerly, Steven; Guo, Huatao; Eskes, Robert; Yang, Jian; Perlman, Philip S.; Lambowitz, Alan M. A group II intron RNA is a catalytic component of a DNA endonuclease involved in intron mobility. Cell (Cambridge, Mass.) (1995), 83(4), 529-38.
xxi. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761-70.
xxii. Michel, Francois; Ferat, Jean Luc. Structure and activities of group II introns. Annu. Rev. Biochem. (1995), 64, 435-61.
xxiii. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410-13.
xxiv. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31-49.
xxv. Guo, Hans C. T.; Collins, Richard A. Efficient transcleavage of a stem-loop RNA substrate by a ribozyme derived from Neurospora VS RNA. EMBO J. (1995), 14(2), 368-76.
xxvi. Scott, W. G., Finch, J. T., Aaron, K. The crystal structure of an all RNA hammerhead ribozyme: A proposed mechanism for RNA catalytic cleavage. Cell, (1995), 81, 991-1002.
xxvii. McKay, Structure and function of the hammerhead ribozyme: an unfinished story. RNA, (1996), 2, 395-403.
xxviii. Long, D., Uhlenbeck, O., Hertel, K. Ligation with hammerhead ribozymes. U.S. Pat. No. 5,633,133.
xxix. Hertel, K. J., Herschlag, D., Uhlenbeck, O. A kinetic and thermodynamic framework for the hammerhead ribozyme reaction. Biochemistry, (1994) 33, 3374-3385. Beigelman, L., et al., Chemical modifications of hammerhead ribozymes. J. Biol. Chem., (1995) 270, 25702-25708.
xxx. Beigelman, L., et al., Chemical modifications of hammerhead ribozymes. J. Biol. Chem., (1995) 270, 25702-25708.
xxxi. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299-304.
xxxii. Chowrira, Bharat M.; Berzal-Herranz, Alfredo; Burke, John M. Novel guanosine requirement for catalysis by the hairpin ribozyme. Nature (London) (1991), 354(6351), 320-2.
xxxiii. Berzal-Herranz, Alfredo; Joseph, Simpson; Chowrira, Bharat M.; Butcher, Samuel E.; Burke, John M. Essential nucleotide sequences and secondary structure elements of the hairpin ribozyme. EMBO J. (1993), 12(6), 2567-73.
xxxiv. Joseph, Simpson; Berzal-Herranz, Alfredo; Chowrira, Bharat M.; Butcher, Samuel E. Substrate selection rules for the hairpin ribozyme determined by in vitro selection, mutation, and analysis of mismatched substrates. Genes Dev. (1993), 7(1), 130-8.

xxxv. Berzal-Herranz, Alfredo; Joseph, Simpson; Burke, John M. In vitro selection of active hairpin ribozymes by sequential RNA-catalyzed cleavage and ligation reactions. Genes Dev. (1992), 6(1), 129-34.

xxxvi. Hegg, Lisa A.; Fedor, Martha J. Kinetics and Thermodynamics of Intermolecular Catalysis by Hairpin Ribozymes. Biochemistry (1995), 34(48), 15813-28.

xxxvii. Grasby, Jane A.; Mersmann, Karin; Singh, Mohinder; Gait, Michael J. Purine Functional Groups in Essential Residues of the Hairpin Ribozyme Required for Catalytic Cleavage of RNA. Biochemistry (1995), 34(12), 4068-76.

xxxviii. Schmidt, Sabine; Beigelman, Leonid; Karpeisky, Alexander; Usman, Nassim; Sorensen, Ulrik S.; Gait, Michael J. Base and sugar requirements for RNA cleavage of essential nucleoside residues in internal loop B of the hairpin ribozyme: implications for secondary structure. Nucleic Acids Res. (1996), 24(4), 573-81.

xxxix. Perrotta, Anne T.; Been, Michael D. Cleavage of oligoribonucleotides by a ribozyme derived from the hepatitis .delta. virus RNA sequence. Biochemistry (1992), 31(1), 16-21.

xl. Perrotta, Anne T.; Been, Michael D. A pseudoknot-like structure required for efficient self-cleavage of hepatitis delta virus RNA. Nature (London) (1991), 350(6317), 434-6.

xli. Puttaraju, M.; Perrotta, Anne T.; Been, Michael D. A circular trans-acting hepatitis delta virus ribozyme. Nucleic Acids Res. (1993), 21(18), 4253-8.

TABLE III

Peptides for Conjugation

| Peptide | Sequence | SEQ ID NO |
|---|---|---|
| ANTENNAPEDIA | RQI KIW FQN RRM KWK K amide | 14 |
| Kaposi fibroblast growth factor | AAV ALL PAV LLA LLA P + VQR KRQ KLMP | 15 |
| caiman crocodylus Ig(5) light chain | MGL GLH LLV LAA ALQ GA | 16 |
| HIVenvelope glycoprotein gp41 | GAL FLG FLG AAG STM GA + PKS KRK 5 (NLS of the SV40) | 17 |
| HIV-1 Tat | RKK RRQ RRR | 18 |
| Influenza hemagglutinin envelop glycoprotein | GLFEAIAGFIENGWEGMIDGGGYC | 19 |
| RGD peptide | X-RGD-X where X is any amino acid or peptide | 20 |

TABLE II

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents: DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 μL | 100 sec | 200 sec | 200 sec |
| Acetonitrile | NA | 1150/1150/1150 μL | NA | NA | NA |

Wait time does not include contact time during delivery.

TABLE III-continued

Peptides for Conjugation

| Peptide | Sequence | SEQ ID NO |
|---|---|---|
| transportan A | GWT LNS AGY LLG KIN LKA LAA LAK KIL | 21 |
| Somatostatin (tyr-3-octreotate) | (S)*FC* YWK TCT | 22 |
| Pre-S-peptide | (S)DH QLN PAF | 23 |

(S) optional Serine for coupling
Italic = optional D isomer for stability

TABLE IV

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | Usually AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | | 2 at 5'-end 1 at 3'-end | Usually AS |
| "Stab 15" | 2'-deoxy | 2'-deoxy | | 2 at 5'-end 1 at 3'-end | Usually AS |
| "Stab 16" | Ribo | 2'-O-Methyl | 5' and 3'-ends | | Usually S |
| "Stab 17" | 2'-O-Methyl | 2'-O-Methyl | 5' and 3'-ends | | Usually S |
| "Stab 18" | 2'-fluoro | 2'-O-Methyl | 5' and 3'-ends | 1 at 3'-end | Usually S |
| "Stab 19" | 2'-fluoro | 2'-O-Methyl | 3'-end | | Usually AS |
| "Stab 20" | 2'-fluoro | 2'-deoxy | 3'-end | | Usually AS |
| "Stab 21" | 2'-fluoro | Ribo | 3'-end | | Usually AS |
| "Stab 22" | Ribo | Ribo | 3'-end- | | Usually AS |

CAP = any terminal cap, such as inverted deoxy abasic, glyceryl, or a conjugate moiety.
All Stab 1-22 chemistries can comprise 3'-terminal thymidine (TT) residues
All Stab 1-22 chemistries typically comprise 21 nucleotides, but can vary as described herein.
S = sense strand
AS = antisense strand

TABLE V

Typical Hydrophobic Interaction Chromatography (HIC) Buffers

| | | | pH | Conductivity |
|---|---|---|---|---|
| Equilibrium (A) | 1.0 M Ammonium Sulfate, | 10 mM Sodium Phosphate, | 7.0 ± 0.3 | |
| Elution (B) | N/A | 100 mM Sodium Phosphate, | 7.0 ± 0.3 | |
| Elution 2 (C) | N/A | N/A | N/A | <20 µS/cm |

TABLE VI

Typical HIC Gradient

| Gradient Step | Buffer | Time |
|---|---|---|
| Step 1 | 100% A to 100% B | 20 cv |
| Step 2 | 100% B to 20% C | 30 cv |
| Step 3 | 20% C to 100% C | 30 cv |

The invention claimed is:

1. A compound having Formula 107:

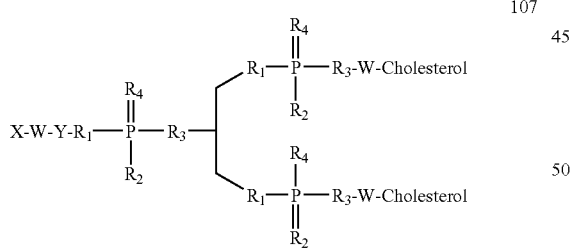

107 wherein X comprises a short interfering nucleic acid (siNA) molecule; each W independently comprises a linker molecule or chemical linkage selected from the group consisting of amide, phosphate, phosphate ester, phosphoramidate, or thiophosphate ester linkage, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N, amide, alkylamine, aminoacid, polyamine, cyclic amine or heterocyclic amine, and Cholesterol comprises cholesterol.

2. A compound having the formula below:

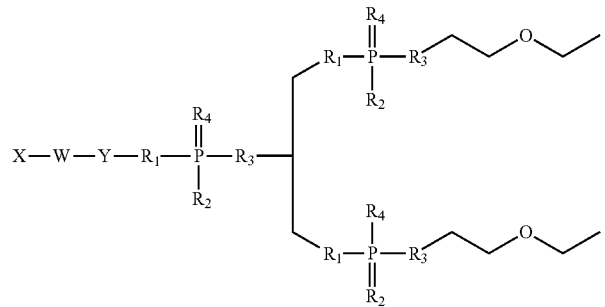

-continued

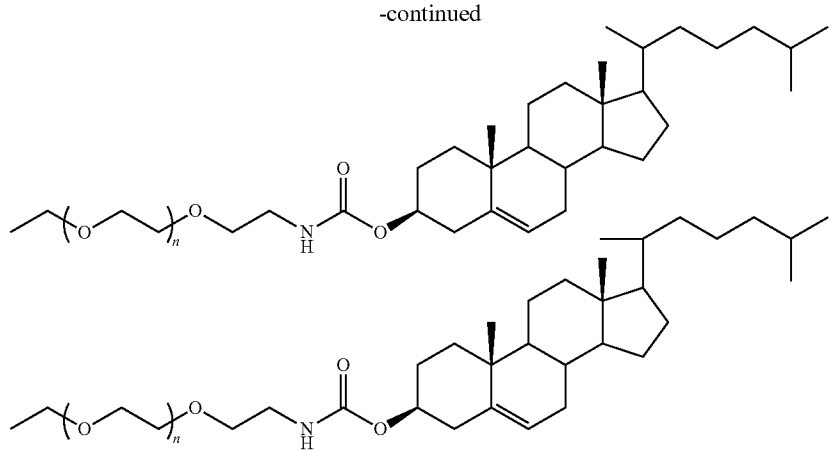

wherein X comprises a short interfering nucleic acid (siNA) molecule; each W independently comprises a linker molecule or chemical linkage selected from the group consisting of amide, phosphate, phosphate ester, phosphoramidate, or thiophosphate ester linkage, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N, amide, alkylamine, aminoacid, polyamine, cyclic amine or heterocyclic amine; and n is independently an integer from about 1 to about 20.

3. A compound having Formula 111:

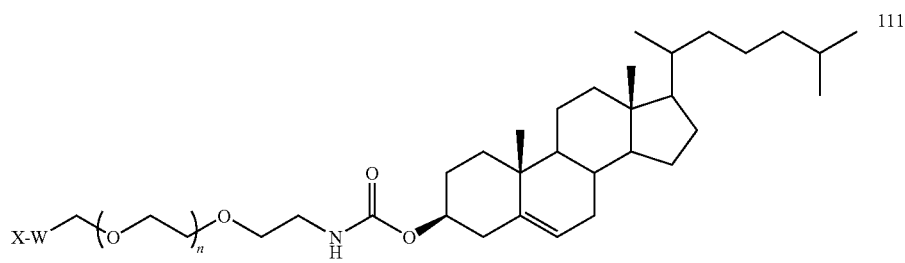

wherein X comprises a short interfering nucleic acid (siNA) molecule capable of mediating RNA interference (RNAi); W comprises a linker molecule or chemical linkage that can be present or absent, and when present, forms only one covalent bond to the siNA molecule; and n is an integer from about 1 to about 20.

4. The compound of claim 1, wherein W comprises a linker molecule or chemical linkage selected from the group consisting of amide, phosphate, phosphate ester, phosphoramidate, or thiophosphate ester linkage.

5. The compound of claim 3, wherein W comprises a linker molecule or chemical linkage selected from the group consisting of amide, phosphate, phosphate ester, phosphoramidate, or thiophosphate ester linkage.

6. The compound of claim 1, wherein said siNA molecule comprises a sense strand and an antisense strand, and wherein said sense strand is conjugated with a compound comprising Formula 107.

7. The compound of claim 3, wherein said siNA molecule comprises a sense strand and an antisense strand, and wherein said sense strand is conjugated with a compound comprising Formula 107.

8. The compound of claim 2, wherein W comprises a linker molecule or chemical linkage selected from the group consisting of amide, phosphate, phosphate ester, phosphoramidate, or thiophosphate ester linkage.

9. The compound of claim 2, wherein the siNA molecule comprises a sense strand and an antisense strand, and wherein the sense strand is conjugated with a compound of claim 2.

* * * * *

SEQUENCE LISTING

<160> NUMBER OF SEQ ID NOS: 24

<210> SEQ ID NO 1
<211> LENGTH: 10
<212> TYPE: RNA
<213> ORGANISM: Artificial Sequence
<220> FEATURE:
<223> OTHER INFORMATION: Synthetic Stem II region

<400> SEQUENCE: 1
gccguuaggc                                                          10

```
<210> SEQ ID NO 2
<211> LENGTH: 15
<212> TYPE: RNA
<213> ORGANISM: Artificial Sequence
<220> FEATURE:
<223> OTHER INFORMATION: Synthetic Generic Target Nucleic Acid
<220> FEATURE:
<221> NAME/KEY: misc_feature
<222> LOCATION: (1)..(6)
<223> OTHER INFORMATION: n stands for a, c, g, or u
<220> FEATURE:
<221> NAME/KEY: misc_feature
<222> LOCATION: (8)..(8)
<223> OTHER INFORMATION: n stands for a, u, or c
<220> FEATURE:
<221> NAME/KEY: misc_feature
<222> LOCATION: (9)..(15)
<223> OTHER INFORMATION: n stands for a, c, g, or u

<400> SEQUENCE: 2
nnnnnnunnn nnnnn                                                    15

<210> SEQ ID NO 3
<211> LENGTH: 36
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (9)..(9)
<223> OTHER INFORMATION: 2'-deoxy-2'-C-Allyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(26)
<223> OTHER INFORMATION: 2'-O-Methyl
<220> FEATURE:
<221> NAME/KEY: misc_feature
<222> LOCATION: (16)..(18)
<223> OTHER INFORMATION: n stands for a, c, g, or u
<220> FEATURE:
<221> NAME/KEY: misc_feature
<222> LOCATION: (23)..(25)
<223> OTHER INFORMATION: n stands for a, c, g, or u
<220> FEATURE:
<221> NAME/KEY: misc_feature
<222> LOCATION: (28)..(29)
<223> OTHER INFORMATION: 2'-O-Methyl
<220> FEATURE:
<221> NAME/KEY: misc_feature
<222> LOCATION: (31)..(36)
<223> OTHER INFORMATION: n stands for a, c, g, or u
<220> FEATURE:
<221> NAME/KEY: misc_feature
<222> LOCATION: (31)..(36)
<223> OTHER INFORMATION: 2'-O-Methyl

<400> SEQUENCE: 3
nnnnnnncug augagnnnga aannncgaaa nnnnnn                             36

<210> SEQ ID NO 4
<211> LENGTH: 14
<212> TYPE: RNA
<213> ORGANISM: Artificial Sequence
```

```
<220> FEATURE:
<223> OTHER INFORMATION: Synthetic Generic Target Nucleic Acid
<220> FEATURE:
<221> NAME/KEY: misc_feature
<222> LOCATION: (1)..(5)
<223> OTHER INFORMATION: n stands for a, c, g, or u
<220> FEATURE:
<221> NAME/KEY: misc_feature
<222> LOCATION: (7)..(7)
<223> OTHER INFORMATION: n stands for a, u, or c
<220> FEATURE:
<221> NAME/KEY: misc_feature
<222> LOCATION: (8)..(14)
<223> OTHER INFORMATION: n stands for a, c, g, or u

<400> SEQUENCE: 4
nnnnncnnnn nnnn                                                              14

<210> SEQ ID NO 5
<211> LENGTH: 35
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (9)..(9)
<223> OTHER INFORMATION: 2'-deoxy-2'-C-Allyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(26)
<223> OTHER INFORMATION: 2'-O-Methyl
<220> FEATURE:
<221> NAME/KEY: misc_feature
<222> LOCATION: (16)..(18)
<223> OTHER INFORMATION: n stands for a, c, g, or u
<220> FEATURE:
<221> NAME/KEY: misc_feature
<222> LOCATION: (23)..(25)
<223> OTHER INFORMATION: n stands for a, c, g, or u
<220> FEATURE:
<221> NAME/KEY: misc_feature
<222> LOCATION: (28)..(29)
<223> OTHER INFORMATION: 2'-O-Methyl
<220> FEATURE:
<221> NAME/KEY: misc_feature
<222> LOCATION: (30)..(30)
<223> OTHER INFORMATION: Inosine
<220> FEATURE:
<221> NAME/KEY: misc_feature
<222> LOCATION: (31)..(35)
<223> OTHER INFORMATION: n stands for a, c, g, or u
<220> FEATURE:
<221> NAME/KEY: misc_feature
<222> LOCATION: (31)..(35)
<223> OTHER INFORMATION: 2'-O-Methyl

<400> SEQUENCE: 5
nnnnnnncug augagnnnga aannncgaan nnnnn                                       35

<210> SEQ ID NO 6
<211> LENGTH: 15
<212> TYPE: RNA
<213> ORGANISM: Artificial Sequence
```

```
<220> FEATURE:
<223> OTHER INFORMATION: Synthetic Generic Target Nucleic Acid
<220> FEATURE:
<221> NAME/KEY: misc_feature
<222> LOCATION: (1)..(6)
<223> OTHER INFORMATION: n stands for a, c, g, or u
<220> FEATURE:
<221> NAME/KEY: misc_feature
<222> LOCATION: (7)..(7)
<223> OTHER INFORMATION: n stands for u or c
<220> FEATURE:
<221> NAME/KEY: misc_feature
<222> LOCATION: (9)..(15)
<223> OTHER INFORMATION: n stands for a, c, g, or u

<400> SEQUENCE: 6
nnnnnnngnn nnnnn                                                      15

<210> SEQ ID NO 7
<211> LENGTH: 35
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (11)..(11)
<223> OTHER INFORMATION: Phosphorothioate 3'-Internucleotide Linkage
<220> FEATURE:
<221> NAME/KEY: misc_feature
<222> LOCATION: (13)..(16)
<223> OTHER INFORMATION: 2'-O-Methyl
<220> FEATURE:
<221> NAME/KEY: misc_feature
<222> LOCATION: (18)..(35)
<223> OTHER INFORMATION: 2'-O-Methyl
<220> FEATURE:
<221> NAME/KEY: misc_feature
<222> LOCATION: (29)..(35)
<223> OTHER INFORMATION: n stands for a, c, g, or u

<400> SEQUENCE: 7
nnnnnnnuga uggcaugcac uaugcgcgnn nnnnn                                 35

<210> SEQ ID NO 8
<211> LENGTH: 48
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (9)..(10)
<223> OTHER INFORMATION: 2'-deoxy-2'-amino
<220> FEATURE:
<221> NAME/KEY: misc_feature
<222> LOCATION: (12)..(21)
<223> OTHER INFORMATION: 2'-O-Methyl
<220> FEATURE:
<221> NAME/KEY: misc_feature
<222> LOCATION: (22)..(26)
<223> OTHER INFORMATION: 2'-deoxy-2'-amino
<220> FEATURE:
<221> NAME/KEY: misc_feature
```

-continued

```
<222> LOCATION: (32)..(37)
<223> OTHER INFORMATION: 2'-O-Methyl
<220> FEATURE:
<221> NAME/KEY: misc_feature
<222> LOCATION: (38)..(40)
<223> OTHER INFORMATION: 2'-deoxy-2'-amino
<220> FEATURE:
<221> NAME/KEY: misc_feature
<222> LOCATION: (44)..(48)
<223> OTHER INFORMATION: 2'-O-Methyl

<400> SEQUENCE: 8
gugugcaacc ggaggaaacu cccuucaagg acgaaagucc gggacggg        48

<210> SEQ ID NO 9
<211> LENGTH: 16
<212> TYPE: RNA
<213> ORGANISM: Artificial Sequence
<220> FEATURE:
<223> OTHER INFORMATION: Synthetic Target Nucleic Acid

<400> SEQUENCE: 9
gccguggguu gcacac        16

<210> SEQ ID NO 10
<211> LENGTH: 35
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(7)
<223> OTHER INFORMATION: 2'-O-Methyl
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (9)..(15)
<223> OTHER INFORMATION: 2'-O-Methyl
<220> FEATURE:
<221> NAME/KEY: misc_feature
<222> LOCATION: (17)..(17)
<223> OTHER INFORMATION: 2'-Deoxy-2'-Amino
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (21)..(21)
<223> OTHER INFORMATION: 2'-O-Methyl
<220> FEATURE:
<221> NAME/KEY: misc_feature
<222> LOCATION: (23)..(23)
<223> OTHER INFORMATION: 2'-O-Methyl
<220> FEATURE:
<221> NAME/KEY: misc_feature
<222> LOCATION: (26)..(26)
<223> OTHER INFORMATION: 2'-O-Methyl
<220> FEATURE:
<221> NAME/KEY: misc_feature
<222> LOCATION: (27)..(27)
<223> OTHER INFORMATION: 2'-Deoxy-2'-Amino
<220> FEATURE:
<221> NAME/KEY: misc_feature
<222> LOCATION: (28)..(35)
<223> OTHER INFORMATION: 2'-O-Methyl
<220> FEATURE:
<221> NAME/KEY: misc_feature
<222> LOCATION: (35)..(35)
<223> OTHER INFORMATION: abasic moiety

<400> SEQUENCE: 10
```

```
gugccuggcc gaaaggcgag ugaggucugc cgcgc                          35
```

<210> SEQ ID NO 11
<211> LENGTH: 15
<212> TYPE: RNA
<213> ORGANISM: Artificial Sequence
<220> FEATURE:
<223> OTHER INFORMATION: Synthetic Target Nucleic Acid

<400> SEQUENCE: 11

```
gcgcggcgca ggcac                                                15
```

<210> SEQ ID NO 12
<211> LENGTH: 16
<212> TYPE: DNA
<213> ORGANISM: Artificial Sequence
<220> FEATURE:
<223> OTHER INFORMATION: Synthetic Enzymatic Nucleic Acid Motif

<400> SEQUENCE: 12

```
rggctagcta caacga                                               16
```

<210> SEQ ID NO 13
<211> LENGTH: 33
<212> TYPE: RNA
<213> ORGANISM: Artificial Sequence
<220> FEATURE:
<223> OTHER INFORMATION: Synthetic Enzymatic Nucleic Acid
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (1)..(15)
<223> OTHER INFORMATION: 2'-O-Methyl
<220> FEATURE:
<221> NAME/KEY: misc_feature
<222> LOCATION: (17)..(22)
<223> OTHER INFORMATION: 2'-O-Methyl
<220> FEATURE:
<221> NAME/KEY: misc_feature
<222> LOCATION: (25)..(25)
<223> OTHER INFORMATION: 2'-O-Methyl
<220> FEATURE:
<221> NAME/KEY: misc_feature
<222> LOCATION: (27)..(33)
<223> OTHER INFORMATION: 2'-O-Methyl
<220> FEATURE:
<221> NAME/KEY: misc_feature
<222> LOCATION: (16)..(16)
<223> OTHER INFORMATION: 2'-deoxy-2'-amino
<220> FEATURE:
<221> NAME/KEY: misc_feature
<222> LOCATION: (26)..(26)
<223> OTHER INFORMATION: 2'-deoxy-2'-amino
<220> FEATURE:
<221> NAME/KEY: misc_feature
<222> LOCATION: (33)..(33)
<223> OTHER INFORMATION: 3'-3 attached terminal deoxyabasic moiety

<400> SEQUENCE: 13

```
gcaguggccg aaaggcgagu gaggucuagc uca                            33
```

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature

```
<222> LOCATION: (16)..(16)
<223> OTHER INFORMATION: Amide-substituted carboxy terminus on the
      lysine residue

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 26
<212> TYPE: PRT
<213> ORGANISM: Artificial
<220> FEATURE:
<223> OTHER INFORMATION: Synthetic

<400> SEQUENCE: 15

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide

<400> SEQUENCE: 16

Met Gly Leu Gly Leu His Leu Leu Val Leu Ala Ala Ala Leu Gln Gly
1               5                   10                  15

Ala

<210> SEQ ID NO 17
<211> LENGTH: 23
<212> TYPE: PRT
<213> ORGANISM: Artificial Sequence
<220> FEATURE:
<223> OTHER INFORMATION: Synthetic peptide

<400> SEQUENCE: 17

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Arg Lys Lys Arg Arg Gln Arg Arg Arg
1               5

<210> SEQ ID NO 19
<211> LENGTH: 24
<212> TYPE: PRT
<213> ORGANISM: Artificial Sequence
<220> FEATURE:
<223> OTHER INFORMATION: Synthetic peptide

<400> SEQUENCE: 19

Gly Leu Phe Glu Ala Ile Ala Gly Phe Ile Glu Asn Gly Trp Glu Gly
```

```
1               5                   10                  15
Met Ile Asp Gly Gly Gly Tyr Cys
            20

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa stands for any amino acid
<220> FEATURE:
<221> NAME/KEY: misc_feature
<222> LOCATION: (5)..(5)
<223> OTHER INFORMATION: Xaa stands for any amino acid

<400> SEQUENCE: 20

Xaa Arg Gly Asp Xaa
1               5

<210> SEQ ID NO 21
<211> LENGTH: 27
<212> TYPE: PRT
<213> ORGANISM: Artificial Sequence
<220> FEATURE:
<223> OTHER INFORMATION: Synthetic peptide

<400> SEQUENCE: 21

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Ser stands for optional Serine for coupling
<220> FEATURE:
<221> NAME/KEY: misc_feature
<222> LOCATION: (2)..(2)
<223> OTHER INFORMATION: Phe stands for optional D isomer for
      stability
<220> FEATURE:
<221> NAME/KEY: misc_feature
<222> LOCATION: (5)..(5)
<223> OTHER INFORMATION: Trp stands for optional D isomer for
      stability

<400> SEQUENCE: 22

Ser Phe Cys Tyr Trp Lys Thr Cys Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Ser stands for optional Serine for coupling
```

```
<400> SEQUENCE: 23

Ser Asp His Gln Leu Asn Pro Ala Phe
1               5

<210> SEQ ID NO 24
<211> LENGTH: 34
<212> TYPE: RNA
<213> ORGANISM: Artificial Sequence
<220> FEATURE:
<223> OTHER INFORMATION: Synthetic Nucleic Acid
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (11)..(11)
<223> OTHER INFORMATION: 2'-deoxy-2'-C-Allyl
<220> FEATURE:
<221> NAME/KEY: misc_feature
<222> LOCATION: (13)..(25)
<223> OTHER INFORMATION: 2'-O-Methyl
<220> FEATURE:
<221> NAME/KEY: misc_feature
<222> LOCATION: (27)..(28)
<223> OTHER INFORMATION: 2'-O-Methyl
<220> FEATURE:
<221> NAME/KEY: misc_feature
<222> LOCATION: (30)..(34)
<223> OTHER INFORMATION: 2'-O-Methyl
<220> FEATURE:
<221> NAME/KEY: misc_feature
<222> LOCATION: (34)..(34)
<223> OTHER INFORMATION: 3'-3 attached terminal deoxyabasic moiety

<400> SEQUENCE: 24
gaguugcuga ugaggccgaa aggccgaaag ucug                               34
```